United States Patent
Mitchell et al.

(10) Patent No.: US 8,680,114 B2
(45) Date of Patent: Mar. 25, 2014

(54) AKT PROTEIN KINASE INHIBITORS

(75) Inventors: Ian S. Mitchell, Lafayette, CO (US);
Keith L. Spencer, Lyons, CO (US);
Peter Stengel, Longmont, CO (US);
Yongxin Han, Longmont, CO (US);
Nicholas C. Kallan, Boulder, CO (US);
Mark Munson, Louisville, CO (US);
Guy P. A. Vigers, Boulder, CO (US);
James Blake, Longmont, CO (US);
Anthony Piscopio, Longmont, CO (US);
John Josey, Longmont, CO (US); Scott Miller, Longmont, CO (US); Dengming Xiao, Longmont, CO (US); Rui Xu, Longmont, CO (US); Chang Rao, Waltham, MA (US); Bing Wang, Longmont, CO (US); April L. Bernacki, Longmont, CO (US)

(73) Assignees: Array Biopharma, Inc., Boulder, CO (US); Genentech, Inc., South San Francisco, CA (US)

(*) Notice: Subject to any disclaimer, the term of this patent is extended or adjusted under 35 U.S.C. 154(b) by 1198 days.

(21) Appl. No.: 12/567,258

(22) Filed: Sep. 25, 2009

(65) Prior Publication Data
US 2010/0168123 A1   Jul. 1, 2010

Related U.S. Application Data

(62) Division of application No. 10/993,173, filed on Nov. 19, 2004, now abandoned.

(60) Provisional application No. 60/524,003, filed on Nov. 21, 2003.

(51) Int. Cl.
*A61K 31/47* (2006.01)
*A01N 43/42* (2006.01)
*C07D 215/00* (2006.01)

(52) U.S. Cl.
USPC ........ 514/311; 514/312; 514/252.1; 546/152; 544/336

(58) Field of Classification Search
USPC ......... 544/336; 546/152; 514/252.1, 311, 312
See application file for complete search history.

(56) References Cited

U.S. PATENT DOCUMENTS

| | | | |
|---|---|---|---|
| 3,885,035 A | 5/1975 | Simpson | |
| 3,956,495 A | 5/1976 | Lacefield | |
| 3,966,936 A | 6/1976 | Cronin et al. | |
| 4,060,615 A | 11/1977 | Matier et al. | |
| 5,051,412 A | 9/1991 | Macor | |
| 5,525,625 A | 6/1996 | Bridges et al. | |
| 5,563,152 A | 10/1996 | Kulagowski et al. | |
| 5,777,112 A * | 7/1998 | Nargund et al. | 544/121 |
| 5,817,671 A | 10/1998 | Filla et al. | |
| 6,310,060 B1 | 10/2001 | Barrett et al. | |
| 6,423,716 B1 | 7/2002 | Matsuno et al. | |
| 6,469,004 B1 | 10/2002 | Barrett et al. | |
| 6,506,798 B1 | 1/2003 | Barrett et al. | |
| 7,074,801 B1 * | 7/2006 | Yoshida et al. | 514/266.23 |
| 2003/0004193 A1 | 1/2003 | Barrett et al. | |
| 2003/0045521 A1 | 3/2003 | Tecle | |
| 2003/0078428 A1 | 4/2003 | Barrett et al. | |
| 2003/0092748 A1 | 5/2003 | Barrett et al. | |
| 2003/0199511 A1 | 10/2003 | Li et al. | |
| 2003/0216460 A1 | 11/2003 | Wallace et al. | |
| 2003/0232869 A1 | 12/2003 | Wallace et al. | |
| 2004/0116710 A1 | 6/2004 | Wallace et al. | |

FOREIGN PATENT DOCUMENTS

| | | |
|---|---|---|
| HU | 207859 B | 6/1993 |
| WO | WO 95/03286 | 2/1995 |
| WO | WO 95/34311 A1 | 12/1995 |
| WO | WO 98/43960 | 10/1998 |
| WO | WO 99/01421 | 1/1999 |
| WO | WO 99/01426 | 1/1999 |
| WO | WO 00/40235 | 7/2000 |
| WO | WO 00/40237 | 7/2000 |
| WO | WO 00/41505 | 7/2000 |
| WO | WO 00/41994 | 7/2000 |
| WO | WO 00/42002 | 7/2000 |
| WO | WO 00/42003 | 7/2000 |
| WO | WO 00/42022 | 7/2000 |
| WO | WO 00/42029 | 7/2000 |
| WO | WO 00/48993 A1 | 8/2000 |
| WO | WO 00/68201 | 11/2000 |
| WO | WO 01/05390 | 1/2001 |
| WO | WO 01/05391 | 1/2001 |
| WO | WO 01/05392 | 1/2001 |
| WO | WO 01/05393 | 1/2001 |
| WO | WO 01/40217 A1 | 6/2001 |
| WO | WO 01/68619 | 9/2001 |
| WO | WO 02/06213 | 1/2002 |

(Continued)

OTHER PUBLICATIONS

Pinedo et al (2000).*
McMahonb et al (2000).*
Vippagunta et al. (2001).*
International Search Report and Written Opinion of the International Searching Authority, PCT/US2004/39094, Dec. 7, 2005, 9 pages.
Agrawal et al., "Antiparasitic Agents. Part VI. Synthesis of 7-chloro-4-(-4-substituted-phenylamino)- and 7-chloro-4-(4-substituted-piperazin-1-yl)Quinolines as potential antiparasitic agents", *Indian Journal of Chemistry*, vol. 26B, 550-555 (1987).
Australian Office Action for Australian Application No. 2011-265309, 12 pages, dated Dec. 7, 2012.
Chemical Abstracts Accession No. 2002:905762.
Chemical Abstracts Accession No. 2002:849613.
Chemical Abstracts Accession No. 1993:449247.
Chemical Abstracts Accession No. 1986:142076.
CAS RN 503428-24-8, Entered STN: Apr. 18, 2003.
CAS RN 462651-41-8, Entered STN: Oct. 18, 2002.

(Continued)

*Primary Examiner* — Paul V. Ward
(74) *Attorney, Agent, or Firm* — Viksnins Harris & Padys PLLP

(57) ABSTRACT

The present invention provides compounds, including resolved enantiomers, diastereomers, solvates and pharmaceutically acceptable salts thereof, comprising the Formula:

A-L-CR where CR is a cyclical core group, L is a linking group and A is as defined herein. Also provided are methods of using the compounds of this invention as AKT protein kinase inhibitors and for the treatment of hyperproliferative diseases such as cancer.

20 Claims, 46 Drawing Sheets

(56) References Cited

FOREIGN PATENT DOCUMENTS

| WO | WO 02/18319 | 3/2002 |
|---|---|---|
| WO | WO 02/44166 | 6/2002 |
| WO | WO 02/083139 | 10/2002 |
| WO | WO 02/088107 A1 | 11/2002 |
| WO | WO 02/094203 A2 | 11/2002 |
| WO | WO 03/022214 | 3/2003 |
| WO | WO 03/064397 | 8/2003 |
| WO | WO 03/077855 | 9/2003 |
| WO | WO 03/077914 | 9/2003 |
| WO | WO 03/086279 | 10/2003 |
| WO | WO 03/086394 | 10/2003 |
| WO | WO 03/086403 | 10/2003 |
| WO | WO 03/086404 | 10/2003 |
| WO | WO 03/105853 A1 | 12/2003 |
| WO | WO 2004/002960 A1 | 1/2004 |
| WO | WO 2004/018453 A1 | 3/2004 |
| WO | WO 2004/078116 | 9/2004 |
| WO | WO 2005/023761 | 3/2005 |

OTHER PUBLICATIONS

CAS RN 328073-76-3, Entered STN: Mar. 20, 2001.
CAS RN 293764-33-7, Entered STN: Oct. 9, 2000.
CAS RN 293759-62-3, Entered STN: Oct. 9, 2000.
CAS RN 292841-57-7, Entered STN: Oct. 5, 2000.
CAS RN 292841-53-3, Entered STN: Oct. 5, 2000.
CAS RN 292152-11-5, Entered STN: Oct. 3, 2000.
CAS RN 291280-13-2, Entered STN: Sep. 27, 2000.
CAS RN 101153-51-9, Entered STN: Mar. 29, 1986.
CAS RN 101153-49-5, Entered STN: Mar. 29, 1986.
Guillory, "Generation of Polymorphs, Hydrates, Solvate and Amorphous Solids", *Polymorphism in Pharmaceutical Solids*, vol. 95, 183-226 (1999).
Jiranusornkul et al., "Synthesis of amino acid derivatives of 6-aminoquinoloine antimalarial agents", *Heterocycles*, 56(1-2), 487-496 (2002).
Peck et al., "Acridine and quinolone analogs of nitrogen mustard with amide side chains", *Journal of Medicinal Chemistry*, 7(4), 480-482 (1964).
Peck et al., "Heterocyclic derivatives of 2-chloroethyl sulfide with antitumor activity", *Journal of Medicinal Chemistry*, 9(2), 217-221 (1966).
Trubitsyna et al., "Comparative anorexigenic activity and other pharmacological properties of quipazine and its N-acyl derivatives", *Farmakologiya*, 49(1), Toksikologlya (Moscow), 44-49 (1986). [English Abstract included on last page.].

\* cited by examiner

AKT PROTEIN KINASE INHIBITORS

CROSS REFERENCE TO RELATED APPLICATIONS

This application is a divisional of U.S. application Ser. No. 10/993,173 filed on Nov. 19, 2004 now abandoned, which claims the benefit of U.S. Provisional Application Ser. No. 60/524,003, filed Nov. 21, 2003, which are incorporated herein by reference in their entireties.

BACKGROUND OF THE INVENTION

1. Field of the Invention

This invention relates to novel inhibitors of serine/threonine protein kinases (e.g., AKT and related kinases), pharmaceutical compositions containing the inhibitors, and methods for preparing these inhibitors. The inhibitors are useful for the treatment of hyperproliferative diseases, such as cancer and inflammation, in mammals and especially in humans.

2. Description of the State of the Art

Protein kinases are a class of enzymes that catalyze the transfer of the γ-phosphorate group from ATP to a recipient protein, acting as a substrate. The specific target of the kinase is the hydroxyl group of a serine, threonine or tyrosine residue. As a result of this specific targeting, kinases are generally referred to as serine/threonine protein kinases or tyrosine protein kinases. The human genome is estimated to encode in excess of 500 distinct protein kinases.

The seemingly insignificant task of phosphorylation of a serine, threonine or tyrosine residue belies the importance of protein kinases in the processes of signal transduction and regulation of cellular functions. Kinases are typically mediated by transmembrane cellular receptors, such as G-protein coupled receptors or growth factor receptors, which when activated by extracellular ligands cause the phosphorylation of intracellular proteins. Often, an interconnected series (or cascade) of protein kinases is necessary to exert the overall effect of this initial signal, which can ultimately result in effects as extreme as cell death (apoptosis).

The ratio of phosphorylated to unphosphorylated protein is a delicate equilibrium, with protein phosphatases acting as the negative regulator of protein kinases, removing the phosphoryl group as it is no longer required. As an example of this interplay, the phosphorylation state of kinases can control whether a cell undergoes division, arrests in the cell cycle or programmed cell death. Should this kinase/phosphatase relationship become disregulated, the potential consequences relating to disease are enormous. For example, abnormal protein kinase activity or expression may be correlated with numerous hyperproliferative diseases, inflammation and tissue repair, and has been associated with a large number of diseases ranging from the relatively non-life threatening, such as psoriasis, to those which are almost always fatal, such as glioblastoma multiforme, an aggressive brain cancer.

Significantly, atypical protein phosphorylation and/or expression is often reported to be one of the causative effects of abnormal cellular proliferation, metastasis and cell survival in cancer. The abnormal regulation and/or expression of various kinases, including VEGF, ILK, AKT, ROCK, p70S6K, Bcl, PKA, PKC, Raf, Src, PDK1, ErbB2, MEK, IKK, Cdk, EGFR, BAD, CHK1, CHK2 and GSK3 amongst numerous others, has been specifically implicated in cancer.

Recent data from the CDC indicate that cancer is the second most common cause of death in the United States, with nearly a quarter of all deaths reported being attributable to malignant neoplasms (Anderson, *National Vital Statistics Report*, 2001, 49 (11):1). Despite recent advances in the understanding of the genesis, progression and treatment of cancer, much still needs to be done to improve the overall prognosis of cancer patients.

The phosphatidylinositol 3'-OH kinase (PI3K) pathway is one of the signaling pathways that exerts its effect on numerous cellular functions including cell cycle progression, proliferation, motility, metabolism and survival. Activation of receptor protein tyrosine kinases (RTKs) cause PI3K to phosphorylate phosphatidylinositol (4,5)-diphosphate[PtdIns (4,5)$P_2$], generating the membrane-bound phosphatidylinositol (3,4,5)-triphosphate[PtdIns(3,4,5)$P_3$]. This in turn promotes the recruitment of a variety of protein kinases from the cytoplasm to the plasma membrane through the binding of PtdIns (3,4,5)$P_3$ to the pleckstrin-homology (PH) domain of the kinase. Kinases notable as key downstream targets of PI3K include phosphoinositide-dependant kinase 1 (PDK1) and AKT (also known as Protein Kinase B.) Phosphorylation of such kinases then permits the activation or deactivation of numerous other pathways involving mediators such as GSK3, mTOR, PRAS40, FKHD, NF-κB, BAD, Caspase-9, etc.

An important negative feedback mechanism for the PI3K pathway is PTEN, a phosphatase that catalyses the dephosphorylation of PtdIns (3,4,5)$P_3$ to PtdIns (4,5)$P_2$ (Furnari, F. B., et al, *Cancer Res.* 1998, 58:5002; Dahia, P. L. M., *Hum. Molec. Genet.* 1999, 8:185). It is of enormous significance that in greater than 60% of all solid tumors, PTEN is mutated into an inactive form, permitting the constitutive-activation of the PI3K pathway. As the majority of cancers are solid tumors, such an observation would suggest that by specifically targeting either PI3K itself or the individual downstream kinases in the PI3K pathway, one might able to mitigate the effects of various cancers and restore normal cellular function.

One of the best-characterized targets of the PI3K lipid products is the AGC serine/threonine protein kinase AKT (Hemmings, B. A., *Science*, 1997, 275:628). AKT is the human homologue of the protooncogene v-akt of the acutely transforming retrovirus AKT8. Its high sequence homology to protein kinases A and C has also earned it the names Protein Kinase B (PKB) and Related to A and C (RAC.) Three isoforms of AKT are known to exist, namely Akt1, Akt2 and Akt3, which exhibit an overall homology of 80% (Staal, S. P, *Proc. Natl. Acad. Sci.*, 1987, 84:5034; Nakatani, K, *Biochem. Biophys. Res. Commun.*, 1999, 257:906). In addition, both Akt2 and Akt3 exhibit splice variants.

Upon recruitment to the cell membrane by PtdInd (3,4,5)$P_3$, AKT is phosphorylated (activated) by PDK1 at T308, T309 and T305 for isoforms Akt1, 2 and 3, respectively, and at S473, S474 and S472 for isoforms Akt1, 2 and 3, respectively. Such phosphorylation occurs by an as yet unknown kinase (putatively named PDK2), although PDK1 (Balendran, A., *Curr. Biol.*, 1999, 9:393), autophosphorylation (Toker, A., *J. Biol. Chem.*, 2000, 275:8271) and integrin-linked kinase (ILK) (Delcommenne, M., *Proc. Natl. Acad. Sci. USA*, 1998, 95:11211) have been implicated in this process. Although monophosphorylation of AKT activates the kinase, bis(phosphorylation) is required for maximal kinase activity.

AKT is believed to assert its effect on cancer by suppressing apoptosis and enhancing both angiogenesis and proliferation. In addition, AKT has been shown to be overexpressed in many forms of human cancer including, but not limited to, colon (Zinda, et al, *Clin. Cancer Res.*, 2001, 7:2475), ovarian (Cheng, J. Q., et al., *Proc. Natl. Acad. Sci. USA*, 1992, 89:9267), brain (Haas Kogan, D., et al, *Curr. Biol.*, 1998, 8:1195), lung (Brognard, J., et al, *Cancer Res.*, 2001, 61:3986), pancreatic (Cheng, J. Q., et al., *Proc. Natl. Acad. Sci.*, 1996, 93:3636), prostate (Graff, J. R., et al, *J. Biol. Chem.*, 2000, 275:24500) and gastric carcinomas (Staal, S. P., et al., *Proc. Natl. Acad. Sci. USA*, 1987, 84:5034).

The development of kinase inhibitors that target abnormally regulated pathways and ultimately result in disease is of enormous ethical and commercial interest to the medical and pharmaceutical community. As such, a compound that inhibits (1) recruitment of AKT to the cell membrane, (2) activation by PDK1 or PDK2, (3) substrate phosphorylation, or (4) one of the downstream targets of AKT would therefore be a valid target as an anticancer agent, either as a stand-alone therapy or in conjunction with other accepted procedures.

SUMMARY OF THE INVENTION

This invention provides novel compounds that inhibit AKT protein kinases, methods for producing these compounds, and pharmaceutical compositions containing such compounds. The compounds of the present invention have utility as therapeutic agents for diseases and conditions that can be treated by the inhibition of AKT protein kinases. More specifically, the present invention includes compounds, including resolved enantiomers and diastereomers, and pharmaceutically acceptable prodrugs, metabolites, salts and solvates thereof, having the general Formula I:

A-L-CR    (I)

where:

CR is heteroaryl, wherein said heteroaryl is optionally substituted with one or more groups selected from halogen, hydroxyl, cyano, nitro, azido, $-NR^{21}SO_2R^{24}$, $-SO_2NR^{21}R^{22}$, $-NR^{21}S(O)R^4$, $-S(O)NR^{21}R^{22}$, $-C(O)R^{21}$, $-C(O)OR^{21}$, $-OC(O)R^{21}$, $-OC(O)OR^{21}$, $-NR^{21}C(O)OR^{24}$, $-NR21C(=NR^{21})NR^{22}R^{23}$, $-NR^{21}C(O)R^{22}$, $-C(O)NR^{21}R^{22}$, $-SR^{21}$, $-S(O)R^{24}$, $-SO_2R^{24}$, $-NR^{21}R^{22}$, $-NR^{21}C(O)NR^{22}R^{23}$, $-NR^{21}C(NCN)NR^{22}R^{23}$, $-OR^{21}$, $C_1$-$C_4$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, $C_3$-$C_6$ cycloalkyl, $C_3$-$C_6$ heterocycloalkyl, aryl, heteroaryl, arylalkyl and heteroarylalkyl, wherein any of said alkyl, heteroalkyl, alkenyl, heteroalkenyl, alkynyl, heteroalkynyl, cycloalkyl, heterocycloalkyl, aryl, heteroaryl, arylalkyl and heteroarylalkyl are further optionally substituted with one or more groups selected from halogen, hydroxyl, cyano, nitro, azido, fluoromethyl, difluoromethyl, trifluoromethyl, $C_1$-$C_6$ alkyl, $C_2$-$C_6$ alkenyl, $C_2$-$C_6$ alkynyl, $C_1$-$C_6$ heteroalkyl, $C_2$-$C_6$ heteroalkenyl, $C_2$-$C_6$ heteroalkynyl, $C_3$-$C_6$ cycloalkyl, $C_3$-$C_6$ heterocycloalkyl, $-SR^{21}$, $-S(O)R^{24}$, $-SO_2R^{24}$, $-C(O)R^{21}$, C(O) $OR^{21}$, $-C(O)NR^{21}R^{22}$, $-NR^{21}R^{22}$ and $-OR^{21}$;

L is selected from:

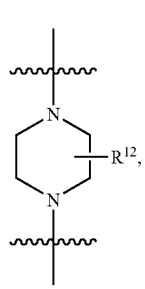 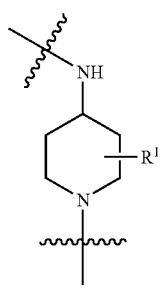 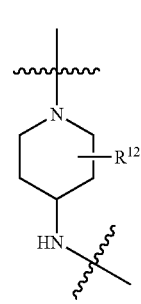

-continued

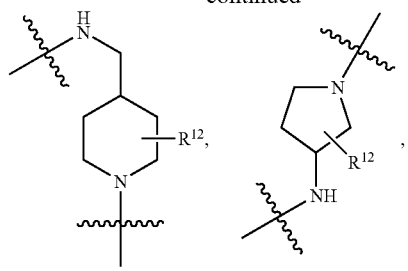

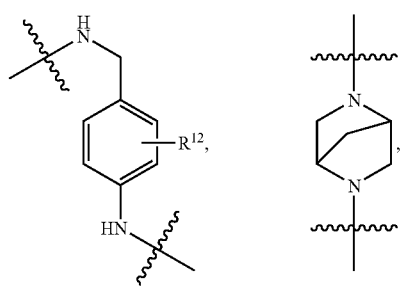

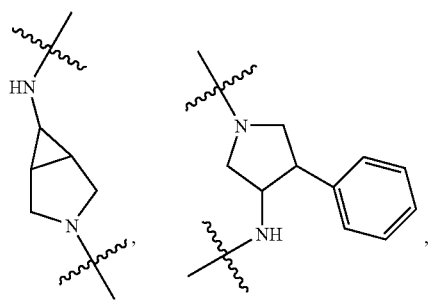

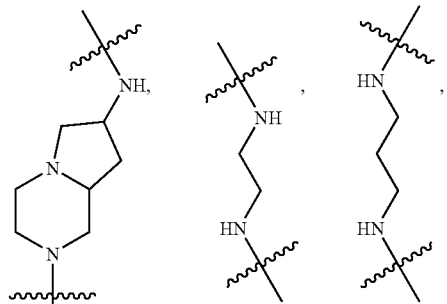

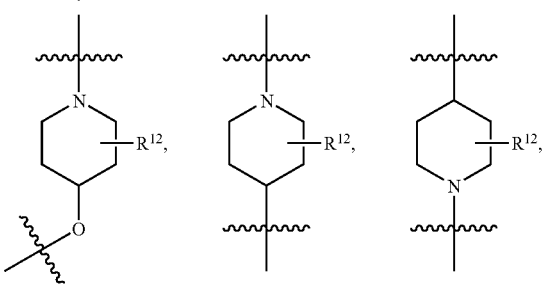

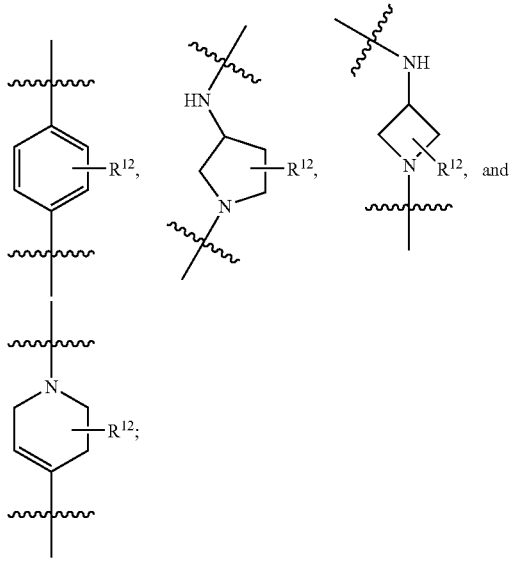

$R^{12}$ is hydrogen, halogen, hydroxy, cyano, nitro, amino, azido, $C_1$-$C_5$ alkyl, $C_2$-$C_5$ alkenyl, $C_2$-$C_5$ alkynyl, $C_1$-$C_5$ heteroalkyl, $C_2$-$C_5$ heteroalkenyl or $C_2$-$C_5$ heteroalkynyl, wherein any of said alkyl, alkenyl, alkynyl, heteroalkyl, heteroalkenyl, and heteroalkynyl are optionally substituted with one or more groups independently selected from halogen, cyano, nitro, amino, azido, $C_1$-$C_4$ alkyl, fluoromethyl, difluoromethyl, trifluoromethyl, methoxy, fluoromethoxy, difluoromethoxy and trifluoromethoxy;

A is

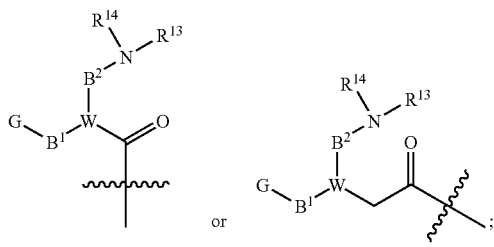

W is N or $CR^{15}$, provided that when L is a substituted or unsubstituted piperazinylene, W must be $CR^{15}$;

G is hydrogen, alkyl, heteroalkyl, alkenyl, heteroalkenyl, alkynyl, heteroalkynyl, cycloalkyl, heterocycloalkyl, aryl or heteroaryl, wherein any of said alkyl, heteroalkyl, alkenyl, heteroalkenyl, alkynyl, heteroalkynyl, cycloalkyl, heterocycloalkyl, aryl or heteroaryl is optionally substituted with one or more groups selected from halogen, hydroxyl, cyano, amino, nitro, azido, $-NR^{21}SO_2R^{24}$, $-SO_2NR^{21}R^{22}$, $-NR^{21}S(O)R^4$, $-S(O)NR^{21}R^{22}$, $-C(O)R^{21}$, $-C(O)OR^{21}$, $-OC(O)R^{21}$, $-OC(O)OR^{21}$, $-NR^{21}C(O)OR^{24}$, $-NR^{21}C(=NR^{21})NR^{22}R^{23}$, $-NR^{21}C(O)R^{22}$, $-C(O)NR^{21}R^{22}$, $-SR^{21}$, $-S(O)R^{24}$, $-SO_2R^{24}$, $-NR^{21}R^{22}$, $-NR^{21}C(O)NR^{22}R^{23}$, $-NR^{21}C(NCN)NR^{22}R^{23}$, $OR^{21}$, $C_1$-$C_4$ alkyl, $C_1$-$C_4$ heteroalkyl, $C_2$-$C_4$ alkenyl, $C_2$-$C_4$ heteroalkenyl, $C_2$-$C_4$ alkynyl, $C_2$-$C_4$ heteroalkynyl, cycloalkyl, heterocycloalkyl aryl and heteroaryl;

$B^1$ and $B^2$ are independently absent or $C_1$-$C_4$ alkylene, $C_1$-$C_4$ heteroalkylene, $C_2$-$C_4$ alkenylene, $C_2$-$C_4$ heteroalkenylene, $C_2$-$C_4$ alkynylene, $C_2$-$C_4$ heteroalkynylene, $C_3$-$C_6$ cycloalkylene, and $C_3$-$C_6$ heterocycloalkylene, wherein any of said alkylene, heteroalkylene, alkenylene, heteroalkenylene, alkynylene, heteroalkynylene, cycloalkylene or heterocycloalkylene is optionally substituted with one or more groups independently selected from halogen, hydroxyl, cyano, nitro, azido, $C_1$-$C_4$ alkyl, $C_1$-$C_4$ heteroalkyl, $C_2$-$C_4$ alkenyl, $C_2$-$C_4$ heteroalkenyl, $C_2$-$C_4$ alkynyl, $C_2$-$C_4$ heteroalkynyl, $NR^{21}R^{22}$ and $OR^{21}$;

$R^{21}$, $R^{22}$ and $R^{23}$ independently are hydrogen, $C_1$-$C_6$ alkyl, $C_2$-$C_6$ alkenyl, $C_2$-$C_6$ alkynyl, $C_1$-$C_6$ heteroalkyl, $C_2$-$C_6$ heteroalkenyl, $C_2$-$C_6$ heteroalkynyl, $C_3$-$C_6$ cycloalkyl, $C_3$-$C_6$ heterocycloalkyl, aryl, arylalkyl, heteroaryl or heteroarylalkyl;

$R^{24}$ is $C_1$-$C_6$ alkyl, $C_2$-$C_6$ alkenyl, $C_2$-$C_6$ alkynyl, $C_1$-$C_6$ heteroalkyl, $C_2$-$C_6$ heteroalkenyl, $C_2$-$C_6$ heteroalkynyl, $C_3$-$C_6$ cycloalkyl, $C_3$-$C_6$ heterocycloalkyl, aryl, arylalkyl, heteroaryl or heteroarylalkyl;

or any two of $R^{21}$, $R^{22}$, $R^{23}$ or $R^{24}$ together with the atom(s) to which they are attached form a 4 to 10 membered carbocyclic, aryl, heteroaryl or heterocyclic ring, wherein any of said carbocyclic, aryl, heteroaryl or heterocyclic rings are optionally substituted with one or more groups independently selected from halogen, cyano, nitro, trifluoromethyl, difluoromethoxy, trifluoromethoxy, azido, aryl, heteroaryl, arylalkyl, heteroarylalkyl, heterocyclyl, and heterocyclylalkyl;

$R^{13}$ and $R^{14}$ are independently hydrogen, hydroxyl, cyano, $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, $C_1$-$C_6$ cycloalkyl, $C_1$-$C_6$ heterocycloalkyl, aryl, heteroaryl, arylalkyl, heteroarylalkyl, $-C(O)R^{21}$, $C(O)OR^{21}$, $C(=NR^{21})NR^{22}R^{23}$ or $-SO_2R^{24}$, wherein any of said alkyl, alkenyl, alkynyl, cycloalkyl, heterocycloalkyl, aryl, heteroaryl, heteroalkyl, heteroalkenyl, heteroalkynyl, arylalkyl or heteroarylalkyl is optionally substituted with one or more groups independently selected from halogen, hydroxyl, cyano, amino, nitro, azido, $-NR^{21}SO_2R^{24}$, $-SO_2NR^{21}R^{22}$, $-NR^{21}S(O)R^4$, $-S(O)NR^{21}R^{22}$, $-C(O)R^{21}$, $C(O)OR^{21}$, $-OC(O)R^{21}$, $-OC(O)OR^{21}$, $-NR^{21}C(O)OR^{24}$, $-NR^{21}C(=NR^{21})NR^{22}R^{23}$, $-NR^{21}C(O)R^{22}$, $-C(O)NR^{21}R^{22}$, $-SR^{21}$, $-S(O)R^{24}$, $-SO_2R^{24}$, $-NR^{21}R^{22}$, $-NR^{21}C(O)NR^{22}R^{23}$, $-NR^{21}C(NCN)NR^{22}R^{23}$, $NR^{21}C(NCN)NR^{22}R^{23}$, $-OR^{21}$, $C_4$ alkyl, $C_1$-$C_4$ heteroalkyl, $C_2$-$C_4$ alkenyl, $C_2$-$C_4$ heteroalkenyl, $C_2$-$C_4$ alkynyl, $C_2$-$C_4$ heteroalkynyl, cycloalkyl, heterocycloalkyl aryl and heteroaryl;

or $R^{13}$ and $R^{14}$ together with the atoms to which they are attached form a 4 to 10 membered carbocyclic, aryl, heteroaryl or heterocyclic ring, wherein any of said carbocyclic, aryl, heteroaryl and heterocyclic rings are optionally substituted with one or more groups independently selected from halogen, cyano, nitro, azido, $C_1$-$C_4$ alkyl, $C_1$-$C_4$ heteroalkyl, $C_2$-$C_4$ alkenyl, $C_2$-$C_4$ heteroalkenyl, $C_2$-$C_4$ alkynyl, $C_2$-$C_4$ heteroalkynyl, $NR^{21}R^{22}$ and $OR^{21}$;

or $R^{13}$ and an atom of $B^2$ together with N form a 4 to 10 membered carbocyclic, aryl, heteroaryl or heterocyclic ring, wherein any of said carbocyclic, aryl, heteroaryl and heterocyclic rings are optionally substituted with one or more groups independently selected from halogen, cyano, nitro, azido, $C_1$-$C_4$ alkyl, $C_1$-$C_4$ heteroalkyl, $C_2$-$C_4$ alkenyl, $C_2$-$C_4$ heteroalkenyl, $C_2$-$C_4$ alkynyl, $C_2$-$C_4$ heteroalkynyl, $NR^{21}R^{22}$ and $OR^{21}$;

$R^{15}$ is hydrogen, $C_1$-$C_4$ alkyl, $C_1$-$C_4$ heteroalkyl, $C_2$-$C_4$ alkenyl, $C_2$-$C_4$ heteroalkenyl, $C_2$-$C_4$ alkynyl or $C_2$-$C_4$ heteroalkynyl, wherein any of said alkyl, heteroalkyl, alkenyl, heteroalkenyl, alkynyl or heteroalkynyl is optionally substituted with one or more groups independently selected from halogen, hydroxyl, cyano, nitro, azido, $NR^{21}R^{22}$ and $OR^{21}$;

or $R^{13}$ and $R^{15}$ together with atoms to which they are attached form a 3 to 10 membered carbocyclic, aryl, heteroaryl or heterocyclic ring, wherein any of said carbocyclic, aryl, heteroaryl and heterocyclic rings are optionally substituted with one or more groups independently selected from halogen, cyano, nitro, azido, $C_1$-$C_4$ alkyl, $C_1$-$C_4$ heteroalkyl, $C_2$-$C_4$ alkenyl, $C_2$-$C_4$ heteroalkenyl, $C_2$-$C_4$ alkynyl, $C_2$-$C_4$ heteroalkynyl, $NR^{21}R^{22}$ and $OR^{21}$;

or, when W is $CR^{15}$, $R^{15}$ and an atom of $B^1$ or $B^2$ together with C, form a 3 to 10 membered carbocyclic, aryl, heteroaryl or heterocyclic ring, wherein any of said carbocyclic, aryl, heteroaryl and heterocyclic rings are optionally substituted with one or more groups independently selected from halogen, cyano, nitro, azido, $C_1$-$C_4$ alkyl, $C_1$-$C_4$ heteroalkyl, $C_2$-$C_4$ alkenyl, $C_2$-$C_4$ heteroalkenyl, $C_2$-$C_4$ alkynyl, $C_2$-$C_4$ heteroalkynyl, $NR^{21}R^{22}$ and $OR^{21}$.

The invention also relates to pharmaceutical compositions comprising an effective amount of an agent selected from compounds of Formula I. Methods of making the compounds of Formula I are also described.

In a further embodiment, the present invention provides methods of inhibiting the activity of AKT protein kinases utilizing compounds of Formula I.

In a further embodiment, the present invention provides a method of treating diseases or medical conditions mediated by AKT protein kinases. For example, this invention provides a method for treatment of a hyperproliferative disorder in a warm-blooded animal which comprises administering to such animal one or more compounds of Formula I, or a pharmaceutically acceptable salt or in vivo cleavable prodrug thereof in an amount effective to treat or prevent said hyperproliferative disorder.

In a further embodiment, the present invention provides a method of inhibiting the production of AKT protein kinases, which comprises administering to a warm-blooded animal an effective amount of a compound of Formula I, or a pharmaceutically acceptable salt or in vivo cleavable prodrug thereof in an amount effective to inhibit production of an AKT protein kinase.

In a further embodiment, the present invention provides a method of providing AKT protein kinase inhibiting effect comprising administering to a warm-blooded animal an effective amount of a compound of Formula I, or a pharmaceutically acceptable salt or in vivo cleavable prodrug thereof.

In a further embodiment, the present invention provides treating or preventing an AKT protein kinase mediated condition, comprising administering to a mammal a compound having Formula I or a pharmaceutically-acceptable salt, in vivo cleavable prodrug or pharmaceutical formulation thereof, in an amount effective to treat or prevent said AKT protein kinase-mediated condition. AKT protein kinase mediated conditions that can be treated according to the methods of this invention include, but are not limited to, cancer, inflammation and various proliferative, cardiovascular, neurodegenerative, gynecological & dermatological diseases.

Hyperproliferative conditions that can be treated according to the methods of this invention include, but are not limited to, cancers of the head, neck, lung, breast, colon, ovary, bladder, stomach, esophagus, uterus or prostate, among other kinds of hyperproliferative disorders. In compounds and methods of this invention can be used to treat diseases and conditions, including rheumatoid arthritis, osteoarthritis, endometriosis, atherosclerosis, vein graft stenosis, peri-anastomatic prothetic graft stenosis, prostate hyperplasia, chronic obstructive pulmonary disease, psoriasis, inhibition of neurological damage due to tissue repair, scar tissue formation (and can aid in wound healing), multiple sclerosis, inflammatory bowel disease, infections, particularly bacterial, viral, retroviral or parasitic infections (by increasing apoptosis), pulmonary disease, neoplasm, Parkinson's disease, transplant rejection (as an immunosupressant), macular degeneration and septic shock.

The compounds of Formula I may be used advantageously in combination with other known therapeutic agents.

Additional advantages and novel features of this invention shall be set forth in part in the description that follows, and in part will become apparent to those skilled in the art upon examination of the following specification, or may be learned by the practice of the invention. The advantages of the invention may be realized and attained by means of the instrumentalities, combinations, compositions, and methods particularly pointed out in the appended claims

BRIEF DESCRIPTION OF THE FIGURES

The accompanying drawings, which are incorporated herein and form a part of the specification, illustrate non-limiting embodiments of the present invention, and together with the description, serve to explain the principles of the invention.

In the Figures.

DETAILED DESCRIPTION OF THE INVENTION

Figure 1:
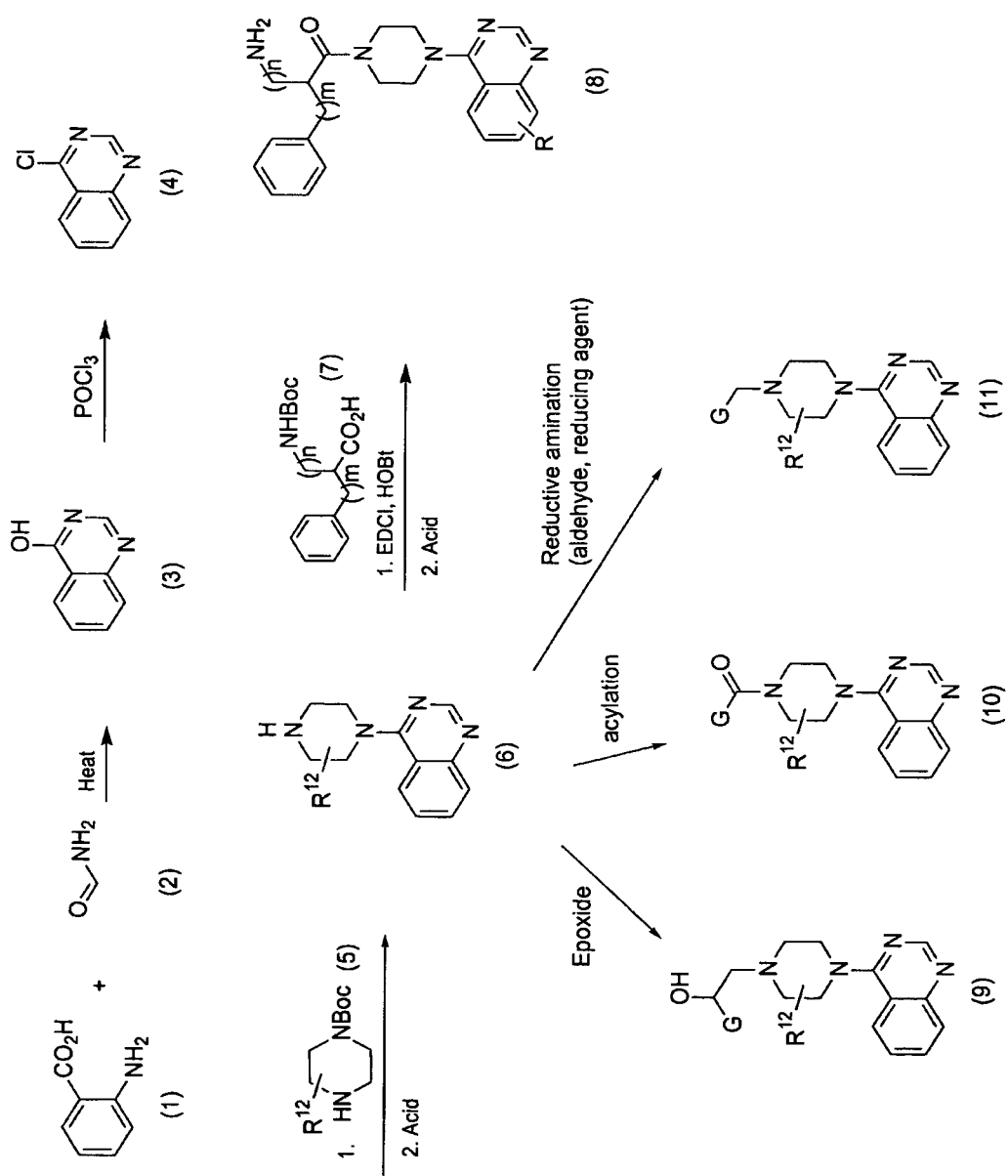
FIG. 1 shows a reaction scheme for the preparation of compounds 8-11.

The inventive compounds of Formula I are useful for inhibiting AKT protein kinases. The compounds of Formula I may also be useful as inhibitors of tyrosine kinases as well as serine and threonine kinases in addition to AKT. Such compounds have utility as therapeutic agents for diseases that can be treated by the inhibition of the AKT protein kinase signaling pathway and tyrosine and serine/threonine kinase receptor pathways. In general, the invention includes compounds, including resolved enantiomers and diastereomers, and pharmaceutically acceptable prodrugs, metabolites, salts and solvates thereof, having the general Formula I:

$$AA\text{-}L\text{-}CR \qquad I$$

where CR is heteroaryl, wherein said heteroaryl is optionally substituted with one or more groups selected from halogen, hydroxyl, cyano, nitro, azido, $-NR^{21}SO_2R^{24}$, $-SO_2NR^{21}R^{22}$, $-NR^{21}S(O)R^4$, $-S(O)NR^{21}R^{22}$, $-C(O)R^{21}$, $-C(O)OR^{21}$, $-OC(O)R^{21}$, $-OC(O)OR^{21}$, $-NR^{21}C(O)OR^{24}$, $-NR^{21}C(=NR^{21})NR^{22}R^{23}$, $-NR^{21}C(O)R^{22}$, $-C(O)NR^{21}R^{22}$, $SR^{21}$, $-S(O)R^{24}$, $-SO_2R^{24}$, $-NR^{21}R^{22}$, $-NR^{21}C(O)NR^{22}R^{23}$, $-NR^{21}C(NCN)NR^{22}R^{23}$, $-OR^{21}$, $C_1$-$C_4$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, $C_3$-$C_6$ cycloalkyl, $C_3$-$C_6$ heterocycloalkyl, aryl, heteroaryl, arylalkyl and heteroarylalkyl, wherein any of said alkyl, heteroalkyl, alkenyl, heteroalkenyl, alkynyl, heteroalkynyl, cycloalkyl, heterocycloalkyl, aryl, heteroaryl, arylalkyl and heteroarylalkyl are further optionally substituted with one or more groups selected from halogen, hydroxyl, cyano, nitro, azido, fluoromethyl, difluoromethyl, trifluoromethyl, $C_1$-$C_6$ alkyl, $C_2$-$C_6$ alkenyl, $C_2$-$C_6$ alkynyl, $C_1$-$C_6$ heteroalkyl, $C_2$-$C_6$ heteroalkenyl, $C_2$-$C_6$ heteroalkynyl, $C_3$-$C_6$ cycloalkyl, $C_3$-$C_6$ heterocycloalkyl, $-SR^{21}$, $-S(O)R^{24}$, $-SO_2R^{24}$, $-C(O)R^{21}$, $C(O)OR^{21}$, $-C(O)NR^{21}R^{22}$, $-NR^{21}R^{22}$ and $-OR^{21}$;

L is selected from:

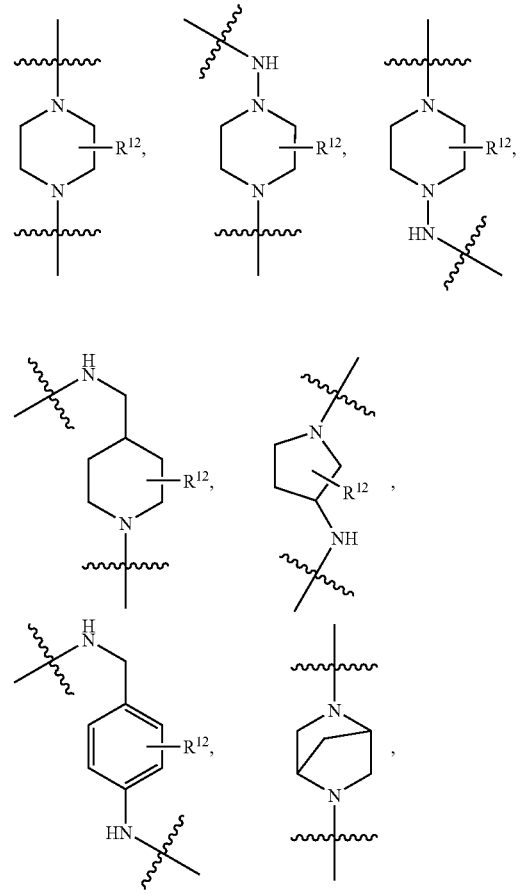

-continued

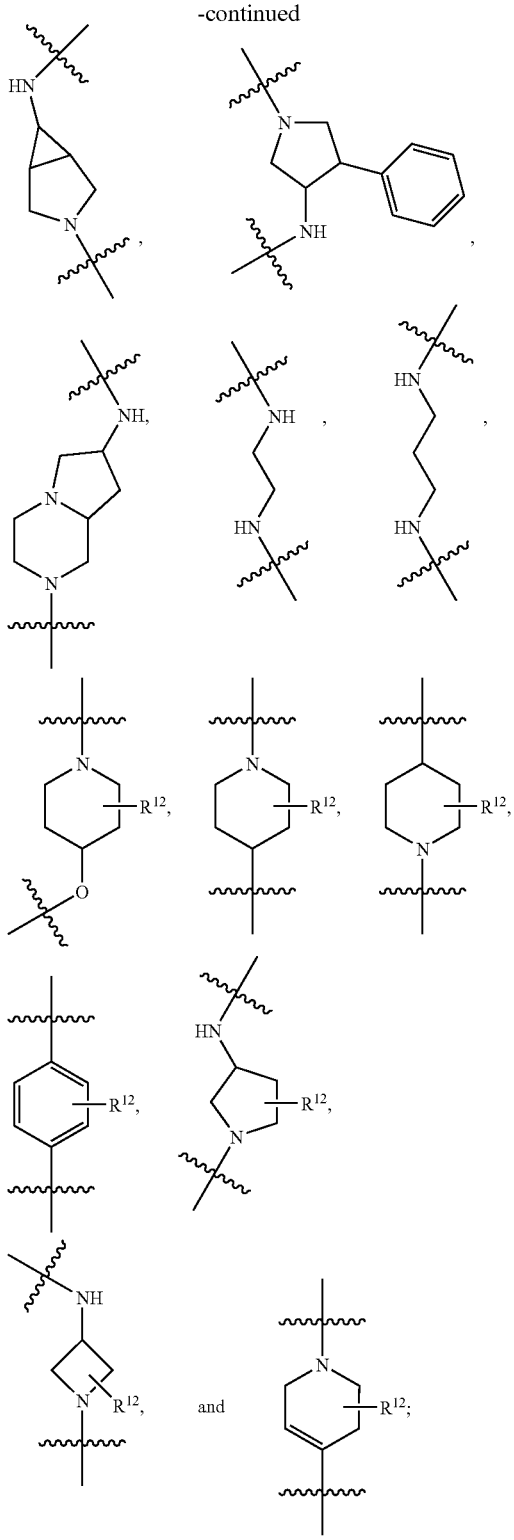

$R^{12}$ is hydrogen, halogen, hydroxy, cyano, nitro, amino, azido, $C_1$-$C_5$ alkyl, $C_2$-$C_5$ alkenyl, $C_2$-$C_5$ alkynyl, $C_1$-$C_5$ heteroalkyl, $C_2$-$C_5$ heteroalkenyl or $C_2$-$C_5$ heteroalkynyl, wherein any of said alkyl, alkenyl, alkynyl, heteroalkyl, heteroalkenyl, and heteroalkynyl are optionally substituted with one or more groups independently selected from halogen, cyano, nitro, amino, azido, $C_1$-$C_4$ alkyl, fluoromethyl, difluoromethyl, trifluoromethyl, methoxy, fluoromethoxy, difluoromethoxy and trifluoromethoxy;

A is

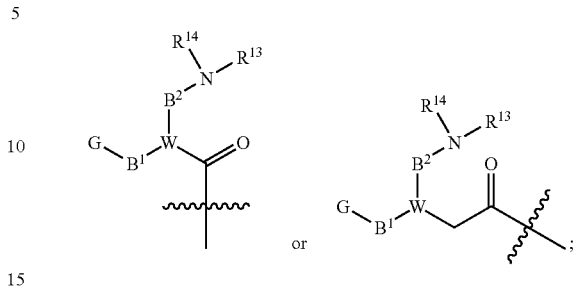

W is N or $CR^{15}$, provided that when L is a substituted or unsubstituted piperazinylene, W must be $CR^{15}$;

G is hydrogen, alkyl, heteroalkyl, alkenyl, heteroalkenyl, alkynyl, heteroalkynyl, cycloalkyl, heterocycloalkyl, aryl or heteroaryl, wherein any of said alkyl, heteroalkyl, alkenyl, heteroalkenyl, alkynyl, heteroalkynyl, cycloalkyl, heterocycloalkyl, aryl or heteroaryl is optionally substituted with one or more groups selected from halogen, hydroxyl, cyano, amino, nitro, azido, $-NR^{21}SO_2R^{23}$, $-SO_2NR^{21}R^{22}$, $-NR^{21}S(O)NR^{21}R^{22}$, $-C(O)R^{21}$, $-C(O)OR^{21}$, $-OC(O)R^{21}$, $-OC(O)OR^{21}$, $-NR^{21}C(O)OR^{24}$, $-NR^{21}C(=NR^{21})NR^{22}R^{23}$, $-NR^{21}C(O)R^{22}$, $-C(O)NR^{21}R^{22}$, $-SR^{21}$, $-S(O)R^{24}$, $-SO_2R^{24}$, $-NR^{21}R^{22}$, $-NR^{21}C(O)NR^{22}R^{23}$, $-NR^{21}C(NCN)NR^{22}R^{23}$, $-OR^{21}$, $C_1$-$C_4$ alkyl, $C_1$-$C_4$ heteroalkyl, $C_2$-$C_4$ alkenyl, $C_2$-$C_4$ heteroalkenyl, $C_2$-$C_4$ alkynyl, $C_2$-$C_4$ heteroalkynyl, cycloalkyl, heterocycloalkyl aryl and heteroaryl;

$B^1$ and $B^2$ are independently absent or $C_1$-$C_4$ alkylene, $C_1$-$C_4$ heteroalkylene, $C_2$-$C_4$ alkenylene, $C_2$-$C_4$ heteroalkenylene, $C_2$-$C_4$ alkynylene, $C_2$-$C_4$ heteroalkynylene, $C_3$-$C_6$ cycloalkylene, and $C_3$-$C_6$ heterocycloalkylene, wherein any of said alkylene, heteroalkylene, alkenylene, heteroalkenylene, alkynylene, heteroalkynylene, cycloalkylene or heterocycloalkylene is optionally substituted with one or more groups independently selected from halogen, hydroxyl, cyano, nitro, azido, $C_1$-$C_4$ alkyl, $C_1$-$C_4$ heteroalkyl, $C_2$-$C_4$ alkenyl, $C_2$-$C_4$ heteroalkenyl, $C_2$-$C_4$ alkynyl, $C_2$-$C_4$ heteroalkynyl, $NR^{21}R^{22}$ and $OR^{21}$;

$R^{21}$, $R^{22}$ and $R^{23}$ independently are hydrogen, $C_1$-$C_6$ alkyl, $C_2$-$C_6$ alkenyl, $C_2$-$C_6$ alkynyl, $C_1$-$C_6$ heteroalkyl, $C_2$-$C_6$ heteroalkenyl, $C_2$-$C_6$ heteroalkynyl, $C_3$-$C_6$ cycloalkyl, $C_3$-$C_6$ heterocycloalkyl, aryl, arylalkyl, heteroaryl or heteroarylalkyl;

$R^{24}$ is $C_1$-$C_6$ alkyl, $C_2$-$C_6$ alkenyl, $C_2$-$C_6$ alkynyl, $C_1$-$C_6$ heteroalkyl, $C_2$-$C_6$ heteroalkenyl, $C_2$-$C_6$ heteroalkynyl, $C_3$-$C_6$ cycloalkyl, $C_3$-$C_6$ heterocycloalkyl, aryl, arylalkyl, heteroaryl or heteroarylalkyl;

or any two of $R^{21}$, $R^{22}$, $R^{23}$ or $R^{24}$ together with the atom(s) to which they are attached form a 4 to 10 membered carbocyclic, aryl, heteroaryl or heterocyclic ring, wherein any of said carbocyclic, aryl, heteroaryl or heterocyclic rings are optionally substituted with one or more groups independently selected from halogen, cyano, nitro, trifluoromethyl, difluoromethoxy, trifluoromethoxy, azido, aryl, heteroaryl, arylalkyl, heteroarylalkyl, heterocyclyl, and heterocyclylalkyl;

$R^{13}$ and $R^{14}$ are independently hydrogen, hydroxyl, cyano, $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, $C_1$-$C_6$ cycloalkyl, $C_1$-$C_6$ heterocycloalkyl, aryl, heteroaryl, arylalkyl, heteroarylalkyl, $-C(O)R^{21}$, $C(O)OR^{21}$, $C(=NR^{21})NR^{22}R^{23}$ or $-SO_2R^{24}$, wherein any of said alkyl, alkenyl, alkynyl, cycloalkyl, heterocycloalkyl, aryl, heteroaryl, heteroalkyl, heteroalkenyl, heteroalkynyl, arylalkyl or heteroarylalkyl is optionally substituted with one or more groups independently selected from halogen, hydroxyl, cyano, amino, nitro, azido, —$NR^{21}SO_2R^{24}$, —$SO_2NR^{21}R^{22}$, —$NR^{21}S(O)R^4$, —$S(O)NR^{21}R^{22}$, —$C(O)R^{21}$, —$C(O)OR^{21}$, —$C(O)R^{21}$, —$OC(O)OR^{21}$, —$NR^{21}C(O)OR^{24}$, —$NR^{21}C(=NR^{21})NR^{22}R^{23}$, —$NR^{21}C(O)R^{22}$, —$C(O)NR^{21}R^{22}$, —$SR^{21}$, —$S(O)R^{24}$, —$SO_2R^{24}$, —$NR^{21}R^{22}$, —$NR^{21}C(O)NR^{22}R^{23}$, —$NR^{21}C(NCN)NR^{22}R^{23}$, —$OR^{21}$, $C_1$-$C_4$ alkyl, $C_1$-$C_4$ heteroalkyl, $C_2$-$C_4$ alkenyl, $C_2$-$C_4$ heteroalkenyl, $C_2$-$C_4$ alkynyl, $C_2$-$C_4$ heteroalkynyl, cycloalkyl, heterocycloalkyl aryl and heteroaryl;

or $R^{13}$ and $R^{14}$ together with the atoms to which they are attached form a 4 to 10 membered carbocyclic, aryl, heteroaryl or heterocyclic ring, wherein any of said carbocyclic, aryl, heteroaryl and heterocyclic rings are optionally substituted with one or more groups independently selected from halogen, cyano, nitro, azido, $C_1$-$C_4$ alkyl, $C_1$-$C_4$ heteroalkyl, $C_2$-$C_4$ alkenyl, $C_2$-$C_4$ heteroalkenyl, $C_2$-$C_4$ alkynyl, $C_2$-$C_4$ heteroalkynyl, $NR^{21}R^{22}$ and $OR^{21}$;

or $R^{13}$ and an atom of $B^2$ together with N form a 4 to 10 membered carbocyclic, aryl, heteroaryl or heterocyclic ring, wherein any of said carbocyclic, aryl, heteroaryl and heterocyclic rings are optionally substituted with one or more groups independently selected from halogen, cyano, nitro, azido, $C_1$-$C_4$ alkyl, $C_1$-$C_4$ heteroalkyl, $C_2$-$C_4$ alkenyl, $C_2$-$C_4$ heteroalkenyl, $C_2$-$C_4$ alkynyl, $C_2$-$C_4$ heteroalkynyl, $NR^{21}R^{22}$ and $OR^{21}$;

$R^{15}$ is hydrogen, $C_1$-$C_4$ alkyl, $C_1$-$C_4$ heteroalkyl, $C_2$-$C_4$ alkenyl, $C_2$-$C_4$ heteroalkenyl, $C_2$-$C_4$ alkynyl or $C_2$-$C_4$ heteroalkynyl, wherein any of said alkyl, heteroalkyl, alkenyl, heteroalkenyl, alkynyl or heteroalkynyl is optionally substituted with one or more groups independently selected from halogen, hydroxyl, cyano, nitro, azido, $NR^{21}R^{22}$ and $OR^{21}$;

or $R^{13}$ and $R^{15}$ together with atoms to which they are attached form a 3 to 10 membered carbocyclic, aryl, heteroaryl or heterocyclic ring, wherein any of said carbocyclic, aryl, heteroaryl and heterocyclic rings are optionally substituted with one or more groups independently selected from halogen, cyano, nitro, azido, $C_1$-$C_4$ alkyl, $C_1$-$C_4$ heteroalkyl, $C_2$-$C_4$ alkenyl, $C_2$-$C_4$ heteroalkenyl, $C_2$-$C_4$ alkynyl, $C_2$-$C_4$ heteroalkynyl, $NR^{21}R^{22}$ and $OR^{21}$;

or, when W is $CR^{15}$, $R^{15}$ and an atom of $B^1$ or $B^2$ together with C, form a 3 to 10 membered carbocyclic, aryl, heteroaryl or heterocyclic ring, wherein any of said carbocyclic, aryl, heteroaryl and heterocyclic rings are optionally substituted with one or more groups independently selected from halogen, cyano, nitro, azido, $C_1$-$C_4$ alkyl, $C_1$-$C_4$ heteroalkyl, $C_2$-$C_4$ alkenyl, $C_2$-$C_4$ heteroalkenyl, $C_2$-$C_4$ alkynyl, $C_2$-$C_4$ heteroalkynyl, $NR^{21}R^{22}$ and $OR^{21}$.

In one embodiment of the invention, CR is selected from:

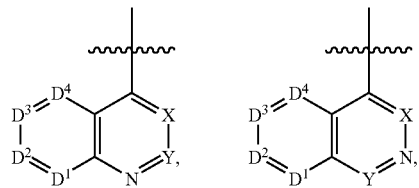

-continued

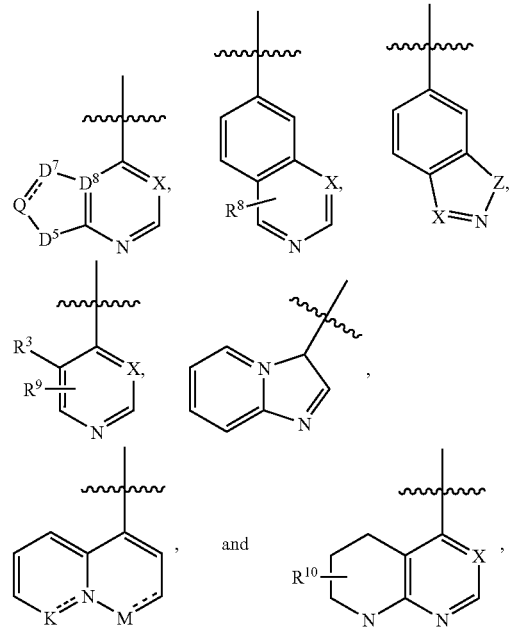

where X is N or $CR^1$;
Y is $CR^2$ or N, provided that when X is N, Y must be $CR^2$;
Z is $CR^3R^{3a}$ or $NR^{2a}$, provided that when X is N, Z must be $CR^3$;
$D^1$, $D^2$, $D^3$ and $D^4$ are independently $CR^4$ or N, provided that no more than two of $D^1$, $D^2$, $D^3$ or $D^4$ are N;
----- is an optional double bond;
$D^5$ is $CR^5R^{5a}$, $NR^{2a}$, O or S, provided that when $D^5$ is O or S, $D^8$ must be C, $D^7$ must be $CR^7$ or N, and either (i) Q must be $CR^6$ or $CR^6R^{6a}$ or (ii) $D^7$ must be $CR^7$ or $CR^7R^{7a}$;
Q is $CR^6$, N or C=O, provided that either (w) when Q is N, one of $D^5$, $D^7$ and $D^8$ must be C, or (x) when Q is C=O, $D^5$ must be $CR^5$ or N, $D^7$ must be $CR^7$ or N, and $D^8$ must be C;
$D^7$ is $CR^7$, N, O or S, provided that when $D^7$ is O or S, $D^8$ must be C, $D^5$ must be $CR^5$ or N, and either (y) Q must be $CR^6$, or (z) $D^5$ must be $CR^5$;
$D^8$ is C or N, provided that when $D^8$ is N, $D^5$ must be $CR^5R^{5a}$ and Q must be $CR^6$ or $CR^6R^{6a}$;
either K or M is carbonyl, provided that both K and M are not carbonyl;
$R^1$, $R^5$, $R^{5a}$ and $R^8$ are independently hydrogen, halogen, hydroxyl, cyano, nitro, azido, fluoromethyl, difluoromethyl, trifluoromethyl, methoxy, fluoromethoxy, difluoromethoxy, trifluoromethoxy, amino, aminomethyl, dimethylamino, aminoethyl, diethylamino or ethoxy;
$R^2$ is hydrogen, halogen, hydroxyl, cyano, nitro, amino, azido, $C_1$-$C_4$ alkyl, $C_1$-$C_4$ heteroalkyl, $C_2$-$C_4$ alkenyl, $C_2$-$C_4$ heteroalkenyl, $C_2$-$C_4$ alkynyl, $C_2$-$C_4$ heteroalkynyl, $C_1$-$C_6$ cycloalkyl, $C_1$-$C_6$ heterocycloalkyl, $C_1$-$C_6$ aryl, or $C_1$-$C_6$ heteroaryl, wherein any of said alkyl, heteroalkyl, alkenyl, heteroalkenyl, alkynyl, heteroalkynyl, cycloalkyl, heterocycloalkyl, aryl or heteroaryl are further optionally substituted with one or more groups independently selected from halogen, hydroxyl, cyano, nitro, azido, fluoromethyl, difluoromethyl, trifluoromethyl, methoxy, fluoromethoxy, difluoromethoxy, trifluoromethoxy, amino, aminomethyl, dimethylamino, aminoethyl, diethylamino and ethoxy;
$R^{2a}$ is hydrogen, hydroxyl, cyano, $C_1$-$C_4$ alkyl, $C_1$-$C_4$ heteroalkyl, $C_2$-$C_4$ alkenyl, $C_2$-$C_4$ heteroalkenyl, $C_2$-$C_4$ alkynyl, $C_2$-$C_6$ heteroalkynyl, $C_3$-$C_6$ cycloalkyl, $C_3$-$C_6$ heterocycloalkyl, aryl or heteroaryl, wherein any of said alkyl, heteroalkyl, alkenyl, heteroalkenyl, alkynyl, heteroalkynyl, cycloalkyl, heterocycloalkyl, aryl or heteroaryl are optionally substituted with one or more groups independently selected from halogen, hydroxyl, cyano, nitro, azido fluoromethyl, difluoromethyl, trifluoromethyl, methoxy, fluoromethoxy, difluoromethoxy, trifluoromethoxy, amino, aminomethyl, dimethylamino, aminoethyl, diethylamino or ethoxy;

$R^3$ and $R^{3a}$ are independently hydrogen, halogen, hydroxyl, cyano, nitro, amino azido, $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, $C_1$-$C_6$ cycloalkyl, $C_1$-$C_6$ heterocycloalkyl, aryl or heteroaryl, wherein any of said alkyl, heteroalkyl, alkenyl, heteroalkenyl, alkynyl, heteroalkynyl, cycloalkyl, heterocycloalkyl, aryl or heteroaryl are further optionally substituted with one or more groups independently selected from halogen, hydroxyl, cyano, nitro, azido, $OR^1$, $NR^1R^2$, and $(C=O)R^2$;

$R^4$, $R^6$, $R^{6a}$, $R^7$, $R^{7a}$ and $R^{10}$ are independently hydrogen, hydroxyl, cyano, amino, nitro, azido, alkyl, heteroalkyl, alkenyl, heteroalkenyl, alkynyl, heteroalkynyl, cycloalkyl, heterocycloalkyl, aryl, arylalkyl, heteroaryl, heteroarylalkyl, —$NR^{21}SO_2R^{24}$, —$SO_2NR^{21}R^{22}$, —$NR^{21}S(O)R^4$, —$S(O)NR^{21}R^{22}$, —$C(O)R^{21}$, —$C(O)OR^{21}$, —$OC(O)R^{21}$, —$OC(O)OR^{21}$, —$NR^{21}C(O)OR^{24}$, —$NR^{21}C(=NR^{21})NR^{22}R^{23}$, —$NR^{21}C(O)R^{22}$, —$C(O)NR^{21}R^{22}$, —$SR^{21}$, —$S(O)R^{24}$, —$SO_2R^{24}$, —$NR^{21}R^{22}$, —$NR^{21}C(O)NR^{22}R^{23}$, —$NR^{21}C(NCN)NR^{22}R^{23}$ or —$OR^{21}$, wherein any of said alkyl, heteroalkyl, alkenyl, heteroalkenyl, alkynyl, heteroalkynyl, cycloalkyl, heterocycloalkyl, aryl, arylalkyl, heteroaryl or heteroarylalkyl, is optionally substituted with one or more groups independently elected from halogen, hydroxyl, cyano, amino, nitro, azido, —$NR^{21}SO_2R^{24}$, —$SO_2NR^{21}R^{22}$, —$NR^{21}S(O)R^4$, —$S(O)NR^{21}R^{22}$, —$C(O)R^{21}$, —$C(O)OR^{21}$, —$OC(O)R^{21}$, —$OC(O)OR^{21}$, —$OC(O)OR^{21}$, —$NR^{21}C(O)OR^{24}$, —$NR^{21}C(=NR^{21})NR^{22}R^{23}$, —$NR^{21}C(O)R^{22}$, —$C(O)NR^{21}R^{22}$, —$SR^{21}$, —$S(O)R^{24}$, —$SO_2R^{24}$, —$NR^{21}R^{22}$, —$NR^{21}C(O)NR^{22}R^{23}$, —$NR^{21}C(NCN)NR^{22}R^{23}$, —$OR^{21}$, $C_1$-$C_4$ alkyl, $C_1$-$C_4$ heteroalkyl, $C_2$-$C_4$ alkenyl, $C_2$-$C_4$ heteroalkenyl, $C_2$-$C_4$ alkynyl, $C_2$-$C_4$ heteroalkynyl, cycloalkyl, heterocycloalkyl, aryl and heteroaryl, and wherein said alkyl, heteroalkyl, alkenyl, heteroalkenyl, alkynyl, heteroalkynyl, cycloalkyl, heterocycloalkyl, aryl and heteroaryl may optionally be further optionally substituted with one or more groups independently selected from halogen, hydroxyl, cyano, amino, nitro, azido, $C_1$-$C_4$ alkyl, $C_1$-$C_4$ heteroalkyl, $C_2$-$C_4$ alkenyl, $C_2$-$C_4$ heteroalkenyl, $C_2$-$C_4$ alkynyl, $C_2$-$C_4$ heteroalkynyl, cycloalkyl, heterocycloalkyl, aryl and heteroaryl, —$NR^{21}R^{22}$, and —$OR^{21}$;

or $R^6$ and $R^7$ together with the atoms to which they are attached form a 4 to 10 membered carbocyclic, aryl, heteroaryl or heterocyclic ring, wherein any of said carbocyclic, aryl, heteroaryl and heterocyclic rings are optionally substituted with one or more groups independently selected from halogen, cyano, nitro, trifluoromethyl, difluoromethoxy, trifluoromethoxy, azido, $OR^1$, $NR^1R^2$, cycloalkyl, heterocycloalkyl, aryl, heteroaryl, arylalkyl, heteroarylalkyl, heterocyclyl, and heterocyclylalkyl; and $R^9$ is hydrogen, halogen, hydroxyl, cyano, nitro, azido, $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, $C_1$-$C_6$ cycloalkyl, $C_1$-$C_6$ heterocycloalkyl, aryl, heteroaryl, —$NR^{21}R^{22}$, —$OR^{21}$, —$NR^{21}SO_2R^{24}$ and —$NR^{21}C(O)R^{22}$, wherein any of said alkyl, heteroalkyl, alkenyl, heteroalkenyl, alkynyl, heteroalkynyl, cycloalkyl, heterocycloalkyl, aryl or heteroaryl are further optionally substituted with one or more groups independently selected from halogen, hydroxyl, cyano, nitro, azido, $OR^1$, $NR^1R^2$, and $(C=O)R^2$.

In one embodiment of the invention, CR is selected from

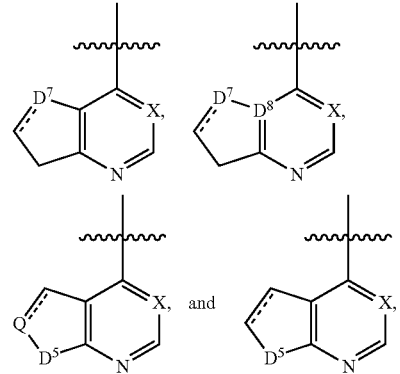

where $D^5$, $D^7$, $D^8$, X and Q are as defined above.

According to another embodiment of the invention, A is:

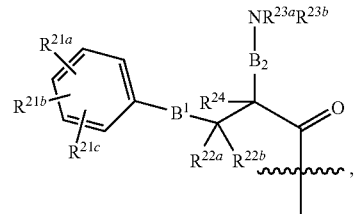

where $B^1$ and $B^2$ are, independently, absent or $C_1$-$C_4$ alkylene;

$R^{21a}$-$R^{21c}$ are independently H, halogen, $CH_3$, $CF_3$, $CH_3O$, CN, $NO_2$, $NH_2$, Ph, OH, or $OCH_2Ph$;

$R^{22a}$, $R^{22b}$, and $R^{24}$ are independently H, $CH_3$, or halogen;

$R^{23a}$ is H; and $R^{23b}$ is H, $CH_3$, $CH_2NH_2$, $CH_2NHCH_2$, $CH_2CH_2NH_2$, $CH_2CH_2NHCH_2$, $CH_2CH_2N(CH_3)_2$, —$(C=O)CH_2NH_2$ or —$(C=O)CH_2CH_2NH_2$;

or $R^{23a}$ and $R^{23b}$ are joined to complete a 5 or 6 membered heterocyclic ring.

In yet another embodiment of this invention, A is

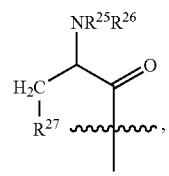

where $R^{25}$ and $R^{26}$ are independently H or $CH_3$, and $R^{27}$ is 1-naphthyl, 2-naphthyl, 3'-benzylthienyl, 2'-thienyl, 2'-pyridyl, 3'-pyridyl, 4'-pyridyl, 4'-thiazolyl, or 3,3-diphenyl.

More specific examples of the A group of Formula I according to this invention include, but are not limited to,

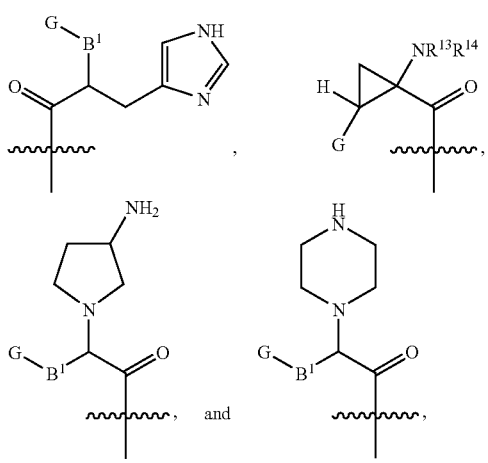

where G, $B^1$, $R^{13}$ and $R^{14}$ are as defined above.

In an alternative embodiment, the A group of Formula I of this invention is a D- or L-amino acid selected from the 20 naturally occurring amino acids commonly designated by three letter symbols, and also includes unnatural amino acids including, but not limited to, 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In one preferred embodiment, the A group of Formula I is alanine, phenylalanine, histidine, or tryptophan.

A specific example of a compound based on Formula I is:

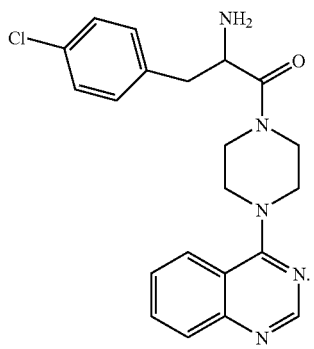 [SMILES: NC(Cc1ccc(Cl)cc1)C(=O)N1CCN(c2ncnc3ccccc23)CC1]

Another example of a compound based on Formula I is:

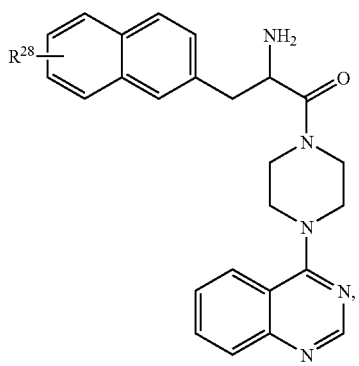

wherein $R^{28}$ is H, halogen, $CH_3$, $CF_3$, $CH_3O$, CN, $NO_2$, $NH_2$, Ph, OH, or $OCH_2Ph$.

Still another example of a compound based on Formula I is:

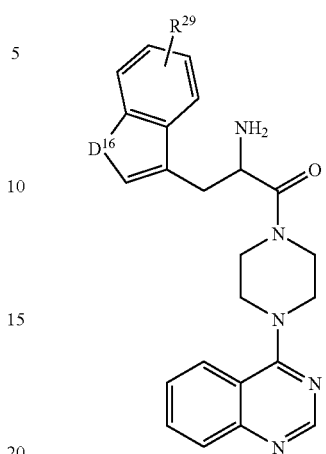

where $D^{16}$ is O or N; and $R^{29}$ is H, halogen, $CH_3$, $CF_3$, $CH_3O$, CN, $NO_2$, $NH_2$, Ph, OH, or $OCH_2Ph$.

The term "alkyl" as used herein refers to a saturated linear or branched-chain monovalent hydrocarbon radical of one to twelve carbon atoms, wherein the alkyl radical may be optionally substituted independently with one or more substituents described below. Examples of alkyl groups include, but are not limited to, methyl, ethyl, n-propyl, isopropyl, butyl, isobutyl, sec-butyl, tert-butyl, pentyl, isopentyl, tert-pentyl, hexyl, isohexyl, and the like.

The term "alkylene" as used herein refers to a linear or branched-chain saturated divalent hydrocarbon radical of one to twelve carbon atoms, e.g., methylene, ethylene, propylene, 2-methylpropylene, pentylene, and the like. The alkylene radical may be optionally substituted independently with one or more substituents described herein.

The term "heteroalkyl" refers to saturated linear or branched-chain monovalent hydrocarbon radical of one to twelve carbon atoms, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkyl radical may be optionally substituted independently with one or more substituents described herein. The term "heteroalkyl" encompasses alkoxy and heteroalkoxy radicals.

The term "heteroalkylene" as used herein refers to a linear or branched-chain saturated divalent hydrocarbon radical of two to twelve carbon atoms, wherein at least one of the carbon atoms is replaced with a heteroatom selected from N, O or S, and wherein the radical may be a carbon radical or heteroatom radical (i.e., the heteroatom may appear in the middle or at the end of the radical). The heteroalkylene radical may be optionally substituted independently with one or more substituents described herein.

"Alkenyl" means a linear or branched-chain monovalent hydrocarbon radical of two to twelve carbon atoms containing at least one double bond, wherein the alkenyl radical may be optionally substituted independently with one or more substituents described below. Examples of alkenyl groups include, but are not limited to: ethylene or vinyl (—CH═$CH_2$), allyl (—$CH_2$CH═$CH_2$), 1-cyclopent-1-enyl, 1-cyclopent-2-enyl, 1-cyclopent-3-enyl, 5-hexenyl (—CH$_2$CH$_2$CH$_2$CH$_2$CH═CH$_2$), 1-cyclohex-1-enyl, 1-cyclohex-2-enyl, and 1-cyclohex-3-enyl.

"Alkenylene" refers to an a linear or branched-chain divalent hydrocarbon radical of one to twelve carbon atoms containing at least one double bond, e.g., 1,2-ethylene (—CH═CH—). The alkenylene radical may be optionally substituted independently with one or more substituents described herein.

The term "heteroalkenyl" refers to a linear or branched-chain monovalent hydrocarbon radical of two to twelve carbon atoms and at least one double bond, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkenyl radical may be optionally substituted independently with one or more substituents described herein. The term "heteroalkenyl" encompasses alkenoxy and heteroalkenoxy radicals.

"Heteroalkenylene" refers to an a linear or branched saturated divalent hydrocarbon radical of one to twelve carbon atoms containing at least one double bond, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkenylene radical may be optionally substituted independently with one or more substituents described herein.

The term "allyl" refers to a radical having the formula RC═CHCHR, wherein R is alkyl, alkenyl, alkynyl, cycloalkyl, heterocycloalkyl, aryl, heteroaryl, or any substituent as defined herein, wherein the allyl radical may be optionally substituted independently with one or more substituents described herein.

The term "alkynyl" means a linear or branched-chain monovalent hydrocarbon radical of two to twelve carbon atoms containing at least one triple bond, wherein the alkynyl radical may be optionally substituted independently with one or more substituents described below. Examples of alkynyl groups include, but are not limited to: acetylene (—C≡CH) and propargyl (—CH$_2$C≡CH).

"Alkynylene" refers to a linear or branched-chain divalent hydrocarbon radical of one to twelve carbon atoms containing at least one triple bond. The alkynylene radical may be optionally substituted independently with one or more substituents described herein. Typical alkynylene radicals include, but are not limited to: acetylene (—C≡C—), propargyl (—CH$_2$C≡C—), and 4-pentynyl (—CH$_2$CH$_2$CH$_2$C≡CH—).

The term "heteroalkynyl" refers to a linear or branched-chain monovalent hydrocarbon radical of two to twelve carbon atoms containing at least one triple bond, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkynyl radical may be optionally substituted independently with one or more substituents described herein. The term "heteroalkynyl" encompasses alkynoxy and heteroalkynoxy radicals.

The term "heteroalkynylene" refers to a linear or branched divalent hydrocarbon radical of two to twelve carbons containing at least one triple bond, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkynylene radical may be optionally substituted independently with one or more substituents described herein.

The terms "carbocycle," "carbocyclyl," or "cycloalkyl" refer to saturated or partially unsaturated cyclic hydrocarbon radical having from three to ten carbon atoms. The term "cycloalkyl" includes monocyclic and polycyclic (e.g., bicyclic and tricyclic) cycloalkyl structures, wherein the polycyclic structures optionally include a saturated or partially unsaturated cycloalkyl fused to a saturated or partially unsaturated cycloalkyl or heterocycloalkyl ring or an aryl or heteroaryl ring. Examples of cycloalkyl groups include, but are not limited to, cyclopropyl, cyclobutyl, cyclopentyl, cyclohexyl, cycloheptyl, and the like. The cycloalkyl may be optionally substituted independently in one or more substitutable positions with various groups. For example, such cycloalkyl groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$)alkyl.

The terms "heterocycloalkyl," "heterocycle" or "hetercyclyl" refer to a saturated or partially unsaturated carbocyclic radical of 3 to 8 ring atoms in which at least one ring atom is a heteroatom selected from nitrogen, oxygen and sulfur, the remaining ring atoms being C, where one or more ring atoms may be optionally substituted independently with one or more substituent described below. The radical may be a carbon radical or heteroatom radical. The term further includes bicyclic and tricyclic fused ring systems which include a heterocycle fused one or more carbocyclic or heterocyclic rings. "Heterocycloalkyl" also includes radicals where heterocycle radicals are fused with aromatic or heteroaromatic rings. Examples of heterocycloalkyl rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl and quinolizinyl. Spiro moieties are also included within the scope of this definition. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). An example of a heterocyclic group wherein 2 ring carbon atoms are substituted with oxo (═O) moieties is 1,1-dioxo-thiomorpholinyl. The heterocycle groups herein are unsubstituted or, as specified, substituted in one or more substitutable positions with various groups. For example, such heterocycle groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$)alkyl.

The terms "heterocycloalkylene" refers to a saturated or partially unsaturated divalent carbocyclic radical of 3 to 8 ring atoms in which at least one ring atom is a heteroatom selected from nitrogen, oxygen and sulfur, the remaining ring atoms being C, where one or more ring atoms may be optionally substituted independently with one or more substituent described herein. Examples include, but are not limited to, substituted and unsubstituted piperidinylenes.

The term "aryl" refers to a monovalent aromatic carbocyclic radical having a single ring (e.g., phenyl), multiple rings (e.g., biphenyl), or multiple condensed rings in which at least one is aromatic, (e.g., 1,2,3,4-tetrahydronaphthyl, naphthyl), which is optionally mono-, di-, or trisubstituted with, e.g., halogen, lower alkyl, lower alkoxy, trifluoromethyl, aryl, heteroaryl, and hydroxy.

The term "heteroaryl" refers to a monovalent aromatic radical of 5-, 6-, or 7-membered rings which includes fused ring systems (at least one of which is aromatic) of 5-10 atoms containing at least one and up to four heteroatoms selected from nitrogen, oxygen, or sulfur. Examples of heteroaryl groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition. Heteroaryl groups are optionally mono-, di-, or trisubstituted with, e.g., halogen, lower alkyl, lower alkoxy, haloalkyl, aryl, heteroaryl, and hydroxy.

The term "halo" represents fluoro, chloro, bromo or iodo. Likewise, the term "halogen" refers to a fluorine, chlorine, bromine, or iodine substituent.

The term "arylalkyl" means an alkyl moiety (as defined above) substituted with one or more aryl moiety (also as defined above). More preferred arylalkyl radicals are aryl-$C_{1-3}$-alkyls. Examples include benzyl, phenylethyl, and the like.

The term "heteroarylalkyl" means an alkyl moiety (as defined above) substituted with a heteroaryl moiety (also as defined above). More preferred heteroarylalkyl radicals are 5- or 6-membered heteroaryl-$C_{1-3}$-alkyls. Examples include, but are not limited to, oxazolylmethyl, pyridylethyl and the like.

The term "heterocyclylalkyl" means an alkyl moiety (as defined above) substituted with a heterocyclyl moiety (also defined above). More preferred heterocyclylalkyl radicals are 5- or 6-membered heterocyclyl-$C_{1-3}$-alkyls. An example includes, but is not limited to, tetrahydropyranylmethyl.

The term "cycloalkylalkyl" means an alkyl moiety (as defined above) substituted with a cycloalkyl moiety (also defined above). More preferred heterocyclyl radicals are 5- or 6-membered cycloalkyl-$C_{1-3}$-alkyls. An example includes, but is not limited to, cyclopropylmethyl.

The term "Me" means methyl, "Et" means ethyl, "Bu" means butyl and "Ac" means acetyl.

In general, the various moieties or functional groups of the compounds of Formula I may be optionally substituted by one or more substituents. Examples of substituents suitable for purposes of this invention include, but are not limited to, halo, alkyl, allyl, alkenyl, alkynyl, heteroalkyl, heteroallyl, heteroalkenyl, heteroalkynyl, alkoxy, heteroalkoxy, $G_n$-cycloalkyl, $G_n$-heterocycloalkyl, $G_n$-OR, $G_n$-NO$_2$, $G_n$-CN, $G_n$-CO$_2$R, $G_n$-(C=O)R, $G_n$-O(C=O)R, $G_n$-O-alkyl, $G_n$-OAr, $G_n$-SH, $G_n$-SR, $G_n$-SOR, $G_n$-SO$^2$R, $G_n$-S—Ar $G_n$-SOAr, $G_n$-C$_2$Ar, aryl, heteroaryl, $G_n$-Ar, $G_n$-(C=O)NR$^2$R$^3$, $G_n$-NR$^2$R$^3$, $G_n$-NR(C=O)R, $G_n$-SO$_2$NR$^2$R$^3$, PO$_3$H$_2$, SO$_3$H$_2$, where G is alkylene having from 1 to 4 carbons, or alkenylene or alkynylene each having from 2 to 4 carbons; n is zero or 1; $R^1$, $R^2$, and $R^3$ are alkyl, allyl, alkenyl, alkynyl, heteroalkyl, heteroallyl, heteroalkenyl, heteroalkynyl, alkoxy, heteroalkoxy, $G_n$-cycloalkyl, or $G_n$-heterocycloalkyl; and Ar is aryl or heteroaryl, wherein said alkyl, allyl, alkenyl, alkynyl, heteroalkyl, heteroallyl, heteroalkenyl, heteroalkynyl, alkoxy, heteroalkoxy, $G_n$-cycloalkyl, $G_n$-heterocycloalkyl, alkylene, alkenylene, alkynylene, Ar, $R^1$, $R^2$, and $R^3$ may be further substituted or unsubstituted.

It is to be understood that in instances where two or more radicals are used in succession to define a substituent attached to a structure, the first named radical is considered to be terminal and the last named radical is considered to be attached to the structure in question. Thus, for example, the radical arylalkyl is attached to the structure in question by the alkyl group.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. Accordingly, this invention also includes racemates and resolved enantiomers, and diastereomers compounds of the Formula I. Methods for determining the stereochemistry and for the separation of stereoisomers are well known in the art (see discussion in Chapter 4 of "Advanced Organic Chemistry", 4th edition J. March, John Wiley and Sons, New York, 1992).

In addition to compounds of the Formula I, the invention also includes solvates, pharmaceutically active metabolites, pharmaceutically acceptable prodrugs, and pharmaceutically acceptable salts of such compounds.

The term "solvate" refers to an aggregate of a molecule with one or more solvent molecules.

A "pharmaceutically active metabolite" is a pharmacologically active product produced through metabolism in the body of a specified compound or salt thereof. Metabolites of a compound may be identified using routine techniques known in the art and their activities determined using tests such as those described herein.

Compounds of the present invention having functional groups including, but not limited to, free amino, amido, hydroxy or carboxylic groups can be converted into pharmaceutically acceptable prodrugs. A "pharmaceutically acceptable prodrug" is a compound that may be converted under physiological conditions or by solvolysis to the specified compound or to a pharmaceutically acceptable salt of such compound. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present invention. The amino acid residues include but are not limited to the 20 naturally occurring amino acids commonly designated by three letter symbols and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. One preferred prodrug of this invention is a compound of Formula I covalently joined to a phosphate residue. Another preferred prodrug of this invention is a compound of Formula I covalently joined to a valine residue.

Additional types of prodrugs are also encompassed. For instance, free carboxyl groups can be derivatized as amides or alkyl esters. As another example, compounds of this invention comprising free hydroxy groups may be derivatized as prodrugs by converting the hydroxy group groups including to a phosphate ester, hemisuccinate, dimethylaminoacetate, or phosphoryloxymethyloxycarbonyl, as outlined in *Advanced Drug Delivery Reviews,* 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including, but not limited to, ether, amine and carboxylic acid functionalities, or where the acyl group is an amino acid ester as described above, are also encompassed. Prodrugs of this type are described in *J. Med. Chem.,* 1996, 39, 10. More specific examples include replacement of the hydrogen atom of the alcohol group with a group such as $(C_1-C_6)$alkanoyloxymethyl, $1-((C_1-C_6)$alkanoyloxy)ethyl, $1$-methyl-$1-(C_1-C_6)$alkanoyloxy)ethyl, $(C_1-C_6)$alkoxycarbonyloxymethyl, $N-(C_1-C_6)$alkoxycarbonylaminomethyl, succinoyl, $(C_1-C_6)$alkanoyl, $\alpha$-amino$(C_1-C_4)$alkanoyl, arylacyl and $\alpha$-aminoacyl, or $\alpha$-aminoacyl-$\alpha$-aminoacyl, where each $\alpha$-aminoacyl group is independently selected from the naturally occurring L-amino acids, $P(O)(OH)_2$, $-P(O)(O(C_1-C_6)$alkyl)$_2$ or glycosyl (the radical resulting from the removal of a hydroxyl group of the hemiacetal form of a carbohydrate).

Free amines can also be derivatized as amides, sulfonamides or phosphonamides. All of these prodrug moieties may incorporate groups including, but not limited to, ether, amine and carboxylic acid functionalities. For example, a prodrug can be formed by the replacement of a hydrogen atom in the amine group with a group such as R-carbonyl, RO-carbonyl, NRR'-carbonyl where R and R' are each independently $(C_1-C_{10})$alkyl, $(C_3-C_7)$cycloalkyl, benzyl, or R-carbonyl is a natural $\alpha$-aminoacyl or natural $\alpha$-aminoacyl-natural $\alpha$-aminoacyl, $-C(OH)C(O)OY$ wherein Y is H, $(C_1-C_6)$alkyl or benzyl, $-C(OY_0)Y_1$ wherein $Y_0$ is $(C_1-C_4)$ alkyl and $Y_1$ is $(C_1-C_6)$alkyl, carboxy$(C_1-C_6)$alkyl, amino$(C_1-C_4)$alkyl or mono-N- or di-N,N-$(C_1-C_6)$alkylaminoalkyl, $-C(Y_2)Y_3$ wherein $Y_2$ is H or methyl and $Y_3$ is mono-N- or di-N,N-$(C_1-C_6)$alkylamino, morpholino, piperidin-1-yl or pyrrolidin-1-yl.

A "pharmaceutically acceptable salt" is a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable sale. Examples of pharmaceutically acceptable salts include those salts prepared by reaction of the compounds of the present invention with a mineral or organic acid or an inorganic base, such salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitromenzoates, hydroxybenzoates, methoxybenzoates, phthalates, sulfonates, xylenesulfonates, pheylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid such as glucuronic acid or galacturonic acid, an alphahydroxy acid such as citric acid or tartaric acid, an amino acid such as aspartic acid or glutamic acid, an aromatic acid such as benzoic acid or cinnamic acid, a sulfonic acid such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The inventive compounds may be prepared using the reaction routes and synthesis schemes as described herein, employing the techniques available in the art using starting materials that are readily available.

Therapeutic Aspects of the Invention

The invention also provides a pharmaceutical composition for the treatment of a hyperproliferative disorder in a mammal which comprises a therapeutically effective amount of a compound of the present invention, or a pharmaceutically acceptable salt, prodrug, metabolite or hydrate thereof, and a pharmaceutically acceptable carrier. In one embodiment, said pharmaceutical composition is for the treatment of cancer such as skin, brain, lung, squamous cell, bladder, gastric, pancreatic, breast, head, neck, renal, kidney, ovarian, prostate, colorectal, esophageal, testicular, gynecological, cardiac, liver, bone, meninges, spinal cord, blood, skin, adrenal or thyroid cancer. In another embodiment, said pharmaceutical composition is for the treatment of a non-cancerous hyperproliferative disorder such as benign hyperplasia of the skin (e.g., psoriasis), restenosis, or prostate (e.g., benign prostatic hypertrophy (BPH)).

The invention also relates to a method for the treatment of a hyperproliferative disorder in a mammal that comprises administering to said mammal a therapeutically effective amount of a compound of the present invention, or a pharmaceutically acceptable salt, prodrug or hydrate thereof, in combination with an anti-tumor agent selected from the group consisting of mitotic inhibitors, alkylating agents, anti-metabolites, intercalating antibiotics, growth factor inhibitors, cell cycle inhibitors, enzyme inhibitors, topoisomerase inhibitors, biological response modifiers, anti-hormones, angiogenesis inhibitors, and anti-androgens.

The invention also relates to a method of treating pancreatitis or kidney disease in a mammal that comprises administering to said mammal a therapeutically effective amount of a compound of the present invention, or a pharmaceutically acceptable salt, prodrug or hydrate thereof.

The invention also relates to a method of preventing blastocyte implantation in a mammal that comprises administering to said mammal a therapeutically effective amount of a compound of the present invention, or a pharmaceutically acceptable salt, prodrug or hydrate thereof.

The invention also relates to a method of treating diseases related to vasculogenesis or angiogenesis in a mammal that comprises administering to said mammal a therapeutically effective amount of a compound of the present invention, or a pharmaceutically acceptable salt, prodrug or hydrate thereof. In one embodiment, said method is for treating a disease selected from the group consisting of tumor angiogenesis, chronic inflammatory disease such as rheumatoid arthritis, atherosclerosis, inflammatory bowel disease, skin diseases such as psoriasis, excema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a pharmaceutical composition for treating a disease or condition related to inflammatory disease, autoimmune disease, destructive bone disorders, proliferative disorders, infectious disease, viral disease, fibrotic disease or neurodegenerative disease in a mammal which comprises a therapeutically effective amount of a compound of the present invention, or a pharmaceutically acceptable salt, prodrug or hydrate thereof, and a pharmaceutically acceptable carrier. Examples of the above diseases and/or conditions include but is not limited to rheumatoid arthritis, atherosclerosis, inflammatory bowel disease, skin diseases such as psoriasis, eczema, and scleroderma, diabetes and diabetic complications, diabetic retinopathy, retinopathy of prematurity, age-related macular degeneration, hemangioma, chronic obstructive pulmonary disease, idiopathic pulmonary fibrosis, allergic responses including asthma allergic rhinitis and atopic dermatitis, renal disease and renal failure, polycystic kidney disease, acute coronary syndrome, congestive heart failure, osteoarthritis, neurofibromatosis, organ transplant rejection, cachexia and pain.

Further provided is a compound of Formula I for use as a medicament in the treatment of the diseases and conditions described above in a warm-blooded animal, preferably a mammal, more preferably a human, suffering from such disorder. Also provided is the use of a compound of Formula I in the preparation of a medicament for the treatment of the diseases and conditions described above in a warm-blooded animal, preferably a mammal, more preferably a human, suffering from such disorder.

Patients that can be treated with compounds of the present invention, or pharmaceutically acceptable salts, prodrugs and hydrates of said compounds, according to the methods of this invention include, for example, patients that have been diagnosed as having psoriasis, restenosis, atherosclerosis, BPH, lung cancer, bone cancer, CMML, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, testicular, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphona, spinal axis tumors, brain stem gliomas or pituitary adenomas).

This invention also relates to a pharmaceutical composition for inhibiting abnormal cell growth in a mammal which comprises an amount of a compound of the present invention, or a pharmaceutically acceptable salt or solvate or prodrug thereof, in combination with an amount of a chemotherapeutic, wherein the amounts of the compound, salt, solvate, or prodrug, and of the chemotherapeutic are together effective in inhibiting abnormal cell growth. Many chemotherapeutics are presently known in the art. In one embodiment, the chemotherapeutic is selected from the group consisting of mitotic inhibitors, alkylating agents, anti-metabolites, antitumor antibiotics, growth factor inhibitors, cell cycle inhibitors, enzymes, topoisomerase inhibitors, biological response modifiers, anti-hormones, angiogenesis inhibitors, and anti-androgens.

This invention further relates to a method for inhibiting abnormal cell growth in a mammal or treating a hyperproliferative disorder which method comprises administering to the mammal an amount of a compound of the present invention, or a pharmaceutically acceptable salt or solvate or prodrug thereof, in combination with radiation therapy, wherein the amounts of the compound, salt, solvate, or prodrug, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

It is believed that the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of the present invention or pharmaceutically acceptable salt or solvate or prodrug thereof, which amount is effective is sensitizing abnormal cells to treatment with radiation. The amount of the compound, salt, or solvate in this method can be determined according to the means for ascertaining effective amounts of such compounds described herein.

Compounds and methods of this invention may also be used to treat other diseases and conditions (e.g., inflammatory disease), including rheumatoid arthritis, osteoarthritis, endometriosis, atherosclerosis, vein graft stenosis, peri-anastomatic prosthetic graft stenosis, prostate hyperplasia, chronic obstructive pulmonary disease, psoriasis, inhibition of neurological damage due to tissue repair, scar tissue formation (and can aid in wound healing), multiple sclerosis, inflammatory bowel disease, infections, particularly bacterial, viral, retroviral or parasitic infections (by increasing apoptosis), pulmonary disease, neoplasm, Parkinson's disease, transplant rejection (as an immunosuppressant), macular degeneration and septic shock.

Therapeutically effective amounts of the compounds of the invention may be used to treat diseases mediated by modulation or regulation of AKT protein kinases, tyrosine kinases, additional serine/threonine kinases, and/or dual specificity kinases. An "effective amount" is intended to mean that amount of compound that, when administered to a mammal in need of such treatment, is sufficient to effect treatment for a disease mediated by the activity of one or more AKT protein kinases, tyrosine kinases, additional serine/threonine kinases, and/or dual specificity kinases. Thus, for example, a therapeutically effective amount of a compound selected from Formula I or a salt, active metabolite or prodrug thereof, is a quantity sufficient to modulate, regulate, or inhibit the activity of one or more AKT protein kinases, tyrosine kinases, additional serine/threonine kinases, and/or dual specificity kinases such that a disease condition which is mediated by that activity is reduced or alleviated.

The terms "abnormal cell growth" and "hyperproliferative disorder" are used interchangeably in this application.

"Abnormal cell growth," as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threoine kinase activation occurs.

The amount of a given agent that will correspond to such an amount will vary depending upon factors such as the particular compound, disease condition and its severity, the identity (e.g., weight) of the mammal in need of treatment, but can nevertheless be routinely determined by one skilled in the art. "Treating" is intended to mean at least the mitigation of a disease condition in a mammal, such as a human, that is affected, at least in part, by the activity of one or more AKT protein kinases, tyrosine kinases, additional serine/threonine kinases, and/or dual specificity kinases, and includes, but is not limited to, preventing the disease condition from occurring in a mammal, particularly when the mammal is found to be predisposed to having the disease condition but has not yet been diagnosed as having it; modulating and/or inhibiting the disease condition; and/or alleviating the disease condition.

In order to use a compound of the Formula I or a pharmaceutically acceptable salt, solvate, metabolite or prodrug thereof, for the therapeutic treatment (including prophylactic treatment) of mammals including humans, it is normally formulated in accordance with standard pharmaceutical practice as a pharmaceutical composition. According to this aspect of the invention there is provided a pharmaceutical composition that comprises a compound of the Formula I, or a pharmaceutically acceptable salt, solvate, metabolite or prodrug thereof, as defined hereinbefore in association with a pharmaceutically acceptable diluent or carrier.

To prepare the pharmaceutical compositions according to this invention, a therapeutically or prophylactically effective amount of a compound of Formula I or pharmaceutically acceptable salt, solvate, metabolite or prodrug thereof (alone or together with an additional therapeutic agent as disclosed herein) is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. Examples of suitable carriers include any and all solvents, dispersion media, adjuvants, coatings, antibacterial and antifungal agents, isotonic and absorption delaying agents, sweeteners, stabilizers (to promote long term storage), emulsifiers, binding agents, thickening agents, salts, preservatives, solvents, dispersion media, coatings, antibacterial and antifungal agents, isotonic and absorption delaying agents, flavoring agents, and miscellaneous materials such as buffers and absorbents that may be needed in order to prepare a particular therapeutic composition. The use of such media and agents with pharmaceutically active substances is well known in the art. Except insofar as any conventional media or agent is incompatible with a compound of Formula I, its use in the therapeutic compositions and preparations is contemplated. Supplementary active ingredients can also be incorporated into the compositions and preparations as described herein.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, or intramuscular dosing or as a suppository for rectal dosing). For example, compositions intended for oral use may contain one or more coloring, sweetening, flavoring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent, and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil such as liquid paraffin, or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient, which is solid at ordinary temperature s but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 μm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulations, see Chapter 25.2 in Volume 5 of Comprehensive Medicinal Chemistry (Corwin Hansch; Chairman of Editorial Board), Pergamon Press 1990, which is specifically incorporated herein by reference.

The amount of a compound of this invention that is combined with one or more excipients to produce a single dosage form will necessarily vary depending upon the host treated and the particular route of administration. For example, a formulation intended for oral administration to humans may contain, for example, from 0.5 mg to 2 g of active agent compounded with an appropriate and convenient amount of excipients, which may vary from about 5 to about 98 percent by weight of the total composition. Dosage unit forms will generally contain about 1 mg to about 500 mg of an active ingredient. For further information on routes of administration and dosage regimes, see Chapter 25.3 in Volume 5 of *Comprehensive Medicinal Chemistry* (Corwin Hansch; Chairman of Editorial Board), Pergamon Press 1990, which is specifically incorporated herein by reference.

The size of the dose for therapeutic or prophylactic purposes of a compound of Formula I will naturally vary according to the nature and severity of the conditions, the age and sex of the animal or patient and the route of administration, according to well known principles of medicine.

The compounds of this invention may be used alone in combination with other drugs and therapies used in the treatment of disease states which would benefit from the inhibition of MEK. Such treatment may involve, in addition to the compounds of the invention, conventional surgery or radiotherapy or chemotherapy. Such chemotherapy may include one or more of the following categories of anti-tumor agents:

(i) antiproliferative/antineoplastic drugs and combinations thereof, as used in medical oncology, such as alkylating agents (for example, cis-platin, carboplatin, cyclophosphamide, nitrogen mustard, melphalan, chlorambucil, busulphan and nitorsoureas); anti-metabolites (for example, antifolates such as such as fluoropyrimidines like 5-fluorouracil and tegafur, raltitrexed, methotrexate, cytosine arabinside, hydroxyurea, or, one of the preferred anti-metabolites disclosed in European Patent Application No. 239362 such as N-(5-[N-(3,4-dihydro-2-methyl-4-oxoquinazolin-6-ylm-ethyl)-N-methylamino]-2-thenoyl)-L-glutamic acid); antitumor antibiotics (for example, anthracyclines like adriamycin, bleomycin, doxorubicin, daunomycin, epirubicin, idarubicin, mitomycin-C, dactinomycin and mithramycin); antimitotic agents (for example, vinca alkaloids like vincristine, vinblastine, vindesine and vinorelbine and taxoids like taxol and taxotere); and topoisomerase inhibitors (for example epipodophyllotoxins like eptoposide and teniposide, amsacrine, topotecan and campothecin):

(ii) cytostatic agents such as antiestrogens (for example, tamoxifen, toremifene, raloxifene, droloxifene and iodoxyfene), estrogen receptor down regulators (for example, fulvestrant), antiandrogens (for example, bicalutamide, flutamide, nilutamide, cyproterone acetate and Casodex™ (4'-cyano-3-(4-fluorophenylsulphonyl)-2-hydroxy-2-methyl-3'-(trifluoromethyl)propionanilide)), LHRH antagonists or LHRH agonists (for example, goserelin, leuporelin and buserelin), progestogens (for example, megestrol acetate), aromatase inhibitors (for example, anastrozole, letrozole, vorazole and exemestane) and inhibitors of 5α-reductase such as finasteride;

(iii) agents which inhibit cancer cell invasion (for example, metalloproteinase inhibitors like marimastat and inhibitors of urokinase plasminogne activator receptor function);

(iv) inhibitors of growth factor function like growth factor antibodies, growth factor receptor antibodies (for example, the anti-erbB2 antibody trastumuzab [Herceptin™] and the anti-erbB1 antibody cetuximab [C225]), farnesyl transferase inhibitors, tyrosine kinase inhibitors and serine-threonine kinase inhibitors (for example, inhibitors of the epidermal growth factor family tyrosine kinases such as N-(3-chloro-4-fluorophenyl)-7-methoxy-6-(3-morpholinopropoxy) quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), inhibitors of the platelet-derived growth factor family and inhibitors of the hepatocyte growth factor family;

(v) antiangiogenic agents such as those which inhibit the effects of vascular endothelial growth factor (for example, the anti-vascular endothelial cell growth factor antibody bevacizumab [Avastin™], compounds such as those disclosed in International Patent Applications WO 97/22596, WO 97/30035, WO 97/32856, and WO 98/13354) and compounds that work by other mechanisms (for example, linomide, inhibitors of integrin αvβ3 function, MMP inhibitors, COX-2 inhibitors and angiostatin);

(vi) vascular damaging agents such as Combretastatin A4 and compounds disclosed in International Patent Applications WO 99/02166, WO 00/40529, WO 00/41669, WO 01/92224, WO 02/04434, and WO 02/08213;

(vii) antisense therapies (for example, those which are directed to the targets listed above such as ISIS 2503, and anti-ras antisense);

(viii) gene therapy approaches, including for example GVAX™, approaches to replace aberrant genes such as aberrant p53 or aberrant BRCA1 or BRCA2, GDEPT (gene-directed enzyme prodrug therapy) approaches such as those using cytosine deaminase, thymidine kinase or a bacterial nitroreductase enzyme and approaches to increase patient tolerance to chemotherapy or radiotherapy such as multi-drug resistance gene therapy;

(ix) interferon; and (x) immunotherapy approaches, including for example ex-vivo and in-vivo approaches to increase the immunogenicity of patient tumor cells, such as transfection with cytokines such as interleukin 2, interleukin 4 or granulocyte-macrophage colony stimulating factor, approaches to decrease T-cell anergy, approaches to using transfected immune cells such as cytokine-transfected dendritic cells, approaches using cytokine-transfected tumor cell lines and approaches using anti-idiotypic antibodies.

Such conjoint treatment may be achieved by way of the simultaneous, sequential or separate dosing of the individual components of treatment. Such combination products employ the compounds of this invention within the dose range described hereinbefore and the other pharmaceutically active agent within its approved dose range.

According to this aspect of the invention there is provided a pharmaceutical product comprising a compound of Formula I as defined hereinbefore and an additional anit-tumor agent as definged hereinbefore for the conjoint treatment of cancer.

Although the compounds of Formula I are primarily of value as therapeutic agents for use in warm-blooded animals (including man), they are also useful whenever it is required to control AKT protein kinases, tyrosine kinases, additional serine/threonine kinases, and/or dual specificity kinases. Thus, they are useful as pharmacological standards for use in the development of new biological tests and in the search for new pharmacological agents.

The activity of the compounds of this invention may be assayed for AKT protein kinases, tyrosine kinases, additional serine/threonine kinases, and/or dual specificity kinases in vitro, in vivo, or in a cell line. In vitro assays include assays that determine inhibition of the kinase activity. Alternate in vitro assays quantitate the ability of the inhibitor to bind to kinases and may be measured either by radiolabelling the inhibitor prior to binding, isolating the inhibitor/kinase complex and determining the amount of radiolabel bound, or by running a competition experiment where new inhibitors are incubated with known radioligands. These and other useful in vitro and cell culture assays are well known to those of skill in the art.

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as hereinafter claimed.

The compounds of the present invention may be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below.

The novel compounds of the present invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used.

The preparation of compounds of the present invention may be carried out in a convergent or sequential synthetic manner. The skills required in preparation and purification of such compounds and the intermediates leading to these compounds are known to those in the art. Purification procedures include, but are not limited to, normal or reverse phase chromatography, crystallization, and distillation.

An illustration of the preparation of compounds (8), (9), (10) and (11) of the present invention is shown in FIG. 1. The synthesis starts with the preparation of a substituted quinazolinone (3) made by, for example, by the condensation of a corresponding substituted aryl amino acid (1) and a corresponding substituted amide (2) (see, for example, LeMahieu, et al, *J. Med. Chem.*, 1983, 26, 420-5 and references cited therein). Introduction of a leaving group into quinazolinone (3) may be accomplished by treatment with a halogenating agent (for example POCl$_3$) to give the chlorinated quinazoline (4.) The halogen leaving group is then displaced with substituted and protected pipera zinc (5) (e.g., Boc, but any suitable protecting group may be used; see, T. W. Greene et al., '*Protective groups in organic synthesis*', John Wiley and Sons, 1999, 3$^{rd}$ Ed., pp. 494-653). The piperazine (5) may be introduced to chlorinated quinazoline (4) either neat or in the presence of base. The piperazine protecting group may then be removed by known methods (see, Greene et al, supra) (6).

Substitution of the piperazine secondary amine in quinazoline intermediate (6) may be accomplished using a variety of electrophiles and reaction conditions. For example, the piperazine may be acylated by a suitably N-substituted or protected amino acid (e.g., Boc, etc.) which may be introduced using a variety of standard peptide coupling procedures under both solution phase and solid phase conditions, to produce a product such as compound (8). For representative examples, see Miklos Bodanszky, 'Principles of Peptide Synthesis,' Springer-Verlag, 1993, 2nd Ed., and C. Najera, *Synlett*, 2002, 9, 1388-1403. As above (and if protected) the N-protected amino acid unit may then be deprotected using representative procedures (e.g., using acid on a Boc-group; Greene et al., supra), and then manipulated as desired according to procedures appreciated by those skilled in the art.

Compounds of the present invention similar to compound (8) may be a prepared from quinazoline intermediate (6) by acylation with a natural or an 'unnatural' amino acid (7). The preparation of 'unnatural' amino acids is also well known to those skilled in the art, and their use is included in the present invention (for representative reviews, see, C. Najera, *Synlett*, 2002, 9, 1388-1403, and J.-A. Ma, *Angew. Chemie, Int. Ed*, 2003, 42, 4290-4299, and references therein).

Alternatively, the piperazine (6) may be acylated with an acid or acid halide in the presence of base to generate a substituted amine (10). Additionally, a substituted tertiary amine (11) can be prepared by treating piperazine (6) with an appropriate aldehyde (or surrogate) in the presence of a reducing agent (e.g., sodium cyanoborohydride). The piperazine (6) can also be treated with an epoxide to give the amino alcohol (9.) All functional groups may be further manipulated under standard conditions (e.g., reductions, alkylations, oxidations, palladium or nickel mediated couplings, etc.) to further functionalize each compound.

The compounds described in FIG. 1 may be prepared either as either the racemate, or as a single enantiomer (for example, using an enantiomerically pure amino acid (7.)) If prepared as the racemate, the corresponding enantiomers may be isolated by separation of the racemic mixture of compound on a chiral stationary phase column utilizing normal or reverse phase HPLC techniques. Alternatively, a diastereomeric mixture of compound (8) can be prepared by treatment of racemic compound (8) with an appropriate chiral acid (or suitably activated derivative), for example dibenzoyl tartrate or the like (see, for example, Kinbara, K., et. al., *J. Chem. Soc., Perkin Trans.* 2, 1996, 2615; and Tomori, H., et. al., *Bull. Chem. Soc. Jpn.,* 1996, 3581). The diastereomers would then be separated by traditional techniques (i.e. silica chromatography, crystallization, HPLC, etc) followed by removal of the chiral auxiliary to afford enantiomerically pure compound (8.)

Figure 2:
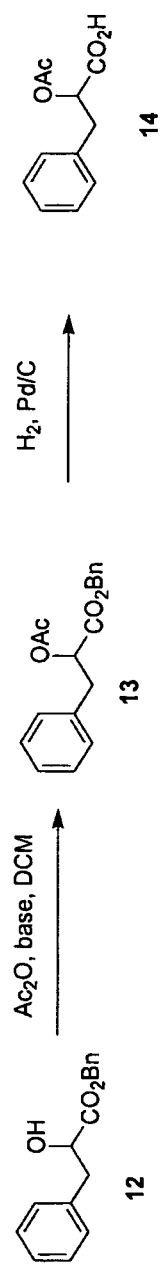
FIG. 2 shows a reaction scheme for the preparation of compound 14.

Other compounds of the present invention can be prepared using the alternatively substituted and functionalised acids, amino acids, hydroxy acids and variants thereof described in FIGS. 2-15. For example, compound (14) of this invention may be prepared as shown in FIG. 2. The hydroxyl group of substituted α-hydroxy benzyl ester (12) is protected with an appropriate protecting group (such as acetate) to give compound 13. The benzyl ester is then converted to the corresponding carboxylic acid (for example by hydrogenolysis) to give compound (14).

Figure 3:
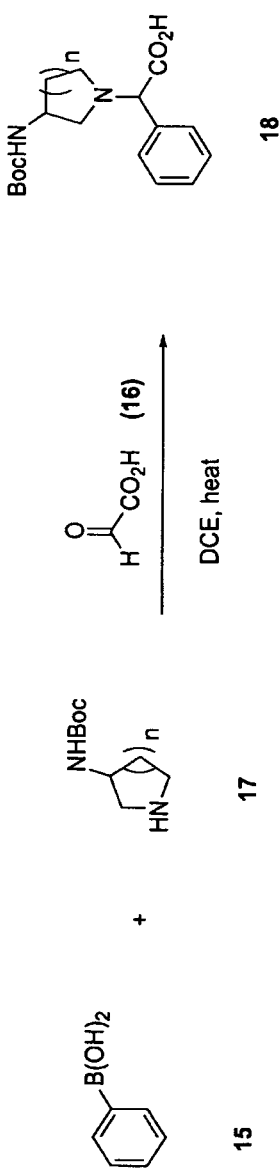
FIG. 3 shows a reaction scheme for the preparation of compound 18.

FIG. 3 shows the preparation of compound (18). Substituted phenyl boronic acid (15), glyoxylic acid (16), and a chiral or achiral mono-protected (using the Boc protecting group, for example) diamine (17) (such as 3-Boc-aminopyrrolidine) are combined in an appropriate solvent such as 1,2-dichloroethane and stirred at elevated temperature to provide carboxylic acids (18).

Figure 4:
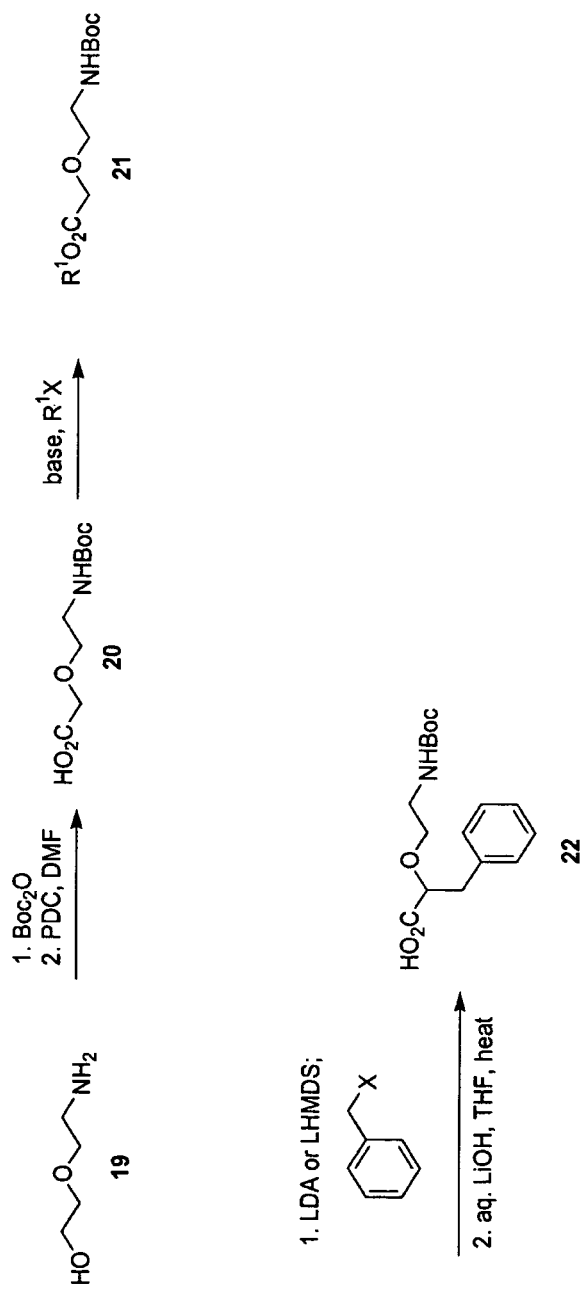
FIG. 4 shows a reaction scheme for the preparation of compound 22.

FIG. 4 shows the preparation of compound (22). 2-(2-Aminoethoxy)ethanol (19) is protected with an appropriate amine protecting group (such as Boc), and the hydroxyl group is oxidized to the carboxylic acid to provide intermediate (20). The acid in compound (20) is then converted to an ester using an appropriate base (such as $K_2CO_3$) and alkyl halide to furnish intermediate compound (21). Enolization of intermediate compound (21) is accomplished with strong base (such as LDA or LHMDS), followed by addition of a substituted benzyl halide yields an alkylated ester, which is then converted by basic hydrolysis to the corresponding acid (22).

Figure 5:
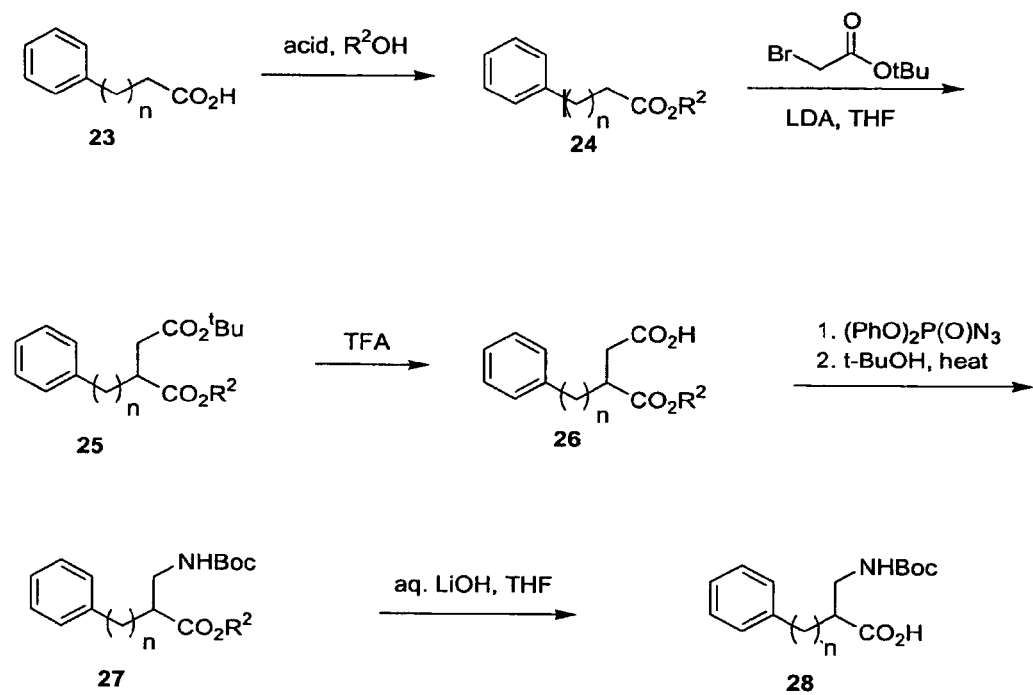
FIG. 5 shows a reaction scheme for the preparation of compound 28.

Compound (28) may be prepared as shown in FIG. 5. The substituted phenyl carboxylic acid (23) is transformed to the appropriate ester (24) under acidic (mineral acid, $R^2OH$) or basic ($K_2CO_3$, $R^2X$) conditions. Enolization of ester (24) is accomplished with strong base (such as LDA), and addition of a haloacetate ester (for example tert-butyl bromoacetate) provides intermediate compound (25). Selective ester deprotection is performed by treating compound (25) with acid (such as TFA) to provide carboxylic acid (26). The carboxylic acid (26) is converted to an acyl azide (using diphenyiphosphoryl azide, for example), which is then transformed to the corresponding carbamate-protected amine by heating in an appropriate alcohol solvent (tert-butyl alcohol, for example) in the presence or absence of a Lewis acid (such as $SnCl_4$) to provide compound (27). The carboxylic acid ester is then converted to the corresponding acid by hydrolysis under basic conditions (such as aq. LiOH in THF) to afford compound (28).

Figure 6:
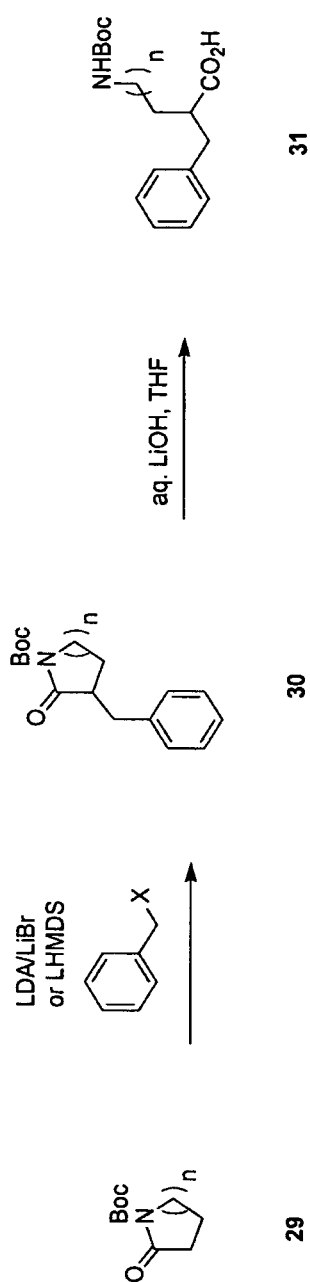
FIG. 6 shows a reaction scheme for the preparation of compound 31.

FIG. 6 shows the preparation of carboxylic acid (31). Lactam (29) is enolized with strong base (such as LDA/LiBr or LHMDS), and addition of a substituted benzyl halide furnishes alkylated intermediate compound (30). The lactam is then opened under basic conditions (such as aq. LiOH, THF) to furnish carboxylic acid (31).

Figure 7:
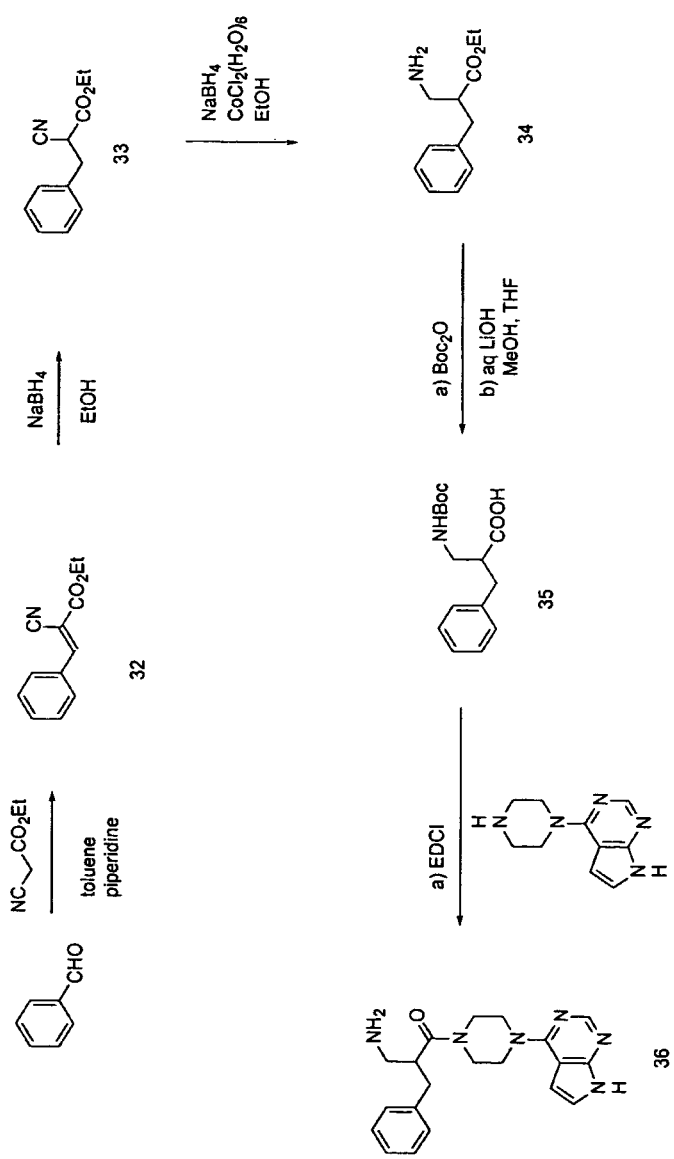
FIG. 7 shows a reaction scheme for the preparation of compounds 35 and 36.

Compound (36) may be prepared as shown in FIG. 7. Condensation of an appropriately substituted benzaldehyde with ethyl cyanoacetate provides compounds of structure (32). Treatment with a reducing agent such as $NaBH_4$ gives the saturated compound (33), which is followed by cobalt-mediated hydride reduction to give compound (34). The amine can then be protected and the ester saponified to give compound (35). Coupling with a piperazine can be accomplished using (for example) EDCI or PyBrop, followed by deprotection to give final compound (36).

Figure 8:
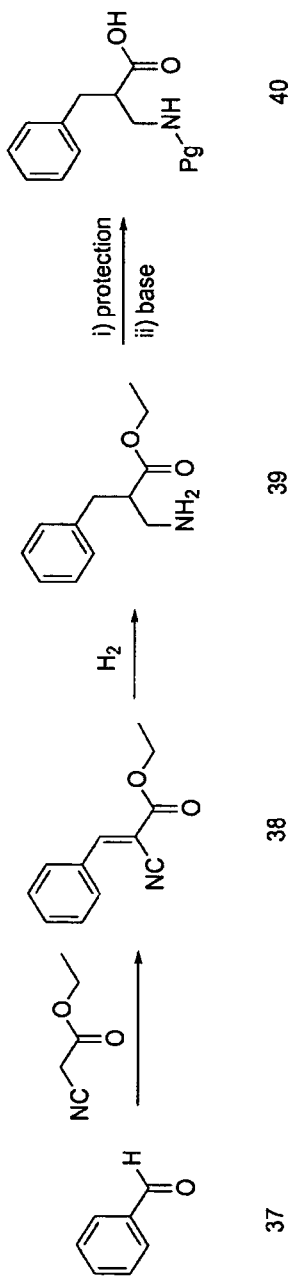
FIG. 8 shows a reaction scheme for the preparation of compounds 39 and 40.

FIG. 8 shows the preparation of amino acid (40). Compound (39) can be prepared by condensation of benzaldehydes with ethyl cyanoacetate followed by catalytic hydrogenation according to the procedures described by Lee, J. et al. (1999), 3060-3065. Compound (39) can be converted to compound amino acid (40) by protection of the primary amine followed by saponification under basic condition (for example, aqueous LiOH solution).

Figure 9:
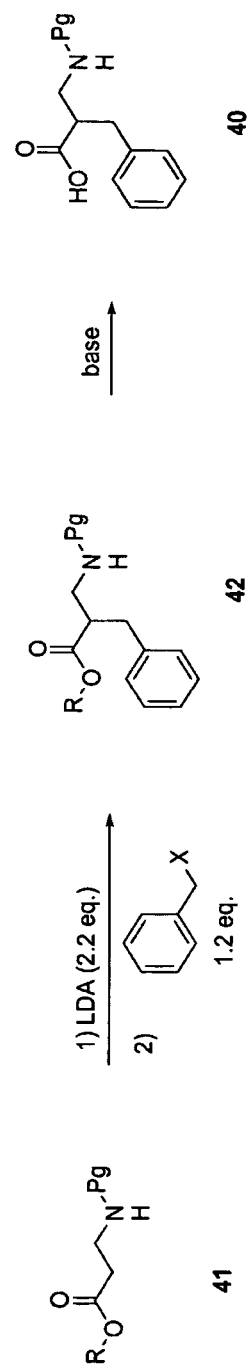
FIG. 9 shows a reaction scheme for the preparation of compound 40.

An alternate approach to amino acid (40) is shown in FIG. 9. Compound (41), where Pg is an appropriate protecting group (for example, Boc), can be treated with a variety of organometallic agents such as LDA in a suitable solvent such as THF or ether at low temperature s to generate a dianion intermediate, which can be quenched by suitable amount of benzyl halides to afford the intermediate compound (42). Saponification under basic conditions such as aqueous LiOH solution furnishes the desired product (40).

Figure 10:
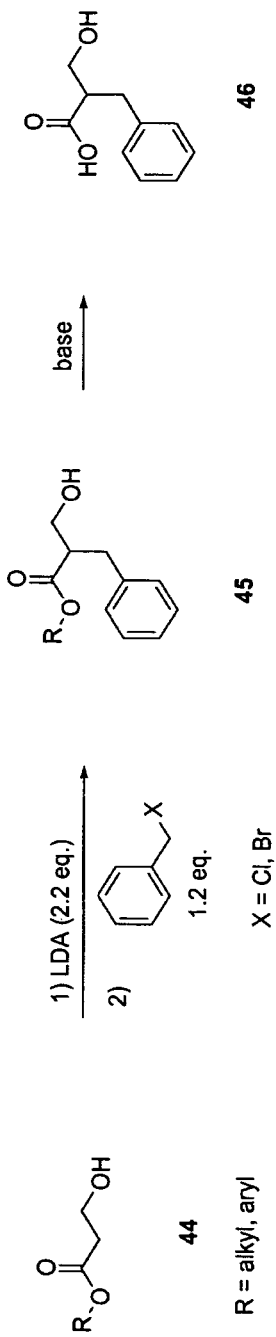
FIG. 10 shows a reaction scheme for the preparation of compound 46.

FIG. 10 summarizes a synthesis of amino alcohols (46) from compound (45). Compound (45) may be prepared from compound (44) by a sequence of deprotonation, alkylation and saponification as described in FIG. 9.

Figure 11:
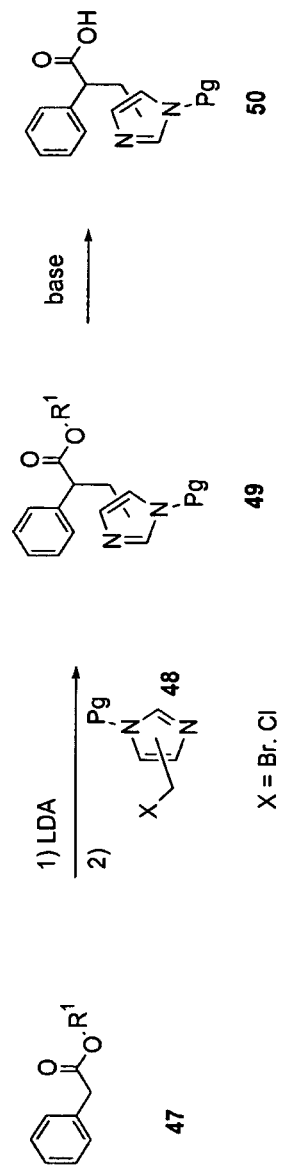
FIG. 11 shows a reaction scheme for the preparation of compound 50.

Preparation of compound (50) is shown in FIG. 11. Phenyl acetic acid derivative (47) can be deprotonated by treatment with a suitable organometallic agent such as LDA in a suitable solvent such as THF or ether at low temperature s, and then reacted with compound (48), where X is a suitable leaving group (for example Br, Cl) and Pg is an appropriate protecting group (for example, Boc or Ts), to yield intermediate compound (49) (Ho-sam A. et al. (1997) J. Med. Chem., 40, 2196; Ohkanda et al. (2004), J. Med Chem., 47, 432). Saponification of compound (49) under basic conditions (for example, aqueous LiOH solution) gives acid (50).

Figure 12:
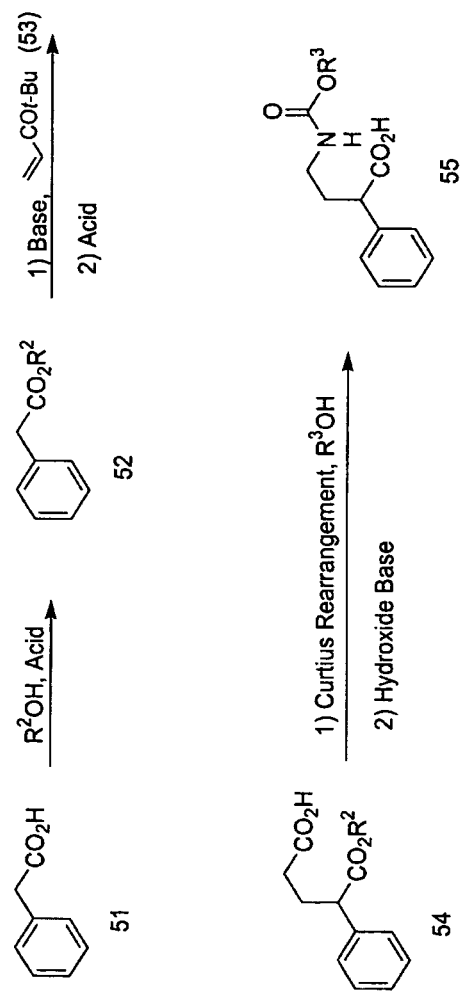
FIG. 12 shows a reaction scheme for the preparation of compound 55.

Compound (55) may be prepared as shown in FIG. 12. Esterification of the appropriately substituted and commercially available acid (51) with an alcohol affords the desired ester (52). Treatment of ester (52) with appropriate base and electrophile (e.g., acrylate, etc. (53)) followed by ester cleavage with acid (see, T. W. Greene et al., supra) affords intermediate compound (54). Introduction of azide (affords acylazide) with activating reagent followed by heating affects rearrangement of acid (54) to the requisite N-protected amino-ester intermediate (for example Boc, but any suitable protecting group may be used with the appropriate alcohol solvent; see, Greene et al., supra. Treatment of ester intermediate with hydroxide base affords the N-protected amino acid (55).

Figure 13:
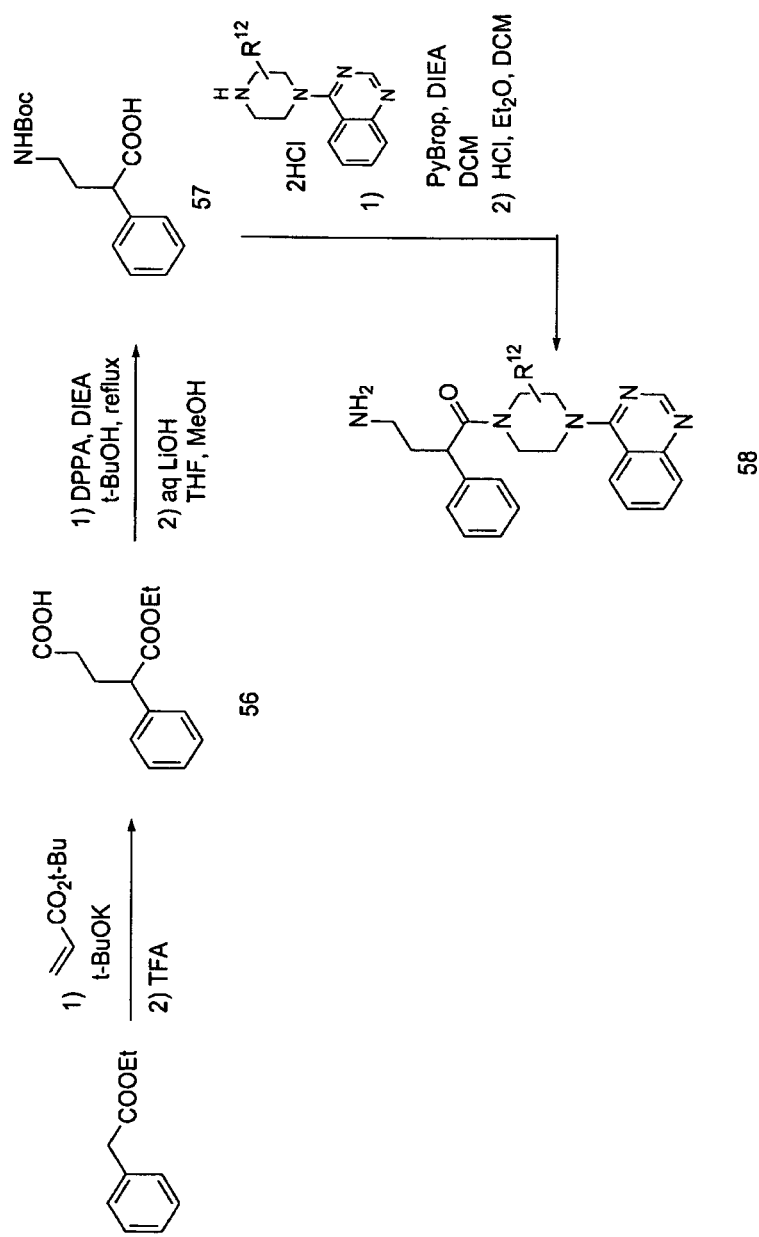
FIG. 13 shows a reaction scheme for the preparation of compounds 57 and 58.

Compound (58) may be prepared as shown in FIG. 13. Michael addition of phenylacetic acid ethyl esters with tert-butyl acrylate using catalytic base such as potassium tert-butoxide followed by acid hydrolysis of the tert-butyl ester provides compound (56). Curtius rearrangement using diphenylphosphorylazide followed by saponification of the ester gives compound (57). Coupling with a piperazine can be accomplished using EDCI or PyBrop, followed by deprotection of the Boc group to give final compound (58).

Figure 14:
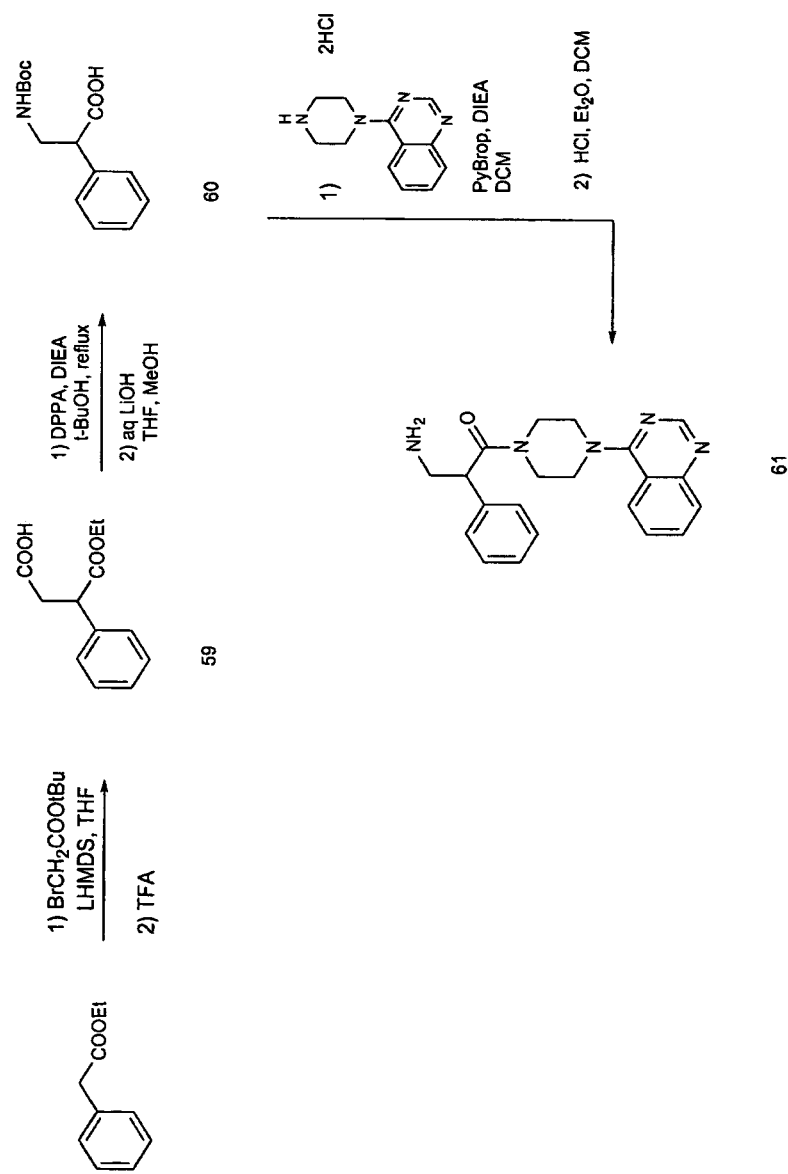
FIG. 14 shows a reaction scheme for the preparation of compounds 60 and 61.

FIG. 14 shows the preparation of compound (61). Alkylation of phenylacetic acid ethyl esters with α-bromoacetate tert-butyl ester using a base such as lithium bis(trimethylsilyl)amide provides compound (59). The remainder of the sequence is as that described in FIG. 13 to provide compound (61).

Figure 15:
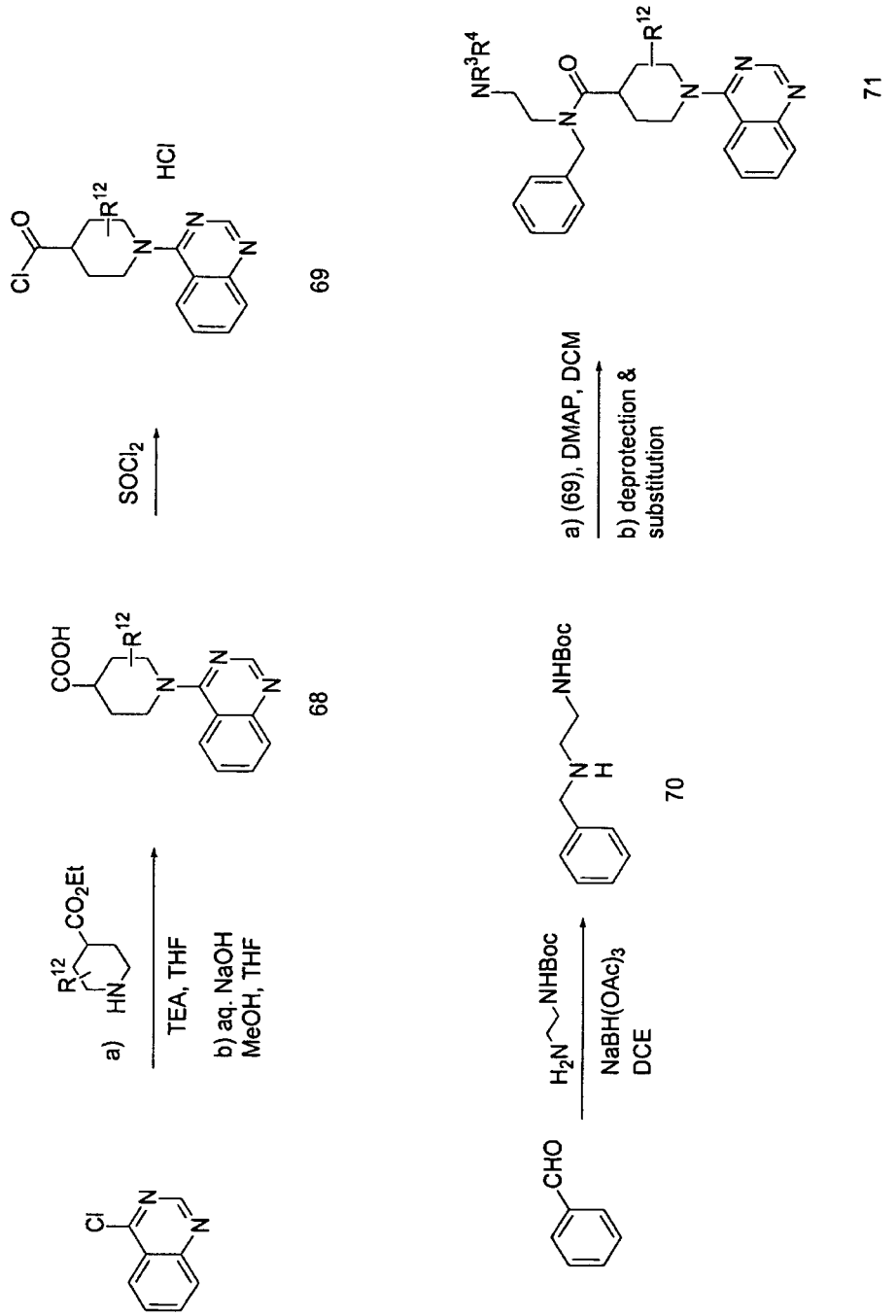
FIG. 15 shows a reaction scheme for the preparation of compounds 69-71.

Compound (71) may be prepared as shown in FIG. 15. The displacement of 4-chloroquinazoline with ethyl isonipecotate followed by saponification of the ester gives intermediate (68). Treatment with a halogenating reagent such as thionyl chloride or oxalyl chloride provides acid chloride (69). Reductive amination of an appropriately substituted benzaldehyde with N-Boc-ethylenediamine using NaCNBH$_3$ or NaH(OAc)$_3$ in MeOH, THF, or DCE as solvent gives the secondary amine (70). Reaction of (69) with amine (70) followed by deprotection of the Boc group provides compound (71).

Figure 16:
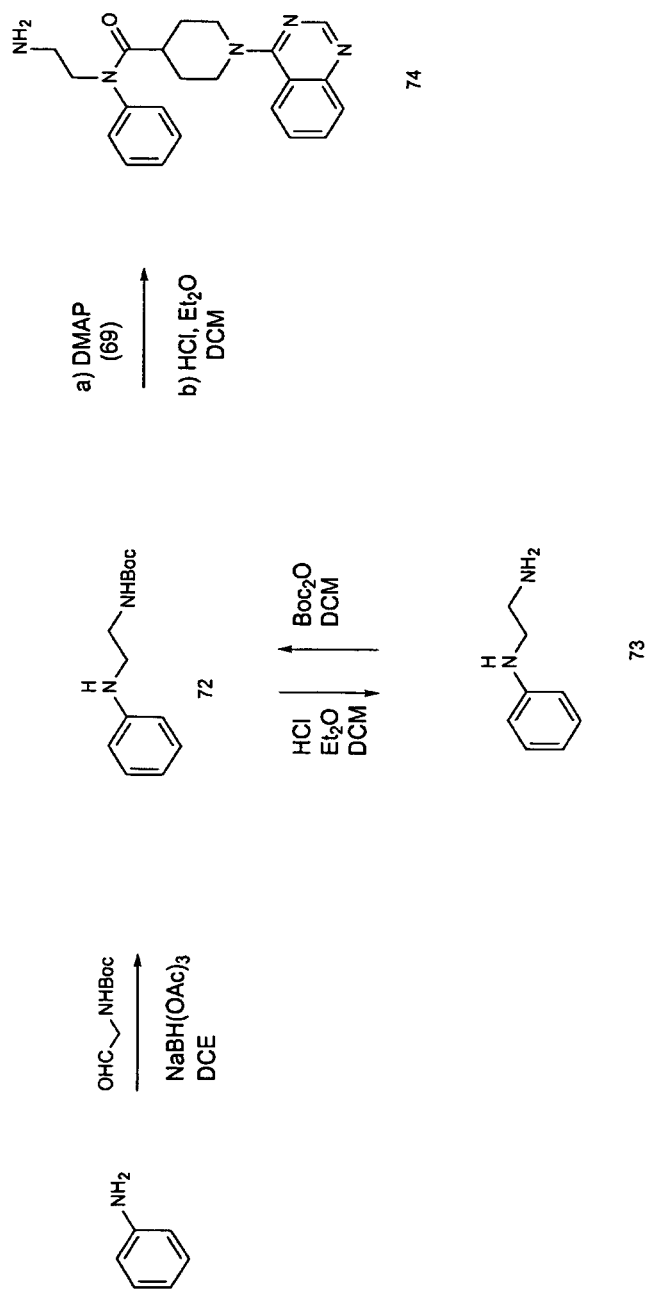
FIG. 16 shows a reaction scheme for the preparation of compounds 72-74.

Alternatively, compound of formula (74) may be prepared as shown in FIG. 16. Reductive amination of an appropriately substituted aniline with tert-butyl N-(2-oxoethyl)carbamate using NaCNBH$_3$ or NaH(OAc)$_3$ in MeOH, THF, or DCE as solvent gives the secondary amine (72). Compound (72) can be purified by removal of the Boc group followed by acid-base extraction and chromatography to give compounds of structure (73) and then converted back to compound (72) by treatment with Boc$_2$O. Reaction with intermediate (69) using DMAP as base followed by deprotection of the Boc group with (for example) ethereal HCl and substitution (if required) gives compound (74).

Figure 17:
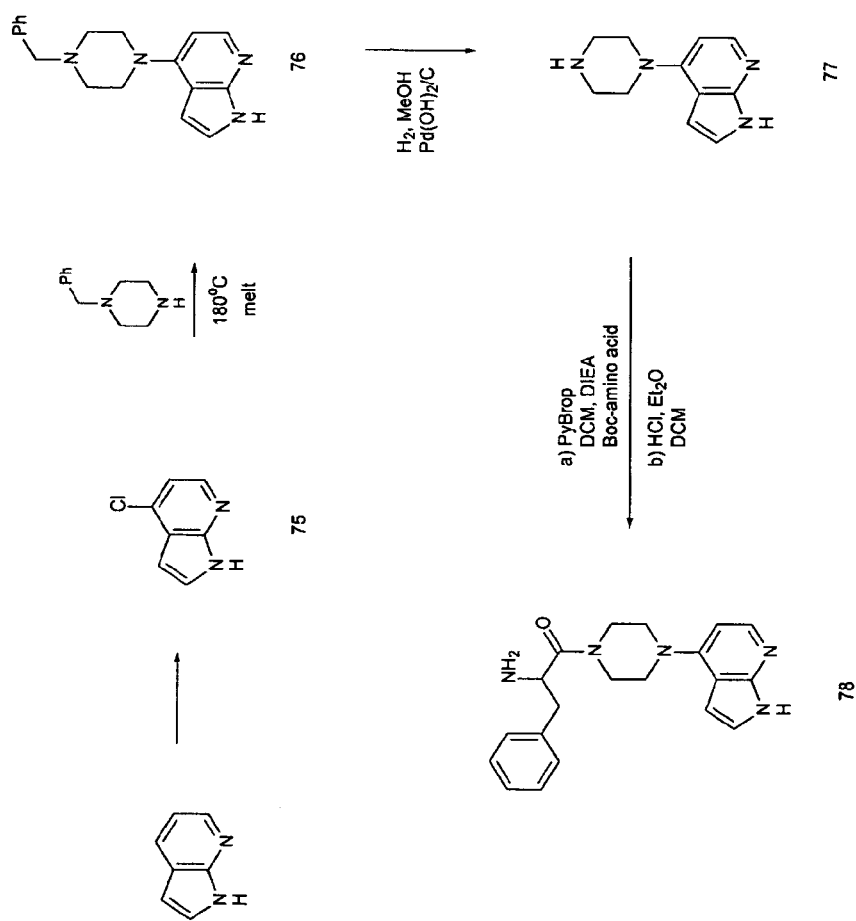
FIG. 17 shows a reaction scheme for the preparation of compound 78.

Compound (78) may be prepared as shown in FIG. 17. Compound (75) can be prepared from 7-azaindole according to literature procedures. Introduction of the piperazine can be accomplished by melting N-benzylpiperidine with intermediate (75) to give intermediate (76). Removal of the benzyl protecting group can be accomplished using (for example) hydrogenation in the presence of Pd—C in methanol. Coupling of a Boc-protected amino acid with intermediate (77) can be accomplished using (for example) EDCI or PyBrop, followed by deprotection of the Boc group to give compound (78).

Figure 18:
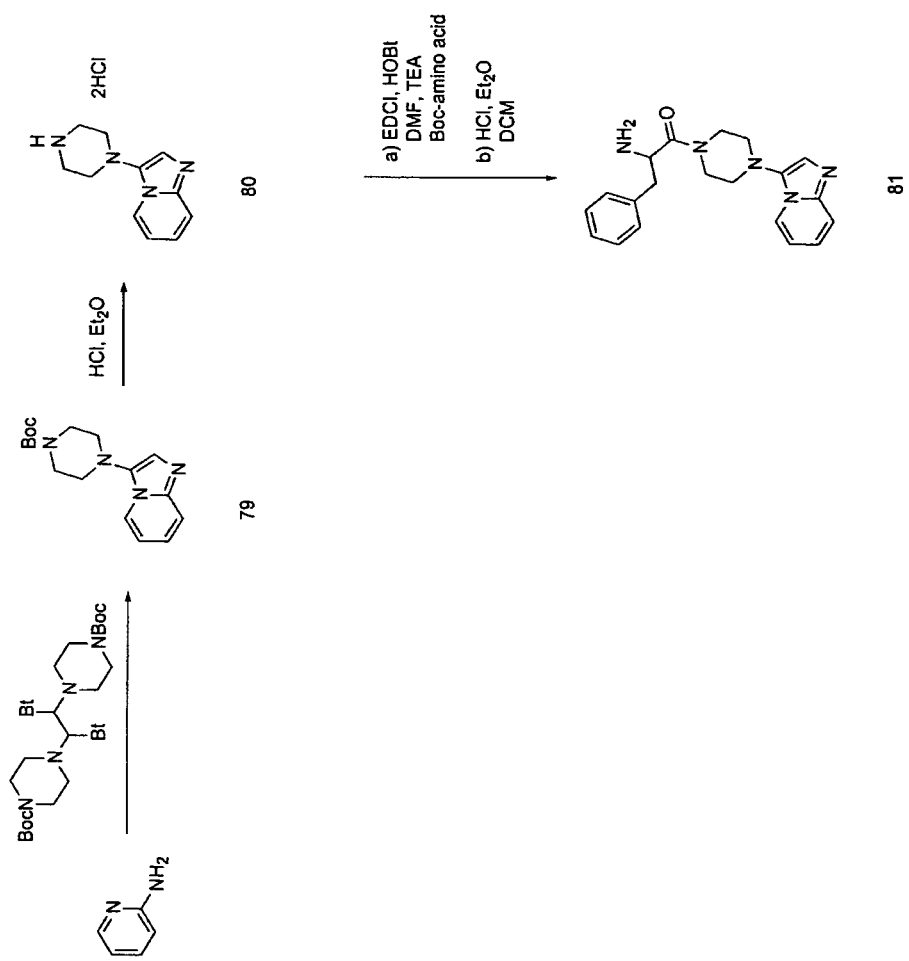
FIG. 18 shows a reaction scheme for the preparation of compounds 80 and 81.

FIG. 18 shows preparation of compound (81). Compound (79) can be prepared from 2-aminopyridine similar to literature procedure (A. R. Katritzky et al., J. Org. Chem., 2003, 68, 4935-4937). Deprotection of the Boc group using (for example) ethereal HCl gives intermediate (80). The piperazine can be coupled to N-protected amino acids using (for example) EDCI or PyBrop followed by deprotection to give final compound (81).

Figure 19:
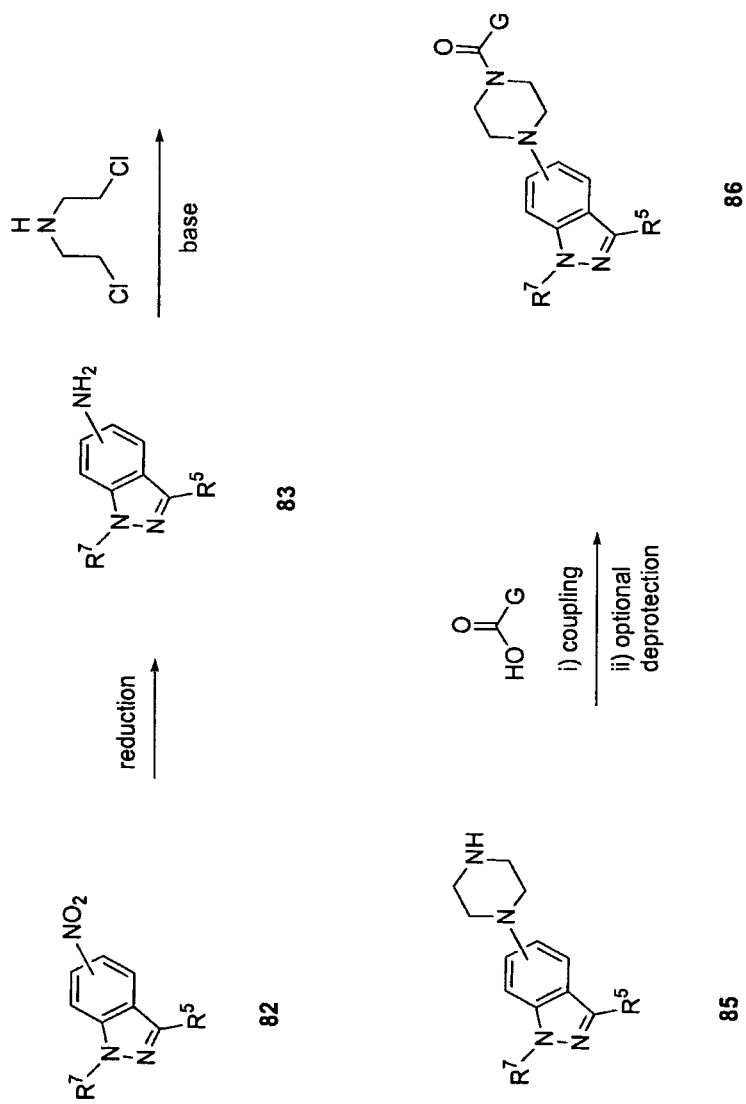
FIG. 19 shows a reaction scheme for the preparation of compounds 85 and 86.

FIG. 19 illustrates the preparation of 5- and 6-substituted indazole (86). Substituted nitro indazole (82), where $R^5$ and $R^7$ are substituents which are suitable for use in the subsequent reactions, may be reduced to amino indazole (83) using standard conditions (for example catalytic hydrogenation, zinc/acetic acid, Fe/HCl, SnCl$_2$/MeOH or FeSO$_4$ in water). Amino indazole (83) can react with compound (84) (for example, bis(2-chloroethyl)amine) in the presence of an acid scavenger (for example, Na$_2$CO$_3$, K$_2$CO$_3$, or the like) to afford the cyclized product (85). This reaction is performed in a suitable solvent (for example, ethanol) by heating at about 50-150° C. The resulting piperazine compound (85) is then acylated by a suitable acid (for example a protected amino acids) which may be introduced using a variety of standard peptide coupling procedures under solution phase or solid phase conditions. The coupling product may require a separate deprotection step to remove any protecting groups in R to afford the product (86). For example, a Boc protecting group may be removed by treating with a strong acid such as trifluoroacetic acid (TFA) or hydrochloric acid in the presence of an inert solvent such as dichloromethane or methanol. Removal of a Cbz group can be carried out by catalytic hydrogenation with hydrogen in the presence of a palladium catalyst or by transfer hydrogenation. An Fmoc group can be removed with a low boiling point amine (for example piperidine or the like) in a solvent such as DMF.

Figure 20:
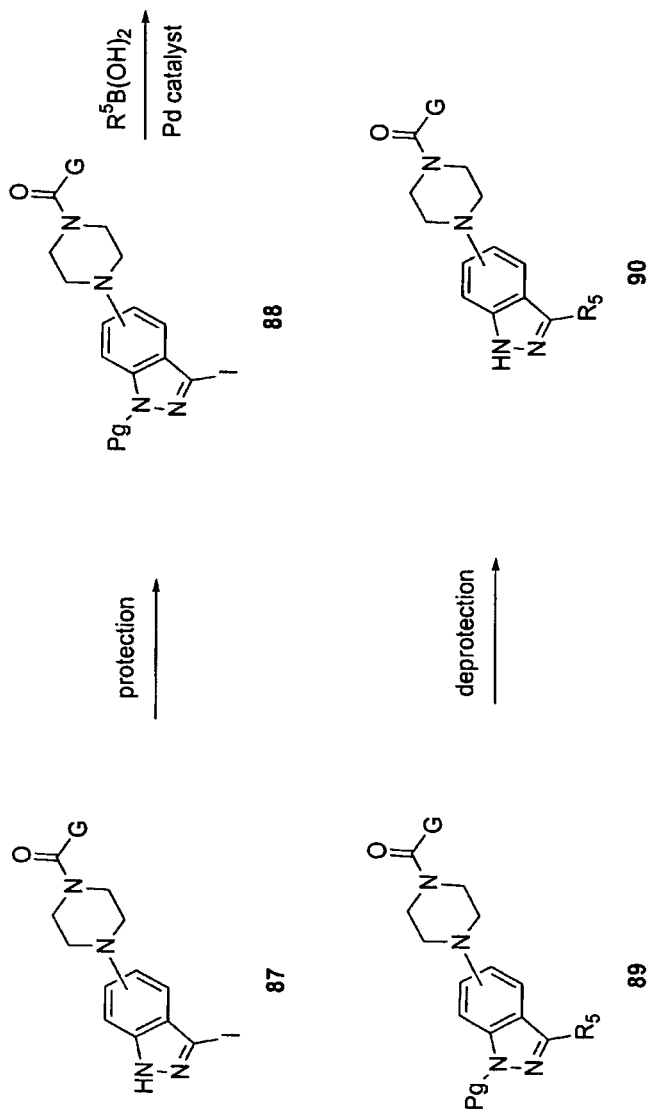
FIG. 20 shows a reaction scheme for the preparation of compound 90.

FIG. 20 describes the synthesis of 3-alkyl and 3-aryl substituted indazole (90). The iodo intermediate (87) can be prepared by the procedures shown in FIG. 20. Compound (87) is protected using a suitable protecting group and treated with an alkyl or aryl boronic acid or ester and a suitable Pd catalyst, for example, Pd(PPh$_3$)$_4$, to afford the desired 3-substituted intermediate (89) which is then deprotected to give compound (90).

Figure 21:
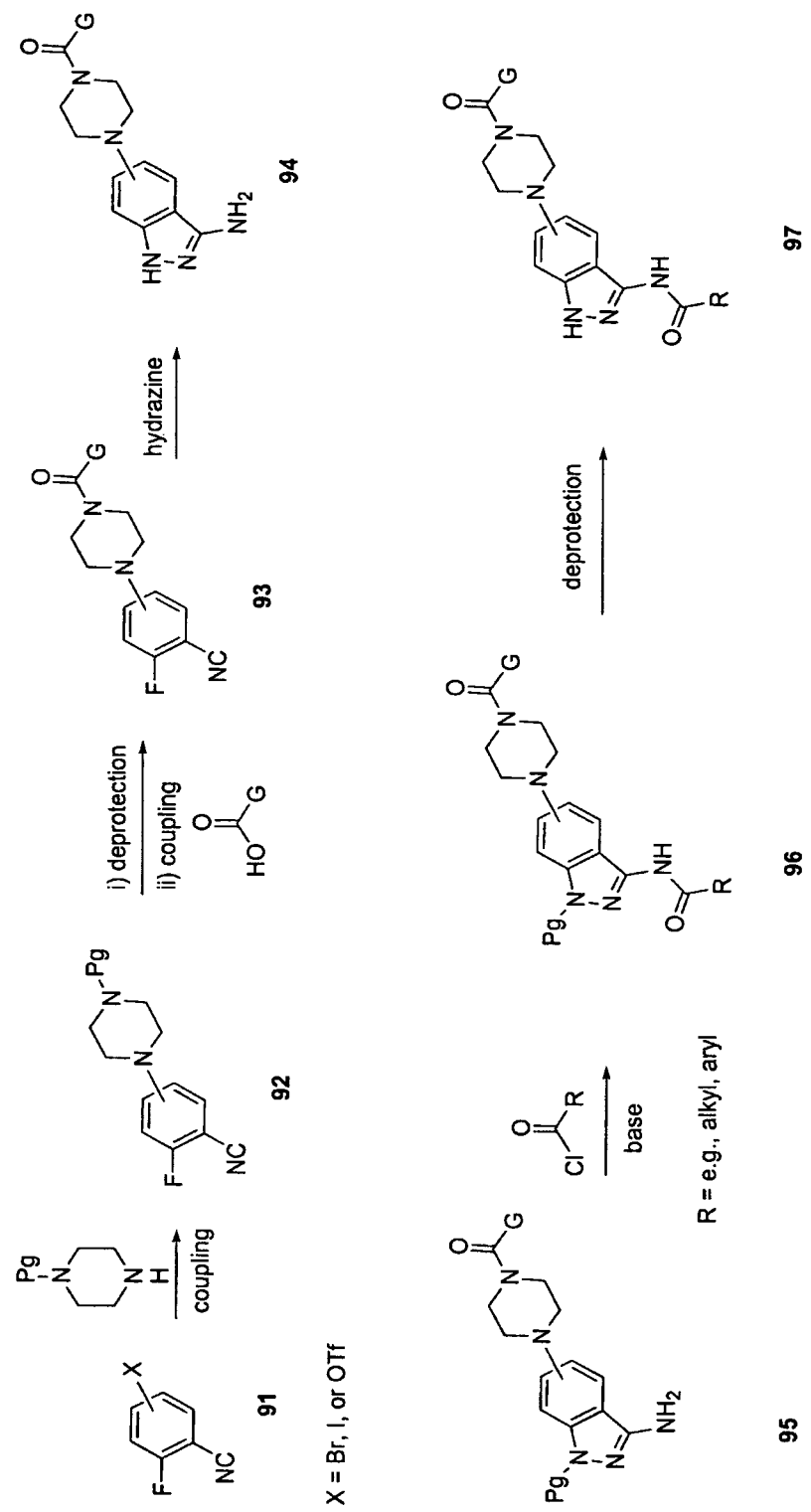
FIG. 21 shows a reaction scheme for the preparation of compounds 93-97.

The preparation of 3-amino substituted indazoles is outlined in FIG. 21. Compound (92) can be prepared by reacting a suitably monoprotected piperazine intermediate with a compound (91), where X is a suitable leaving group (for example, bromo, iodo or OTD, via Pd or Cu-mediated coupling (Buchwald et al. (2000), J. Org. Chem., 65, 1144; Hartwig et al. (1998) Angew. Chem. Int. Ed. Eng., 37, 2046) to furnish intermediate (92). Removal of the protecting group followed by amide coupling with an acid affords compound (93), which is then treated with hydrazine to give 3-amino indazole intermediate (94). Selective protection of the N-1 nitrogen affords compound (95), which can be acylated with an acid halide in an inert solvent (for example, dichloromethane, or the like) to afford the amide (96). An organic base, such as diisopropylethylamine, triethylamine, pyridine, or DMAP, may be added as an acid scavenger to facilitate the coupling reaction. Transformation of compound (96) into compound (97) can be accomplished by removal of the protecting groups.

Figure 22:
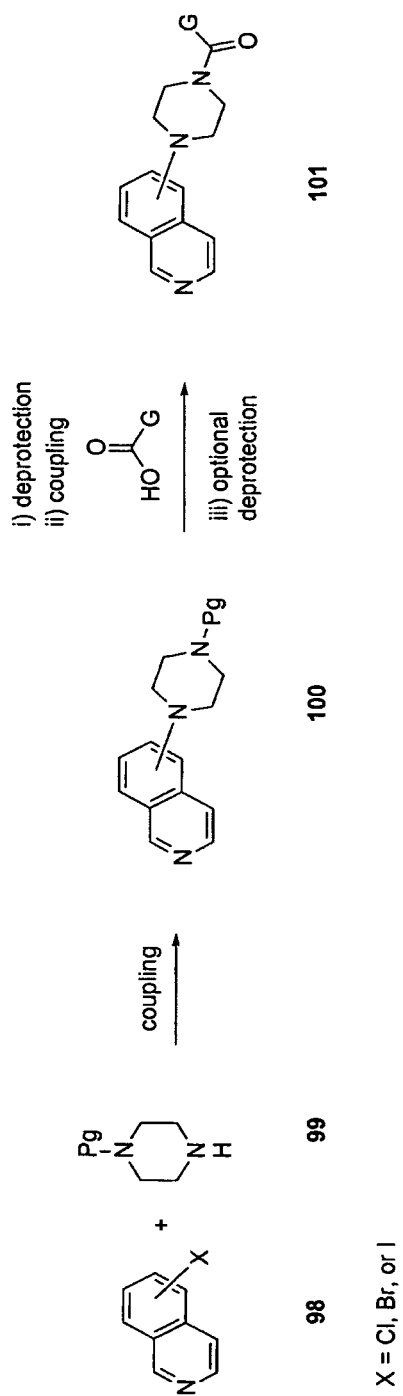
FIG. 22 shows a reaction scheme for the preparation of compounds 100 and 101.

FIG. 22 describes a synthesis of a particular class of compounds bearing an isoquinoline ring. Compound (100) can be prepared by reacting suitably mono-protected piperazine (99) with an isoquinoline compound substituted with a leaving group X, where X is halide (for example, chloro, bromo, and iodo), or sulfonate (for example $OSO_2CF_3$), in the presence of a base and a palladium or a copper catalyst, according to known methods. Removal of the protecting group Pg of compound (100) affords an amine intermediate, which can be conveniently converted to compound (101) by amide coupling with acids followed by optional removal of protecting groups as described in FIG. 19.

Figure 23:
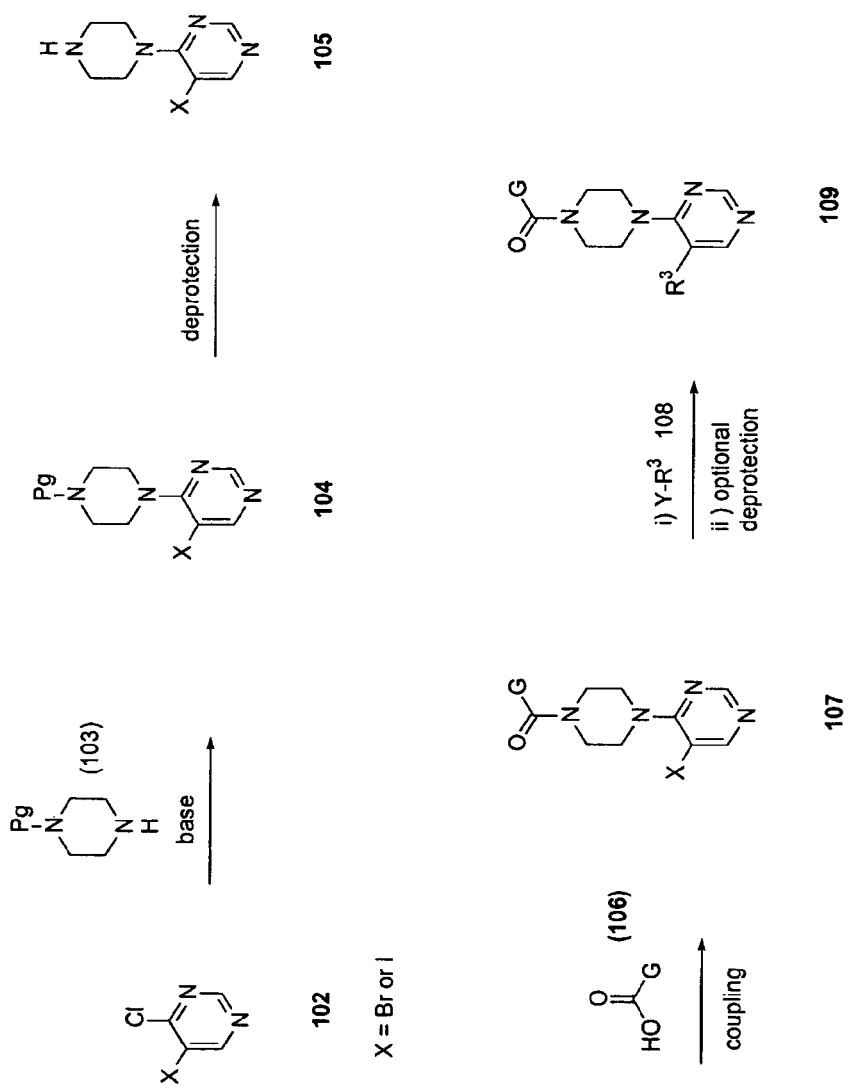
FIG. 23 shows a reaction scheme for the preparation of compounds 104-109.

FIG. 23 presents a synthesis of a particular class of pyrimidines bearing a substituent at the 5-position. Compound (104) can be prepared by $S_NAr$ reaction between a suitably mono-protected piperazine compound (103) and a 4-chloro substituted pyrimidine intermediate (102), where X is Br or I, in the presence of an acid scavenger (for example, diisopropylethylamine or triethylamine). Removal of the protecting group Pg followed by amide coupling with an acid (106) affords intermediate (107). Intermediate (107) can react with various coupling components (108) via metal-mediated reactions to furnish product (109). For example, compounds bearing an O- or S-linked substituent at the 5-position of the pyrimidine ring can be prepared by reactions between intermediate (107) and an alcohol or thiol in the presence of a base (for example, $Cs_2CO_3$) and a Cu catalyst (for example, CuCl, CuI, or the like) under modified Ullman coupling conditions (Wolter, M. et. al. *Org. Lett.* 2002, 4, 973-976). In some cases, an additive (for example, 2,2,6,6-tetramethyl-heptane-3,5-dione, pentane-2,4-dione, 1,10-phenethroline, or the like) is added to accelerate the reaction. Alternatively, if sodium thiolates are available, base is not required for the reaction. The coupling between compound (107) and a thiol may also be accomplished by palladium-catalyzed reactions (Kondo, T. et al. *Chem. Rev.,* 2000, 100, 3205-3220; Zheng, N. et al. *J. Org. Chem.,* 1998, 63, 9606-9607). Compounds bearing a N-linked substituent at the 5-position of the pyrimidine ring can be prepared by a Pd or Cu mediated coupling between intermediate (107) and amines (Buchwald et al. (2000), *J. Org. Chem.,* 65, 1144; Hartwig et al. (1998) *Angew. Chem. Int. Ed. Eng.* 37, 2046). Compounds bearing an alkyl or an aryl substituent at the 5-position of the pyrimidine ring can be prepared by Suzuki coupling (Miyaura, N. Suzuki A. (1995), *Chem. Rev.* 95, 2457; *Org. React.* (1997), 50, 1) between intermediates (107) and (108), wherein Y is a boronic acid or boronic ester, in the presence of a base (for example, $Na_2CO_3$ and $Et_3N$), a catalytic Pd(O) species (for example, $Pd(PPh_3)_4$, $Pd(PPh_3)_2Cl_2$, $Pd_2(dba)_3$ and $Pd(OAc)_2$) and a suitable ligand (such as $PPh_3$ and $AsPh_3$). Alternatively, 5-alkyl and aryl substituted pyrimidines (109) may also be prepared by Nigeshi or Kumada couplings between compounds (107) and (108), wherein Y—R' is an organo zinc reagent, in the presence of a Pd (for example, $Pd(PPh_3)_4$) or Ni (for example $Ni(acac)_2$) catalyst. Alternatively, 5-alkyl and aryl substituted pyrimidines (109) may also be prepared by Stille coupling between compounds (107) and (108), wherein Y—R' is an organostannane reagent, in the presence of a Pd catalyst.

Figure 24:
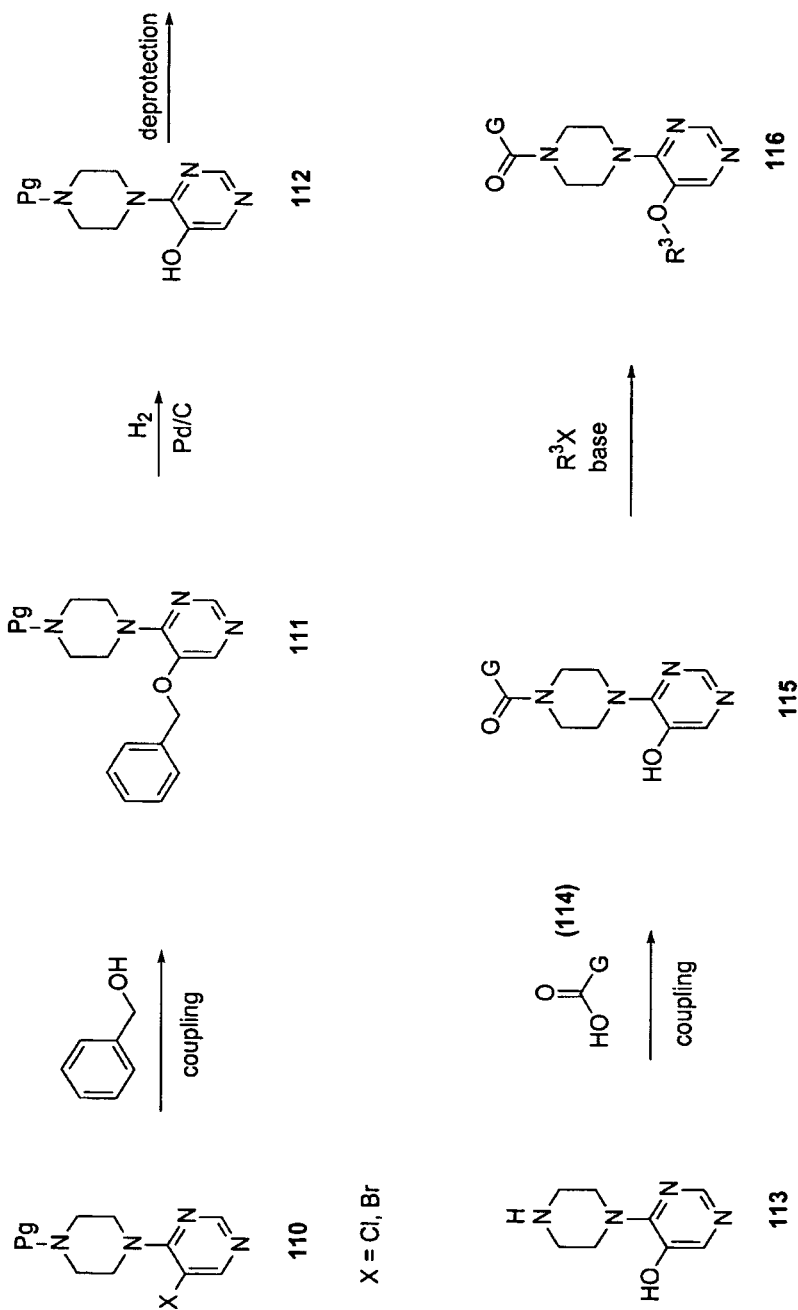
FIG. 24 shows a reaction scheme for the preparation of compounds 112-116.

FIG. 24 describes an alternate synthesis of compounds bearing an O-linked substituent at the 5-position. Compound (111) can be prepared by Cu-catalyzed coupling of intermediate (110) with benzyl alcohol. Removal of the benzyl group by hydrogenation affords 5-hydroxylpyrimidine intermediate (112), which can be converted to compound (115) by deprotection and amide coupling as described in FIG. 19. Alkylation of compound (115) with alkyl halides in the presence of a base (for example, $K_2CO_3$, $Cs_2CO_3$, or the like) in an inert solvent (for example, DMF) provides the desired compound (116).

Figure 25:
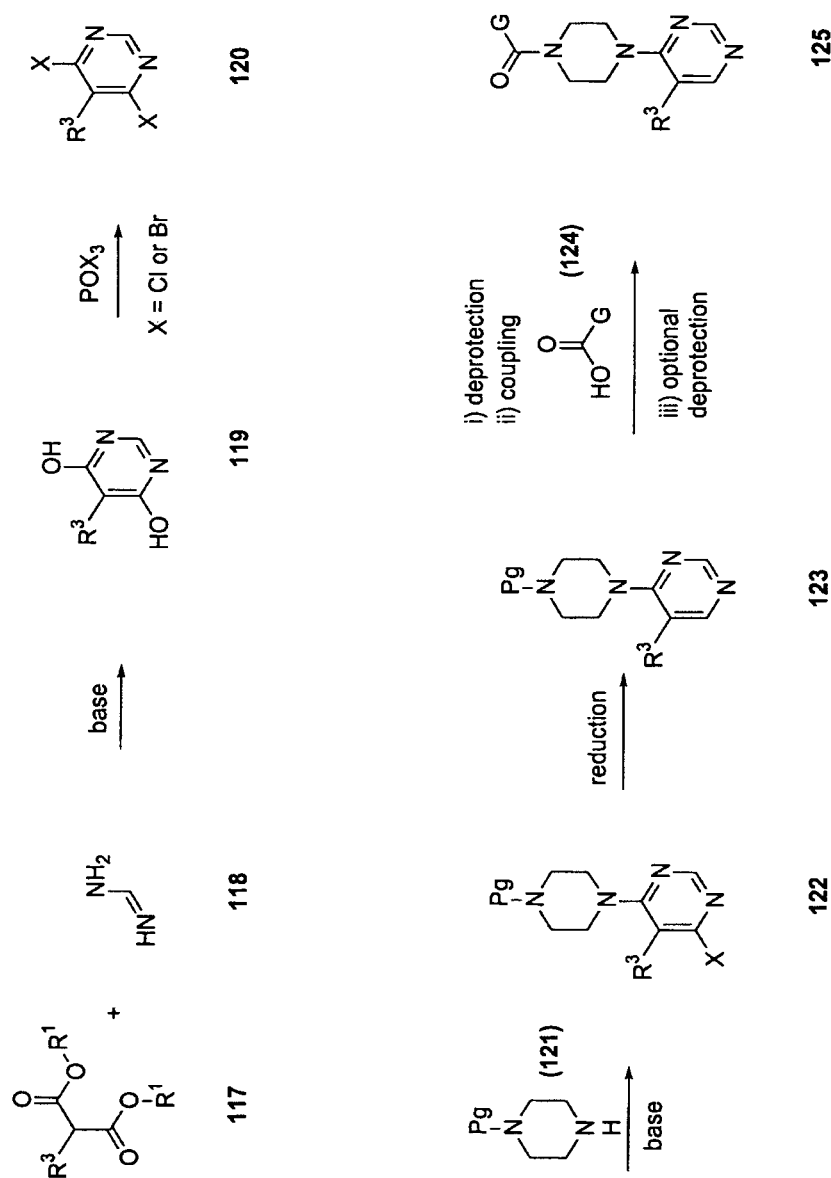
FIG. 25 shows a reaction scheme for the preparation of compounds 120-125.

Compound (125) can be synthesized as described in FIG. 25. An appropriately substituted pyrimidine (119) may be prepared by the condensation of a corresponding substituted malonic acid diester (117) and a corresponding substituted formamidine (118) in the presence of a base (for example, NaOEt). Treatment of pyrimidine (119) with a halogenating agent (for example, $POCl_3$ or $POBr_3$) affords the dihalide (120). Displacing one of the halogens with protected piperazine (121) gives the mono-substituted compound (122), which can be converted to compound (123) by reduction (for example, catalytic hydrogenation) of the second halogen. Transformation of compound (123) into desired compound (125) can be accomplished by the procedures described in FIG. 22.

Figure 26:
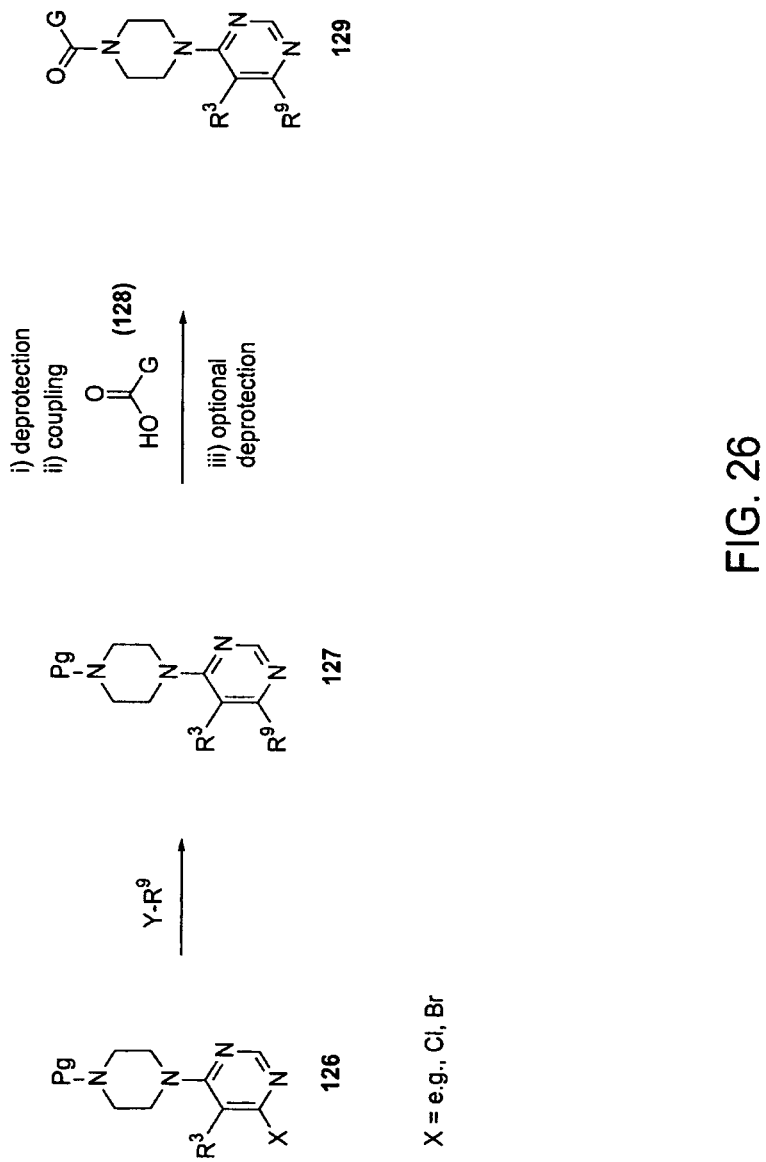
FIG. 26 shows a reaction scheme for the preparation of compounds 127 and 129.

FIG. 26 illustrates an approach to preparation of 5,6-disubstituted pyrimidines (129). Treatment of compound (126) with a nucleophile (for example, an amine) either neat or in the presence of a base can give the $SN_A$, product (127). Alternatively, compound (126) can be converted to compound (127) via various metal mediated coupling reactions such as described in FIG. 23. Transformation of compound (127) into desired compound (129) can be accomplished by a sequence of deprotection, amide coupling and optional deprotection as described in FIG. 22.

Figure 27:
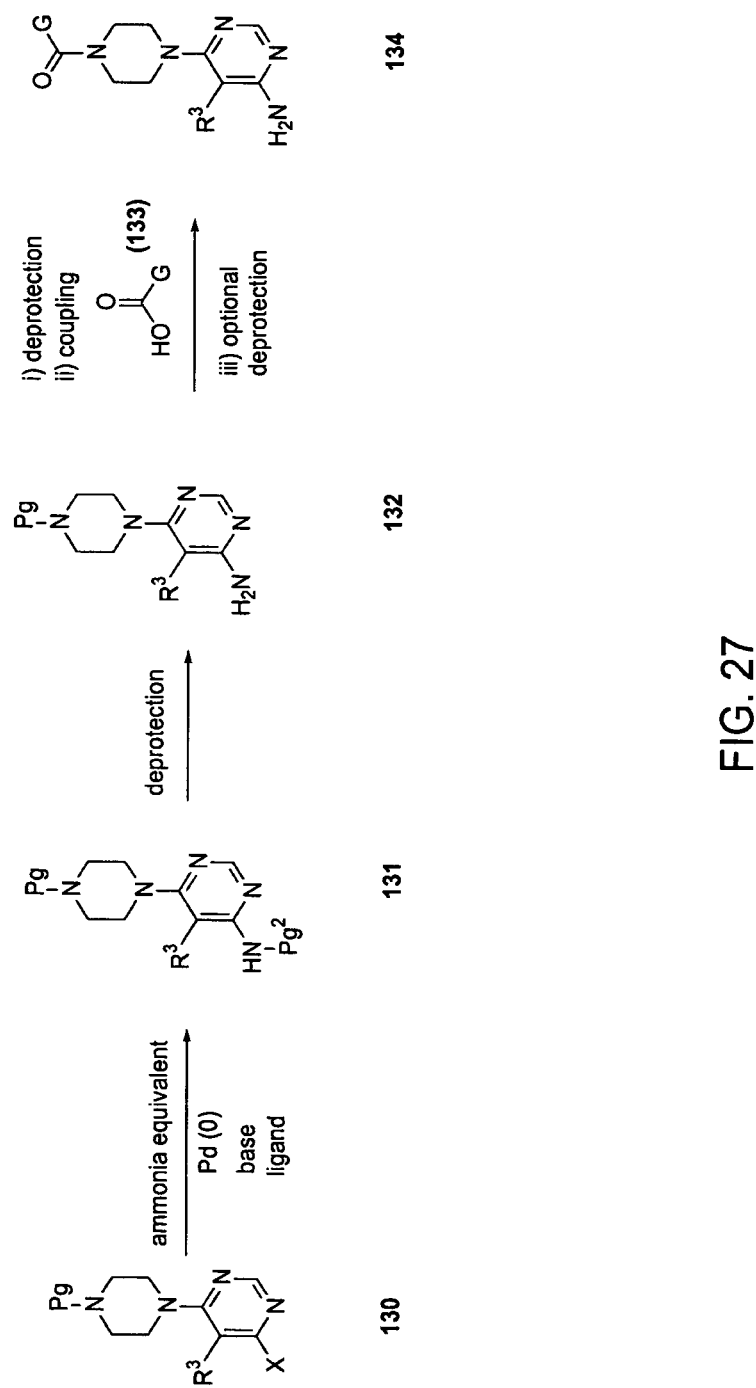
FIG. 27 shows a reaction scheme for the preparation of compounds 132 and 134.

The preparation of compounds with an amino group at the 6-position of the pyrimidine ring is shown in FIG. 27. Compounds of formula (131) can be prepared by palladium catalyzed coupling reactions between intermediate (130) and an ammonia equivalent (for example, benzophenone imine) For a review and leading references for arylation of ammonia equivalents, see Muci, A. R., Buchwald, S. L., *Topics in Current Chemistry,* 2002, 219, 131. Removal of the protecting group $Pg^2$ in compound (131) furnishes the amino intermediate (132). Transformation of (132) into desired compound (134) can be accomplished by the procedures described in FIG. 22.

Figure 28:
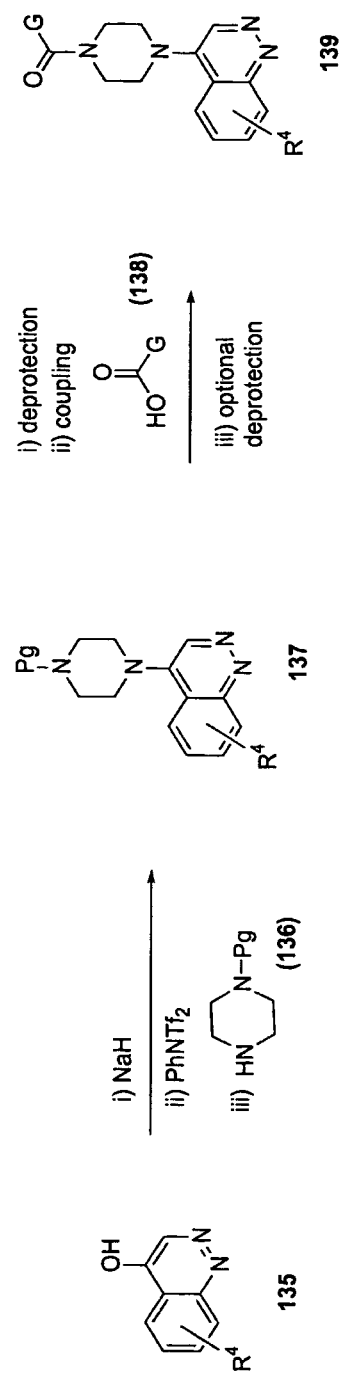
FIG. 28 shows a reaction scheme for the preparation of compounds 137 and 139.

FIG. 28 summarizes the preparation of compounds of the invention bearing a cinnoline ring. Compound (137) can be prepared by a one-pot process from 4-hydroxyl cinnoline (135) and protected piperazine (136) through a triflate intermediate (Cacchi, S. et al. *Synlett,* 1997, 1400). Sequential removal of the protecting group in compound (137) followed by amide coupling and optional deprotection affords compound (139).

Figure 29:
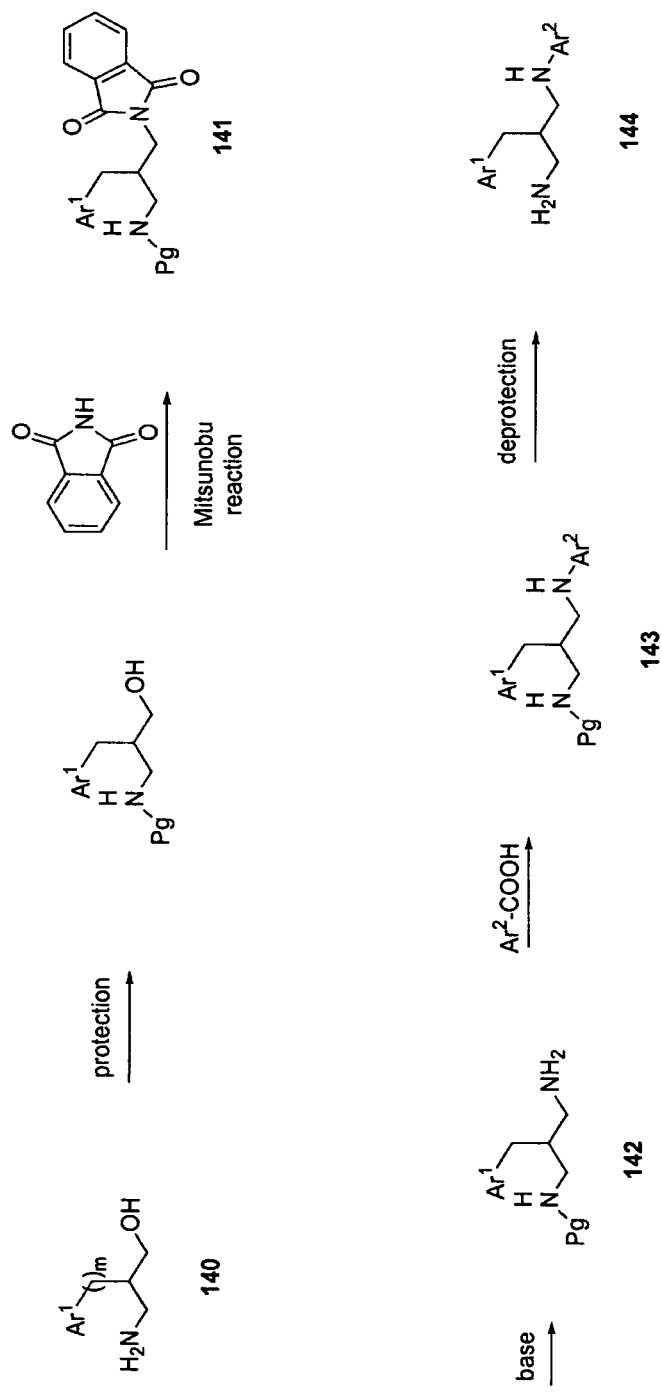
FIG. 29 shows a reaction scheme for the preparation of compounds 141-144.

FIG. 29 describes a synthesis of a compound containing a diamino group. Protection of the amino group in compound (140) gives a protected intermediate, which is subjected to Mitsunobu reaction with pthalimide to furnish compound (141). The phthalimide group can be selectively removed with a base (for example, hydrazine and low boiling point amines). Acylation of compound (142) with a acids using standard peptide coupling procedures followed by removal of the protecting group affords the product (144).

Figure 30:
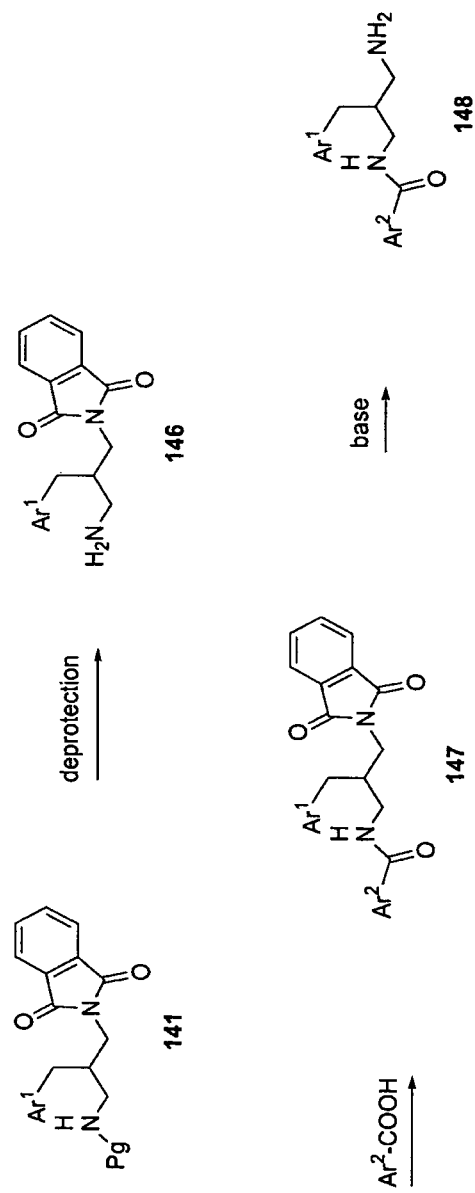
FIG. 30 shows a reaction scheme for the preparation of compound 148.

As shown in FIG. 30, the protecting group in compound (141) can alternatively be first selectively removed under known conditions to give compound (146), which can be coupled with an acid to afford the amide (147). Removal of the phthalimide group with a base (for example, hydrazine and a low boiling point amine) leads to the product (148).

Figure 31:
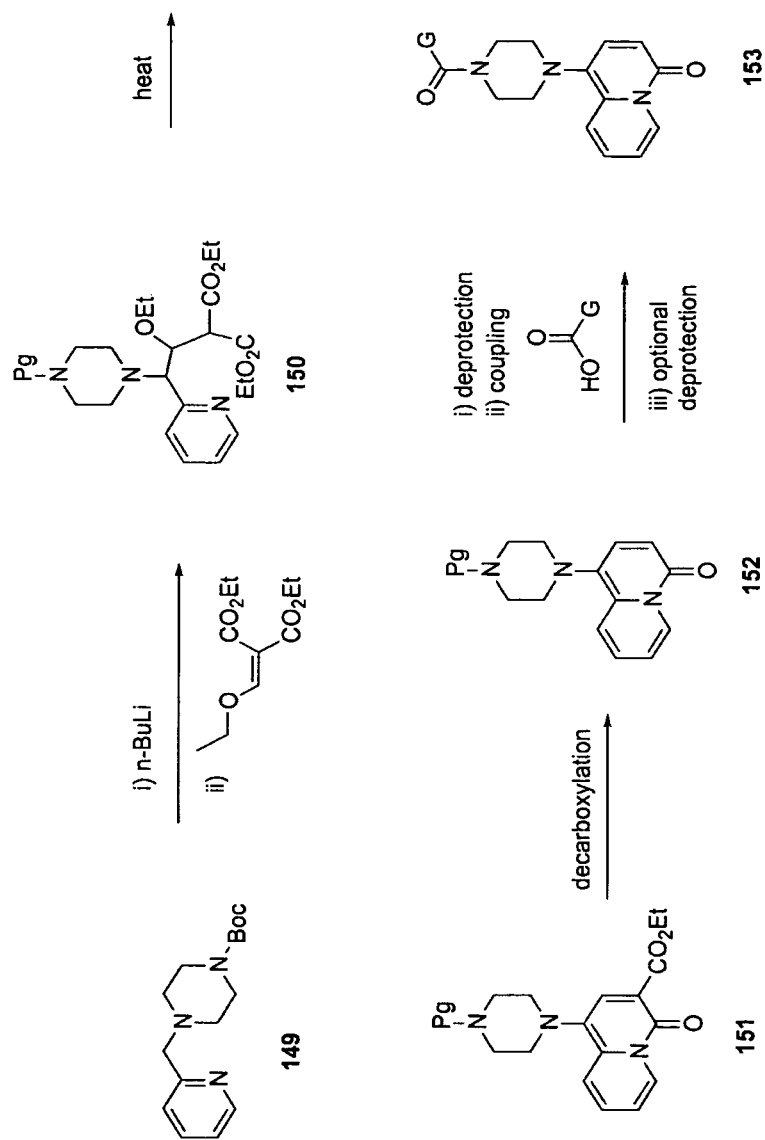
FIG. 31 shows a reaction scheme for the preparation of compounds 151-153.

FIG. 31 summarizes a preparation of 1-substituted quinolizinones (153). Treatment of compound (149) with an organometallic base (for example, n-BuLi) followed by quenching with 2-ethoxymethylenemalonic acid diethyl ester yields the Michael addition product (150). Cyclization occurs when heating compound (150) in an inert solvent (for example, xylene) to give intermediate (151). The carboxylate group in intermediate (151) may be removed by heating in an acidic solution (for example, aqueous HCl or $H_2SO_4$ solution). Sequential removal of the protecting group in compound (152) followed by amide coupling and optional deprotection affords compound (153).

Figure 32:
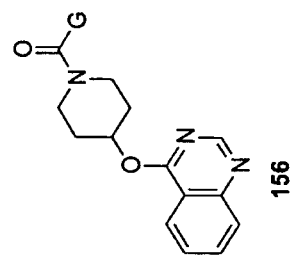
FIG. 32 shows a reaction scheme for the preparation of compounds 155 and 156.
Figure 32:
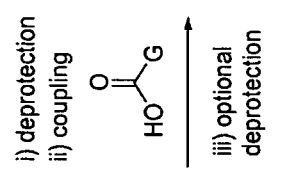
Figure 32:
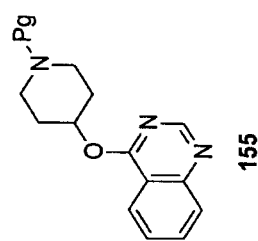
Figure 32:
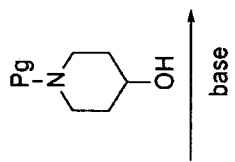
Figure 32:
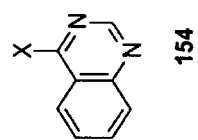

FIG. 32 describes a synthesis of compounds with a 4-hydroxyl piperidine linker. Compound (155) can be prepared by $S_NAr$ reaction between a suitably N-protected 4-hydroxyl piperidine compound and a substituted quinazoline intermediate (154) where X is leaving group (for example Cl or Br), in the presence of a base (for example, NaH or triethylamine) in a suitable solvent such as DMF, THF etc. Removal of the protecting group Pg in compound (155) followed by amide coupling with an acid and optional deprotection affords the desired compound (156).

Figure 33:
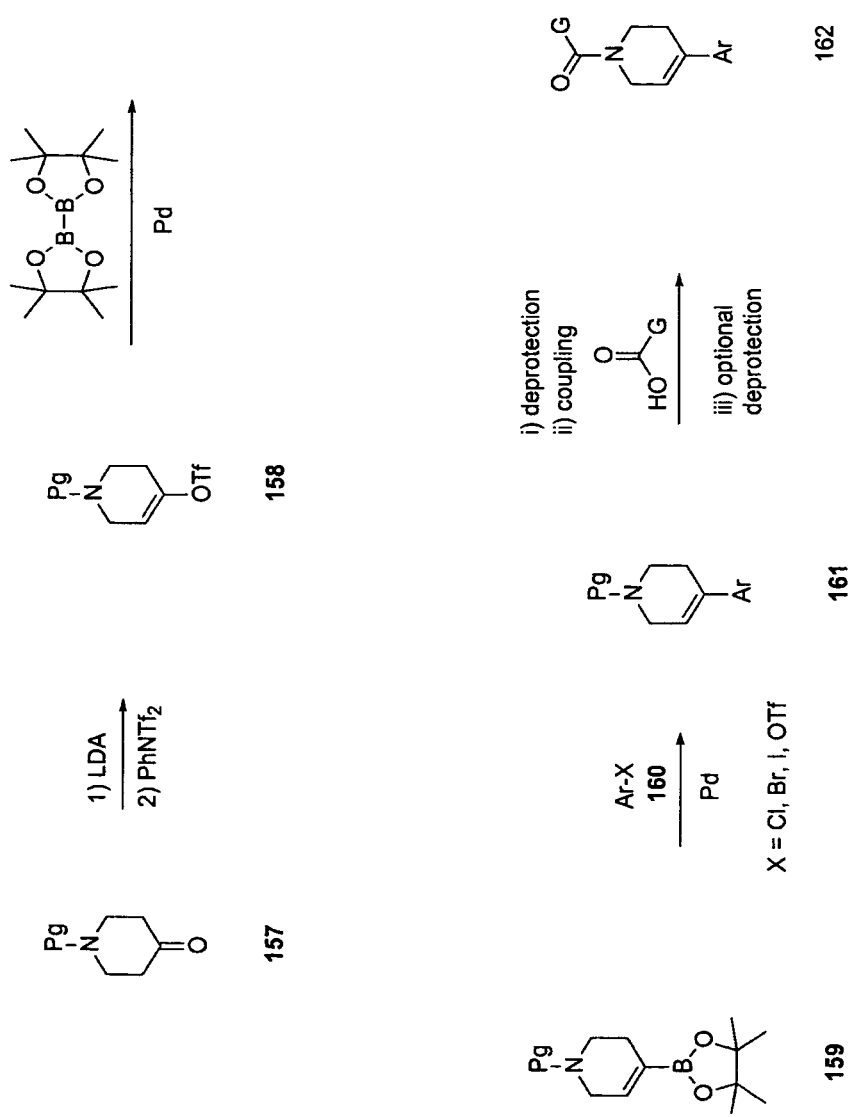
FIG. 33 shows a reaction scheme for the preparation of compounds 161 and 162.

Synthesis of compounds with a tetrahydropyridine linker is described in FIG. 33. Compound (157), where Pg is an appropriate protecting group, is treated with an organometallic agent (for example, LDA) and N-phenyltrifluoromethanesulfonimide to give the triflate (158) (Eastwood, P. R. (2000), *Tetrahedron Lett.*, 3705). Conversion of triflate (158) to the corresponding borinate ester (159) is accomplished by reacting with a suitable diboron species, such as dipinacolatodiboron, or other electrophilic source of boron, with an appropriate palladium catalyst. Ester (159) is then reacted with compound (160), where X is a leaving group (for example, chloro, bromo, iodo or OTf), under palladium catalysis to give intermediate (161). Alternatively, the cross-coupling reaction also can be performed in the reverse direction by switching the leaving group and boron species. For example, intermediate (161) can be prepared by the reaction between compound (160), where X is a boronic acid or ester, with the triflate (158). Sequential removal of the protecting group in compound (161) followed by amide coupling and optional deprotection affords compound (162).

Figure 34:
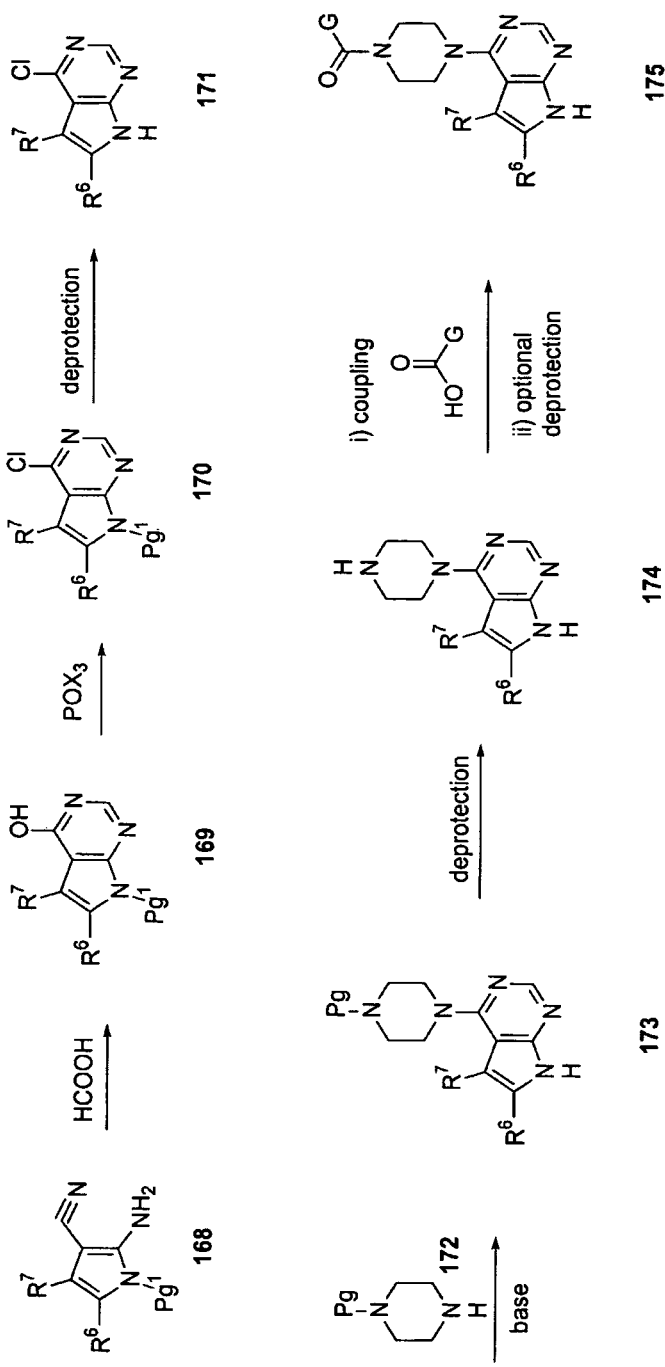
FIG. 34 shows a reaction scheme for the preparation of compounds 171-175.

FIG. 34 describes the preparation of 5,6-disubstituted pyrrolopyrimidine (175). Compound (168) can be obtained from commercial sources or can be prepared by literature methods (for example, Eger, K. et al. (1987), *J. Heterocycl. Chem.* 24, 425-430; Roth, H. J. et al. (1975), *Arch. Pharm.* 308, 179-185; Pichler, H. et al. (1986), *Liebigs Ann. Chem.* 1986, 1485-1505). Condensation of compound (168) with formic acid at elevated temperature affords intermediate (169) (Traxler, P. M. et al. (1996), *J. Med. Chem.*, 39, 2285-2292). Treating compound (169) with a halogenating agent (for example, $POCl_3$) yields the halide (170). Removal of the protecting group Pg followed by displacement of the halogen with suitably protected piperazine (172), either neat or in the presence of an acid scavenger (for example, diisopropylethylamine or triethylamine), leads to intermediate (173). Transformation of intermediate (173) into compound (175) can be accomplished by the procedures described in FIG. 22.

Figure 35:
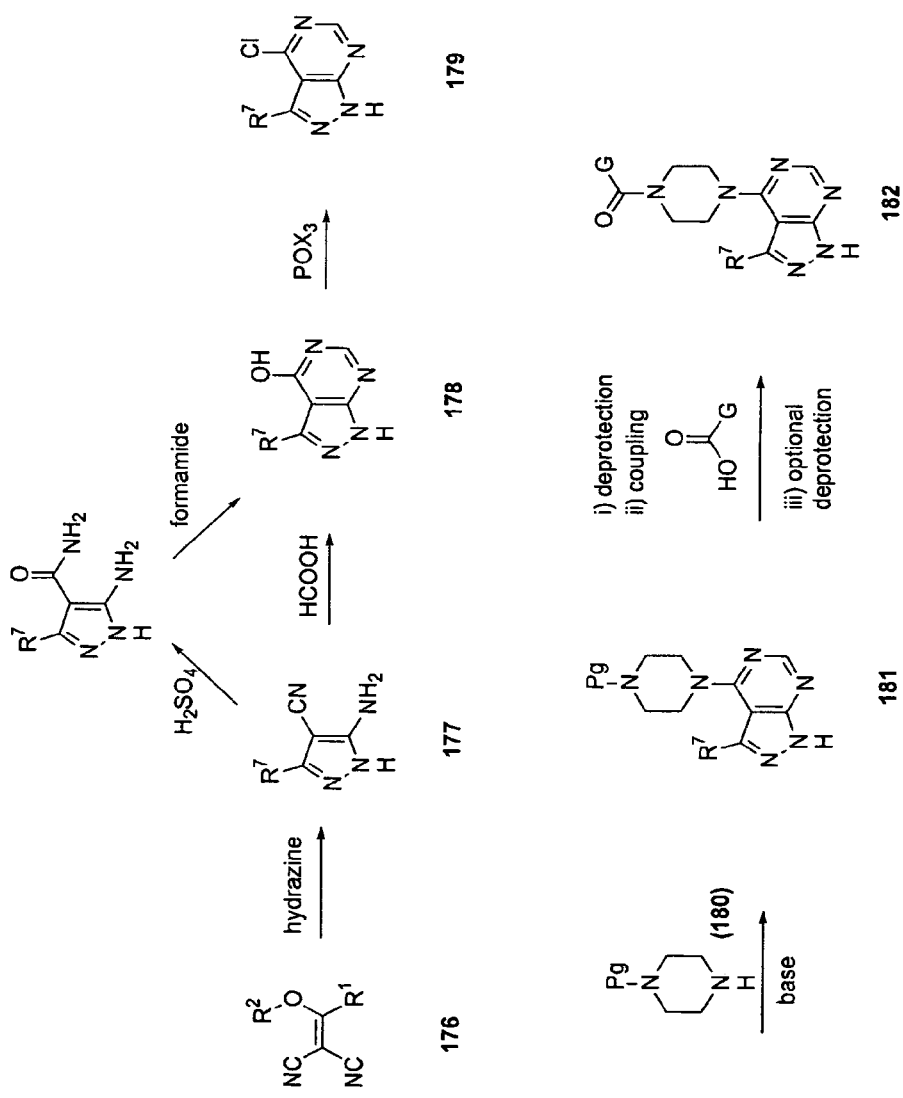
FIG. 35 shows a reaction scheme for the preparation of compounds 178-182.

The preparation of 3-substituted pyrazolopyrimidines (182) is described in FIG. 35. Compound (176) can be obtained from commercial sources or can be prepared by literature methods (for example, Hamaguchi, M. et al. (1986), *Heterocycles*. 24, 2111-2115; MaCall, M. A. et al. (1962), *J. Org. Chem.* 27, 2433-2439). Condensation of compound (176) with hydrazine affords the cyano intermediate (177), which can be converted to compound (178) by condensing with formic acid at elevated temperature. Alternatively, compound (96) can first be hydrolyzed to afford the primary amide, which is then condensed with formamide at elevated temperature to give the cyclized product (178). Treatment of (178) with a halogenating agent (for example, $POCl_3$) gives the halide (179). Transformation of (179) into desired compound (182) can be accomplished by the procedures described in FIG. 22.

Figure 36:
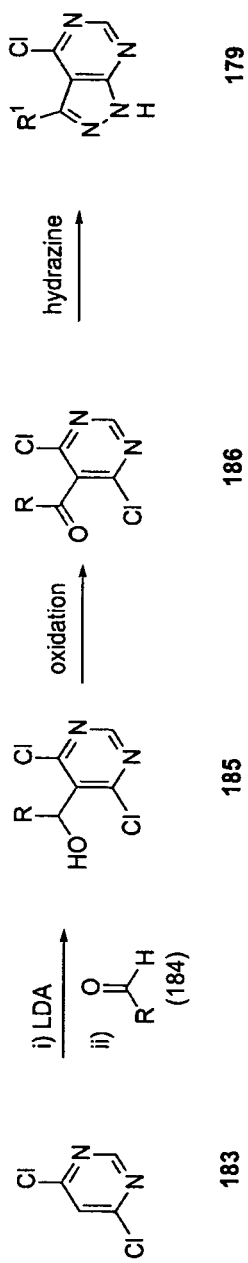
FIG. 36 shows a reaction scheme for the preparation of compounds 179.

An alternate route to the intermediate (179) for the synthesis of 3-substituted pyrazolopyrimidines is shown in FIG. 36. Regioselective deprotonation of 4,6-dichloropyrimidine at the C-5 position by treatment with an organometallic agent (for example, LDA), followed by quenching with aldehyde (184) furnishes the hydroxyl intermediate (185) (Radinov, R. et al. (1986), *Synthesis*, 11, 886-891; Radinov, R. et al. (1991), *J. Org. Chem.*, 56, 4793-4796). Intermediate (185) can be oxidized with an oxidizing agent (for example, $CrO_3$ or $MnO_2$) to give ketone (186). Treatment with hydrazine in an inert solvent such as THF or DCM yields the cyclized product (179). Transformation of (179) into desired compound (182) can be accomplished by the procedures described in FIG. 22.

Figure 37:
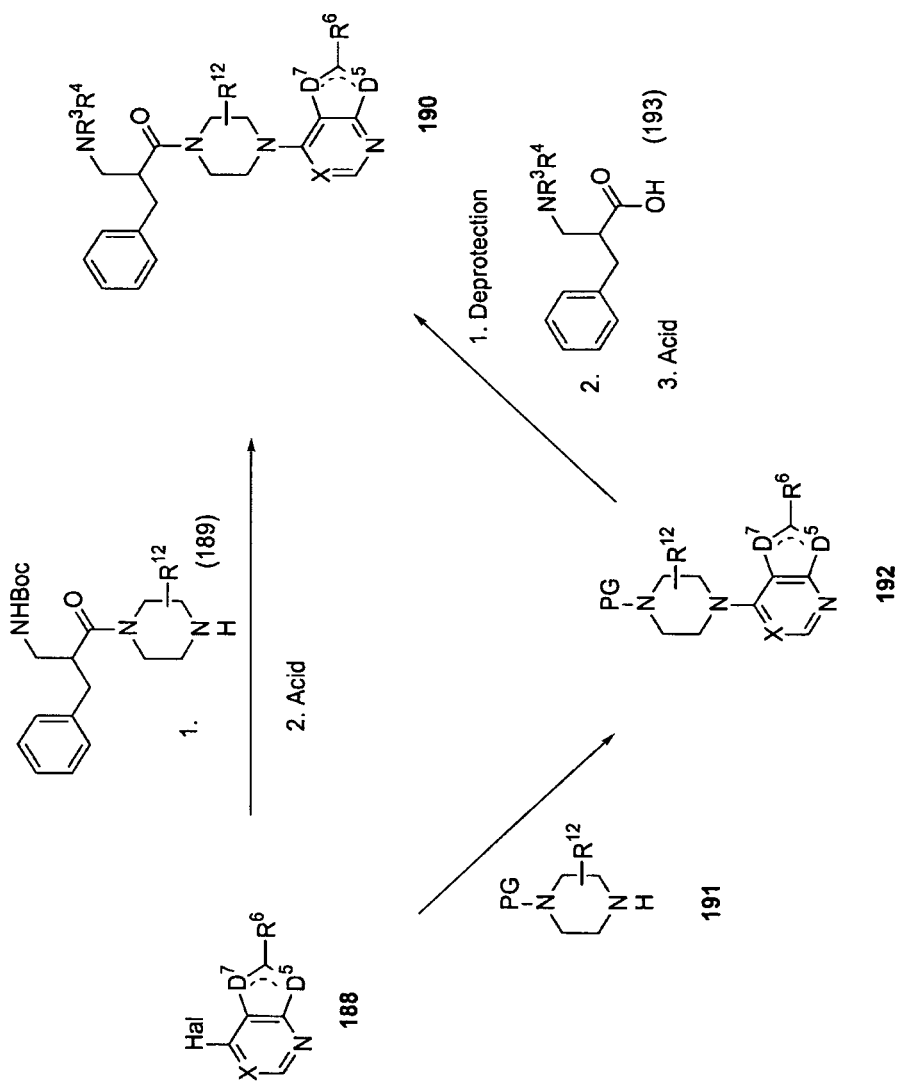
FIG. 37 shows a reaction scheme for the preparation of compound 190.

As shown in FIG. 37, compound (190) may be prepared in two ways. First, the substitution of heterocyclic core (188) with arninoamido piperazine (189) followed by deprotection with acid affords the desired product (190). Second, substitution of the heterocyclic core (188) with N-protected piperazine (191) gives the intermediate (192), which was subject to deprotection, coupling with amino acid (193) and deprotection again with acid to provide the final compound (190). The halide (188) may be obtained from commercial sources or prepared by means known to those in the art.

Figure 38:
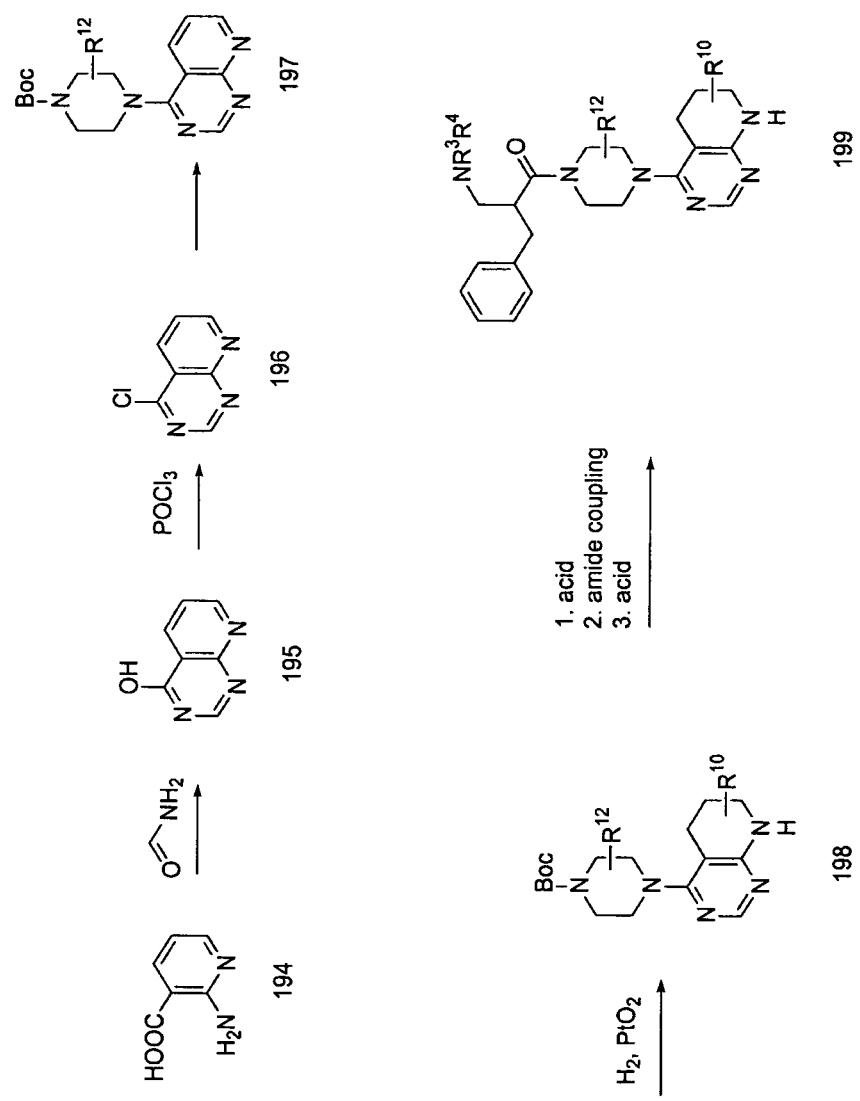
FIG. 38 shows a reaction scheme for the preparation of compounds 197-199.

The tetrahydropyrado[2,3-d]pyrimidine derivative (199) may be prepared as shown in FIG. 38. A 2-amino-3-pyradocarboxylic acid (194) was heated with formamide to give the 4-hydroxypyradopyrimidine derivative (195), which was subject to chlorination with (for example) $POCl_3$ to afford the 4-chloro pyridopyrimidine derivative (196). $S_NAr$ reactions of the compounds (196) with 1-Boc-piperazine gave the intermediates (197). Reduction of the intermediate (197) in the presence of catalytic amount of (for example) $PtO_2$ under hydrogen yielded the tetrahydropyrido[2,3-d]pyrimidine derivatives (198). After deprotection, the compounds (198) were subject to amide coupling with N-protected amino acids and followed by deprotection with acid to offer the product (199).

Figure 39:
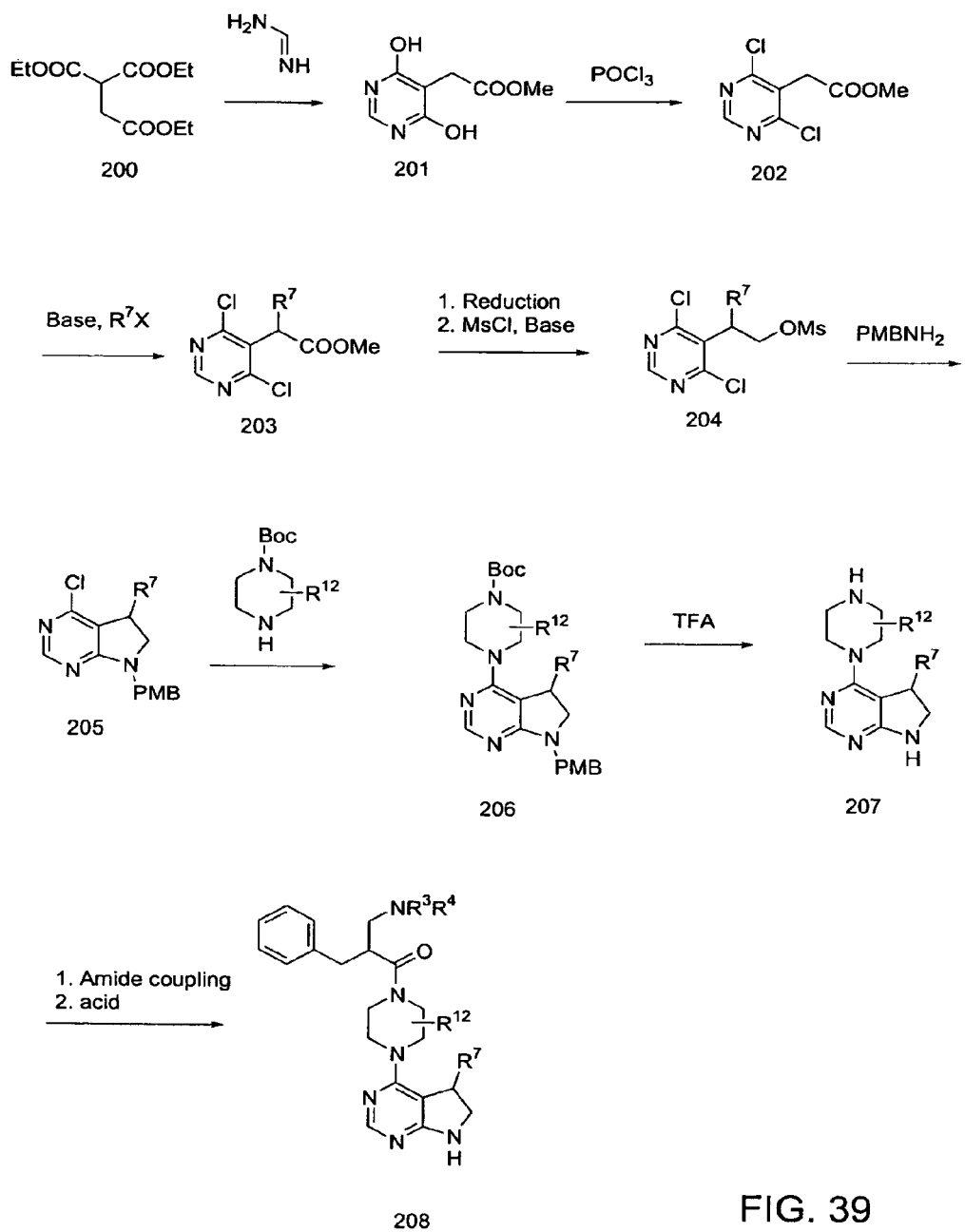
FIG. 39 shows a reaction scheme for the preparation of compounds 205-208.

Dihydropyrrolo[2,3-d]pyrimidine derivatives may be prepared as shown in FIG. 39. 2-Ethoxycarbonyl-succinic acid diethyl ester (200) was heated with formamidine to provide (4,6-Dihydroxypyrimidin-5-yl)-acetic acid methyl ester (201). Halogenation of compound (201) with (for example) $POCl_3$ gave the dichloropyrimidine derivative (202). Treating compound (142) with base (e.g., KH) in THF and an electrophile $R^3X$ affords the intermediate (203). Reduction with an agent such as DIBAL-H gives the alcohol, which was activated with (for example) MsCl in the presence of base (e.g., TEA) to provide the mesylate intermediate (204). Treating the mesylate (204) with (for example) p-methoxybenzylamine yielded the dihydropyrrolo[2,3-d]pyrimidine derivative (205). $S_NAr$ reaction of the compound (205) with 1-Boc-piperazine formed the intermediate (206). Deprotection of the compound (206) with acid (e.g., TFA) gave the free amine (207). Amide coupling of the free amine (207) with an appropriately substituted/protected amino acid and followed by deprotection (if necessary) gave the product (208).

Figure 40:
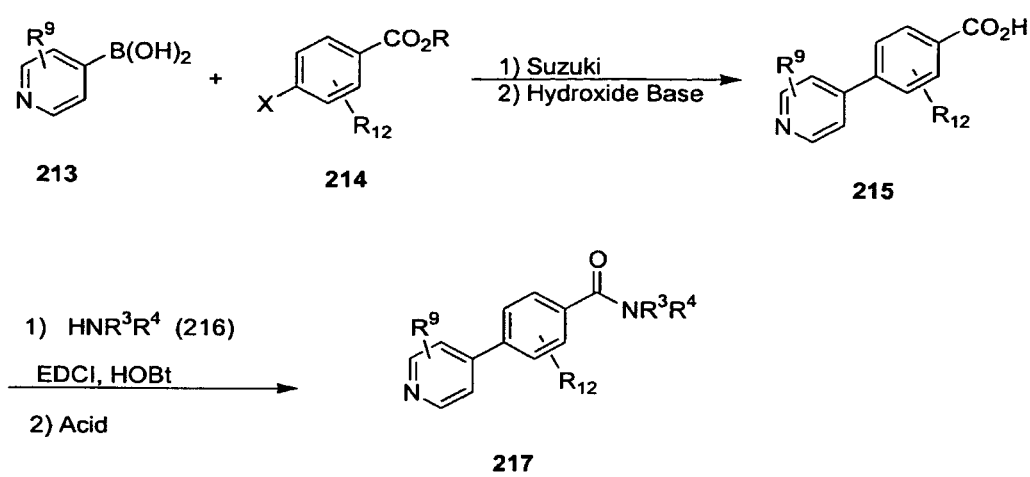
FIG. 40 shows a reaction scheme for the preparation of compounds 215 and 217.

Compound (217) of this invention may be prepared as shown in FIG. 40. Thus palladium-catalyzed cross coupling of boronic acid (213) and properly substituted aryl halide (214) affords the ester intermediate, which is saponified by hydroxide base leading to acid (215). The coupling of acid (215) and amine (216) under standard conditions (e.g., EDCI, HOBt, etc.) gives the N-protected/substituted advanced intermediate (for example Boc, but any suitable protecting group may be used; see, Greene et al., supra. The N-protected/substituted intermediate (e.g., Boc) is cleaved if necessary to afford product (217).

Figure 41:
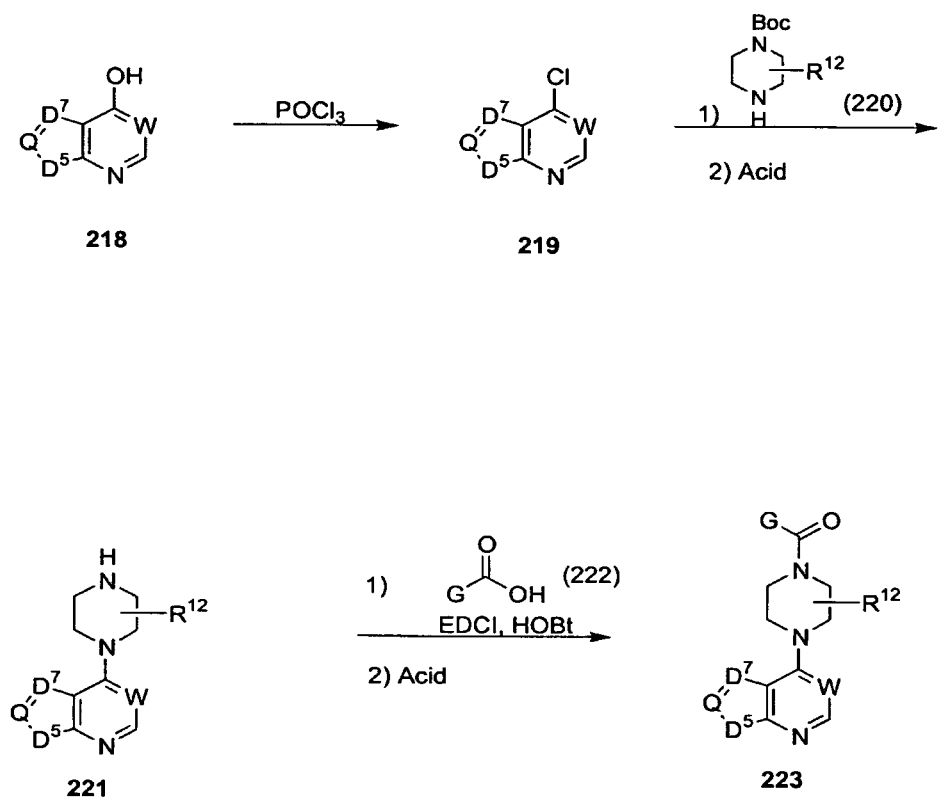
FIG. 41 shows a reaction scheme for the preparation of compounds 219, 221 and 223.

Compound (223) may be prepared as shown in FIG. 41. Introduction of a leaving group into the appropriately substituted and commercially available 4,3,0-heterocycle (218) may be accomplished, for example, by treatment with a halogenating agent (for example $POCl_3$) to give the chloride (219). Displacement of the leaving group with an appropriately substituted and protected piperazine (220) (for example Boc, but any suitable protecting group may be used; see, Greene et al., supra) either, for example, neat or in the presence of base, followed by removal of the piperazine protecting group (using references from the above book) can give the advanced quinazoline intermediate (221). Substitution of the piperazine secondary amine may then be accomplished using a variety of electrophiles and reaction conditions. The piperazine may be acylated by a suitably N-substituted or protected amino acid (e.g., Boc, etc. (162)) which may be introduced using a variety of standard peptide coupling procedures under both solution phase and solid phase conditions to yield compound (223). For representative examples, see Miklos Bodanszky, '*Principles of Peptide Synthesis*,' Springer-Verlarg, 1993, 2nd Ed., and C. Najera, Synlett, 2002, 9, 1388-1403. As above (and if protected) the N-protected amino acid unit may then be deprotected using representative procedures (e.g., acid, for a Boc-group) referenced in Greene et al., supra, and then manipulated as desired according to procedures appreciated by those skilled in the art. Alternatively (and as in FIG. 1), the amine (221) may be reacted with any other electrophile, including (but not limited to) epoxides, acid halides, aldehydes, etc., using procedures known to those in the art of organic synthesis.

Figure 42:
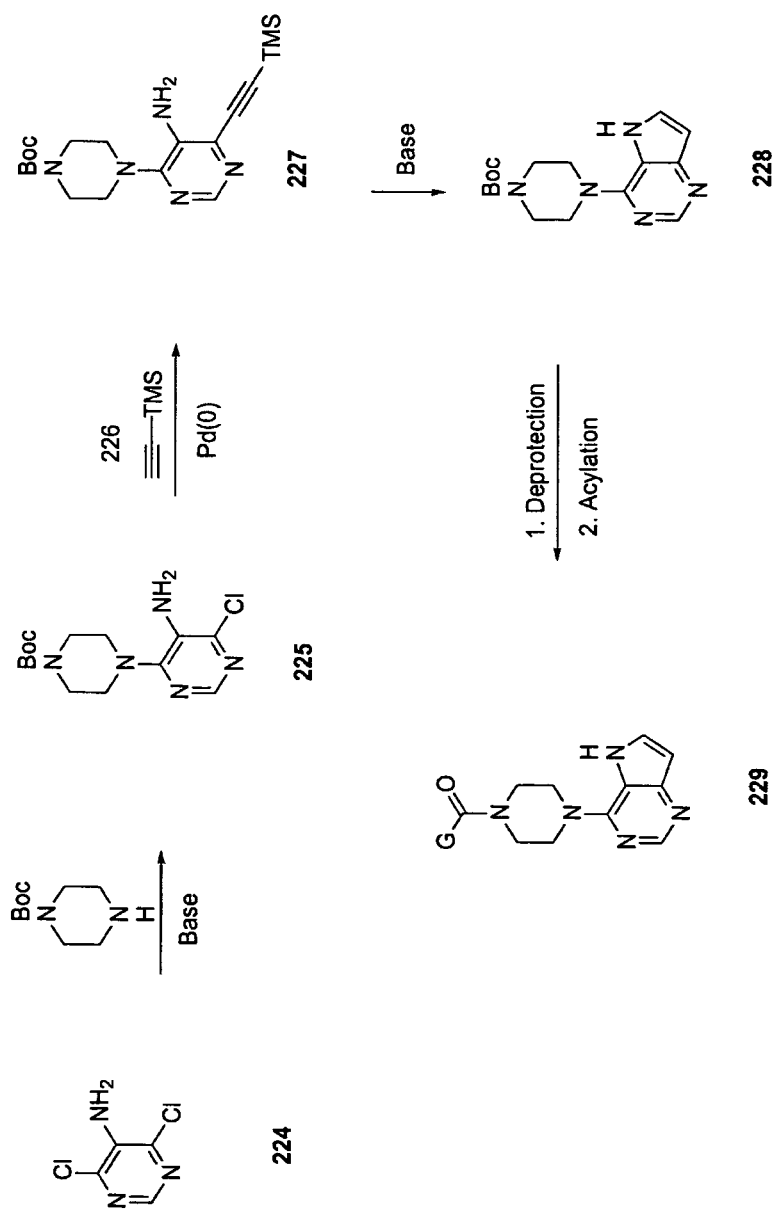
FIG. 42 shows a reaction scheme for the preparation of compound 229.

Compounds of formula (229) may be prepared as shown in FIG. 42. An $S_NAr$ reaction of compound (224) with a protected linker (eg. Boc-piperazine) gives the piperazine (225). An organometallic-mediated reaction may be used to install an activated acetylene group (226) and treatment with base (for example, KOtBu) gives the pyrrolopyrimidine (228). Deprotection of the piperazine protecting group (with, for example in the case of a Boc group, acid) and acylation (with for example a protected amino acid, followed by deprotection if necessary) gives the desired product (229).

Figure 43:
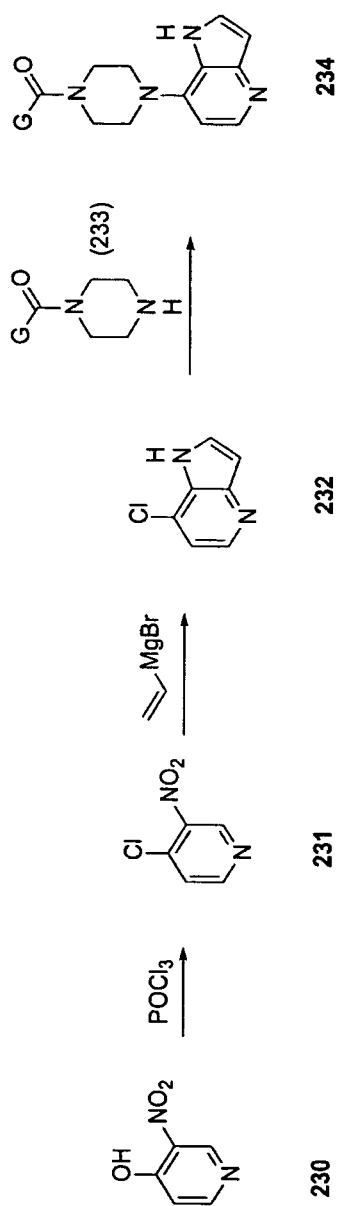
FIG. 43 shows a reaction scheme for the preparation of compounds 232 and 234.

Compounds of formula (234) may be prepared as shown in FIG. 43. Thus halogenation (eg. $POCl_3$) of a suitably substituted nitropyridone, (230), and subsequent treatment with a vinyl Grignard reagent gives the appropriately halogenated pyrrolopyridine (232). Subsequent $S_NAr$ displacement (or alternatively a transition metal mediated reaction) with a suitably substituted piperazine derivative (233) gives the desired product (234).

Figure 44:
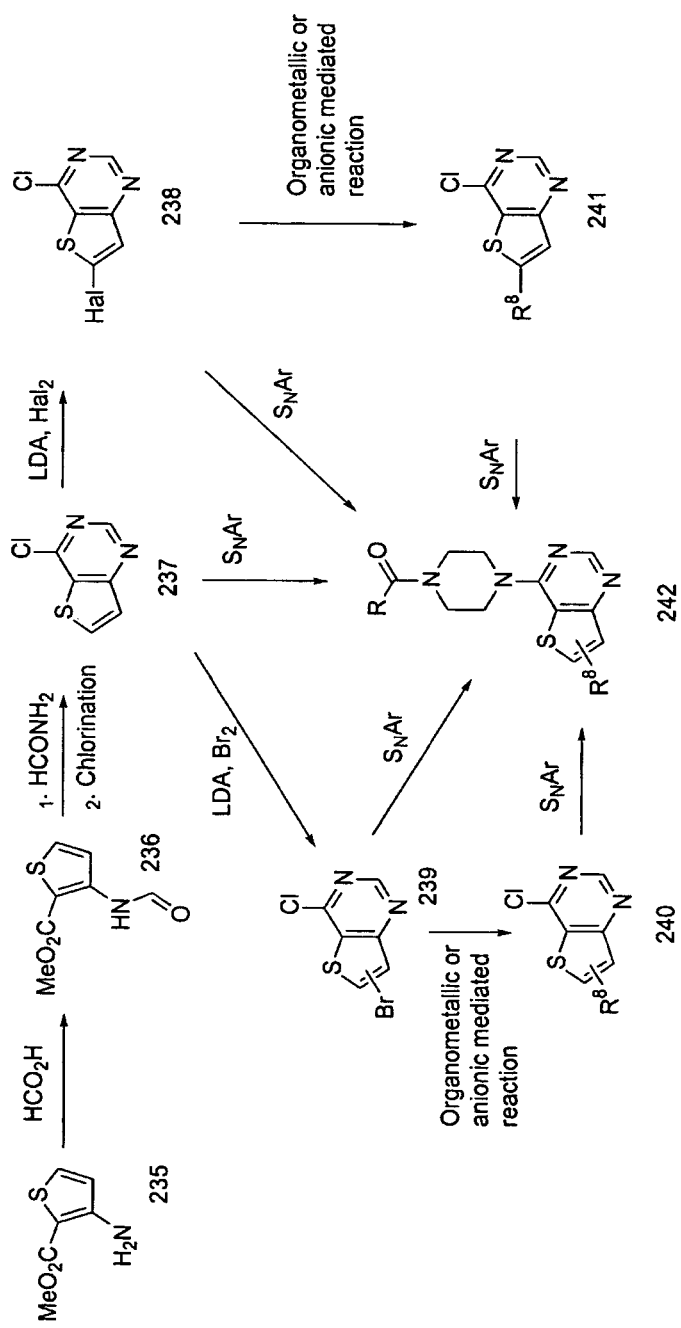
FIG. 44 shows a reaction scheme for the preparation of compounds 237-242.

FIG. 44 illustrates the general preparation of compounds of the formula (242). Acylation of an appropriately substituted aminothiophene (235) (using, for example, formic acid and ammonium acetate under heat) and cyclisation using (for example) formamide and ammonium formate at high temperature gives the appropriate heterocycle. Halogenation, using (for example) oxalyl chloride then gives the appropriately halogenated intermediate (237). This intermediate may then be functionalised in multiple ways. For example, displacement with an appropriately substituted piperazine (using either heat or transition metal mediated reactions) will give the desired product (242). Alternatively, the core may be halogenated, using (for example) an organolithium base and a halogen source (e.g., NCS, $Br_2$, $I_2$, etc.) to give compound (238). In the case of bromination, both non-regioselective and polybromination are observed, allowing an entry into more fully substituted and functionalised derivatives, (239). These may then be subjected to any number of anionic or transition metal-mediated reactions (eg. Suzuki, Stille, Negishi, etc.) to provide further functionality (e.g., (240) or (241)). In all cases, subsequent displacement with an appropriately substituted piperazine (along with subsequent functionalisation, if desired) gives rise to the desired products (242).

Figure 45:
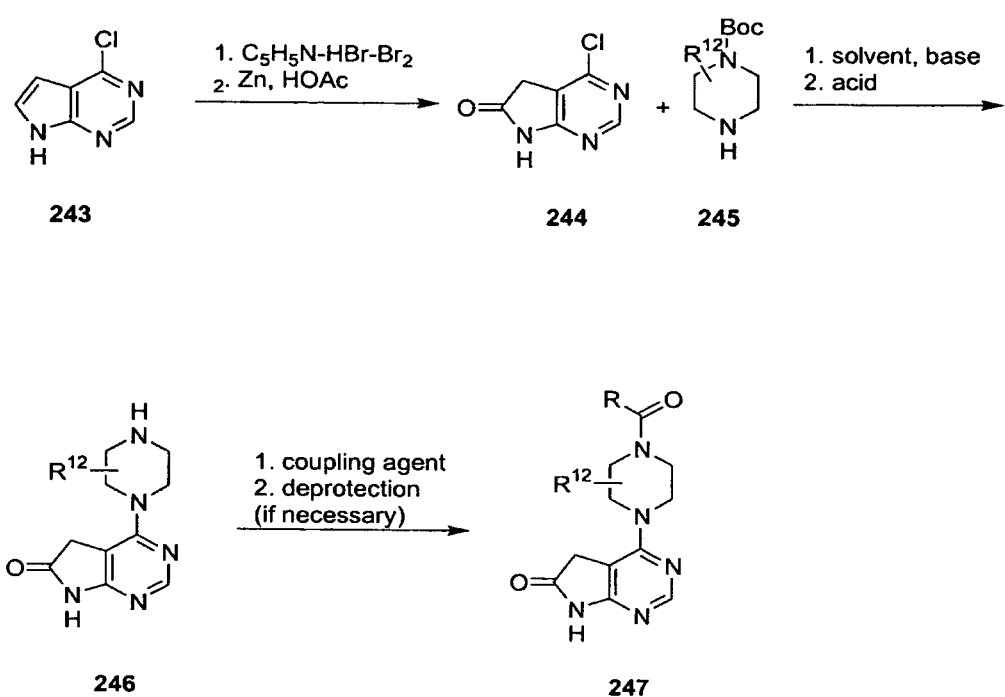
FIG. 45 shows a reaction scheme for the preparation of compounds 244 and 247.

Compounds (247) may be prepared as shown in FIG. 45. 4-Chloropynolo[2,3-d]pyrimidine (243) is oxidized with an appropriate oxidizing agent (pyridinium tribromide, for example) in an appropriate solvent (such as t-butanol), and the resulting gem-dibromide is reduced under appropriate conditions (using Zn/HOAc, for example) in an appropriate solvent (e.g., MeOH) to give the lactam 244. Reaction of compound (244) with a monoprotected diamine (245) (using the Boc protecting group, for example) in an appropriate solvent (such as IPA or NMP) in the presence or absence of base (such as triethylamine), followed by deprotection with mineral acid (HCl, for example) furnishes intermediate (246). Compound (246) is then combined with (for example) a protected amino acid (using the Boc protecting group, for example) in an appropriate solvent (such as DCM or DMF) with or without base (such as triethylamine or DIEA) and treated with an appropriate coupling agent (such as DCC, HBTU, or EDCI) to furnish compound (247) after deprotection with acid (in the case of a Boc-protecting group.)

Figure 46:
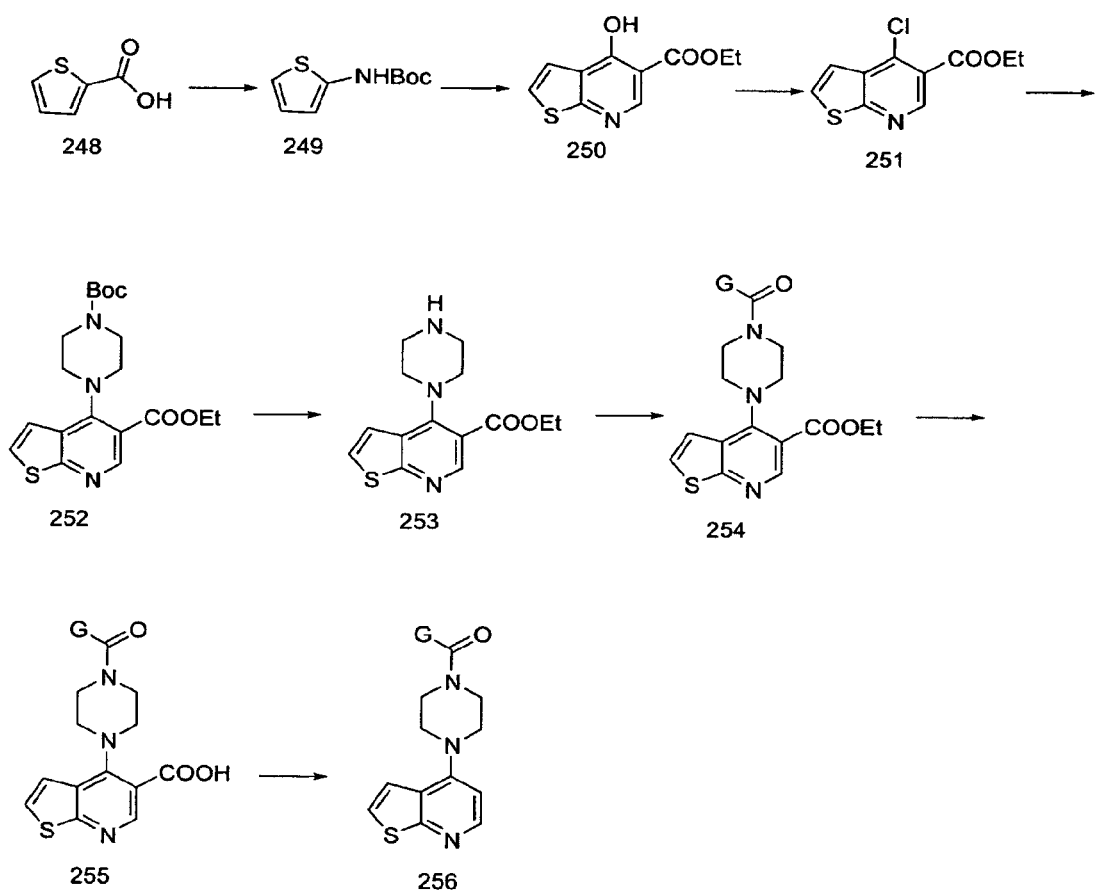
FIG. 46 shows a reaction scheme for the preparation of compounds 250, 251 and 254-256.

FIG. 46 shows the general preparation of compounds (256). A suitably substituted thiophenecarboxylic acid (248) may be converted to the protected aminothiophene (249) by means of a rearrangement, using (for example) diphenylphosphorylazide in the presence of a suitable base and solvent (e.g., t-BuOH) at elevated temperature. This can be treated with a suitable malonate derivative (eg. 2-ethoxymethylene malonate) at high temperature to give the pyridothiophene (250). Halogenation using (for example) $POCl_3$ in the presence of base (eg. $NEt_3$) gives the chloride (251) which may then be treated with an appropriate linker (eg. Boc-piperazine) and appropriately deprotected to give the piperazine intermediate (252). Acylation (using, for example, a suitably protected amino acid under standard conditions) followed by deprotection (if needed), gives the desired product (254). Alternatively, in place of deprotection, the ester may be saponified using aqueous basic conditions (e.g., LiOH in water and methanol) to give the acid (255) which may then be removed by decarboxylation by heating at high temperature in an appropriate solvent (e.g., diphenyl ether.) After any additional and necessary deprotection, the desired product is attained (256).

Figure 47:
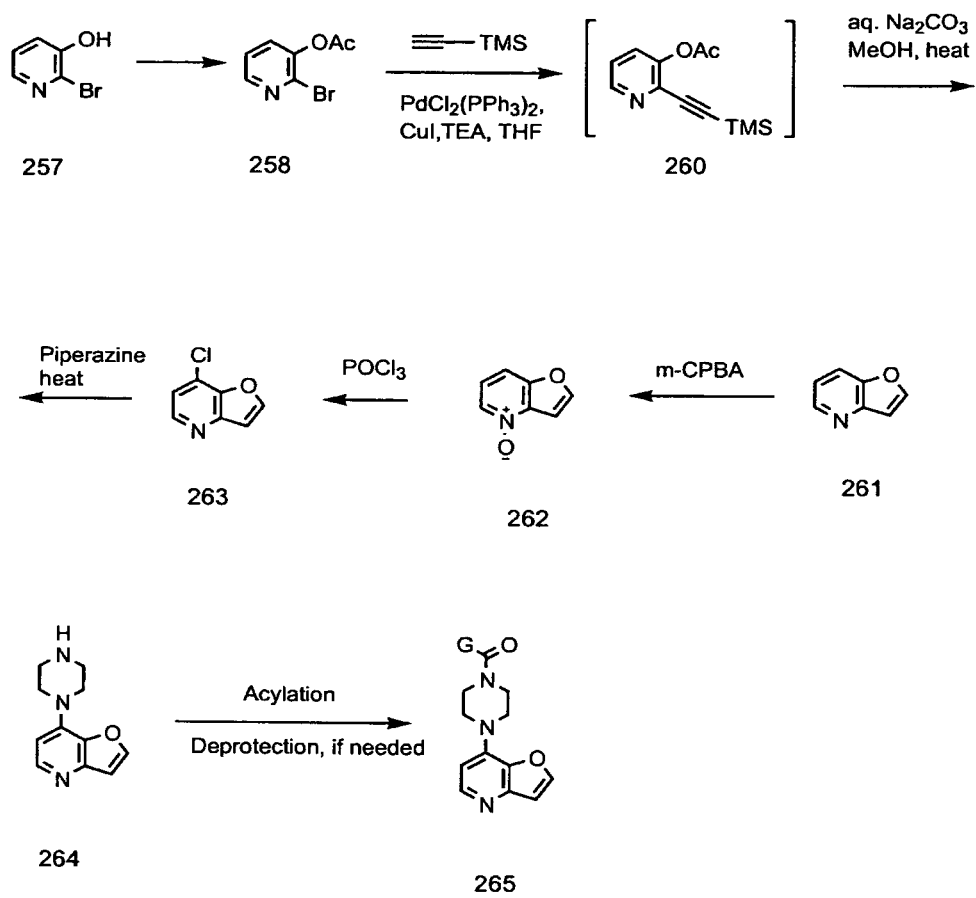
FIG. 47 shows a reaction scheme for the preparation of compounds 263 and 265.

The general preparation of compounds (265) is shown in FIG. 47. Hence protection of an appropriately substituted halopyridone (257) with (for example) an acetate group under standard conditions) and a subsequent transition metal mediated introduction of a functionalized actyylene (258) (for example, using $PdCl_2(PPh_3)_2$ and CuI) gives the intermediate acetylene (260). Treatment with base (e.g., aqueous $Na_2CO_3$ and heat) effects cyclisation to give the pyridylfuran core (261). Halogenation, via N-oxidation (eg. mcpba oxidation) and treatment with a halogenating agent (eg. $POCl_3$) gives the halide (263), which is then displaced by (for example) piperazine to give (264), and then subsequently further functionalised by (for example) the introduction of a suitably protected amino acid, followed by deprotection to give the desired product (265).

Figure 48:
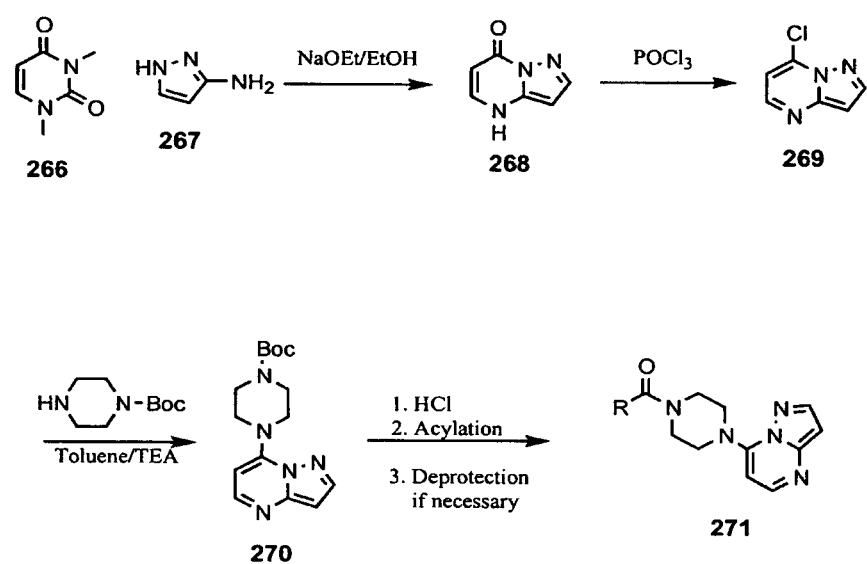
FIG. 48 shows a reaction scheme for the preparation of compounds 269 and 271.

FIG. 48 illustrates the general preparation of compound (271). Coupling of the uracil derivative (266) with 3-aminopyrazole (267) in the presence of base gives the pyrazolopyridone (268). Halogenation (for example, using POCl₃) gives the halide (269), displacement with a suitably substituted linker (e.g., Boc-piperazine using heat) and removal of the protecting group (e.g., TFA, for a Boc-group), followed by acylation using (for example) a protected amino acid (followed by the appropriate deprotection) gives the desired product (271).

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other analogs of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

Biological Examples

Example of AKT-1 Kinase Assay

The activity of the compounds described in the present invention may be determined by the following procedure: This procedure describes a kinase assay that measures the phosphorylation of a fluorescently-labeled peptide by full-length human recombinant active AKT-1 by fluorescent polarization using a commercially available IMAP kit.

The assay materials come from an IMAP AKT Assay Bulk Kit, product #R8059, from Molecular Devices, Sunnyvale, Calif. The kit materials include an IMAP Reaction Buffer (5×): The diluted 1×IMAP Reaction Buffer contains 10 mM Tris-HCl, pH 7.2, 10 mM MgCl₂, 0.1% BSA, 0.05% NaN3. DTT is routinely added to a final concentration of 1 mM immediately prior to use.

Also included are IMAP Binding Buffer (5×), and IMAP Binding Reagent. The Binding Solution is prepared as a 1:400 dilution of IMAP Binding Reagent into 1×IMAP Binding Buffer.

Fluorescein-labeled AKT Substrate (Crosstide), having the sequence (F1)-GRPRTSSFAEG. A stock solution of 20 μM is made up in 1×IMAP Reaction Buffer.

The plates used include a Costar 3657 (382-well made of polypropylene and having a white, v-bottom) that is used for compound dilution and for preparing the compound-ATP mixture. The assay plate was the Packard ProxyPlate™-384 F.

The AKT-1 used was made from full-length, human recombinant AKT-1 that is activated with PDK1 and MAP kinase 2.

The assay procedure starts the preparation of stock solutions of compounds at 10 mM in DMSO. The stock solutions and the control compound are serially diluted 1:2 nine times into DMSO (10 μL of compound+10 μL of DMSO) to give 50× dilution series over the desired dosing range. Then, 2.1-μL aliquots of the compounds in DMSO are transferred to a Costar 3657 plate containing 50 μL of 10.4 μM ATP in 1×IMAP Reaction Buffer containing 1 mM DTT. After thorough mixing, 2.5-μL aliquots are transferred to a Proxy-Plate™-384 F plate.

The assay is initiated by the addition of 2.5-μL aliquots of a solution containing 200 nM of fluorescently-labeled peptide substrate and 4 nM AKT-1. The plate is centrifuged for 1 minute at 1000 g and incubated for 60 minute at ambient temperature. The reaction is then quenched by the addition of 15 μL of Binding Solution, centrifuged again and incubated for an additional 30 minutes at ambient temperature prior to reading on a Victor 1420 Multilabel HTS Counter configured to measure fluorescence polarization.

Several compounds of Formula I tested in the assay showed activity for inhibiting AKT protein kinases, including (2R)-2-amino-3-(4-chlorophenyl)-1-(4-quinazolin-4-yl-piperazin-1-yl)-propan-1-one, (2R)-2-amino-3-(2-napthyl)-1-(4-quinazolin-4-yl-piperazin-1-yl)-propan-1-one, and (2R)-2-amino-3-(4-chlorophenyl)-1-(4-thieno[3,2,b]pyridin-7-yl-piperazin-1-yl)-propan-1-one.

Preparative Examples

The compounds of the present invention may be prepared either as either the racemate or as a single enantiomer (for example, using enantiomerically pure reagents. If prepared as the racemate, the corresponding enantiomers may be isolated by separation of the racemic mixture of on a chiral stationary phase column utilizing normal or reverse phase HPLC techniques. Alternatively, a diastereomeric mixture can be prepared by treatment of the racemic mixture with an appropriate chiral acid (or suitably activated derivative), for example dibenzoyl tartrate or the like (see, for example, Kinbara, K., et. al., *J. Chern. Soc., Perkin Trans.* 2, 1996, 2615; and Tomori, H., et. al., *Bull. Chem. Soc. Jpn.*, 1996, 3581). The diastereomers would then be separated by traditional techniques (i.e. silica chromatography, crystallization, HPLC, etc) followed by removal of the chiral auxiliary to afford enantiomerically pure material.

The examples below describe the synthesis of some of the compounds of the invention. Unless otherwise indicated all temperature s are set forth in degrees Celsius. Reagents were purchased from commercial suppliers such as Aldrich Chemical Company, Lancaster, TCI or Maybridge, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

HPLC retention times ($R_t$) are reported in minutes. Unless stated otherwise, the following HPLC conditions were used to obtain the reported retention times: column: Waters YMC ODS-AQ, 3.0×50 mm; 5-95% gradient MeCN in water (0.01% HFBA, 1% IPA); flow rate: 1.00 mL/min; detected at 220 nm.

¹H-NMR spectra were recorded on a Varian instrument operating at 400 MHz. ¹H-NMR spectra were obtained as CDCl₃ solutions (reported in ppm), using chloroform as the reference standard (7.25 ppm). Other NMR solvents were used as needed. When peak multiplicities are reported, the following abbreviations are used: s (singlet), d (doublet), t (triplet), m (multiplet), br (broadened), dd (doublet of doublets), dt (doublet of triplets).

Example 1A

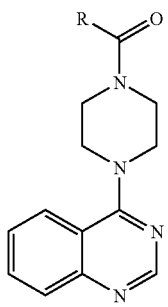

Preparation of 4-Piperazinylquinazoline Amino Amides

Step 1: To a solution of 4-chloroquinazoline (2.0 g, 12.2 mmol) (Tobe, Masanori, et al., *Bioorg. Med. Chem.* 2003, 11(3), 383) and DIEA (3.2 mL, 18.2 mmol) in 40 mL IPA was added Boc-piperazine (1.96 g, 12.81 mmol). The reaction mixture was heated to reflux and stirred for 20 hours, after which it was cooled to room temperature and concentrated by rotary evaporation. The residue was dissolved in dichloromethane (DCM) and washed with 1N NaOH. The organic layer was dried ($Na_2SO_4$), filtered, and concentrated by rotary evaporation. The resulting oil was dissolved in 25 mL dioxane, and 4M HCl/dioxane (46 mL, 182 mmol) was added dropwise. The suspension was sonicated for 2 minutes and stirred 13 hours at room temperature, after which the reaction mixture was concentrated to dryness by rotary evaporation. The resulting amine HCl salt was dissolved in 2N NaOH and extracted with DCM. The organic layer was dried ($Na_2SO_4$), filtered, and concentrated by rotary evaporation. The resulting oil was purified on silica (9:1:0.02 DCM/MeOH/$NR_4OH$) to give 4-piperazinylquinazoline as a yellow oil (2.5 g, 96%). $^1$H NMR ($CDCl_3$, 400 MHz) δ 8.74 (s, 1H), 7.92-7.86 (m, 2H), 7.76-7.70 (m, 1H), 7.48-7.42 (m, 1H), 3.75 (t, J=4.9 Hz, 4H), 3.09 (t, J=4.9 Hz, 4H), 1.89 (br s, 1H). $R_f$ 0.70. MS (ESI+) [M+H]$^+$ 215.

Step 2: To a Jones tube containing PS-CDI (Argonaut, 1.04 mmol/g, 2.2 equivalents) suspended in a solution of the 4-piperazinylquinazoline (1.0 equivalent) in $CHCl_3$ was added a solid Boc-protected amino acid (1.5 equivalents) (see Example 1B). The reaction mixture was shaken for 15 hours at room temperature, after which it was vacuum filtered, the resin rinsed with $CHCl_3$, and the filtrate concentrated by rotary evaporation. If necessary, the crude coupled product was purified on silica (DCM/EtOAc or DCM/MeOH). The resulting Boc-amino amide was dissolved in minimal dioxane, and 4M HCl/dioxane (10 equivalents) was added. The suspension was sonicated 5 minutes and stirred at room temperature for 12 hours, after which it was concentrated by rotary evaporation. The solids were dispersed in ether, isolated by filtration with nitrogen pressure, and dried under reduced pressure to give the corresponding 4-piperazinylquinazoline amino amide as the hydrochloride salt. If necessary, the hydrochloride salts were free-based with 1N NaOH, extracted with DCM, and the combined organic layers were dried ($Na_2SO_4$), filtered, concentrated by rotary evaporation, and dried under reduced pressure.

Example 1B

The following amino acids were introduced as Boc-protected amino acids to the 4-piperazinylquinazoline in Example 1, Step 2:

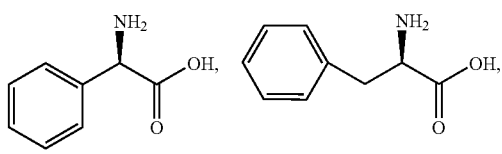

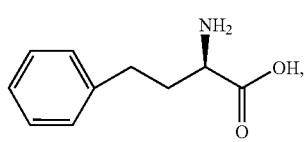

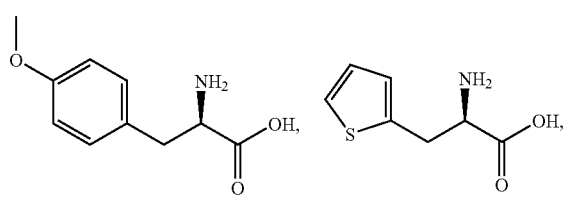

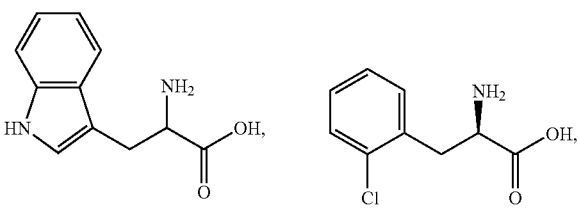

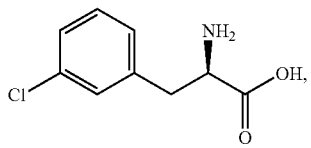

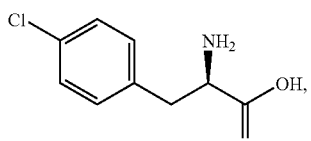

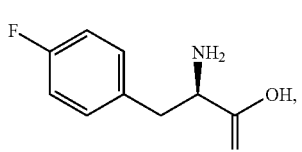

-continued
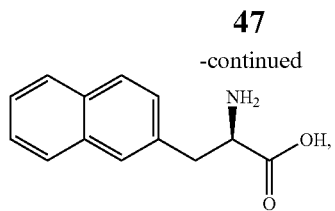
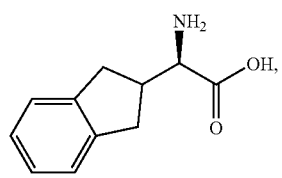
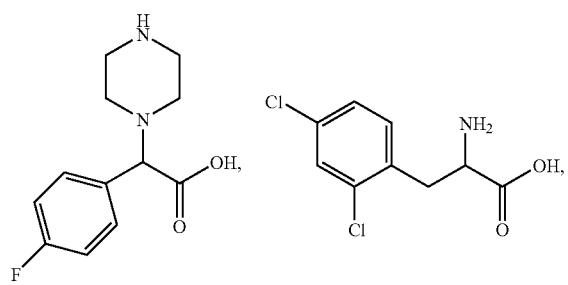
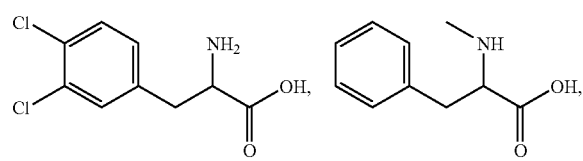
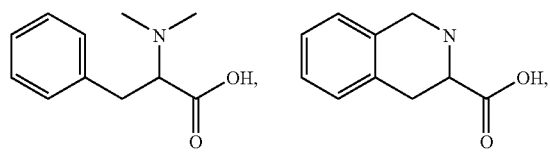
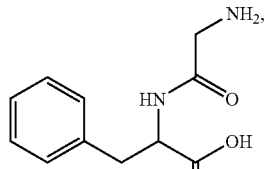
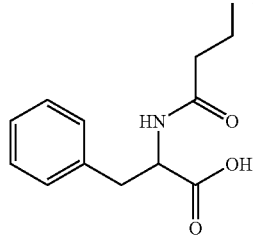
-continued
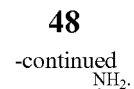
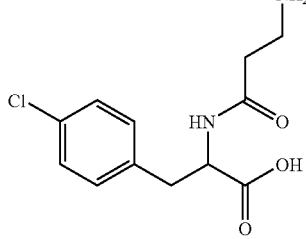
The compounds described in Examples 2-21 were prepared as described in Example 1, Step 2, using 4-piperazinylquinazoline and the appropriate amino acid shown in Example 1B.
Example 2
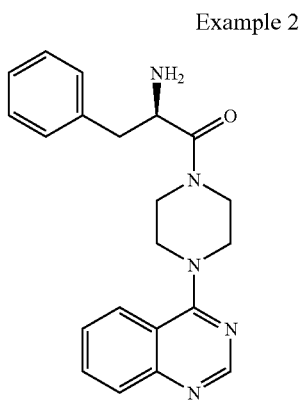
(2R)-2-Amino-3-phenyl-1-(4-quinazolin-4-yl-piperazin-1-yl)-propan-1-one
$R_t$ 2.15. MS (ESI+) [M+H]$^+$ 362.
Example 3
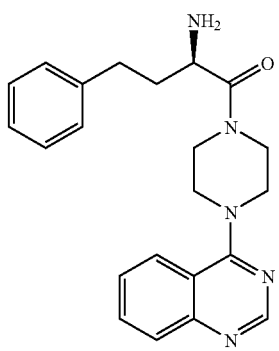 [SMILES: N[C@H](CCc1ccccc1)C(=O)N1CCN(c2ncnc3ccccc23)CC1]

(2R)-2-Amino-4-phenyl-1-(4-quinazolin-4-yl-piperazin-1-yl)-butan-1-one

R$_t$ 2.26. MS (ESI+) [M+H]$^+$ 376.

Example 4

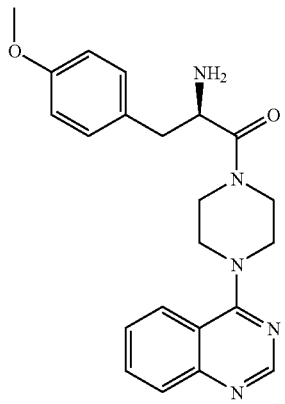 [SMILES: COc1ccc(C[C@@H](N)C(=O)N2CCN(c3ncnc4ccccc34)CC2)cc1]

(2R)-2-Amino-3-(4-methoxyphenyl)-1-(4-quinazolin-4-yl-piperazin-1-yl)-propan-1-one R$_t$ 2.15. MS (ESI+) [M+H]$^+$ 392.

Example 5

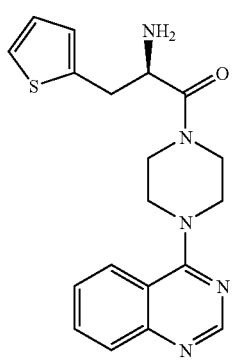 [SMILES: N[C@H](Cc1cccs1)C(=O)N1CCN(c2ncnc3ccccc23)CC1]

(2R)-2-Amino-1-(4-quinazolin-4-yl-piperazin-1-yl)-3-(2-thienyl)-propan-1-one

R$_t$ 2.10. MS (ESI+) [M+H]$^+$ 368.

Example 6

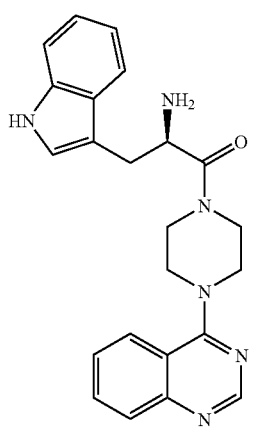 [SMILES: N[C@H](Cc1c[nH]c2ccccc12)C(=O)N1CCN(c2ncnc3ccccc23)CC1]

(2R)-2-Amino-3-(3-indolyl)-1-(4-quinazolin-4-yl-piperazin-1-yl)-propan-1-one

R$_t$ 2.24. MS (ESI+) [M+H]$^+$ 401.

Example 7

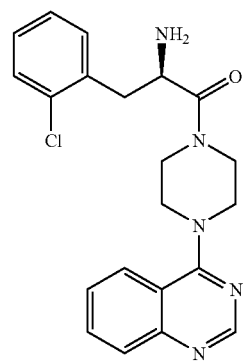 [SMILES: N[C@H](Cc1ccccc1Cl)C(=O)N1CCN(c2ncnc3ccccc23)CC1]

(2R)-2-Amino-3-(2-chlorophenyl)-1-(4-quinazolin-4-yl-piperazin-1-yl)-propan-1-one R$_t$ 2.23. MS (ESI+) [M+H]$^+$ 396.

Example 8

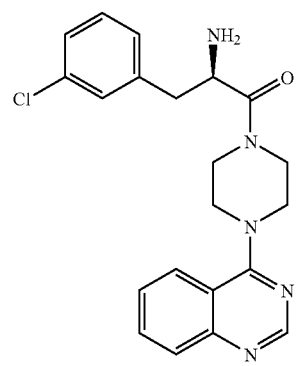 [SMILES: N[C@H](Cc1cccc(Cl)c1)C(=O)N1CCN(c2ncnc3ccccc23)CC1]

(2R)-2-Amino-3-(3-chlorophenyl)-1-(4-quinazolin-4-yl-piperazin-1-yl)-propan-1-one R$_t$ 2.30. MS (ESI+) [M+H]$^+$ 396.

Example 9

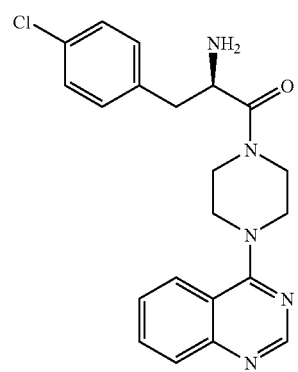

(2R)-2-Amino-3-(4-chlorophenyl)-1-(4-quinazolin-4-yl-piperazin-1-yl)-propan-1-one R$_t$ 2.36. MS (ESI+) [M+H]$^+$ 396. $^1$H NMR (free base; CDCl$_3$, 400 MHz) δ 8.73 (s, 1H), 7.89 (d, J=8.4 Hz, 1H), 7.78 (d, J=8.4 Hz, 1H), 7.77-7.71 (m, 1H), 7.49-7.43 (m, 1H), 7.31-7.26 (m, 2H), 7.23-7.19 (m, 2H), 4.37 (br s, 1H), 3.92-

3.82 (m, 1H), 3.73-3.57 (m, 6H), 3.39-3.30 (m, 1H), 3.29-3.19 (m, 1H), 3.12-3.02 (m, 2H).

Example 10

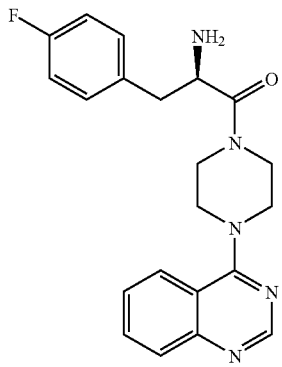 [SMILES: N[C@H](Cc1ccc(F)cc1)C(=O)N1CCN(c2ncnc3ccccc23)CC1]

(2R)-2-Amino-3-(4-fluorophenyl)-1-(4-quinazolin-4-yl-piperazin-1-yl)-propan-1-one (12)

R$_t$ 2.23. MS (ESI+) [M+H]$^+$ 380.

Example 11

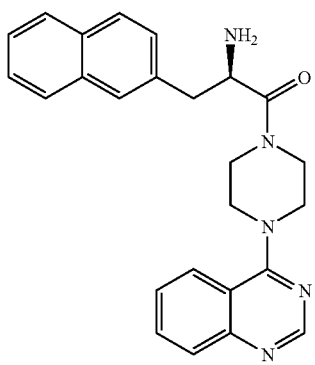 [SMILES: N[C@H](Cc1ccc2ccccc2c1)C(=O)N1CCN(c2ncnc3ccccc23)CC1]

(2R)-2-Amino-3-(2-naphthyl)-1-(4-quinazolin-4-yl-piperazin-1-yl)-propan-1-one

R$_t$ 2.39. MS (ESI+) [M+H]$^+$ 412.

Example 12

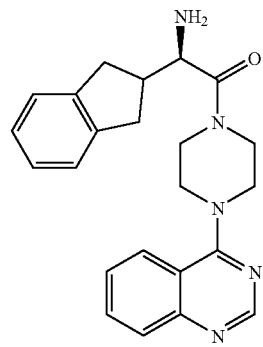 [SMILES: N[C@@H](C(=O)N1CCN(c2ncnc3ccccc23)CC1)C1Cc2ccccc2C1]

(2R)-2-Amino-2-(2-indanyl)-1-(4-quinazolin-4-yl-piperazin-1-yl)-ethan-1-one

R$_t$ 2.33. MS (ESI+) [M+H]$^+$ 388.

Example 13

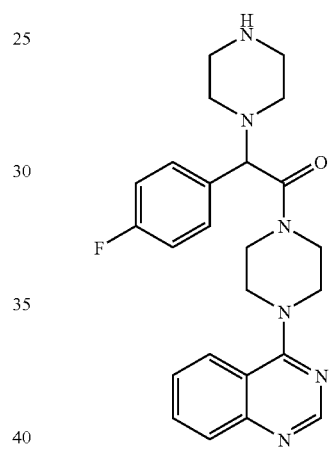

(±)-2-(4-Fluorophenyl)-2-piperazinyl-1-(4-quinazolin-4-yl-piperazin-1-yl)-ethan-1-one R$_t$ 2.21 minutes. MS (ESI+) [M+H]$^+$ 435.

Example 14

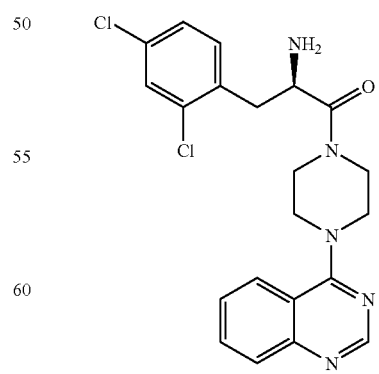

(2R)-2-Amino-3-(2,4-dichlorophenyl)-1-(4-quinazolin-4-yl-piperazin-1-yl)-propan-1-one R$_t$ 2.39. MS (ESI+) [M+H]$^+$ 430.

Example 15

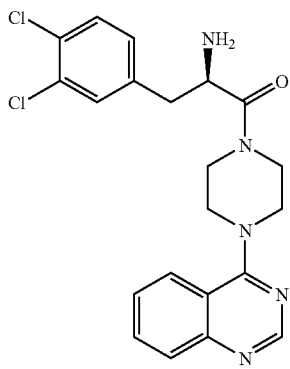 [SMILES: N[C@H](Cc1ccc(Cl)c(Cl)c1)C(=O)N1CCN(c2ncnc3ccccc23)CC1]

(2R)-2-Amino-3-(3,4-dichlorophenyl)-1-(4-quinazolin-4-yl-piperazin-1-yl)-propan-1-one $R_t$ 2.43. MS (ESI+) [M+H]$^+$ 430.

Example 16

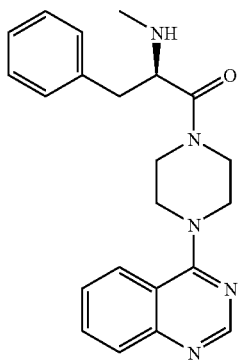 [SMILES: CN[C@H](Cc1ccccc1)C(=O)N1CCN(c2ncnc3ccccc23)CC1]

(2R)-2-(N-Methylamino)-3-phenyl-1-(4-quinazolin-4-yl-piperazin-1-yl)-propan-1-one $R_t$ 2.15. MS (ESI+) [M+H]$^+$ 376.

Example 17

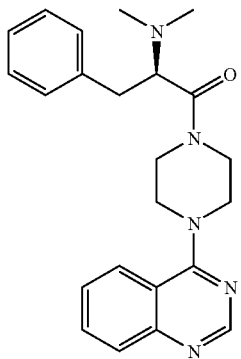

Preparation of (2R)-2-(N,N-Dimethylamino)-3-phenyl-1-(4-quinazolin-4-yl-piperazin-1-yl)-propan-1-one To a solution of (2R)-2-(N-Methylamino)-3-phenyl-1-(4-quinazolin-4-yl-piperazin-1-yl)-propan-1-one (free-base, 14 mg, 0.037 mmol) in 1,2-dichloroethane was added a solution of formaldehyde (37% w/w, 50 µL, 0.61 mmol) and then Na(OAc)$_3$BH (0.12 mmol). The reaction mixture was stirred at room temperature for 3 hours, after which saturated NaHCO$_3$ was added, and the reaction mixture was stirred 10 minutes. The suspension was extracted with DCM, and the combined extracts were dried (Na$_2$SO$_4$), filtered, and concentrated by rotary evaporation. The residue was filtered through a Fluorosil plug with ETOAC, and the filtrate was concentrated by rotary evaporation. The resulting residue was dissolved in ether and excess 4M HCl/dioxane was added. The yellow solids were isolated by filtration with nitrogen pressure and dried under reduced pressure to afford the desired product (7 mg, 41%) as the dihydrochloride salt. $R_t$ 2.20. MS (ESI+) [M+H]$^+$ 390.

Example 18

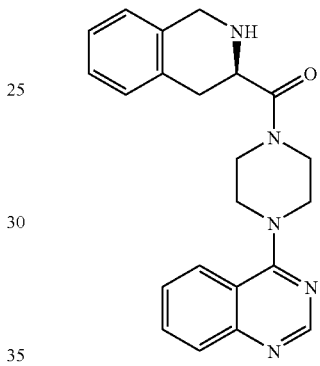

(4-Quinazolin-4-yl-piperazin-1-yl)-((3R)-1,2,3,4-tetrahydro-isoquinolin-3-yl)-methanone $R_t$ 2.21. MS (ESI+) [M+H]$^+$ 374.

Example 19

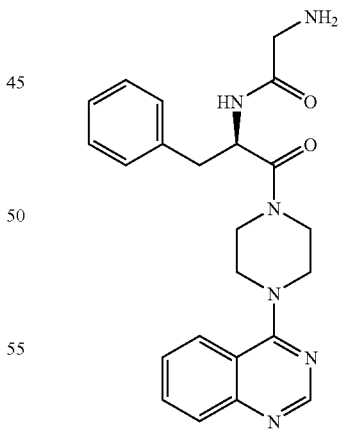

Preparation of (2R)-2-(2-Aminoacetamido)-3-phenyl-1-(4-quinazolin-4-yl-piperazin-1-yl)-propan-1-one (2R)-2-Amino-3-phenyl-1-(4-quinazolin-4-yl-piperazin-1-yl)-propan-1-one (free-base) was acylated with Boc-glycine and deprotected according to Step 2 of Example 1 to furnish (2R)-2-(2-Aminoacetamido)-3-phenyl-1-(4-quinazolin-4-yl-piperazin-1-yl)-propan-1-one. $R_t$ 2.23. MS (ESI+) [M+H]$^+$ 419.

Example 20

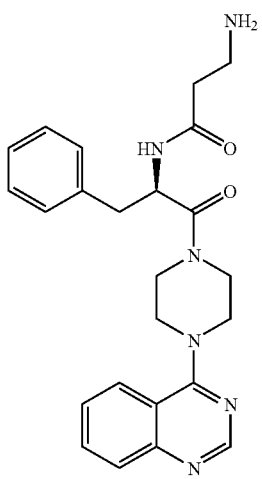 [SMILES: NCCC(=O)N[C@H](Cc1ccccc1)C(=O)N1CCN(c2ncnc3ccccc23)CC1]

Preparation of (2R)-2-(3-aminopropionamido)-3-phenyl-1-(4-quinazolin-4-yl-piperazin-1-yl)-propan-1-one (2R)-2-Amino-3-phenyl-1-(4-quinazolin-4-yl-piperazin-1-yl)-propan-1-one (free-base) was acylated with Boc-homoalanine and deprotected according to according to Step 2 of Example 1 to furnish (2R)-2-(3-Aminopropionamido)-3-phenyl-1-(4-quinazolin-4-yl-piperazin-1-yl)-propan-1-one. $R_t$ 2.24. MS (ESI+) [M+H]$^+$ 433.

For the compounds prepared below, the HPLC conditions used to obtain the reported retention times (minutes) were: column: Waters YMC ODS-AQ, 4.6×50 mm; 5-95% gradient MeCN in water (0.01% HFBA, 1% IPA); flow rate: 2.00 mL/min; detected at 220 nm.

Example 21

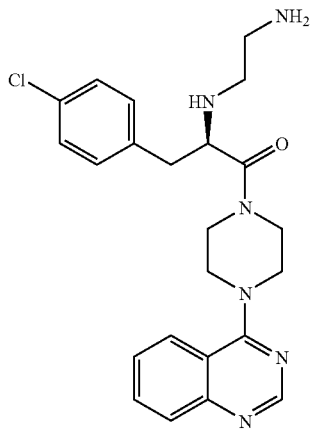 [SMILES: NCCN[C@H](Cc1ccc(Cl)cc1)C(=O)N1CCN(c2ncnc3ccccc23)CC1]

Preparation of (2R)-2-[(2-Aminoethyl)amino]-3-(4-chlorophenyl)-1-(4-quinazolin-4-yl-piperazin-1-yl)-propan-1-one (2R)-2-Amino-3-(4-chlorophenyl)-1-(4-quinazolin-4-yl-piperazin-1-yl)-propan-1-one (free-base, 41 mg, 0.104 mmol) was stirred at room temperature with Boc-2-aminoacetaldehyde (16 mg, 0.104 mmol) in 0.7 mL methanol for 1 hour, after which NaBH$_4$ (6 mg, 0.160 mmol) was added. The reaction mixture was stirred for 3 hours and then quenched with 1N NaOH. The reaction mixture was extracted with DCM, and the combined extracts were dried (Na$_2$SO$_4$), filtered, and concentrated by rotary evaporation. The crude residue was purified on silica (15:1 DCM/MeOH). The resulting Boc-amine intermediate was treated with 1.4 mL 4M HCl/dioxane and stirred at room temperature for 14 hours, after which the reaction mixture was diluted with ether. The solids were isolated by filtration with nitrogen pressure and dried under reduced pressure to give the desired product (29 mg, 51%) as the trihydrochloride salt. $R_t$ 1.69. MS (CI+) [M+H]$^+$ 439.

Example 22

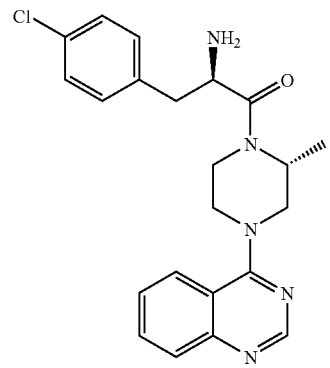 [SMILES: C[C@@H]1CN(c2ncnc3ccccc23)CCN1C(=O)[C@H](N)Cc1ccc(Cl)cc1]

Preparation of (2R)-2-Amino-3-(4-chlorophenyl)-1-((2R)-2-methyl-4-quinazolin-4-yl-piperazin-1-yl)-propan-1-one 4-((3R)-3-methylpiperazinyl)quinazoline was prepared in a similar fashion to Step 1 of Example 1, which was then acylated with Boc-4-chloro-D-phenylalanine and deprotected according to Step 2 of Example 1 to furnish (2R)-2-Amino-3-(4-chlorophenyl)-1-((2R)-2-methyl-4-quinazolin-4-yl-piperazin-1-yl)-propan-1-one. $R_t$ 1.72. MS (CI+) [M+H]$^+$ 410.

Example 23

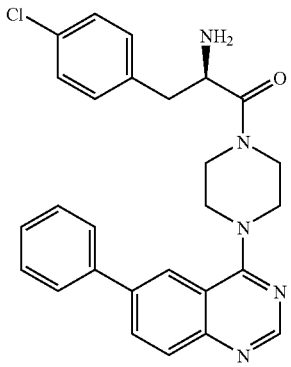 [SMILES: N[C@H](Cc1ccc(Cl)cc1)C(=O)N1CCN(c2ncnc3ccc(-c4ccccc4)cc23)CC1]

Preparation of 2-Amino-3-(4-chlorophenyl)-1-[4-(6-phenylquinazolin-4-yl)-piperazin-1-yl]-propan-1-one Step 1: A solution of 6-bromoquinazolin-4-ol (1.0 g, 4.44 mmol) in POCl₃ (10 mL) was stirred and heated at 110° C. in a sealed tube overnight. The solution was cooled to room temperature and poured onto ice (200 g.) The solution was extracted with DCM (300 mL), washed with water (200 mL), dried over Na₂SO₄ and concentrated in vacuo to give the impure 6-bromo-4-chloroquinazoline as a brown solid that was not purified further (1.5 g.) MS (APCI+) [M+H]⁺ 243.1.

Step 2: A solution of the crude product from Step 1 (1.5 g), piperazine-1-carboxylic acid tert-butyl ester (2.29 g, 12.3 mmol) and triethylamine (2.15 mL, 15.4 mmol) in N-methylpyrrolidinone (50 mL) was stirred and heated at 80° C. for 2 hours. The solution was cooled to room temperature, diluted with EtOAc (200 mL), washed with water (3×200 mL) and dried over Na₂SO₄. The mixture was purified by silica gel column chromatography (50% EtOAc/hexanes) to give 4-(6-bromo-quinazolin-4-yl)-piperazine-1-carboxylic acid tert-butyl ester as a colorless oil (1.5 g, 3.8 mmol, 85% from Step 1.) MS (APCI+) [M+H]⁺ 394.9 and 392.9. ¹H NMR (CDCl₃, 400 MHz) δ 8.76 (1H, s), 8.02 (1H, s), 7.84-7.78 (2H, m), 3.74 (4H, s), 3.66 (4H, s), 1.51 (9H, s.)

Step 3: HCl (1.0 M in Et₂O, 30 mL) was added to a solution of 4-(6-bromo-quinazolin-4-yl)-piperazine-1-carboxylic acid tert-butyl ester (1.50 g, 3.81 mmol) in MeOH (50 mL) and stirred at room temperature overnight. The mixture was concentrated in vacuo to give 6-bromo-4-piperazin-1-yl-quinazoline as the bis-hydrochloride salt (1.3 g, 93%.) MS (APCI+) [M+H]⁺ 295.1.

Step 4: EDCI.HCl (230 mg, 1.2 mmol), HOBt (160 mg, 1.2 mmol) and Boc-D-4-chlorophenylalanine (240 mg, 1.2 mmol) were added to a stirred solution of 6-bromo-4-piperazin-1-yl-quinazoline bis-hydrochloride (360 mg, 0.98 mmol) and triethylamine (0.30 mL, 1.2 mmol) in DMF (8 mL) at room temperature under nitrogen. Stirred at room temperature overnight. Diluted with EtOAc (100 mL) and washed with water (3×50 mL.) Dried over Na₂SO₄ and concentrated in vacuo. The mixture was purified by silica gel column chromatography (100% EtOAc) to give [2-[4-(6-bromoquinazolin-4-yl)-piperazin-1-yl]-1-(4-chlorobenzyl)-2-oxo-ethyl]-carbamic acid tert-butyl ester as a yellow solid (320 mg, 57%.) MS (APCI+) [M+H]⁺ 575.9. ¹H NMR (CDCl₃, 400 MHz) δ 8.75 (1H, s), 7.95 (1H, s), 7.85-7.79 (2H, m), 7.30-7.27 (2H, m), 7.17 (2H, d, J7.1 Hz), 5.39 (1H, app. d, J8.2 Hz), 4.86 (1H, app. d, J 7.3 Hz), 3.83-3.60 (6H, m), 3.36-3.26 (2H, m), 3.04-2.96 (2H, m), 1.43 (9H, s).

Step 5: THF (5 mL) was added to a stirred mixture of Pd₂dba₃ (8.0 mg, 0.0087 mmol) and triphenylarsine (11 mg, 0.035 mmol) at room temperature under nitrogen. The yellow solution was stirred at room temperature for 2 minutes and then transferred via cannula to a stirred solution of [2-[4-(6-bromoquinazolin-4-yl)-piperazin-1-yl]-1-(4-chlorobenzyl)-2-oxo-ethyl]-carbamic acid tert-butyl ester (50 mg, 0.087 mmol) and phenylboronic acid (21 mg, 0.17 mmol) in ethylene glycol dimethyl ether (5 mL) and aqueous sodium carbonate (2M, 5 mL) and stirred and heated at 80° C. under nitrogen overnight. The reaction was cooled to room temperature, extracted into EtOAc (100 mL), washed with water (50 mL), dried over Na₂SO₄ and concentrated in vacuo. The mixture was purified by silica gel column chromatography (100% EtOAc) to give {1-(4-chlorobenzyl)-2-oxo-2-[4-(6-phenylquinazolin-4-yl)-piperazin-1-yl]-ethyl}-carbamic acid tert-butyl ester as an oil (30 mg, 60%.) MS (APCI+) [M+H]⁺ 574.0 and 572.0.

Step 6: Trifluoroacetic acid (4 mL) was added to a stirred solution of {1-(4-chlorobenzyl)-2-oxo-2-[4-(6-phenylquinazolin-4-yl)-piperazin-1-yl]-ethyl}-carbamic acid tert-butyl ester (30 mg) in DCM (10 mL) at room temperature. The solution was stirred at room temperature for 4 hours, quenched with aqueous NaOH (1N, 10 mL), diluted with EtOAc (100 mL) and washed with aqueous NaOH (2×50 mL.) The organic phase was dried over Na₂SO₄ and concentrated in vacuo to give 2-amino-3-(4-chlorophenyl)-1-[4-(6-phenyl-quinazolin-4-yl)-piperazin-1-yl]-propan-1-one as a colorless oil (23 mg.) ¹H NMR (CDCl₃, 400 MHz.) δ 8.77 (1H, s), 8.02-8.00 (2H, m), 7.98 (1H, s), 7.64 (2H, d, J7.4 Hz), 7.53 (2H, t, J7.7 Hz), 7.44 (1H, t, J7.3 Hz), 7.30 (2H, d, J8.6 Hz), 7.17 (2H, d, J8.6 Hz), 3.98 (1H, t, J7.3 Hz), 3.87-3.60 (6H, m), 3.42-3.34 (2H, m), 2.97 (1H, dd, J7.4 and 13.3 Hz), 2.84 (1H, dd, J7.0 and 13.7 Hz.) The oil was taken up into THF (10 mL) and treated with HCl (1.0M in Et₂O, 10 mL) and concentrated in vacuo to give the bis hydrochloride salt of 2-amino-3-(4-chlorophenyl)-1-[4-(6-phenyl-quinazolin-4-yl)-piperazin-1-yl]-propan-1-one as a solid (21 mg).

Example 24

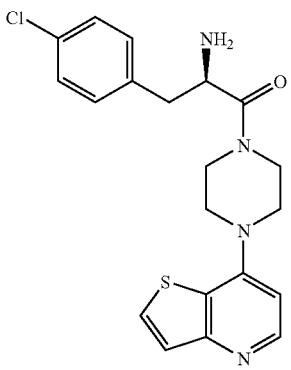 [SMILES: N[C@H](Cc1ccc(Cl)cc1)C(=O)N1CCN(c2ccnc3ccsc23)CC1]

Preparation of (2R)-2-amino-3-(4-chlorophenyl)-1-(4-thieno[3,2,b]pyridin-7-yl-piperazin-1-yl)-propan-1-one dihydochloride Step 1: NaH (60% in mineral oil, 0.24 g) in DMF (15 mL) was added Thieno[3,2-b]pyridin-7-ol (0.756 g) portionwise.

The reaction mixture was warmed at 40° C. and stirred for 30 minutes. After cooling, N-phenyltrifluoromethanesulfonimide (2.1 g) was added, the reaction mixture was stirred at room temperature for 1 hour, and the Boc-piperazine (1.9 g) was added. The mixture was stirred at 80° C. for 2 hours. Ethyl acetate (100 mL) was added and the resulting solution was washed with brine (2×50 mL), dried over sodium sulfate, concentrated under reduced pressure and purified by chromatography (1:4 hexane/EtOAc) to give the product as yellow oil 1.32 g (82.5%). $R_t$ 2.10 minutes. MS (ESI+) [M+H]$^+$ 320.

Step 2: The 4-thieno [3,2-b]pyridin-7-piperazine-1-carboxylic tert-butyl ester (1.32 g) in DCM (20 mL) was added the 4N HCl in dioxane (21 mL). The reaction was stirred at room temperature for 10 hours. The solvent was removed under reduced pressure and the resulting amine HCl salt was dissolved in saturated sodium bicarbonate (20 mL) and extracted with DCM (30 mL). The organic layer was dried (Na$_2$SO$_4$), filtered, and concentrated by rotary evaporation. to give 7-Piperazin-1-yl-thieno[3,2-b]pyridine as an off-white solid (0.85 g, 93.8%). $R_t$ 1.40 minutes. MS (ESI+) [M+H]$^+$ 220.

Step 3: DIEA (0.07 mL) and HBTU (0.12 g) was added to the solution of the (2R)-2-tert-butoxycarbonylamino-3-(4-chlorophenyl)-propionic acid (0.092 g) in THF (5 mL) at 0° C. The mixture was stirred at room temperature for 20 minutes, then 7-Piperazin-1-yl-thieno[3,2-b]pyridine (0.056 g) was added. The reaction was stirred at room temperature for 1 hr. 20 mL of EtOAc was added and the organic layer was separated. The aqueous layer extracted with EtOAc (20 mL). The combined organic layer was washed with saturated sodium bicarbonate (20 mL) and dried over sodium sulfate. After removal of solvent, the residue was purified by flash chromatography (EtOAc) to give the product as white foam solid (0.126 g, 98.5%). $R_t$ 2.43 minutes. MS (ESI+) [M+H]$^+$ 501.

Step 4: The resulting Boc-amino amide (0.056 mg) was dissolved in dioxane, and 4M HCl/dioxane (0.5 mL) was added. The suspension was stirred at room temperature for 3 hours, after which it was concentrated to give the corresponding amino amide as the hydrochloride salt (0.53 g, 98%). $R_t$ 1.77 minutes. MS (ESI+) [M+H]$^+$ 401.

Example 25

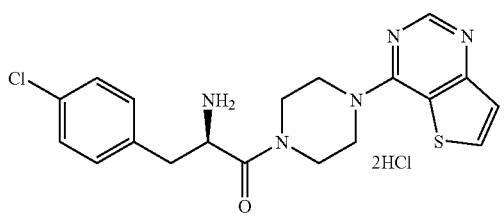 [SMILES: N[C@H](Cc1ccc(Cl)cc1)C(=O)N1CCN(c2ncnc3ccsc23)CC1 ; "2HCl"]

Preparation of 2-Amino-3-(4-chlorophenyl)-1-(4-thieno[3,2-d]pyrimidin-4-yl-piperazin-1-yl)-propan-1-one dihydrochloride Step 1: To a solution of Boc-D-Phe(4-Cl)—OH (3.65 g, 12.2 mmol), piperazine (10 g, 116 mmol) in DCM (200 mL) were added HOBT (3.3 g, 24 mmol) and EDCI (4.7 g, 25 mmol). The mixture was stirred at room temperature for 12 hours. The solution was washed with water, brine and dried over magnesium sulfate. After filtration, the organic solvent was evaporated and the residue was subject to silica gel chromatography to afford the product [1-(4-chlorobenzyl)-2-oxo-2-piperazin-1-yl-ethyl]-carbamic acid tert-butyl ester (0.58 g, 13%). $^1$H NMR (CDCl$_3$, 400 Hz) δ 7.25 (d, J=8.4 Hz, 2H), 7.12 (d, J=8.0 Hz, 2H), 5.52 (d, J=8.4 Hz, 1H), 4.83-4.77 (m, 1H), 3.63-3.45 (m, 2H), 3.37-3.32 (m, 1H), 3.08-3.04 (m, 1H), 2.99-2.90 (m, 2H), 2.81-2.70 (m, 3H), 2.42-2.38 (m, 1H), 1.41 (s, 9H). MS (ESI+) [M+H]$^+$ 369.

Step 2: To a solution of 3-aminothiophene-2-carboxylic methyl ester (20 g, 127 mmol) in formic acid (100 mL) was added ammonium acetate (13 g, 169 mmol). The mixture was refluxed for 3 hours. After cooling to room temperature, the precipitate was filtered, washed with water and dried under vacuum to afford 3-formylaminothiophene-2-carboxylic acid methyl ester (20.5 g, 87%). $^1$H NMR (DMSO, 400 Hz) δ 10.38 (s, 1H), 8.42 (s, 1H), 8.00 (d, J=5.2 Hz, 1H), 7.90 (d, J=5.6 Hz, 1H), 3.84 (s, 3H). MS (ESI+) [M+H]$^+$ 186.

Step 3: To a mixture of 3-formylaminothiophene-2-carboxylic acid methyl ester (20.5 g, 111 mmol) and ammonium formate (21 g, 333 mmol) was added formamide (29.8 g, 662 mmol). The slurry was heated to 140° C. for 10 hours. After cooling, the solid was filtered, washed with water and dried under vacuum to afford the product 3H-Thieno[3,2-d]pyrimidin-4-one (12.5 g, 74%). $^1$H NMR (DMSO, 400 Hz) δ 12.31 (br, 1H), 8.18 (d, J=5.2 Hz, 1H), 8.16 (s, 1H), 7.41 (d, J=5.2 Hz, 1H). MS (ESI+) [M+H]$^+$ 153

Step 4: To a solution of DMF (13.2 mL, 170 mmol) in DCM (100 mL) at 0° C. was added oxalyl chloride (22 mL, 252 mmol) in DCM (100 mL) very slowly over 1 hour. To the resulting white gel solution was added the 3H-thieno[3,2-d] pyrimidin-4-one (12 g, 79 mmol). The mixture was refluxed for 4 hours. After cooling, the mixture was purred into water (500 mL) and extracted with DCM (3×250 mL). Then the organic phase was dried over magnesium sulfate, filtered and concentrated to afford 7-chloro-thieno[3,2-b]pyridine as white solid (13.4 g, 99%). $^1$H NMR (CDCl$_3$, 400 Hz) δ 9.00 (s, 1H), 8.06 (d, J=5.6 Hz, 1H), 7.61 (d, J=5.6 Hz, 1H). MS (ESI+) [M+H]$^+$ 170

Step 5: The solution of [1-(4-chlorobenzyl)-2-oxo-2-piperazin-1-yl-ethyl]-carbamic acid tert-butyl ester (60 mg, 0.163 mmol) and 4-Chlorothieno[3,2-d]pyrimidine 950 mg, 0.293 mmol) in Toluene (5 mL)/TEA (1 mL) was refluxed for 12 hours. After the solvent was removed, the residue was subject to chromatography on silica gel to afford [1-(4-chlorobenzyl)-2-oxo-2-(4-thieno[3,2-d]pyrimidin-4-yl-piperazin-1-yl)-ethyl]-carbamic acid tert-butyl ester (71 mg, 86.7%). $^1$H NMR (CDCl$_3$, 400 Hz) δ 8.60 (s, 1H), 7.76 (d, J=5.2 Hz, 1H), 7.45 (d, J=5.2 Hz, 1H), 7.26 (d, J=8.4 Hz, 1H), 7.15 (d, J=8.4 Hz, 1H), 5.39 (d, J=8.8 Hz, 1H), 4.88-4.82 (m, 1H), 3.94-3.76 (m, 4H), 3.69-3.58 (m, 3H), 3.25-3.22 (m, 1H), 2.98 (d, J=7.2 Hz, 2H), 1.43 (s, 9H). MS (ESI+) [M+H]$^+$ 503.

Step 6: To a solution of [1-(4-chlorobenzyl)-2-oxo-2-(4-thieno[3,2-d]pyrimidin-4-yl-piperazin-1-yl)-ethyl]-carbamic acid tert-butyl ester in DCM (2 mL) was added HCl in Dioxane (4M, 1 mL). The mixture was stirred at room temperature for 4 hours. The solvent was removed to afford 2-amino-3-(4-chlorophenyl)-1-(4-thieno[3,2-d]pyrimidin-4- yl-piperazin-1-yl)-propan-1-one dihydrochloride quantitatively. MS (ESI+) [M+H]+ 402.

Example 26

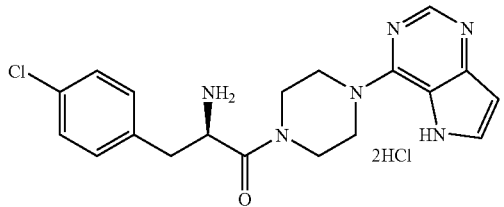

Preparation of 2-amino-3-(4-chlorophenyl)-1-[4-(5H-pyrrolo[3,2-d]pyrimidin-4-yl)-piperazin-1-yl]-propan-1-one dihydrochloride Step 1: To a solution of 4,6-dichloro-5-aminopyrimidine (1 g, 6.1 mmol) in TEA (2 mL) and toluene (10 mL) was added 1-Boc-piperazine (2.3 g, 12.3 mmol). The mixture was refluxed for 12 hours. The solvent was removed and the residue was subject to chromatography on silica gel to afford the product 4-(5-amino-6-chloropyrimidin-4-yl)-piperazin-1-carboxylic acid tert-butyl ester (1.9 g, 99%). $^1$H NMR (CDCl$_3$, 400 Hz) δ 8.16 (s, 1H), 3.87 (s, 2H), 3.56 (m, 4H), 3.29 (m, 4H), 1.49 (s, 9H). MS (ESI+) [M+H]+ 314.

Step 2: To a solution of 4-(5-amino-6-chloropyrimidin-4-yl)-piperazine-1-carboxylic acid tert-butyl ester (1 g, 3.19 mmol) and TMS-acetylene (1.5 g, 15 mmol) in TEA (10 mL) and THF (30 mL) were added PdCl$_2$(PPh$_3$)$_2$ (0.33 g, 0.47 mmol) and CuI (0.1 g, 0.53 mmol) under N$_2$. The mixture was heated to 80° C. for 20 hours. The solvent was removed and the residue was subject to chromatography on silica gel to afford the product 4-(5-Amino-6-trimethylsilanylethynyl-pyrimidin-4-yl)-piperazine-1-carboxylic acid tert-butyl ester (0.3 g, 25%). $^1$H NMR (CDCl$_3$, 400 Hz) δ 8.00 (s, 1H), 3.74 (s, 2H), 3.28-3.25 (m, 4H), 3.02-2.99 (m, 4H), 1.20 (s, 9H), 0.00 (s, 9H). MS (ESI+) [M+H]+ 376.

Step 3: To a solution of $^t$BuOK (0.063 g, 0.56 mmol) in NMP (4 mL) was added 4-(5-Amino-6-trimethylsilanylethynyl-pyrimidin-4-yl)-piperazine-1-carboxylic acid tert-butyl ester (0.1 g, 0.27 mmol) in NMP (1 mL) under N$_2$. The mixture was vigorously stirred at room temperature for 4 hours. The reaction was quenched with water (1 mL) and ethyl acetate (50 mL). The organic phase was washed brine and water until NMP was gone, then dried over MgSO$_4$, filtered and concentrated. The residue was subject to chromatography on silica gel to afford the product 4-(5H-Pyrrolo[3,2-d]pyrimidin-4-yl)-piperazine-1-carboxylic acid tert-butyl ester (43 mg, 53%). $^1$H NMR (CDCl$_3$, 400 Hz) δ 9.47 (s, 1H), 8.49 (s, 1H), 7.37 (d, J=2.4 Hz, 1H), 6.62 (d, J=2.8 Hz, 1H), 3.85-3.82 (m, 4H), 3.61-3.58 (m, 4H). 1.49 (s, 9H). MS (ESI+) [M+H]+ 304.

Step 4: To a solution of 4-(5H-Pyrrolo[3,2-d]pyrimidin-4-yl)-piperazine-1-carboxylic acid tert-butyl ester (43 mg, 0.14 mmol) in DCM (4 mL) was added HCl in Dioxane (4M, 1 mL). The mixture was stirred at room temperature for 4 hours. The solvent was removed and the residue was treated with TEA (2 mL), Boc-D-Phe(4-Cl)—OH (43 mg, 0.14 mmol), HOBT (30 mg, 0.222 mmol) and EDCI (41 mg, 0.214 mmol) in DCM (5 mL). The mixture was stirred at room temperature for 12 hours. The solvent was removed and the residue was subject to chromatography on silica gel to give product {1-(4-chlorobenzyl)-2-oxo-2-[4-(5H-pyrrolo[3,2-d]pyrimidin-4-yl)-piperazin-1-yl]-ethyl}-carbamic acid tert-butyl ester (30 mg, 44%). $^1$H NMR (CDCl$_3$, 400 Hz) δ 9.85 (s, 1H), 8.48 (s, 1H), 7.37 (s, 1H), 7.25-7.23 (d, J=8.4 Hz, 2H), 7.13-7.11 (d, J=8.4 Hz, 2H), 6.60 (s, 1H), 5.39-5.37 (d, J=8.8 Hz, 1H), 4.83-4.78 (m, 1H), 3.81-3.43 (m, 7H), 3.31-3.27 (m, 1H), 3.00-2.91 (m, 2H), 1.41 (s, 9H). MS (ESI+) [M+H]+ 485.

Step 5: To a solution of {1-(4-chlorobenzyl)-2-oxo-2-[4-(5H-pyrrolo[3,2-d]pyrimidin-4-yl)-piperazin-1-yl]-ethyl}-carbamic acid tert-butyl ester in DCM (4 mL) was added HCl in Dioxane (4M, 1 mL) and stirred for 4 hours. The solvent was removed to afford 2-Amino-3-(4-chlorophenyl)-1-[4-(5H-pyrrolo[3,2-d]pyrimidin-4-yl)-piperazin-1-yl]-propan-1-one dihydrochloride quantitatively. MS (ESI+) [M+H]+ 385.

Example 27

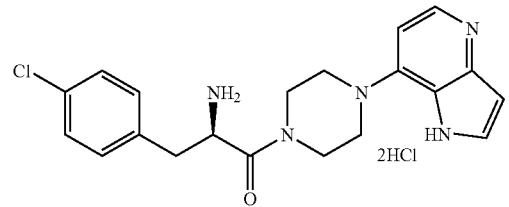 [SMILES: N[C@H](Cc1ccc(Cl)cc1)C(=O)N1CCN(c2ncnc3cc[nH]c23)CC1 ; "2HCl"]

Preparation of 2-Amino-3-(4-chlorophenyl)-1-[4-(1H-pyrrolo[3,2-b]pyridin-7-yl)-piperazin-1-yl]-propan-1-one Step 1: To a solution of 4-hydroxy-3-nitro-pyridine (2 g, 14 mmol) in POCl$_3$ (6 mL) was added PCl$_5$ (2.5 g, 12 mmol). The mixture was heated to reflux for 3 hours. The solvent was evaporated and the residue was cooled with ice-water and vigorously stirred with water (3 mL) and CHCl$_3$ (6 mL). The aqueous was extracted CHCl$_3$ (5×5 mL). The organic phase was combined and dried over MgSO$_4$. After filtration, the solvent was removed to afford the product 4-Chloro-3-nitro-pyridine (2.24 g, 99%). $^1$H NMR (CDCl$_3$, 400 Hz) δ 9.13 (s, 1H), 8.70 (d, J=5.2 Hz, 1H), 7.55 (d, J=5.6 Hz, 1H). MS (ESI+) [M+H]+ 159.

Step 2: To a solution of 4-chloro-3-nitro-pyridine (2 g, 13 mmol) in dry THF (100 mL) under N$_2$ at −78° C. was added excess vinyl magnesium bromide (1.0M, 40 mL, 40 mmol). The mixture was stirred at −20° C. for 8 hours before the reaction was quenched with 20% NH$_4$Cl (75 mL). The aqueous phase was extracted with ethyl acetate (3×100 mL). The combined organic layer was dried over MgSO$_4$, filtered and concentrated. The residue was subject to chromatography on silica gel to afford 7-Chloro-1H-pyrrolo[3,2-b]pyridine (0.3 g, 16%). $^1$H NMR (CD$_3$OD, 400 Hz) δ 8.22 (d, J=5.2 Hz, 1H), 7.64 (d, J=3.2 Hz, 1H), 7.23 (d, J=5.2 Hz, 1H), 6.67 (d, J=3.2 Hz, 1H). MS (ESI+) [M+H]+ 153.

Step 3: To a solution of 7-Chloro-1H-pyrrolo[3,2-b]pyridine (40 mg, 0.262 mmol) in xylene (4 mL) and TEA (1 mL) was added [1-(4-chlorobenzyl)-2-oxo-2-piperazin-1-yl-ethyl]-carbamic acid tert-butyl ester (0.1 g, 0.27 mol). The mixture was refluxed for 6 days. The solvent was removed under vacuum and the residue was subject to purification by HPLC to afford {1-(4-chlorobenzyl)-2-oxo-2-[4-(1H-pyrrolo[3,2-b]pyridin-7-yl)-piperazin-1-yl]-ethyl}-carbamic acid tert-butyl ester (10 mg, 8%). $^1$H NMR (CDCl$_3$, 400 Hz) δ 11.81 (s, 1H), 7.95 (d, J=6.4 Hz, 1H), 7.40 (s, 1H), 7.15 (d, J=8.00 Hz, 2H), 6.46 (d, J=6.8 Hz, 2H), 5.42 (d, J=8.4 Hz, 1H), 4.82 (d, J=7.2 Hz, 1H), 3.87-3.28 (m, 8H), 2.98 (d, J=6.4 Hz, 2H), 1.41 (s, 9H). MS (ESI+) [M+H]+ 484.

Step 4: To a solution of {1-(4-chlorobenzyl)-2-oxo-2-[4-(1H-pyrrolo[3,2-b]pyridin-7-yl)-piperazin-1-yl]-ethyl}-carbamic acid tert-butyl ester in DCM (4 mL) was added HCl in Dioxane (4M, 1 mL). The mixture was stirred at room temperature for 4 hours. The solvent removed to afford the product 2-Amino-3-(4-chlorophenyl)-1-[4-(1H-pyrrolo[3,2-b]pyridin-7-yl)-piperazin-1-yl]-propan-1-one quantitatively. MS (ESI+) [M+H]+ 384.

Example 28

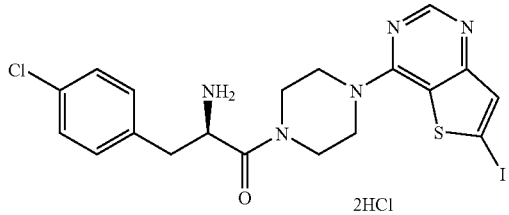 [SMILES: N[C@H](Cc1ccc(Cl)cc1)C(=O)N1CCN(c2ncnc3cc(I)sc23)CC1 ; "2HCl"]

2HCl

Preparation of 2-Amino-3-(4-chlorophenyl)-1-[4-(6-iodothieno[3,2-d]pyrimidin-4-yl)-piperazin-1-yl]-propan-1-one Step 1: To a solution of LDA (1.8M, 20.6 mL, 37.1 mmol) in THF (65 mL) at −78° C. was added 4-chloro-thieno[3,2-d]pyrimidine (5.26 g, 31 mmol) in THF (50 mL) dropwise over 1 hour. After stirring for 20 minutes, I$_2$ (12.7 g, 50 mmol) in THF (40 mL) was added to the mixture at −78° C. dropwise. The mixture was stirred at the same temperature for 20 minutes and then warmed up to room temperature for 2 hours. The mixture was poured into water (100 mL) and stirred for 30 minutes. The solid was filtered and washed with water and Hexane-Hexanes/DCM (50:1) to afford the product 4-Chloro-6-iodothieno[3,2-d]pyrimidine (6.86 g, 75%). $^1$H NMR (DMSO, 400 Hz) δ 8.97 (s, 1H), 8.15 (s, 1H).

Step 2: To a solution of 4-chloro-6-iodothieno[3,2-d]pyrimidine (0.22 g, 0.742 mmol) in DCE (5 mL)/TEA (2 mL) was added [1-(4-chlorobenzyl)-2-oxo-2-piperazin-1-yl-ethyl]-carbamic acid tert-butyl ester (25 mg, 0.68 mmol). The mixture was refluxed for 2 hours. The solvent was removed and the residue was subject to chromatography on silica gel to afford the product {1-(4-chlorobenzyl)-2-[4-(6-iodothieno[3,2-d]pyrimidin-4-yl)-piperazin-1-yl]-2-oxo-ethyl}-carbamic acid tert-butyl ester (44 mg, 95%). $^1$H NMR (CDCl$_3$, 400 Hz) δ 8.47 (s, 1H), 7.64 (s, 1H), 7.27-7.25 (d, J=8.4 Hz, 2H), 7.17-7.15 (d, J=8.0 Hz, 2H), 5.44 (d, J=8.8 Hz, 1H), 4.85-4.81 (m, 1H), 3.86-3.50 (m, 7H), 3.24-3.19 (m, 1H), 2.99-2.97 (d, J=7.2 Hz, 2H), 1.43 (s, 9H). MS (ESI+) [M+H]+ 628.

Step 3: To a solution of {1-(4-chlorobenzyl)-2-[4-(6-iodothieno[3,2-d]pyrimidin-4-yl)-piperazin-1-yl]-2-oxo-ethyl}-carbamic acid tert-butyl ester in DCM (4 mL) was added HCl in Dioxane (4M, 1 mL). The mixture was stirred at room temperature for 4 hours. The solvent was removed to afford the product 2-Amino-3-(4-chlorophenyl)-1-[4-(6-iodothieno[3,2-d]pyrimidin-4-yl)-piperazin-1-yl]-propan-1-one quantitatively. MS (ESI+) [M+H]+ 528.

Example 29

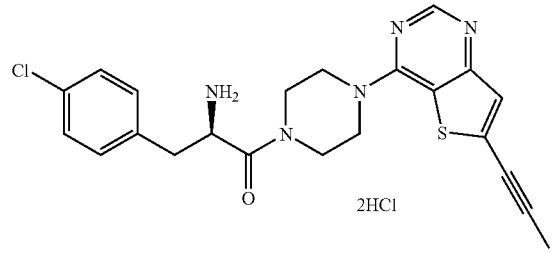 [SMILES: CC#Cc1cc2ncnc(N3CCN(C(=O)[C@H](N)Cc4ccc(Cl)cc4)CC3)c2s1 ; "2HCl"]

2HCl

Preparation of 2-Amino-3-(4-chlorophenyl)-1-[4-(6-prop-1-ynyl-thieno[3,2-d]pyrimidin-4-yl)-piperazin-1-yl]-propan-1-one dihydrochloride Step 1: To a solution of ZnBr$_2$ (70 mg, 0.311 mmol) in THF (2 mL) was added propargyl magnesium bromide (0.5M, 0.6 mL, 0.3 mmol) at room temperature. After stirring for 20 minutes, the 6-iodothieno[3,2-d]pyrimidine (50 mg, 0.08 mmol) was added. The mixture was flushed with N$_2$ and PdCl$_2$(dppf) was added. The mixture was stirred at room temperature under N$_2$ for 12 hours. After filtration, the filtrate was concentrated and the residue was subject to chromatography on silica gel to afford the product {1-(4-chlorobenzyl)-2-oxo-2-[4-(6-prop-1-ynyl-thieno[3,2-d]pyrimidin-4-yl)-piperazin-1-yl]-ethyl}-carbamic acid tert-butyl ester (17 mg, 40%). $^1$H NMR (CDCl$_3$, 400 Hz) δ 8.56 (s, 1H), 7.37 (s, 1H), 7.27-7.25 (d, J=8 Hz, 2H), 7.16-7.14 (d, J=8.4 Hz, 2H), 5.37-5.35 (d, J=8.4 Hz, 1H), 4.85-4.82 (m, 1H), 3.86-3.51 (m, 7H), 3.23-3.20 (m, 1H), 3.00-2.94 (m, 2H), 2.15 (s, 3H), 1.42 (s, 9H). MS (ESI+) [M+H]+ 540.

Step 2: To a solution of {1-(4-chlorobenzyl)-2-oxo-2-[4-(6-prop-1-ynyl-thieno[3,2-d]pyrimidin-4-yl)-piperazin-1-yl]-ethyl}-carbamic acid tert-butyl ester in DCM (4 mL) was added HCl in Dioxane (4M, 1 mL). The mixture was stirred for 4 hours. The solvent was removed to afford the product 2-Amino-3-(4-chlorophenyl)-1-[4-(6-prop-1-ynyl-thieno[3,2-d]pyrimidin-4-yl)-piperazin-1-yl]-propan-1-one dihydrochloride quantitatively. MS (ESI+) [M+H]+ 440.

Example 30

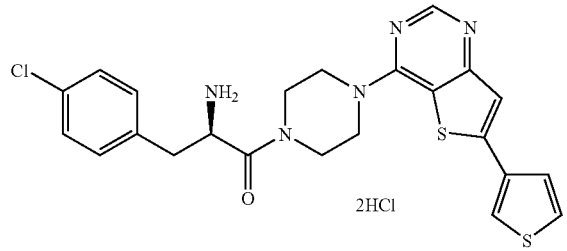 [SMILES: N[C@H](Cc1ccc(Cl)cc1)C(=O)N1CCN(c2ncnc3cc(-c4ccsc4)sc23)CC1 ; "2HCl"]

2HCl

Preparation of 2-Amino-3-(4-chlorophenyl)-1-[4-(6-thiophen-3-yl-thieno [3,2-d]pyrimidin-4-yl)-piperazin-1-yl]-propan-1-one dihydrochloride Step 1: To a solution of {1-(4-chlorobenzyl)-2-[4-(6-iodothieno[3,2-d]pyrimidin-4-yl)-piperazin-1-yl]-2-oxoethyl}-carbamic acid tert-butyl ester (50 mg, 0.080 mmol) in DMF (3 mL) were added 2M Na₂CO₃ (0.1 mL) and 3-thiophenyl boronic acid (15 mg, 0.117 mmol). The mixture was bubbled N₂ for 20 minutes and then Pd(PPh₃)₄ (10 mg, 0.012 mmol) was added. The mixture was heated to 90° C. for 12 hours. The solvent was removed under vacuum and the residue was subject to chromatography on silica gel to afford the product {1-(4-chlorobenzyl)-2-oxo-2-[4-(6-thiophen-3-yl-thieno[3,2-d]pyrimidin-4-yl)-piperazin-1-yl]-ethyl}-carbamic acid tert-butyl ester (16 mg, 34.4%). ¹H NMR (CDCl₃, 400 Hz) δ 8.57 (s, 1H), 7.70-7.42 (m, 4H), 7.27 (d, J=8.4, 2H), 7.16 (d, J=8.4 Hz, 2H), 5.36 (d, J=8.8 Hz, 1H), 4.87-4.84 (m, 1H), 3.91-3.59 (m, 7H), 3.27-3.24 (d, J=11.2 Hz, 1H), 3.00-2.99 (d, J=7.2 Hz, 2H), 1.43 (s, 9H). MS (ESI+) [M+H]⁺ 584.

Step 2: To a solution of product {1-(4-chlorobenzyl)-2-oxo-2-[4-(6-thiophen-3-yl-thieno[3,2-d]pyrimidin-4-yl)-piperazin-1-yl]-ethyl}-carbamic acid tert-butyl ester in DCM (4 mL) was added HCl in Dioxane (4M, 1 mL). The mixture was stirred at room temperature for 4 hours. The solvent was removed to afford the product 2-Amino-3-(4-chlorophenyl)-1-[4-(6-thiophen-3-yl-thieno[3,2-d]pyrimidin-4-yl)-piperazin-1-yl]-propan-1-one dihydrochloride quantitatively. MS (ESI+) [M+H]⁺ 484.

Example 31

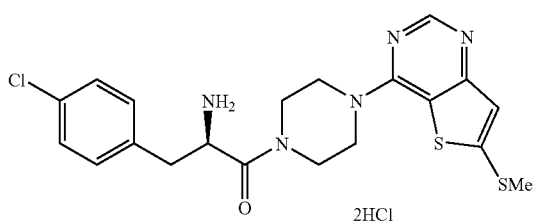 [SMILES: CSc1cc2ncnc(N3CCN(C(=O)[C@H](N)Cc4ccc(Cl)cc4)CC3)c2s1 ; "2HCl"]

Preparation of 2-Amino-3-(4-chlorophenyl)-1-[4-(6-methylsulfanyl-thieno [3,2-d]pyrimidin-4-yl)-piperazin-1-yl]-propan-1-one dihydrochloride Step 1: To a solution of {1-(4-chlorobenzyl)-2-[4-(6-iodothieno[3,2-d]pyrimidin-4-yl)-piperazin-1-yl]-2-oxo-ethyl}-carbamic acid tert-butyl ester (50 mg, 0.080 mmol), sodium methylthiolate (12 mg, 2.15 mmol) and 1,3-di-tert-butyl-propane-dione 940 mg, 0.22 mmol) was purged with N₂. NMP (2 mL) and CuCl (5 mg, 0.05 mmol) were added. The mixture was heated to 130° C. for 3 hours. After cooling down, the reaction was diluted with ethyl acetate and filtered. The filtrate was washed with water, brine and dried over MgSO₄. After filtration, the solvent was removed and the residue was subject to chromatography on silica gel to afford the product {1-(4-chlorobenzyl)-2-[4-(6-methylsulfanyl-thieno[3,2-d]pyrimidin-4-yl)-piperazin-1-yl]-2-oxo-ethyl}-carbamic acid tert-butyl ester. (20 mg, 46%). ¹H NMR (CDCl₃, 400 Hz) δ 8.61 (s, 1H), 7.57 (s, 1H), 7.28-7.26 (d, J=6.4 Hz, 2H), 7.18-7.16 (d, J=8.4 Hz, 2H), 5.33-5.31 (d, J=8.8 Hz, 1H), 4.81-4.79 (m, 1H), 4.01-3.71 (m, 7H), 3.24-3.19 (m, 1H), 3.03-2.98 (m, 2H), 2.74 (s, 3H), 1.43 (s, 9H). MS (ESI+) [M+H]⁺ 548.

Step 2: To a solution of {1-(4-chlorobenzyl)-2-[4-(6-methylsulfanyl-thieno[3,2-d]pyrimidin-4-yl)-piperazin-1-yl]-2-oxo-ethyl}-carbamic acid tert-butyl ester in DCM (4 mL) was added HCl in Dioxane (4M, 1 mL). The mixture was stirred at room temperature for 4 hours. The solvent was removed to afford the product 2-Amino-3-(4-chlorophenyl)-1-[4-(6-methylsulfanyl-thieno[3,2-d]pyrimidin-4-yl)-piperazin-1-yl]-propan-1-one dihydrochloride quantitatively. MS (ESI+) [M+H]⁺ 448.

Example 32

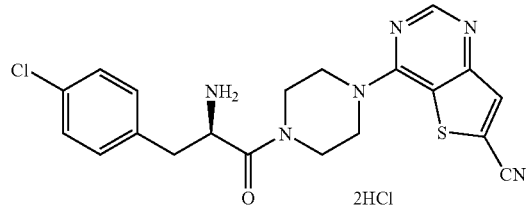 [SMILES: N#Cc1cc2ncnc(N3CCN(C(=O)[C@H](N)Cc4ccc(Cl)cc4)CC3)c2s1 ; "2HCl"]

Preparation of 4-{4-[2-Amino-3-(4-chlorophenyl)-propionyl]-piperazin-1-yl}-thieno[3,2-d]pyrimidine-6-carbonitrile dihydrochloride Step 1: To a solution of {1-(4-chlorobenzyl)-2-[4-(6-iodothieno[3,2-d]pyrimidin-4-yl)-piperazin-1-yl]-2-oxo-ethyl}-carbamic acid tert-butyl ester (50 mg, 0.080 mmol) in Pyridine (5 mL) was added CuCN (20 mg, 0.223 mmol). The mixture was refluxed under N₂ for 12 hours. The solvent was removed and the residue was subject to chromatography on silica gel to afford {1-(4-chlorobenzyl)-2-[4-(6-cyanothieno[3,2-d]pyrimidin-4-yl)-piperazin-1-yl]-2-oxo-ethyl}-carbamic acid tert-butyl ester (29 mg, 69%). ¹H NMR (CDCl₃, 400 Hz) δ 8.65 (s, 1H), 7.95 (s, 1H), 7.28-7.26 (d, J=7.6 Hz, 2H), 7.18-7.16 (d, J=8.4 Hz, 2H). 5.35-5.33 (d, J=8.4 Hz, 1H), 4.85-4.80 (m, 1H), 3.91-3.56 (m, 7H, 3.24-3.19 (m, 1H), 3.01-2.99 (d, J=8.0 Hz, 2H), 1.44 (s, 9H). MS (ESI+) [M+H]⁺ 527.

Step 2: To a solution of {1-(4-chlorobenzyl)-2-[4-(6-cyanothieno[3,2-d]pyrimidin-4-yl)-piperazin-1-yl]-2-oxo-ethyl}-carbamic acid tert-butyl ester in DCM (4 mL) was added HCl in Dioxane (4M, 1 mL). The mixture was stirred at room temperature for 10 hours. The solvent was removed and the residue was subject to purification by HPLC to afford the product 4-{4-[2-Amino-3-(4-chlorophenyl)-propionyl]-piperazin-1-yl}-thieno[3,2-d]pyrimidine-6-carbonitrile dihydrochloride (12 mg, 44%). MS (ESI+) [M+H]⁺ 427.

Example 33

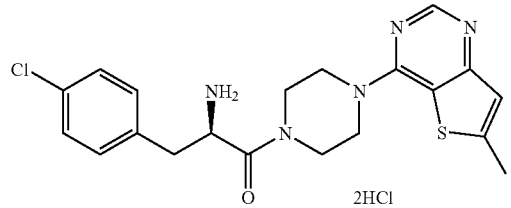 [SMILES: Cc1cc2ncnc(N3CCN(C(=O)[C@H](N)Cc4ccc(Cl)cc4)CC3)c2s1 ; "2HCl"]

Preparation of 2-Amino-3-(4-chlorophenyl)-1-[4-(6-methylthieno[3,2-d]pyrimidin-4-yl)-piperazin-1-yl]-propan-1-one dihydrochloride Step 1: To a solution of 4-chloro-6-iodothieno[3,2-d]pyrimidine (0.5 g, 1.7 mmol) in DCE (5 mL)/TEA (1 mL) was added 1-Benzyl-piperazine (0.3 g, 1.69 mmol). The mixture was refluxed for 1 hour. The solvent was removed and the residue was subject to chromatography on silica gel to afford (4-Benzyl-piperazin-1-yl)-6-iodothieno[3,2-d]pyrimidine (0.65 g, 88%). $^1$H NMR (CDCl$_3$, 400 Hz) δ 8.47 (s, 1H) 7.60 (s, 1H), 7.35-7.23 (m, 5H), 3.95-3.92 (m, 4H), 3.51 (s, 2H), 2.59-2.54 (m, 4H). MS (ESI+) [M+H]$^+$ 437.

Step 2: To a suspension of ZnBr$_2$ (0.5 g, 2.2 mmol) dried under vacuum in THF (10 mL) was added MeMgBr (3M, 0.6 mL, 1.8 mmol) at room temperature dropwise. After addition, the mixture was stirred for 1 hour, then (4-Benzyl-piperazin-1-yl)-6-iodothieno[3,2-d]pyrimidine (0.4 g, 0.92 mmol) was added followed by PdCl$_2$(dppf) (30 mg) under N$_2$. The mixture was heated to 60° C. for 2 hours. The reaction was quenched with water. The organic phase was separated and dried over MgSO$_4$. After filtration, the solvent was removed and the residue was subject to chromatography on silica gel to give the product 4-(4-Benzyl-piperazin-1-yl)-6-methylthieno[3,2-d]pyrimidine (0.16 g, 54%). $^1$H NMR (CDCl$_3$, 400 Hz) δ 8.52 (s, 1H), 7.35-7.26 (m, 5H), 7.07 (s, 1H), 3.98-3.95 (m, 4H), 3.56 (s, 2H), 2.59-2.57 (m, 7H). MS (ESI+) [M+H]$^+$ 325.

Step 3: To a solution of 4-(4-Benzyl-piperazin-1-yl)-6-methylthieno[3,2-d]pyrimidine (65 mg, 0.20 mmol) in MeOH (10 mL) was added Pd/C (10%, 20 mg) and two drop of TFA. The mixture was stirred under H$_2$ balloon for 4 hours. The catalyst was filtered off and the filtrate was concentrated. The residue was dissolved in DCM (6 mL) and TEA (2 mL), then Boc-D-Phe(4-Cl)—OH (59 mg, 0.20 mmol) was added, followed by HOBT (50 mg, 0.37 mmol) and EDCI (74 mg, 0.39 mmol). The mixture was stirred at room temperature for 12 hours. The solvent was removed and the residue was subject to chromatography on silica gel to give the product {1-(4-chlorobenzyl)-2-[4-(6-methylthieno[3,2-d]pyrimidin-4-yl)-piperazin-1-yl]-2-oxo-ethyl}-carbamic acid tert-butyl ester (60 mg, 59%). $^1$H NMR (CDCl$_3$, 400 Hz) δ 8.54 (s, 1H), 7.28-7.26 (d, J=7.2 Hz, 2H), 7.17-7.15 (d, J=8.4 Hz, 2H), 7.08 (s, 1H), 5.37-5.35 9d, J=8.8 Hz, 1H), 4.86-4.84 (m, 1H), 3.87-3.57 (m, 7H), 3.24-3.22 (m, 1H), 3.00-2.98 (d, J=7.2 Hz, 2H), 2.63 (s, 3H), 1.43 (s, 9H). MS (ESI+) [M+H]$^+$ 516.

Step 4: To a solution of {1-(4-chlorobenzyl)-2-[4-(6-methylthieno[3,2-d]pyrimidin-4-yl)-piperazin-1-yl]-2-oxo-ethyl}-carbamic acid tert-butyl ester in DCM (4 mL) was added HCl in Dioxane (4M, 1 mL). The mixture was stirred for 4 hours. The solvent was removed to afford the product 2-Amino-3-(4-chlorophenyl)-1-[4-(6-methylthieno[3,2-d]pyrimidin-4-yl)-piperazin-1-yl]-propan-1-one dihydrochloride quantitatively. MS (ESI+) [M+H]$^+$ 416.

Example 34

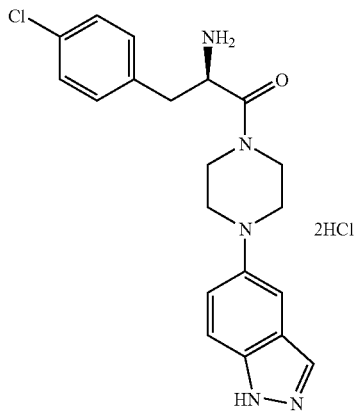 [SMILES: N[C@H](Cc1ccc(Cl)cc1)C(=O)N1CCN(c2ccc3[nH]ncc3c2)CC1 ; "2HCl"]

Preparation of (2R)-2-Amino-3-(4-chlorophenyl)-1-[4-(1H-indazol-5-yl)-piperazin-1-yl]-propan-1-one dihydrochloride Step 1: A mixture of 5-aminoindazole (2.53 g, 19.0 mmol), bis(2-chloroethyl)amine hydrochloride (3.60 g, 20.1 mmol) and ethanol (30 mL) was heated at reflux overnight. The mixture was allowed to cool to room temperature. Na$_2$CO$_3$ (2.14 g, 20.2 mmol) was added and the reaction mixture heated at reflux for 8 hours. After cooling, the mixture was filtered and the filtrate evaporated in vacuo. The residue was dissolved in 1N HCl (100 mL) and extracted with DCM (2×50 mL). The aqueous phase was made basic with 4N NaOH (30 mL) and extracted with EtOAc (2×100 mL). The combined organic layers were washed with brine, dried and concentrated. The residue was purified by column chromatography (20:1 DCM/MeOH to 20:1:0.5 DCM/MeOH/Et$_3$N) to 5-Piperazin-1-yl-1H-indazole (1.26 g, 33%) as a brown solid. $^1$H NMR (DMSO-d$_6$, 400 MHz) δ 12.80 (s, 1H), 7.89 (s, 1H), 7.40 (d, J=8.8 Hz, 1H), 7.16 (dd, J=8.8 Hz, J=2.0 Hz, 1H), 7.07 (s, 1H), 3.17 (s, 1H), 2.99 (m, 4H), 2.89 (m, 4H). LCMS (APCI+) m/z 203 [M$^1$H]$^+$; Rt=1.33 minutes.

Step 2: To a solution of (D)-Boc-4-chlorophenylalanine (0.119 g, 0.396 mmol) and 5-Piperazin-1-yl-1H-indazole (0.100 g, 0.494 mmol) in DMF (5 mL) was added EDCI (0.152 g, 0.791 mmol), HOBt (0.121 g, 0.791 mmol) and triethylamine (0.110 mL, 0.791 mmol). The reaction mixture was stirred at room temperature overnight. The mixture was partitioned between water and EtOAc. The aqueous phase was extracted with EtOAc. The combined organic layers were washed with aqueous NaHCO$_3$, brine, dried and concentrated. The residue was purified by column chromatography (80:1 to 50:1 DCM/MeOH) to give (2R)-{1-(4-chlorobenzyl)-2-[4-(1H-indazol-5-yl)-piperazin-1-yl]-2-oxo-ethyl}-carbamic acid tert-butyl ester (0.176 g, 92%) as a white solid. $^1$H NMR (CDCl$_3$, 400 MHz) δ 10.12 (s, 1H), 7.98 (s, 1H), 7.41 (d, J=8.8 Hz, 1H), 7.28 (d, J=8.4 Hz, 2H), 7.16 (d, J=8.4 Hz, 2H), 7.12 (dd, J=8.8 Hz, J=2.0 Hz, 1H), 7.07 (s, 1H), 5.46 (m, 1H), 4.88 (m, 1H), 3.74 (m, 2H), 3.53 (m, 1H), 3.31 (m, 1H), 3.07 (m, 1H), 2.99 (d, J=6.8 Hz, 2H), 2.91 (m, 2H), 2.49 (m, 1H), 1.43 (s, 9H). LCMS (APCI+) m/z 484, 486 [M+H]$^+$; Rt=3.01 minutes.

Step 3: To a solution of (2R)-{1-(4-chlorobenzyl)-2-[4-(1H-indazol-5-yl)-piperazin-1-yl]-2-oxo-ethyl}-carbamic acid tert-butyl ester (0.176 g, 0.364 mmol) in DCM (10 mL) was added 4N HCl in dioxane (1 mL). The mixture was stirred at room temperature overnight and then evaporated. The resulting solid was suspended in isopropyl alcohol-ether (1:5) and stirred for 30 minutes. The mixture was filtered to give (2R)-2-Amino-3-(4-chlorophenyl)-1-[4-(1H-indazol-5-yl)-piperazin-1-yl]-propan-1-one dihydrochloride (0.151 g, 91%) as a white solid. $^1$H NMR (CD$_3$OD, 400 MHz) δ 8.24 (s, 1H), 8.03 (s, 1H), 7.75 (d, J=9.2 Hz, 1H), 7.65 (d, J=9.2 Hz, 1H), 7.47 (d, J=8.0 Hz, 2H), 7.37 (d, J=8.0 Hz, 2H), 4.82 (m, 1H), 4.12 (m, 1H), 3.94 (m, 2H), 3.73 (m, 2H), 3.51 (m, 2H), 3.22 (dd, J=13.2 Hz, J=6.0 Hz, 1H), 3.15 (dd, J=13.2 Hz, J=9.2 Hz, 1H), 2.87 (m, 1H). LCMS (APCI+) m/z 384, 386 [M+H]$^+$; Rt=1.92 minutes.

Example 35

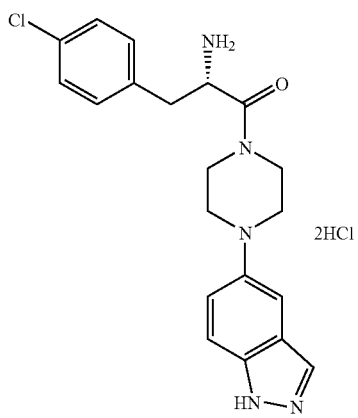 [SMILES: N[C@@H](Cc1ccc(Cl)cc1)C(=O)N1CCN(c2ccc3[nH]ncc3c2)CC1 ; "2HCl"]

Preparation of (2S)-2-Amino-3-(4-chlorophenyl)-1-[4-(1H-indazol-5-yl)-piperazin-1-yl]-propan-1-one dihydrochloride Step 1: (2S)-{1-(4-chlorobenzyl)-2-[4-(1H-indazol-5-yl)-piperazin-1-yl]-2-oxo-ethyl}-carbamic acid tert-butyl ester was prepared by the procedures described in Example 34, Step 2, substituting (D)-Boc-4-chlorophenylalanine with (L)-Boc-4-chlorophenylalanine. $^1$H NMR (CDCl$_3$, 400 MHz) δ 10.03 (s, 1H), 7.98 (s, 1H), 7.41 (d, J=8.8 Hz, 1H), 7.28 (d, J=8.4 Hz, 2H), 7.16 (d, J=8.4 Hz, 2H), 7.12 (dd, J=8.8 Hz, J=2.0 Hz, 1H), 7.07 (s, 1H), 5.46 (m, 1H), 4.88 (m, 1H), 3.74 (m, 2H), 3.53 (m, 1H), 3.31 (m, 1H), 3.07 (m, 1H), 2.99 (d, J=6.8 Hz, 2H), 2.91 (m, 2H), 2.49 (m, 1H), 1.43 (s, 9H).

Step 2: (2S)-2-Amino-3-(4-chlorophenyl)-1-[4-(1H-indazol-5-yl)-piperazin-1-yl]-propan-1-one dihydrochloride was prepared by the procedures described in Example 34, Step 3, substituting (2R)-{1-(4-chlorobenzyl)-2-[4-(1H-indazol-5-yl)-piperazin-1-yl]-2-oxo-ethyl}-carbamic acid tert-butyl ester with (2S)-{1-(4-chlorobenzyl)-2-[4-(1H-indazol-5-yl)-piperazin-1-yl]-2-oxo-ethyl}-carbamic acid tert-butyl ester. $^1$H NMR (CD$_3$OD, 400 MHz) δ 8.24 (s, 1H), 8.03 (s, 1H), 7.75 (d, J=9.2 Hz, 1H), 7.65 (d, J=9.2 Hz, 1H), 7.47 (d, J=8.0 Hz, 2H), 7.37 (d, J=8.0 Hz, 2H), 4.82 (m, 1H), 4.12 (m, 1H), 3.94 (m, 2H), 3.73 (m, 2H), 3.51 (m, 2H), 3.22 (dd, J=13.2 Hz, J=6.0 Hz, 1H), 3.15 (dd, J=13.2 Hz, J=9.2 Hz, 1H), 2.87 (m, 1H). LCMS (APCI+) m/z 384, 386 [M+H]$^+$; Rt=1.92 minutes.

Example 36

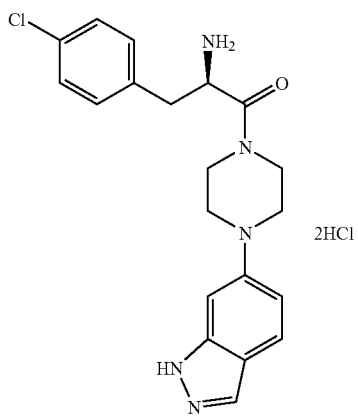 [SMILES: N[C@H](Cc1ccc(Cl)cc1)C(=O)N1CCN(c2ccc3cn[nH]c3c2)CC1 ; "2HCl"]

Preparation of (2R)-2-Amino-3-(4-chlorophenyl)-1-[4-(1H-indazol-6-yl)-piperazin-1-yl]-propan-1-one dihydrochloride Step 1: 6-Piperazin-1-yl-1H-indazole was prepared by the procedures described in Example 34, Step 1, substituting 5-aminoindazole with 6-aminoindazole. LCMS (APCI+) m/z 203 [M+H]$^+$; Rt=1.53 minutes.

Step 2: (2R)-{1-(4-chlorobenzyl)-2-[4-(1H-indazol-6-yl)-piperazin-1-yl]-2-oxo-ethyl}-carbamic acid tert-butyl ester was prepared by the procedures described in Example 34, Step 2, substituting 5-Piperazin-1-yl-1H-indazole with 6-Piperazin-1-yl-1H-indazole. $^1$H NMR (CDCl$_3$, 400 MHz) δ 9.91 (s, 1H), 7.94 (d, J=2.0 Hz, 1H), 7.61 (dd, J=8.8 Hz, J=2.0 Hz, 1H), 7.28 (d, J=8.4 Hz, 2H), 7.16 (d, J=8.4 Hz, 2H), 6.86 (dd, J=8.8 Hz, J=2.0 Hz, 1H), 6.73 (s, 1H), 5.42 (m, 1H), 4.88 (m, 1H), 3.74 (m, 2H), 3.53 (m, 1H), 3.29 (m, 1H), 3.19 (m, 1H), 3.00 (m, 4H), 2.59 (m, 1H), 1.43 (s, 9H). LCMS (APCI+) m/z 484, 486 [M+H]$^+$; Rt=3.40 minutes.

Step 3: (2R)-2-Amino-3-(4-chlorophenyl)-1-[4-(1H-indazol-6-yl)-piperazin-1-yl]-propan-1-one dihydrochloride was prepared by the procedures described in Example 34, Step 3, substituting (2R)-{1-(4-chlorobenzyl)-2-[4-(1H-indazol-5-yl)-piperazin-1-yl]-2-oxo-ethyl}-carbamic acid tert-butyl ester with (2R)-{1-(4-chlorobenzyl)-2-[4-(1H-indazol-6-yl)-piperazin-1-yl]-2-oxo-ethyl}-carbamic acid tert-butyl ester. $^1$H NMR (CD$_3$OD, 400 MHz) δ 8.30 (s, 1H), 7.78 (d, J=9.2 Hz, 1H), 7.40 (d, J=8.4 Hz, 2H), 7.32 (d, J=8.4 Hz, 2H), 7.15 (d, J=9.2 Hz, 1H), 6.97 (s, 1H), 4.76 (m, 1H), 3.80 (m, 2H), 3.62 (m, 1H), 3.40 (m, 1H), 3.10-3.30 (m, 5H), 2.72 (m, 1H). LCMS (APCI+) m/z 384, 386 [M+H]$^+$; Rt=2.02 minutes.

Example 37

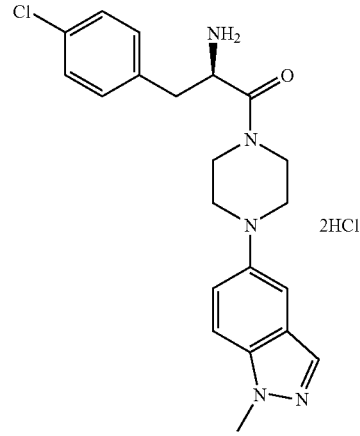 [SMILES: Cn1ncc2cc(N3CCN(C(=O)[C@H](N)Cc4ccc(Cl)cc4)CC3)ccc21 ; "2HCl"]

Preparation of (2R)-2-Amino-3-(4-chlorophenyl)-1-[4-(1-methyl-1H-indazol-5-yl)-piperazin-1-yl]-propan-1-one dihydrochloride Step 1: To a solution of 5-Piperazin-1-yl-1H-indazole (0.34 g, 1.3 mmol) in 1,4-dioxane (5 mL) was added 3N NaOH (0.42 mL, 1.3 mmol). After cooling to 0° C., a solution of tert-butylcarbonate (0.25 g, 1.3 mmol) in 1,4-dioxane (1 mL) was added dropwise. The reaction mixture was stirred at room temperature overnight and then poured into water and extracted with EtOAc. The combined organic layers were washed with saturated aqueous NaHCO$_3$, water, brine, dried and concentrated. The residue was purified by column chromatography (EtOAc:hexanes, 1:1) to give 4-(1H-Indazol-5-yl)-piperazine-1-carboxylic acid tert-butyl ester (0.31 g, 82%) as a white solid. $^1$H NMR (CDCl$_3$, 400 MHz) δ 10.01 (s, 1H), 7.80 (s, 1H), 7.42 (d, J=9.2 Hz, 1H), 7.21 (dd, J=9.2 Hz, J=2.0 Hz, 1H), 7.16 (d, J=2.0 Hz, 1H), 3.62 (m, 4H), 3.09 (m, 4H), 1.50 (s, 9H). LCMS (APCI+) m/z 303 [M+H]$^+$; Rt=2.50 minutes.

Step 2: To a stirred suspension of NaH (60%, 4 mg, 0.1 mmol) in DMF (0.5 mL) was added dropwise a solution of 4-(1H-Indazol-5-yl)-piperazine-1-carboxylic acid tert-butyl ester (0.100 g, 0.33 mmol) in DMF (1 mL). After stirring for 30 minutes, methyl iodide (0.026 g, 0.18 mmol) was added dropwise. The mixture was stirred at room temperature for 2 hours and then partitioned between EtOAc and water. The aqueous phase was extracted with EtOAc. The combined organic layers were washed with brine, dried and concentrated. The residue was purified by column chromatography (hexanes:EtOAc, 2:1) to give 4-(1-Methyl-1H-indazol-5-yl)-piperazine-1-carboxylic acid tert-butyl ester (0.023 g, 22%) as a white solid. $^1$H NMR (CDCl$_3$, 400 MHz) δ 7.87 (s, 1H), 7.32 (d, J=9.2 Hz, 1H), 7.20 (d, J=9.2 Hz, 1H), 7.12 (s, 1H), 4.04 (s, 3H), 3.62 (m, 4H), 3.09 (m, 4H), 1.50 (s, 9H). LCMS (APCI+) m/z 317 [M+H]$^+$; Rt=3.31 minutes.

Step 3: 1-Methyl-5-piperazin-1-yl-1H-indazole dihydrochloride was prepared by the procedures described in Example 34, Step 3, substituting (2R)-{1-(4-chlorobenzyl)-2-[4-(1H-indazol-5-yl)-piperazin-1-yl]-2-oxo-ethyl}-carbamic acid tert-butyl ester with 4-(1-Methyl-1H-indazol-5-yl)-piperazine-1-carboxylic acid tert-butyl ester. LCMS (APCI+) m/z 217 [M+H]$^+$; Rt=1.15 minutes.

Step 4: (2R)-{1-(4-chlorobenzyl)-2-[4-(1-methyl-1H-indazol-5-yl)-piperazin-1-yl]-2-oxo-ethyl}-carbamic acid tert-butyl ester was prepared by the procedures described in Example 34, Step 2, substituting 5-Piperazin-1-yl-1H-indazole with 1-Methyl-5-piperazin-1-yl-1H-indazole dihydrochloride. $^1$H NMR (CDCl$_3$, 400 MHz) δ 7.87 (s, 1H), 7.31 (d, J=9.2 Hz, 1H), 7.28 (d, J=8.0 Hz, 2H), 7.17 (d, J=8.0 Hz, 2H), 7.12 (d, J=9.2 Hz, 1H), 7.04 (s, 1H), 5.41 (m, 1H), 4.87 (m, 1H), 4.04 (s, 3H), 3.73 (m, 2H), 3.50 (m, 1H), 3.31 (m, 1H), 3.07 (m, 1H), 2.99 (d, J=7.2 Hz, 2H), 2.94 (m, 2H), 2.48 (m, 1H), 1.43 (s, 9H). LCMS (APCI+) m/z 498, 500 [M+H]$^+$; Rt=3.27 minutes.

Step 5: (2R)-2-Amino-3-(4-chlorophenyl)-1-[4-(1-methyl-1H-indazol-5-yl)-piperazin-1-yl]-propan-1-one dihydrochloride was prepared by the procedures described in Example 34, Step 3, substituting (2R)-{1-(4-chlorobenzyl)-2-[4-(1H-indazol-5-yl)-piperazin-1-yl]-2-oxo-ethyl}-carbamic acid tert-butyl ester with (2R)-{1-(4-chlorobenzyl)-2-[4-(1-methyl-1H-indazol-5-yl)-piperazin-1-yl]-2-oxo-ethyl}-carbamic acid tert-butyl ester. $^1$H NMR (CD$_3$OD, 400 MHz) δ 8.13 (s, 1H), 7.96 (s, 1H), 7.76 (d, J=9.2 Hz, 1H), 7.62 (dd, J=9.2 Hz, J=2.0 Hz, 1H), 7.47 (d, J=8.4 Hz, 2H), 7.37 (d, J=8.4 Hz, 2H), 4.81 (m, 1H), 4.11 (m, 4H), 3.98 (m, 1H), 3.90 (m, 1H), 3.69 (m, 2H), 3.49 (m, 2H), 3.16 (m, 2H), 2.84 (m, 1H). LCMS (APCI+) m/z 398, 400 [M+H]$^+$; Rt=2.05 minutes.

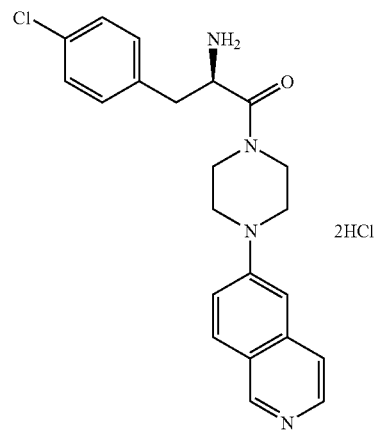 [SMILES: N[C@H](Cc1ccc(Cl)cc1)C(=O)N1CCN(c2ccc3cnccc3c2)CC1 ; "2HCl"]

Preparation of (2R)-2-Amino-3-(4-chlorophenyl)-1-(4-isoquinolin-6-yl-piperazin-1-yl)-propan-1-one dihydrochloride Step 1: A round bottom flask charged with 6-bromo isoquinoline (prepared from 4-bromobenzaldehyde according to the literature: Neiko Nerenz, et al. (1998) *J. Chem. Soc. Perkin Trans.* 2, 437-447, 0.200 g, 0.961 mmol), 1-Boc piperazine (0.215 g, 1.15 mmol), K$_3$PO$_4$ (0.286 g, 1.35 mmol), (2'-dicyclohexylphosphanyl-biphenyl-2-yl)-dimethylamine (0.028 g, 0.072 mmol) and Pd$_2$dba$_3$ (0.022 g, 0.024 mmol) in dry DME (2 mL) was purged under N$_2$ and heated at reflux for 5 hours. After cooling, the mixture was partitioned between EtOAc and H$_2$O. The organic layer was washed with brine, dried and concentrated. The residue was purified by column chromatography (1:1 hexanes/EtOAc,) to give 4-Isoquinolin-6-yl-piperazine-1-carboxylic acid tert-butyl ester (0.210 g, 70%) as a white solid. $^1$H NMR (CDCl$_3$, 400 MHz) δ 9.04 (s, 1H), 8.39 (dd, J=6.8 Hz, J=2.8 Hz, 1H), 7.83 (dd, J=9.2 Hz, J=2.8 Hz, 1H), 7.45 (d, J=6.8 Hz, 1H), 7.32 (dd, J=9.2 Hz, J=2.4 Hz, 1H), 6.98 (s, 1H), 3.64 (m, 4H), 3.35 (m, 4H), 1.50 (s, 9H). LCMS (APCI+) m/z 314 [M+H]$^+$; Rt=2.14 minutes.

Step 2: 6-Piperazin-1-yl-isoquinoline dihydrochloride was prepared by the procedures described in Example 34, Step 3, substituting (2R)-{1-(4-chlorobenzyl)-2-[4-(1H-indazol-5-yl)-piperazin-1-yl]-2-oxo-ethyl}-carbamic acid tert-butyl ester with 4-Isoquinolin-6-yl-piperazine-1-carboxylic acid tert-butyl ester. $^1$H NMR (CD$_3$OD, 400 MHz) δ 9.28 (s, 1H), 8.30 (d, J=9.2 Hz, 1H), 8.24 (d, J=7.2 Hz, 11-1), 8.04 (d, J=6.8 Hz, 1H), 7.83 (dd, J=9.2 Hz, J=2.4 Hz, 1H), 7.49 (s, 1H), 3.98 (m, 4H), 3.45 (m, 4H). LCMS (APCI+) m/z 214 [M+H]$^+$; Rt=1.76 minutes.

Step 3: (2R)-[1-(4-chlorobenzyl)-2-(4-isoquinolin-6-yl-piperazin-1-yl)-2-oxo-ethyl]-carbamic acid tert-butyl ester was prepared by the procedures described in Example 34, Step 2, substituting 5-Piperazin-1-yl-1H-indazole with 6-Piperazin-1-yl-isoquinoline dihydrochloride. $^1$H NMR (CDCl$_3$, 400 MHz) δ 9.04 (s, 1H), 8.40 (dd, J=5.6 Hz, J=3.2 Hz, 1H), 7.83 (dd, J=9.2 Hz, J=2.4 Hz, 1H), 7.46 (d, J=6.0 Hz, 1H), 7.27 (m, 3H), 7.17 (d, J=8.0 Hz, 2H), 6.90 (s, 1H), 5.41 (m, 1H), 4.87 (m, 1H), 3.76 (m, 2H), 3.58 (m, 1H), 3.31 (m, 2H), 3.20 (m, 2H), 2.99 (d, J=6.8 Hz, 2H), 2.78 (m, 1H), 1.43 (s, 9H). LCMS (APCI+) m/z 495, 497 [M+H]$^+$; Rt=2.50 minutes.

Step 4: (2R)-2-Amino-3-(4-chlorophenyl)-1-(4-isoquinolin-6-yl-piperazin-1-yl)-propan-1-one dihydrochloride was prepared by the procedures described in Example 34, Step 3, substituting (2R)-{1-(4-chlorobenzyl)-2-[4-(1H-indazolo-5-yl)-piperazin-1-yl]-2-oxo-ethyl}-carbamic acid tert-butyl ester with (2R)-[1-(4-chlorobenzyl)-2-(4-isoquinolin-6-yl-piperazin-1-yl)-2-oxo-ethyl]-carbamic acid tert-butyl ester. $^1$H NMR (CD$_3$OD, 400 MHz) δ 9.18 (s, 1H), 8.22 (d, J=9.2 Hz, 1H), 8.16 (d, J=6.8 Hz, 1H), 7.95 (d, J=6.8 Hz, 1H), 7.69 (dd, J=9.2 Hz, J=2.4 Hz, 1H), 7.38 (d, J=8.4 Hz, 2H), 7.32 (d, J=8.4 Hz, 2H), 7.27 (s, 1H), 4.75 (m, 1H), 3.58-3.84 (m, 6H), 3.10-3.30 (m, 4H). LCMS (APCI+) m/z 395, 397 [M+H]$^+$; Rt=2.68 minutes.

Example 39

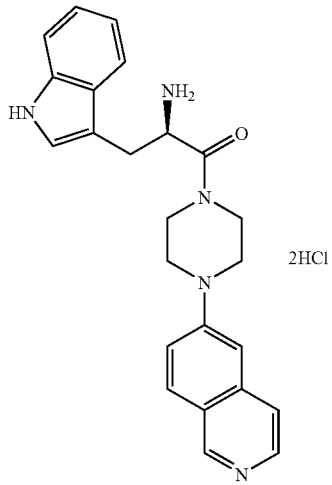 [SMILES: N[C@H](Cc1c[nH]c2ccccc12)C(=O)N1CCN(c2ccc3cnccc3c2)CC1 ; "2HCl"]

Preparation of (2R)-2-Amino-3-(1H-indol-3-yl)-1-(4-isoquinolin-6-yl-piperazin-1-yl)-propan-1-one dihydrochloride Step 1: (2R)-[1-(1H-Indol-3-ylmethyl)-2-(4-isoquinolin-6-yl-piperazin-1-yl)-2-oxo-ethyl]-carbamic acid tert-butyl ester was prepared by the procedures described in Example 34, Step 2, substituting 5-Piperazin-1-yl-1H-indazole with 6-Piperazin-1-yl-isoquinoline dihydrochloride and substituting (D)-Boc-4-chlorophenylalanine with (D)-Boc-tryptophan. $^1$H NMR (CDCl$_3$, 400 MHz) δ 9.00 (s, 1H), 8.37 (d, J=6.4 Hz, 1H), 8.19 (s, 1H), 7.76 (d, J=9.2 Hz, 1H), 7.72 (d, J=7.6 Hz, 1H), 7.41 (d, J=6.0 Hz, 1H), 7.30 (d, J=7.6 Hz, 1H), 7.18 (m, 2H), 7.12 (d, J=8.8 Hz, 1H), 7.08 (s, 1H), 6.70 (s, 1H), 5.53 (d, J=8.4 Hz, 1H), 5.03 (m, 1H), 3.79 (m, 1H), 3.47 (m, 1H), 3.05-3.40 (m, 6H), 2.73 (m, 1H), 1.97 (m, 1H), 1.46 (s, 9H). LCMS (APCI+) m/z 500 [M+H]$^+$; Rt=2.75 minutes.

Step 2: (2R)-2-Amino-3-(1H-indol-3-yl)-1-(4-isoquinolin-6-yl-piperazin-1-yl)-propan-1-one dihydrochloride was prepared by the procedures described in Example 34, Step 3, substituting (2R)-{1-(4-chlorobenzyl)-2-[4-(1H-indazol-5-yl)-piperazin-1-yl]-2-oxo-ethyl}-carbamic acid tert-butyl ester with (2R)-[1-(1H-Indol-3-ylmethyl)-2-(4-isoquinolin-6-yl-piperazin-1-yl)-2-oxo-ethyl]-carbamic acid tert-butyl ester. $^1$H NMR (CD$_3$OD, 400 MHz) δ 10.65 (s, 1H), 9.14 (s, 1H), 8.15 (m, 2H), 7.89 (d, J=6.8 Hz, 1H), 7.56 (d, J=5.6 Hz, 1H), 7.51 (d, J=9.2 Hz, 1H), 7.30 (m, 2H), 7.07 (m, 3H), 4.70 (m, 1H), 3.74 (m, 1H), 3.64 (m, 1H), 3.39 (m, 5H), 3.01 (m, 1H), 2.86 (m, 1H), 2.36 (m, 1H). LCMS (APCI+) m/z 400 [M+H]$^+$; Rt=1.73 minutes.

Example 40

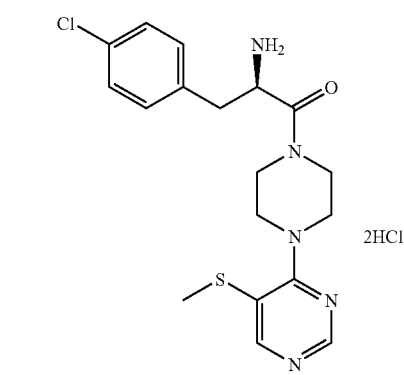 [SMILES: CSc1cncnc1N1CCN(C(=O)[C@H](N)Cc2ccc(Cl)cc2)CC1 ; "2HCl"]

Preparation of (2R)-2-Amino-3-(4-chlorophenyl)-1-[4-(5-methylsulfanylpyrimidin-4-yl)-piperazin-1-yl]-propan-1-one dihydrochloride Step 1: A mixture of 4-chloro-5-iodopyrimidine (3.00 g, 12.5 mmol) (prepared from 4(3H)-pyrimidinone according to the literature: Takao Sakamoto, et al. (1986) *Chem. Pharm. Bull.*, 2719-2724), Et$_3$N (5.22 mL, 37.4 mmol), 1-Boc piperazine (2.79 g, 15.0 mmol) and NMP (30 mL) was heated at 75° C. for 6 hours. After cooling, the reaction mixture was partitioned between EtOAc and water. The aqueous phase was extracted with EtOAc. The combined organic layers were washed with brine, dried and concentrated. The residue was purified by column chromatography (2:1 hexanes/EtOAc) to give 4-(5-Iodo-pyrimidin-4-yl)-piperazine-1-carboxylic acid tert-butyl ester (4.81 g, 99%) as a white solid. $^1$H NMR (CDCl$_3$, 400 MHz) δ 8.70 (s, 1H), 8.62 (s, 1H), 3.57 (s, 8H), 1.49 (s, 9H). LCMS (APCI+) m/z 391 [M+H]$^+$; Rt=2.96 minutes.

Step 2: 5-Iodo-4-piperazin-1-yl-pyrimidine dihydrochloride was prepared by the procedures described in Example 34, Step 3, substituting (2R)-{1-(4-chlorobenzyl)-2-[4-(1H-indazol-5-yl)-piperazin-1-yl]-2-oxo-ethyl}-carbamic acid tert-butyl ester with 4-(5-Iodo-pyrimidin-4-yl)-piperazine-1-carboxylic acid tert-butyl ester. $^1$H NMR (CD$_3$OD, 400 MHz) δ 8.87 (s, 1H), 8.84 (s, 1H), 4.36 (t, J=4.2 Hz, 4H), 3.47 (t, J=4.2 Hz, 4H). LCMS (APCI+) m/z 291 [M+H]$^+$; Rt=1.45 minutes.

Step 3: (2R)-{1-(4-chlorobenzyl)-2-[4-(5-iodopyrimidin-4-yl)-piperazin-1-yl]-2-oxo-ethyl}-carbamic acid tert-butyl ester was prepared by the procedures described in Example 34, Step 2, substituting 5-Piperazin-1-yl-1H-indazole with 5-Iodo-4-piperazin-1-yl-pyrimidine dihydrochloride. $^1$H NMR (CDCl$_3$, 400 MHz) δ 8.70 (s, 1H), 8.62 (s, 1H), 7.27 (d, J=8.0 Hz, 2H), 7.15 (d, J=8.0 Hz, 2H), 5.38 (m, 1H), 4.84 (m, 1H), 3.73 (m, 2H), 3.65 (m, 1H), 3.53 (m, 2H), 3.45 (m, 2H), 3.24 (m, 1H), 3.12 (m, 1H), 2.98 (m, 2H), 1.42 (s, 9H). LCMS (APCI+) m/z 572, 574 [M+H]$^+$; Rt=3.25 minutes.

Step 4: A round bottom flask was charged with sodium methanethiolate (17 mg, 0.25 mmol), (2R)-{1-(4-chlorobenzyl)-2-[4-(5-iodopyrimidin-4-yl)-piperazin-1-yl]-2-oxo-ethyl}-carbamic acid tert-butyl ester (71 mg, 0.12 mmol) and 2,2,6,6-tetramethyl-heptane-3,5-dione (6 mg, 0.25 equivalents). After vacuum purging and refilling of N$_2$, NMP (3 mL)

and CuCl (6 mg, 0.06 mmol) was added to this mixture. The reaction was stirred at 130° C. for 1 hour. After cooling, the reaction mixture was diluted with EtOAc and filtered through Celite. The filtrate was washed with brine, dried over $Na_2SO_4$, filtered and concentrated in vacuo. The residue was purified by flash column chromatography (1:1 hexanes/EtOAc) to give (2R)-{1-(4-chlorobenzyl)-2-[4-(5-methylsulfanylpyrimidin-4-yl)-piperazin-1-yl]-2-oxo-ethyl}-carbamic acid tert-butyl ester (24 mg, 39%) as a colorless gum. $^1$H NMR ($CDCl_3$, 400 MHz) δ 8.56 (s, 1H), 8.29 (s, 1H), 7.26 (d, J=8.4 Hz, 2H), 7.14 (d, J=8.4 Hz, 2H), 5.37 (m, 1H), 4.84 (m, 1H), 3.70 (m, 1H), 3.61 (m, 2H), 3.51 (m, 4H), 3.20 (m, 2H), 2.97 (m, 2H), 2.42 (s, 3H), 1.42 (s, 9H). LCMS (APCI+) m/z 492, 494 [M+H]$^+$; Rt=3.57 minutes.

Step 5: (2R)-2-Amino-3-(4-chlorophenyl)-1-[4-(5-methylsulfanylpyrimidin-4-yl)-piperazin-1-yl]-propan-1-one dihydrochloride was prepared by the procedures described in Example 34, Step 3, substituting (2R)-{1-(4-chlorobenzyl)-2-[4-(1H-indazol-5-yl)-piperazin-1-yl]-2-oxo-ethyl}-carbamic acid tert-butyl ester with (2R)-{1-(4-chlorobenzyl)-2-[4-(5-methylsulfanylpyrimidin-4-yl)-piperazin-1-yl]-2-oxo-ethyl}-carbamic acid tert-butyl ester. $^1$H NMR ($CD_3OD$, 400 MHz) δ 8.64 (s, 1H), 8.30 (s, 1H), 7.39 (d, J=8.0 Hz, 2H), 7.32 (d, J=8.0 Hz, 2H), 4.75 (m, 1H), 4.09 (m, 2H), 4.00 (m, 1H), 3.83 (m, 1H), 3.68 (m, 3H), 3.17 (m, 3H), 2.55 (s, 3H). LCMS (APCI+) m/z 392, 394 [M+H]$^+$; Rt=1.85 minutes.

Example 41

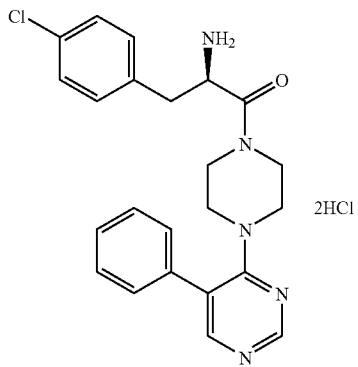 [SMILES: N[C@H](Cc1ccc(Cl)cc1)C(=O)N1CCN(c2ncncc2-c2ccccc2)CC1 ; "2HCl"]

Preparation of (2R)-2-Amino-3-(4-chlorophenyl)-1-[4-(5-phenylpyrimidin-4-yl)-piperazin-1-yl]-propan-1-one dihydrochloride Step 1: (2R)-{1-(4-chlorobenzyl)-2-[4-(5-iodopyrimidin-4-yl)-piperazin-1-yl]-2-oxo-ethyl}-carbamic acid tert-butyl ester (0.150 g, 0.262 mmol), phenylboronic acid (0.042 g, 0.341 mmol) and 2N sodium carbonate solution (0.34 mL, 0.68 mmol) were stirred in DME (3 mL) and the mixture was degassed with $N_2$ for 15 minutes. Tetrakis(triphenylphosphine) palladium (0) (0.015 g, 0.013 mmol) was added and the mixture heated at 80° C. for 24 hours. The mixture was cooled to room temperature and partitioned between DCM and water. The aqueous layer was extracted with DCM. The combined organic layers were washed with saturated aqueous $NaHCO_3$ and brine, dried and concentrated. The residue was purified by flash chromatography on silica gel, eluting with hexanes:EtOAc (3:1 to 1:1) to give (2R)-{1-(4-chlorobenzyl)-2-oxo-2-[4-(5-phenylpyrimidin-4-yl)-piperazin-1-yl]-ethyl}-carbamic acid tert-butyl ester (0.074 g, 54%) as a colorless oil. $^1$H NMR ($CDCl_3$, 400 MHz) δ 8.65 (s, 1H), 8.21 (s, 1H), 7.46 (m, 2H), 7.38 (m, 2H), 7.25 (m, 3H), 7.09 (d, J=8.4 Hz, 2H), 5.30 (m, 1H), 4.73 (m, 1H), 3.50 (m, 1H), 3.43 (m, 1H), 3.30 (m, 2H), 3.16 (m, 2H), 2.97 (m, 1H), 2.91 (d, J=7.6 Hz, 2H), 2.85 (m, 1H), 1.39 (s, 9H). LCMS (APCI+) m/z 522, 524 [M+H]$^+$; Rt=2.72 minutes.

Step 2: (2R)-2-Amino-3-(4-chlorophenyl)-1-[4-(5-phenylpyrimidin-4-yl)-piperazin-1-yl]-propan-1-one dihydrochloride was prepared by the procedures described in Example 34, Step 3, substituting (2R)-{1-(4-chlorobenzyl)-2-[4-(1H-indazol-5-yl)-piperazin-1-yl]-2-oxo-ethyl}-carbamic acid tert-butyl ester with (2R)-{1-(4-chlorobenzyl)-2-oxo-2-[4-(5-phenylpyrimidin-4-yl)-piperazin-1-yl]-ethyl}-carbamic acid tert-butyl ester. $^1$H NMR ($CD_3OD$, 400 MHz) δ 8.75 (s, 1H), 8.20 (s, 1H), 7.56 (m, 3H), 7.44 (d, J=6.8 Hz, 2H), 7.37 (d, J=8.0 Hz, 2H), 7.25 (d, J=8.0 Hz, 2H), 4.62 (m, 1H), 3.47-3.54 (m, 6H), 3.38-3.44 (m, 4H). LCMS (APCI+) m/z 422, 424 [M+H]$^+$; Rt=2.40 minutes.

Example 42

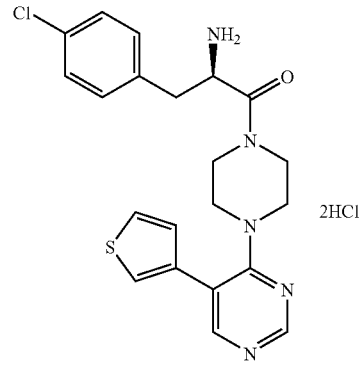 [SMILES: N[C@H](Cc1ccc(Cl)cc1)C(=O)N1CCN(c2ncncc2-c2ccsc2)CC1 ; "2HCl"]

Preparation of (2R)-2-Amino-3-(4-chlorophenyl)-1-[4-(5-thiophen-3-yl-pyrimidin-4-yl)-piperazin-1-yl]-propan-1-one dihydrochloride Step 1: (2R)-{1-(4-chlorobenzyl)-2-oxo-2-[4-(5-thiophen-3-yl-pyrimidin-4-yl)-piperazin-1-yl]-ethyl}-carbamic acid tert-butyl ester was prepared by the procedures described in Example 41, Step 1, substituting phenylboronic acid with 3-thiopheneboronic acid. $^1$H NMR ($CDCl_3$, 400 MHz) δ 8.64 (s, 1H), 8.27 (s, 1H), 7.46 (d, J=4.8 Hz, 1H), 7.33 (s, 1H), 7.26 (d, J=8.4 Hz, 21-1), 7.16 (d, J=4.8 Hz, 1H), 7.11 (d, J=8.4 Hz, 2H), 5.33 (m, 1H), 4.76 (m, 1H), 3.55 (m, 1H), 3.48 (m, 1), 3.27 (m, 2H), 3.16 (m, 2H), 2.98 (m, 1H), 2.92 (d, J=6.8 Hz, 2H), 2.82 (m, 1H), 1.40 (s, 9H). LCMS (APCI+) m/z 528, 530 [M+H]$^+$; Rt=2.75 minutes.

Step 2: (2R)-2-Amino-3-(4-chlorophenyl)-1-[4-(5-thiophen-3-yl-pyrimidin-4-yl)-piperazin-1-yl]-propan-1-one dihydrochloride was prepared by the procedures described in Example 34, Step 3, substituting (2R)-{1-(4-chlorobenzyl)-2-[4-(1H-indazol-5-yl)-piperazin-1-yl]-2-oxo-ethyl}-carbamic acid tert-butyl ester with (2R)-{1-(4-chlorobenzyl)-2-oxo-2-[4-(5-thiophen-3-yl-pyrimidin-4-yl)-piperazin-1-yl]-ethyl}-carbamic acid tert-butyl ester. $^1$H NMR ($CD_3OD$, 400 MHz) δ 8.74 (s, 1H), 8.24 (s, 1H), 7.70 (s, 1H), 7.65 (s, 1H), 7.39 (d, J=8.0 Hz, 2H), 7.27 (d, J=8.0 Hz, 2H), 7.22 (d, J=4.8 Hz, 1H), 4.62 (m, 1H), 3.48-3.55 (m, 6H), 3.38-3.44 (m, 4H). LCMS (APCI+) m/z 428, 430 [M+H]$^+$; Rt=2.76 minutes.

Example 43

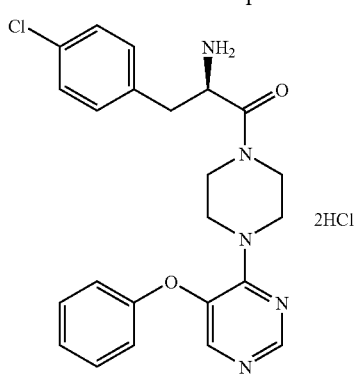

Preparation of (2R)-2-Amino-3-(4-chlorophenyl)-1-[4-(5-phenoxypyrimidin-4-yl)-piperazin-1-yl]-propan-1-one dihydrochloride A round bottom flask was charged with phenol (33 mg, 0.35 mmol), (2R)-{1-(4-chlorobenzyl)-2-[4-(5-iodopyrimidin-4-yl)-piperazin-1-yl]-2-oxo-ethyl}-carbamic acid tert-butyl ester (100 mg, 0.175 mmol), $Cs_2CO_3$ (114 mg, 0.350 mmol) and 2,2,6,6-tetramethyl-heptane-3,5-dione (8 mg, 0.25 equivalents). After vacuum purging and refilling of $N_2$, NMP (3 mL) and CuCl (9 mg, 0.09 mmol) was added to this mixture. The reaction was stirred at 130° C. for 2 hours. After cooling, the reaction was diluted with EtOAc and filtered. The filtrate was washed with water, brine and dried. Evaporation of the solvent followed by flash column chromatography (10:1 DCM/MeOH) gave the title compound as a free base, which was converted to dihydrochloride salt (36 mg, 38%) by treatment with 4N HCl in dioxane. $^1$H NMR ($CD_3OD$, 400 MHz) δ 8.64 (s, 1H), 7.96 (s, 1H), 7.70 (s, 1H), 7.65 (s, 1H), 7.49 (m, 2H), 7.37 (m, 2H), 7.29 (m, 3H), 7.14 (d, J=8.0 Hz, 2H), 4.70 (m, 1H), 4.11 (m, 2H), 4.00 (m, 1H), 3.76 (m, 2H), 3.57 (m, 2H), 3.10 (m, 3H). LCMS (APCI+) m/z 438, 440 [M+H]$^+$; Rt=2.13 minutes.

Example 44

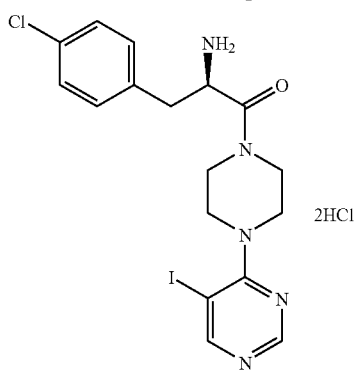 [SMILES: N[C@H](Cc1ccc(Cl)cc1)C(=O)N1CCN(c2ncncc2I)CC1 ; "2HCl"]

Preparation of (2R)-2-Amino-3-(4-chlorophenyl)-1-[4-(5-iodopyrimidin-4-yl)-piperazin-1-yl]-propan-1-one dihydrochloride The title compound was prepared by the procedures described in Example 34, Step 3, substituting (2R)-{1-(4-chlorobenzyl)-2-[4-(1H-indazol-5-yl)-piperazin-1-yl]-2-oxo-ethyl}-carbamic acid tert-butyl ester with (2R)-{1-(4-chlorobenzyl)-2-[4-(5-iodopyrimidin-4-yl)-piperazin-1-yl]-2-oxo-ethyl}-carbamic acid tert-butyl ester. $^1$H NMR ($CD_3OD$, 400 MHz) δ 8.77 (s, 1H), 8.73 (s, 1H), 7.41 (d, J=8.4 Hz, 2H), 7.33 (d, J=8.4 Hz, 2H), 4.74 (m, 1H), 4.05 (m, 2H), 3.95 (m, 1H), 3.84 (m, 1H), 3.69 (m, 3H), 3.22 (m, 1H), 3.13 (m, 2H). LCMS (APCI+) m/z 472, 474 [M+H]$^+$; Rt=2.06 minutes.

Example 45

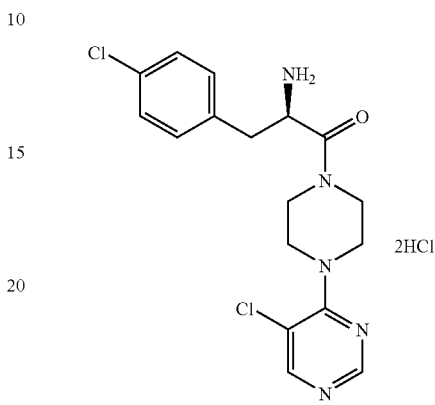

Preparation of (2R)-2-Amino-3-(4-chlorophenyl)-1-[4-(5-chloropyrimidin-4-yl)-piperazin-1-yl]-propan-1-one dihydrochloride Step 1: (2R)-{1-(4-chlorobenzyl)-2-[4-(5-chloropyrimidin-4-yl)-piperazin-1-yl]-2-oxo-ethyl}-carbamic acid tert-butyl ester was prepared by the procedures described in Example 40, Step 1, substituting 4-chloro-5-iodopyrimidine with 4,5-dichloropyrimidine (prepared from 5-chloropyrimidin-4-ol according to the literature: Chestfield J. et al. (1955) *J. Chem. Soc. Abstracts*, 3478-3481), and substituting 1-Boc piperazine with [1-(4-chlorobenzyl)-2-oxo-2-piperazin-1-yl-ethyl]-carbamic acid tert-butyl ester. $^1$H NMR ($CDCl_3$, 400 MHz) δ 8.57 (s, 1H), 8.32 (s, 1H), 7.27 (d, J=8.0 Hz, 2H), 7.15 (d, J=8.0 Hz, 2H), 5.36 (m, 1H), 4.85 (m, 1H), 3.50-3.80 (m, 6H), 3.24 (m, 2H), 2.98 (m, 2H), 1.43 (s, 9H). LCMS (APCI+) m/z 480, 482, 484 [M+H]$^+$; Rt=3.24 minutes.

Step 2: (2R)-2-Amino-3-(4-chlorophenyl)-1-[4-(5-chloropyrimidin-4-yl)-piperazin-1-yl]-propan-1-one dihydrochloride was prepared by the procedures described in Example 34, Step 3, substituting (2R)-{1-(4-chlorobenzyl)-2-[4-(1H-indazol-5-yl)-piperazin-1-yl]-2-oxo-ethyl}-carbamic acid tert-butyl ester with (2R)-{1-(4-chlorobenzyl)-2-[4-(5-chloropyrimidin-4-yl)-piperazin-1-yl]-2-oxo-ethyl}-carbamic acid tert-butyl ester. $^1$H NMR ($CD_3OD$, 400 MHz) δ 8.74 (s, 1H), 8.57 (s, 1H), 7.40 (d, J=7.6 Hz, 2H), 7.33 (d, J=7.6 Hz, 2H), 4.74 (m, 1H), 4.13 (m, 2H), 4.03 (m, 1H), 3.85 (m, 1H), 3.72 (m, 3H), 3.22 (m, 1H), 3.16 (m, 2H). LCMS (APCI+) m/z 380, 382, 384 [M+H]$^+$; Rt=2.01 minutes.

Example 46

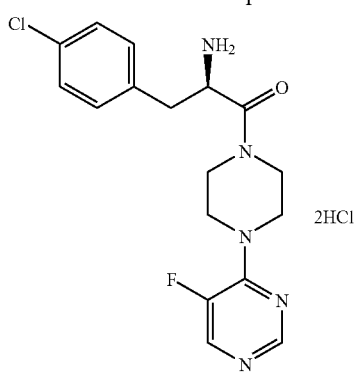

Preparation of (2R)-2-Amino-3-(4-chlorophenyl)-1-[4-(5-fluoropyrimidin-4-yl)-piperazin-1-yl]-propan-1-one dihydrochloride Step 1: (2R)-{1-(4-chlorobenzyl)-2-[4-(5-fluoropyrimidin-4-yl)-piperazin-1-yl]-2-oxo-ethyl}-carbamic acid tert-butyl ester was prepared by the procedures described in Example 40, Step 1, substituting 4-chloro-5-iodopyrimidine with 4-chloro-5-fluoropyrimidine (prepared from 5-fluoropyrimidin-4-ol according to the literature (Kheifets, G. M. et al., 2000, *Russian J. Org. Chem.*, 1373-1387), and substituting 1-Boc piperazine with [1-(4-chlorobenzyl)-2-oxo-2-piperazin-1-yl-ethyl]-carbamic acid tert-butyl ester. $^1$H NMR (CDCl$_3$, 400 MHz) δ 8.41 (d, J=2.8 Hz, 1H), 8.12 (d, J=6.4 Hz, 1H), 7.27 (d, J=8.0 Hz, 2H), 7.15 (d, J=8.0 Hz, 2H), 5.35 (m, 1H), 4.83 (m, 1H), 3.45-3.75 (m, 6H), 3.35 (m, 1H), 3.18 (m, 1H), 2.98 (d, J=7.2 Hz, 2H), 1.43 (s, 9H). LCMS (APCI+) m/z 464, 466 [M+H]$^+$; Rt=2.93 minutes.

Step 2: (2R)-2-Amino-3-(4-chlorophenyl)-1-[4-(5-fluoropyrimidin-4-yl)-piperazin-1-yl]-propan-1-one dihydrochloride was prepared by the procedures described in Example 34, Step 3, substituting (2R)-{1-(4-chlorobenzyl)-2-[4-(1H-indazol-5-yl)-piperazin-1-yl]-2-oxo-ethyl}-carbamic acid tert-butyl ester with (2R)-{1-(4-chlorobenzyl)-2-[4-(5-fluoropyrimidin-4-yl)-piperazin-1-yl]-2-oxo-ethyl}-carbamic acid tert-butyl ester. $^1$H NMR (CD$_3$OD, 400 MHz) δ 8.66 (s, 1H), 8.50 (s, 1H), 7.39 (d, J=8.0 Hz, 2H), 7.32 (d, J=8.0 Hz, 2H), 4.75 (m, 1H), 4.05 (m, 2H), 3.97 (m, 1H), 3.88 (m, 1H), 3.70 (m, 3H), 3.23 (m, 1H), 3.15 (m, 2H). LCMS (APCI+) m/z 364, 366 [M+H]$^+$; Rt=1.88 minutes.

Example 47

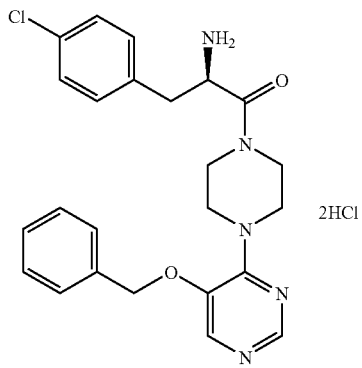 [SMILES: N[C@H](Cc1ccc(Cl)cc1)C(=O)N1CCN(c2ncncc2OCc2ccccc2)CC1 ; "2HCl"]

Preparation of (2R)-2-Amino-1-[4-(5-benzyloxypyrimidin-4-yl)-piperazin-1-yl]-3-(4-chlorophenyl)-propan-1-one dihydrochloride Step 1: A sealed tube charged with 4-(5-Iodo-pyrimidin-4-yl)-piperazine-1-carboxylic acid tert-butyl ester (780 mg, 2.00 mmol), CuI (38 mg, 0.20 mmol), 1,10-phenathroline (72 mg, 0.4 mmol), Cs$_2$CO$_3$ (912 mg, 2.8 mmol), benzyl alcohol (0.62 mL, 6.0 mmol) and toluene (2 mL) was heated at 110° C. for 40 hours. The resulting suspension was cooled to room temperature and filtered through a silica gel pad, eluting with EtOAc. Evaporation of the solvent followed by flash chromatography on silica gel (10:1 hexanes/EtOAc) provided 4-(5-benzyloxypyrimidin-4-yl)-piperazine-1-carboxylic acid tert-butyl ester (0.640 g, 86%) as a white solid. $^1$H NMR (CDCl$_3$, 400 MHz) δ 8.36 (s, 1H), 7.99 (s, 1H), 7.39 (m, 5H), 5.08 (s, 2H), 3.73 (m, 4H), 3.48 (m, 4H), 1.47 (s, 9H). LCMS (APCI+) m/z 371 [M+H]$^+$; Rt=2.52 minutes.

Step 2: 5-Benzyloxy-4-piperazin-1-yl-pyrimidine dihydrochloride was prepared by the procedures described in Example 34, Step 3, substituting (2R)-{1-(4-chlorobenzyl)-2-[4-(1H-indazol-5-yl)-piperazin-1-yl]-2-oxo-ethyl}-carbamic acid tert-butyl ester with 4-(5-Benzyloxypyrimidin-4-yl)-piperazine-1-carboxylic acid tert-butyl ester. LCMS (APCI+) m/z 271 [M+H]$^+$; Rt=1.64 minutes.

Step 3: (2R)-[2-[4-(5-Benzyloxypyrimidin-4-yl)-piperazin-1-yl]-1-(4-chlorobenzyl)-2-oxo-ethyl]-carbamic acid tert-butyl ester was prepared by the procedures described in Example 34, Step 2, substituting 5-Piperazin-1-yl-1H-indazole with 5-Benzyloxy-4-piperazin-1-yl-pyrimidine dihydrochloride. $^1$H NMR (CDCl$_3$, 400 MHz) δ 8.34 (s, 1H), 8.00 (s, 1H), 7.38 (m, 5H), 7.24 (d, J=8.0 Hz, 2H), 7.12 (d, J=8.0 Hz, 2H), 5.37 (d, J=8.8 Hz, 1H), 5.06 (s, 2H), 4.81 (m, 1H), 3.64 (m, 5H), 3.44 (m, 1H), 3.34 (m, 1H), 3.13 (m, 1H), 2.96 (m, 2H), 1.41 (s, 9H). LCMS (APCI+) m/z 552, 554 [M+H]$^+$; Rt=2.79 minutes.

Step 4: (2R)-2-Amino-1-[4-(5-benzyloxypyrimidin-4-yl)-piperazin-1-yl]-3-(4-chlorophenyl)-propan-1-one dihydrochloride was prepared by the procedures described in Example 34, Step 3, substituting (2R)-{1-(4-chlorobenzyl)-2-[4-(1H-indazol-5-yl)-piperazin-1-yl]-2-oxo-ethyl}-carbamic acid tert-butyl ester with (2R)-[2-[4-(5-benzyloxypyrimidin-4-yl)-piperazin-1-yl]-1-(4-chlorobenzyl)-2-oxo-ethyl]-carbamic acid tert-butyl ester. $^1$H NMR (CD$_3$OD, 400 MHz) δ 8.49 (s, 1H), 8.11 (s, 1H), 7.48 (m, 5H), 7.36 (d, J=8.4 Hz, 2H), 7.28 (d, J=8.4 Hz, 2H), 5.20 (s, 2H), 4.68 (m, 1H), 4.07 (m, 2H), 3.97 (m, 1H), 3.69 (m, 2H), 3.59 (m, 2H), 3.12 (m, 3H). LCMS (APCI+) m/z 452, 454 [M+H]$^+$; Rt=2.02 minutes.

Example 48

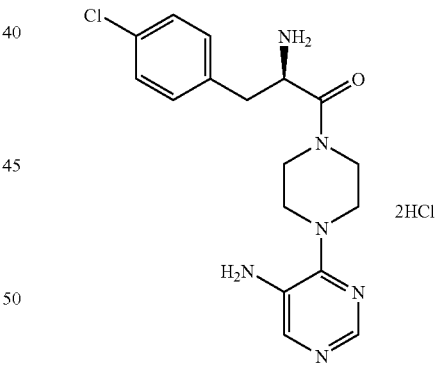

Preparation of (2R)-2-Amino-1-[4-(5-aminopyrimidin-4-yl)-piperazin-1-yl]-3-(4-chlorophenyl)-propan-1-one dihydrochloride Step 1: 4-Piperazin-1-yl-pyrimidin-5-ylamine dihydrochloride was prepared by the procedures described in Example 34, Step 3, substituting (2R)-{1-(4-chlorobenzyl)-2-[4-(1H-indazol-5-yl)-piperazin-1-yl]-2-oxo-ethyl}-carbamic acid tert-butyl ester with 4-(5-aminopyrimidin-4-yl)-piperazine-1-carboxylic acid tert-butyl ester (prepared from 4,6-dichloro-nitropyrimidine according to the procedures described in U.S. Pat. No. 5,563,142). LCMS (APCI+) m/z 180 [M+H]$^+$; Rt=1.12 minutes.

Step 2: (2R)-[2-[4-(5-aminopyrimidin-4-yl)-piperazin-1-yl]-1-(4-chlorobenzyl)-2-oxo-ethyl]-carbamic acid tert-butyl ester was prepared by the procedures described in Example 34, Step 2, substituting 5-Piperazin-1-yl-1H-indazole with 4-Piperazin-1-yl-pyrimidin-5-ylamine dihydrochloride. $^1$H NMR (CDCl$_3$, 400 MHz) δ 8.38 (s, 1H), 7.97 (s, 1H), 7.27 (d, J=8.0 Hz, 2H), 7.14 (d, J=8.0 Hz, 2H), 5.38 (d, J=8.4 Hz, 1H), 4.85 (m, 1H), 3.66 (m, 2H), 3.52 (m, 2H), 3.44 (s, 2H), 3.23 (m, 4H), 2.93 (m, 2H), 1.42 (s, 9H). LCMS (APCI+) m/z 461, 463 [M+H]$^+$; Rt=2.38 minutes.

Step 3: (2R)-2-Amino-1-[4-(5-aminopyrimidin-4-yl)-piperazin-1-yl]-3-(4-chlorophenyl)-propan-1-one dihydrochloride was prepared by the procedures described in Example 34, Step 3, substituting (2R)-{1-(4-chlorobenzyl)-2-[4-(1H-indazol-5-yl)-piperazin-1-yl]-2-oxo-ethyl}-carbamic acid tert-butyl ester with (2R)-[2-[4-(5-aminopyrimidin-4-yl)-piperazin-1-yl]-1-(4-chlorobenzyl)-2-oxo-ethyl]-carbamic acid tert-butyl ester. $^1$H NMR (CD$_3$OD, 400 MHz) δ 8.41 (s, 1H), 7.80 (s, 1H), 7.40 (d, J=8.4 Hz, 2H), 7.32 (d, J=8.4 Hz, 2H), 4.77 (m, 1H), 3.84 (m, 4H), 3.63 (m, 2H), 3.50 (m, 1H), 3.18 (m, 3H). LCMS (APCI+) m/z 361, 363 [M+H]$^+$; Rt=1.68 minutes.

Example 49

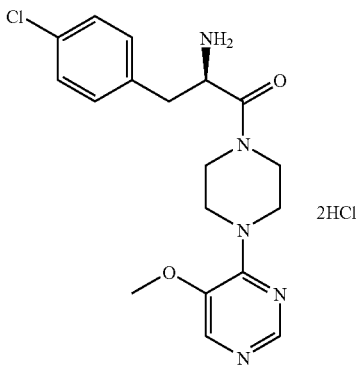 [SMILES: COc1cncnc1N1CCN(C(=O)[C@H](N)Cc2ccc(Cl)cc2)CC1 ; "2HCl"]

Preparation of (2R)-2-Amino-3-(4-chlorophenyl)-1-[4-(5-methoxypyrimidin-4-yl)-piperazin-1-yl]-propan-1-one dihydrochloride Step 1: To a stirred solution of 4-(5-benzyloxypyrimidin-4-yl)-piperazine-1-carboxylic acid tert-butyl ester (0.540 g, 1.46 mmol) in MeOH (20 mL) under N$_2$ was cautiously added 10% Pd on carbon (40 mg). The reaction vessel was evacuated under vacuum and then put under an atmosphere of hydrogen using a balloon. The mixture was stirred for 2 hours at room temperature. At this time the hydrogen gas was evacuated and the catalyst was removed by filtration. The filtrate was concentrated. The residue was purified by flash chromatography (1:1 hexanes/EtOAc) to give 4-(5-Hydroxypyrimidin-4-yl)-piperazine-1-carboxylic acid tert-butyl ester (0.390 g, 95%) as a white solid. $^1$H NMR (CDCl$_3$, 400 MHz) δ 8.18 (s, 1H), 7.75 (s, 1H), 3.93 (m, 4H), 3.54 (m, 4H), 1.41 (s, 9H). LCMS (APCI+) m/z 281 [M+H]$^+$; Rt=2.01 minutes.

Step 2: 4-Piperazin-1-yl-pyrimidin-5-ol dihydrochloride was prepared by the procedures described in Example 34, Step 3, substituting (2R)-{1-(4-chlorobenzyl)-2-[4-(1H-indazol-5-yl)-piperazin-1-yl]-2-oxo-ethyl}-carbamic acid tert-butyl ester with 4-(5-Hydroxypyrimidin-4-yl)-piperazine-1-carboxylic acid tert-butyl ester. LCMS (APCI+) m/z 181 [M+H]$^+$; Rt=1.15 minutes.

Step 3: (2R)-{1-(4-chlorobenzyl)-2-[4-(5-hydroxypyrimidin-4-yl)-piperazin-1-yl]-2-oxo-ethyl}-carbamic acid tert-butyl ester was prepared by the procedures described in Example 34, Step 2, substituting 5-Piperazin-1-yl-1H-indazole with 4-Piperazin-1-yl-pyrimidin-5-ol dihydrochloride. $^1$H NMR (CDCl$_3$, 400 MHz) δ 8.18 (s, 1H), 7.76 (s, 1H), 7.25 (d, J=8.0 Hz, 2H), 7.14 (d, J=8.0 Hz, 2H), 5.39 (d, J=8.4 Hz, 1H), 4.84 (m, 1H), 3.55-3.95 (m, 5H), 3.51 (m, 2H), 3.21 (m, 1H), 2.96 (m, 2H), 1.42 (s, 9H). LCMS (APCI+) m/z 462, 464 [M+H]$^+$; Rt=2.41 minutes.

A mixture of methyl iodide (18 mg, 0.13 mmol), K$_2$CO$_3$ (18 mg, 0.13 mmol) and (2R)-{1-(4-chlorobenzyl)-2-[4-(5-hydroxypyrimidin-4-yl)-piperazin-1-yl]-2-oxo-ethyl}-carbamic acid tert-butyl ester (50 mg, 0.11 mmol) in DMF (2 mL) was stirred at room temperature for 1 hour. The reaction mixture was diluted with water and extracted with EtOAc. The combined organic layers were washed with brine, dried and concentrated. The residue was purified by flash chromatography (hexanes:EtOAc, 1:1) to give (2R)-{1-(4-chlorobenzyl)-2-[4-(5-methoxypyrimidin-4-yl)-piperazin-1-yl]-2-oxo-ethyl}-carbamic acid tert-butyl ester (20 mg, 39%) as a colorless oil. $^1$H NMR (CDCl$_3$, 400 MHz) δ 8.34 (s, 1H), 7.94 (s, 1H), 7.26 (d, J=8.4 Hz, 2H), 7.14 (d, J=8.4 Hz, 2H), 5.37 (d, J=8.4 Hz, 1H), 4.84 (m, 1H), 3.87 (s, 3H), 3.65 (m, 5H), 3.48 (m, 1H), 3.33 (m, 1H), 3.20 (m, 1H), 2.96 (m, 2H), 1.42 (s, 9H). LCMS (APCI+) m/z 476, 478 [M+H]$^+$; Rt=2.44 minutes.

(2R)-2-Amino-3-(4-chlorophenyl)-1-[4-(5-methoxypyrimidin-4-yl)-piperazin-1-yl]-propan-1-one dihydrochloride was prepared by the procedures described in Example 34, Step 3, substituting (2R)-{1-(4-chlorobenzyl)-2-[4-(1H-indazol-5-yl)-piperazin-1-yl]-2-oxo-ethyl}-carbamic acid tert-butyl ester with (2R)-{1-(4-chlorobenzyl)-2-[4-(5-methoxypyrimidin-4-yl)-piperazin-1-yl]-2-oxo-ethyl}-carbamic acid tert-butyl ester $^1$H NMR (CD$_3$OD, 400 MHz) δ 8.50 (s, 1H), 8.01 (s, 1H), 7.38 (d, J=8.0 Hz, 2H), 7.32 (d, J=8.0 Hz, 2H), 4.75 (m, 1H). 4.12 (m, 2H), 4.04 (m, 1H), 3.97 (s, 3H), 3.81 (m, 2H), 3.67 (m, 2H), 3.16 (m, 3H). LCMS (APCI+) m/z 376, 378 [M+H]$^+$; Rt=1.77 minutes.

Example 50

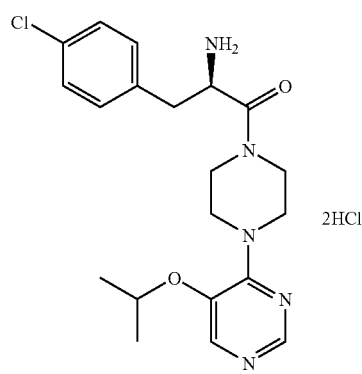 [SMILES: CC(C)Oc1cncnc1N1CCN(C(=O)[C@H](N)Cc2ccc(Cl)cc2)CC1 ; "2HCl"]

Preparation of (2R)-2-Amino-3-(4-chlorophenyl)-1-[4-(5-isopropoxypyrimidin-4-yl)-piperazin-1-yl]-propan-1-one dihydrochloride Step 1: (2R)-{1-(4-chlorobenzyl)-2-[4-(5-isopropoxypyrimidin-4-yl)-piperazin-1-yl]-2-oxo-ethyl}-carbamic acid tert-butyl ester was prepared by the procedures described in Example 49, Step 2, substituting methyl iodide with isopropyl bromide. $^1$H NMR (CDCl$_3$, 400 MHz) δ 8.33 (s, 1H), 7.94 (s, 1H), 7.26 (d, J=8.0 Hz, 2H), 7.14 (d, J=8.0 Hz, 2H), 5.39 (d, J=8.8 Hz, 1H), 4.84 (m, 1H), 4.48 (m, 1H), 3.63 (m, 5H), 3.48 (m, 1H), 3.33 (m, 1H), 3.14 (m, 1H), 2.97 (m, 2H), 1.42 (s, 9H), 1.34 (d, J=6.4 Hz, 6H). LCMS (APCI+) m/z 504, 506 [M+H]$^+$; Rt=2.61 minutes.

Step 2: (2R)-2-Amino-3-(4-chlorophenyl)-1-[4-(5-isopropoxypyrimidin-4-yl)-piperazin-1-yl]-propan-1-one dihydrochloride was prepared by the procedures described in Example 34, Step 3, substituting (2R)-{1-(4-chlorobenzyl)-2-[4-(1H-indazol-5-yl)-piperazin-1-yl]-2-oxo-ethyl}-carbamic acid tert-butyl ester with (2R)-{1-(4-chlorobenzyl)-2-[4-(5-isopropoxypyrimidin-4-yl)-piperazin-1-yl]-2-oxo-ethyl}-carbamic acid tert-butyl ester. $^1$H NMR (CD$_3$OD, 400 MHz) δ 8.47 (s, 1H), 8.03 (s, 1H), 7.39 (d, J=8.0 Hz, 2H), 7.33 (d, J=8.0 Hz, 2H), 4.73 (m, 2H), 4.13 (m, 2H), 4.02 (m, 1H), 3.81 (m, 2H), 3.66 (m, 2H), 3.17 (m, 3H), 1.42 (d, J=6.4 Hz, 6H). LCMS (APCI+) m/z 404, 406 [M+H]$^+$; Rt=1.86 minutes.

Example 51

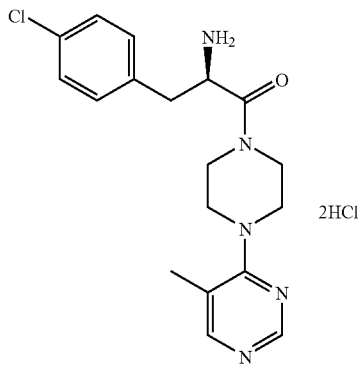 [SMILES: Cc1cncnc1N1CCN(C(=O)[C@H](N)Cc2ccc(Cl)cc2)CC1 ; "2HCl"]

Preparation of (2R)-2-Amino-3-(4-chlorophenyl)-1-[4-(5-methylpyrimidin-4-yl)-piperazin-1-yl]-propan-1-one dihydrochloride Step 1: A mixture of (2R)-{1-(4-chlorobenzyl)-2-[4-(5-iodopyrimidin-4-yl)-piperazin-1-yl]-2-oxo-ethyl}-carbamic acid tert-butyl ester (0.070 g, 0.12 mmol), methylboronic acid (0.022 g, 0.37 mmol), K$_2$CO$_3$ (0.085 g, 0.61 mmol) and PdCl$_2$(PPh$_3$)$_2$ (0.0086 g, 0.012 mmol) in DMF (2 mL) was heated at 100° C. for 16 hours under nitrogen. The mixture was cooled to room temperature and partitioned between EtOAc and water. The organic layer was washed with saturated aqueous NaHCO$_3$ and brine, dried and concentrated. The residue was purified by flash chromatography on silica gel, eluting with DCM/MeOH (70:1) to give (2R)-{1-(4-chlorobenzyl)-2-[4-(5-methylpyrimidin-4-yl)-piperazin-1-yl]-2-oxo-ethyl}-carbamic acid tert-butyl ester (0.022 g, 39%) as a colorless oil. $^1$H NMR (CDCl$_3$, 400 MHz) δ 8.62 (s, 1H), 8.20 (s, 1H), 7.26 (d, J=8.0 Hz, 2H), 7.14 (d, J=8.0 Hz, 2H), 5.37 (d, J=8.4 Hz, 1H), 4.84 (m, 1H), 3.70 (m, 1H), 3.60 (m, 1H), 3.42 (m, 1H), 3.32 (m, 4H), 3.02 (m, 3H), 2.20 (s, 3H), 1.42 (s, 9H). LCMS (APCI+) m/z 460, 462 [M+H]$^+$; Rt=2.38 minutes.

Step 2: (2R)-2-Amino-3-(4-chlorophenyl)-1-[4-(5-methylpyrimidin-4-yl)-piperazin-1-yl]-propan-1-one dihydrochloride was prepared by the procedures described in Example 34, Step 3, substituting (2R)-{1-(4-chlorobenzyl)-2-[4-(1H-indazol-5-yl)-piperazin-1-yl]-2-oxo-ethyl}-carbamic acid tert-butyl ester with (2R)-{1-(4-chlorobenzyl)-2-[4-(5-methylpyrimidin-4-yl)-piperazin-1-yl]-2-oxo-ethyl}-carbamic acid tert-butyl ester. $^1$H NMR (CD$_3$OD, 400 MHz) δ 8.65 (s, 1H), 8.13 (s, 1H), 7.39 (d, J=8.4 Hz, 2H), 7.32 (d, J=8.4 Hz, 2H), 4.73 (m, 1H), 3.40 (m, 2H), 3.96 (m, 1H), 3.80 (m, 1H), 3.67 (m, 3H), 3.21 (m, 1H), 3.14 (m, 2H). LCMS (APCI+) m/z 360, 362 [M+H]$^+$; Rt=1.70 minutes.

Example 52

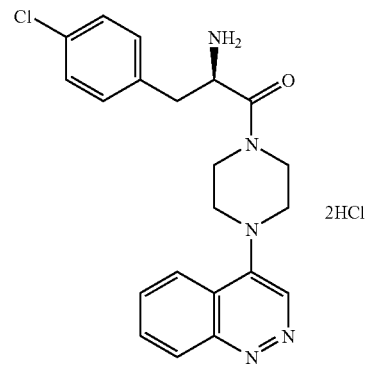 [SMILES: N[C@H](Cc1ccc(Cl)cc1)C(=O)N1CCN(c2cnnc3ccccc23)CC1 ; "2HCl"]

Preparation of (2R)-2-Amino-3-(4-chlorophenyl)-1-(4-cinnolin-4-yl-piperazin-1-yl)-propan-1-one dihydrochloride Step 1: To a suspension of NaH (60% in mineral oil, 0.099 g, 2.46 mmol) in DMF (5 mL) was added cinnolin-4-ol (prepared from 2-aminoacetophenone according to the procedures described in U.S. Pat. No. 4,620,000), 0.300 g, 2.05 mmol) in DMF (2 mL) dropwise. The reaction mixture was warmed at 40° C. and stirred for 30 minutes. After cooling, N-phenyltrifluoromethanesulfonimide (0.880 g, 2.46 mmol) in DMF (2 mL) was added, and the reaction mixture was stirred at room temperature for 1 hour. 1-Boc piperazine (0.765 g, 4.11 mmol) was added to the mixture. The reaction was stirred at 80° C. for 4 hours. After cooling, the mixture was partitioned between EtOAc and water. The aqueous phase was extracted with EtOAc. The combined organic layers were washed with water, brine, dried and concentrated. The residue was purified by column chromatography (1:1 to 1:3 hexanes/EtOAc) to give 4-Cinnolin-4-yl-piperazine-1-carboxylic acid tert-butyl ester (0.246 g, 38%) as a yellow oil. $^1$H NMR (CDCl$_3$, 400 MHz) δ 8.91 (s, 1H), 8.47 (d, J=8.4 Hz, 1H), 7.97 (d, J=8.4 Hz, 1H), 7.80 (t, J=7.2 Hz, 1H), 7.69 (t, J=7.2 Hz, 1H), 3.74 (m, 4H), 3.34 (m, 4H), 1.51 (s, 9H). LCMS (APCI+) m/z 315 [M+H]$^+$; Rt=2.14 minutes.

Step 2: 4-Piperazin-1-yl-cinnoline dihydrochloride was prepared by the procedures described in Example 34, Step 3, substituting (2R)-{1-(4-chlorobenzyl)-2-[4-(1H-indazol-5-yl)-piperazin-1-yl]-2-oxo-ethyl}-carbamic acid tert-butyl ester with 4-Cinnolin-4-yl-piperazine-1-carboxylic acid tert-butyl ester. $^1$H NMR (CD$_3$OD, 400 MHz) δ 8.96 (s, 1H), 8.33 (d, J=8.8 Hz, 1H), 8.15 (t, J=7.2 Hz, 1H), 8.07 (d, J=8.4 Hz, 1H), 7.88 (t, J=7.2 Hz, 1H), 4.42 (m, 4H), 3.64 (m, 4H). LCMS (APCI+) m/z 215 [M+H]$^+$; Rt=1.46 minutes.

Step 3: (2R)-[1-(4-chlorobenzyl)-2-(4-cinnolin-4-yl-piperazin-1-yl)-2-oxo-ethyl]carbamic acid tert-butyl ester was prepared by the procedures described in Example 34, Step 2, substituting 5-Piperazin-1-yl-1H-indazole with 4-Piperazin-1-yl-cinnoline dihydrochloride. $^1$H NMR (CDCl$_3$, 400 MHz) δ 8.82 (s, 1H), 8.48 (d, J=8.4 Hz, 1H), 7.89 (d, J=8.4 Hz, 1H), 7.80 (t, J=7.2 Hz, 1H), 7.70 (t, J=7.2 Hz, 1H), 7.31 (d, J=8.4 Hz, 2H), 7.18 (d, J=8.4 Hz, 2H), 5.36 (m, 1H), 4.88 (m, 1H), 3.85 (m, 2H), 3.69 (m, 1H), 3.40 (m, 1H), 3.28 (m, 1H), 3.17 (m, 2H), 3.01 (d, J=7.2 Hz, 2H), 2.78 (m, 1H), 1.43 (s, 9H). LCMS (APCI+) m/z 496, 498 [M+H]$^+$; Rt=2.44 minutes.

Step 4: (2R)-2-Amino-3-(4-chlorophenyl)-1-(4-cinnolin-4-yl-piperazin-1-yl)-propan-1-one dihydrochloride was prepared by the procedures described in Example 34, Step 3, substituting (2R)-{1-(4-chlorobenzyl)-2-[4-(1H-indazol-5-yl)-piperazin-1-yl]-2-oxo-ethyl}-carbamic acid tert-butyl ester with (2R)-[1-(4-chlorobenzyl)-2-(4-cinnolin-4-yl-piperazin-1-yl)-2-oxo-ethyl]carbamic acid tert-butyl ester. $^1$H-NMR (CD$_3$OD, 400 MHz) δ 8.75 (s, 1H), 8.27 (d, J=8.4 Hz, 1H), 8.10 (t, J=7.2 Hz, 1H), 7.99 (d, J=8.4 Hz, 1H), 7.82 (t, J=7.2 Hz, 1H), 7.42 (d, J=8.0 Hz, 2H), 7.34 (d, J=8.0 Hz, 2H), 4.74 (m, 1H), 4.19 (m, 3H), 3.89 (m, 4H), 3.41 (m, 1H), 3.18 (d, J=7.6 Hz, 2H). LCMS (APCI+) m/z 396, 398 [M+H]$^+$; Rt=2.46 minutes.

Example 53

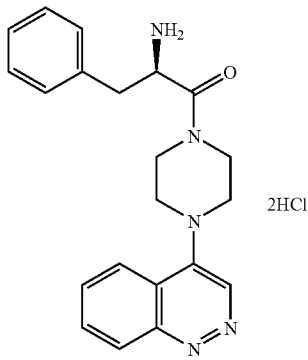 [SMILES: N[C@H](Cc1ccccc1)C(=O)N1CCN(c2cnnc3ccccc23)CC1 ; "2HCl"]

Preparation of (2R)-2-Amino-1-(4-cinnolin-4-yl-piperazin-1-yl)-3-phenylpropan-1-one dihydrochloride Step 1: (2R)-[1-Benzyl-2-(4-cinnolin-4-yl-piperazin-1-yl)-2-oxo-ethyl]-carbamic acid tert-butyl ester was prepared by the procedures described in Example 34, Step 2, substituting 5-Piperazin-1-yl-1H-indazole with 4-Piperazin-1-yl-cinnoline dihydrochloride, and substituting (D)-Boc-4-chlorophenylalanine with (D)-Boc-phenylalanine. $^1$H NMR (CDCl$_3$, 400 MHz) δ 8.73 (s, 1H), 8.46 (d, J=8.4 Hz, 1H), 7.85 (d, J=8.4 Hz, 1H), 7.79 (t, J=8.0 Hz, 1H), 7.68 (t, J=8.0 Hz, 1H), 7.29 (m, 5H), 5.42 (d, J=8.4 Hz, 1H), 4.91 (m, 1H), 3.89 (m, 1H), 3.67 (m, 1H), 3.57 (m, 1H), 3.32 (m, 2H), 3.08 (m, 2H), 2.99 (m, 2H), 2.32 (m, 1H), 1.45 (s, 9H). LCMS (APCI+) m/z 462 [M+H]$^+$; Rt=2.30 minutes.

Step 2: (2R)-2-Amino-1-(4-cinnolin-4-yl-piperazin-1-yl)-3-phenylpropan-1-one dihydrochloride was prepared by the procedures described in Example 34, Step 3, substituting (2R)-{1-(4-chlorobenzyl)-2-[4-(1H-indazol-5-yl)-piperazin-1-yl]-2-oxo-ethyl}-carbamic acid tert-butyl ester with (2R)-[1-Benzyl-2-(4-cinnolin-4-yl-piperazin-1-yl)-2-oxo-ethyl]-carbamic acid tert-butyl ester. $^1$H NMR (CD$_3$OD, 400 MHz) δ 8.72 (s, 1H), 8.25 (d, J=8.4 Hz, 1H), 8.09 (t, J=8.0 Hz, 1H), 7.99 (d, J=8.4 Hz, 1H), 7.80 (t, J=8.0 Hz, 1H), 7.37 (m, 2H), 4.75 (m, 1H), 4.24 (m, 1H), 4.12 (m, 2H), 3.89 (m, 3H), 3.65 (m, 1H), 3.23 (m, 3H). LCMS (APCI+) m/z 362 [M+H]$^+$; Rt=2.38 minutes.

Example 54

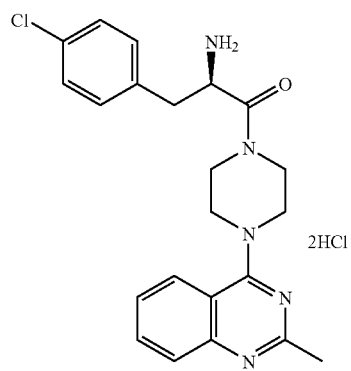 [SMILES: Cc1nc(N2CCN(C(=O)[C@H](N)Cc3ccc(Cl)cc3)CC2)c2ccccc2n1 ; "2HCl"]

Preparation of (2R)-2-Amino-3-(4-chlorophenyl)-1-[4-(2-methylquinazolin-4-yl)-piperazin-1-yl]-propan-1-one-dihyrdochlorie Step 1: (2R)-{1-(4-chlorobenzyl)-2-[4-(2-methylquinazolin-4-yl)-piperazin-1-yl]-2-oxo-ethyl}-carbamic acid tert-butyl ester was prepared by the procedures described in Example 40, Step 1, substituting 4-chloro-5-iodopyrimidine with 4-chloro-2-methylquinazoline, and substituting 1-Boc piperazine with [1-(4-chlorobenzyl)-2-oxo-2-piperazin-1-yl-ethyl]-carbamic acid tert-butyl ester. $^1$H NMR (CDCl$_3$, 400 MHz) δ 7.84 (d, J=8.4 Hz, 1H), 7.77 (d, J=8.4 Hz, 1H), 7.71 (t, J=8.4 Hz, 1H), 7.41 (t, J=8.4 Hz, 1H), 7.28 (d, J=8.4 Hz, 2H), 7.16 (d, J=8.4 Hz, 2H), 5.37 (d, J=8.4 Hz, 1H), 4.87 (m, 1H), 3.73 (m, 3H), 3.60 (m, 4H), 3.29 (m, 2H), 2.98 (m, 2H), 2.84 (s, 3H), 1.43 (s, 9H). LCMS (APCI+) m/z 510, 512 [M+H]$^+$; Rt=2.50 minutes.

Step 2: (2R)-2-Amino-3-(4-chlorophenyl)-1-[4-(2-methylquinazolin-4-yl)-piperazin-1-yl]-propan-1-one dihydrochloride was prepared by the procedures described in Example 34, Step 3, substituting (2R)-{1-(4-chlorobenzyl)-2-[4-(1H-indazol-5-yl)-piperazin-1-yl]-2-oxo-ethyl}-carbamic acid tert-butyl ester with (2R)-{1-(4-chlorobenzyl)-2-[4-(2-methylquinazolin-4-yl)-piperazin-1-yl]-2-oxo-ethyl}-carbamic acid tert-butyl ester. $^1$H NMR (CD$_3$OD, 400 MHz) δ 8.19 (d, J=8.0 Hz, 1H), 8.01 (t, J=8.0 Hz, 1H), 7.77 (d, J=8.0 Hz, 1H), 7.72 (t, J=8.0 Hz, 1H), 7.40 (d, J=8.4 Hz, 2H), 7.34 (d, J=8.4 Hz, 2H), 4.76 (m, 1H), 4.27 (m, 2H), 4.19 (m, 1H), 3.70-3.95 (m, 4H), 3.17 (m, 3H). LCMS (APCI+) m/z 410, 412 [M+H]⁺; Rt=1.80 minutes.

Example 55

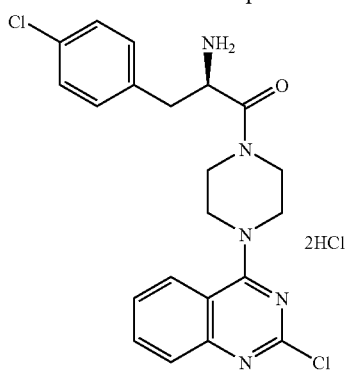

Preparation of (2R)-2-Amino-3-(4-chlorophenyl)-1-[4-(2-chloroquinazolin-4-yl)-piperazin-1-yl]-propan-1-one dihydrochloride Step 1: (2R)-{1-(4-chlorobenzyl)-2-[4-(2-chloroquinazolin-4-yl)-piperazin-1-yl]-2-oxo-ethyl}-carbamic acid tert-butyl ester was prepared by the procedures described in Example 40, Step 1, substituting 4-chloro-5-iodopyrimidine with 2,4-dichloroquinazoline, and substituting 1-Boc piperazine with [1-(4-chlorobenzyl)-2-oxo-2-piperazin-1-yl-ethyl]-carbamic acid tert-butyl ester. $^1$H NMR (CDCl$_3$, 400 MHz) δ 7.84 (d, J=8.0 Hz, 1H), 7.77 (m, 2H), 7.47 (t, J=8.0 Hz, 1H), 7.29 (d, J=8.4 Hz, 2H), 7.16 (d, J=8.4 Hz, 2H), 5.35 (d, J=8.8 Hz, 1H), 4.84 (m, 1H), 3.74 (m, 5H), 3.40 (m, 1H), 3.31 (m, 1H), 2.99 (d, J=8.0 Hz, 2H), 1.43 (s, 9H). LCMS (APCI+) m/z 530, 532, 534 [M+H]⁺; Rt=3.74 minutes.

Step 2: (2R)-2-Amino-3-(4-chlorophenyl)-1-[4-(2-chloroquinazolin-4-yl)-piperazin-1-yl]-propan-1-one dihydrochloride was prepared by the procedures described in Example 34, Step 3, substituting (2R)-{1-(4-chlorobenzyl)-2-[4-(1H-indazol-5-yl)-piperazin-1-yl]-2-oxo-ethyl}-carbamic acid tert-butyl ester with (2R)-{1-(4-chlorobenzyl)-2-[4-(2-chloroquinazolin-4-yl)-piperazin-1-yl]-2-oxo-ethyl}-carbamic acid tert-butyl ester. $^1$H NMR (CD$_3$OD, 400 MHz) δ 8.16 (d, J=8.4 Hz, 1H), 7.97 (t, J=8.4 Hz, 1H), 7.74 (d, J=8.4 Hz, 1H), 7.69 (t, J=8.4 Hz, 1H), 7.40 (d, J=8.0 Hz, 2H), 7.33 (d, J=8.0 Hz, 2H), 4.74 (m, 1H), 4.14 (m, 2H), 4.06 (m, 1H), 3.91 (m, 1H), 3.78 (m, 3H), 3.33 (m, 1H), 3.17 (m, 2H. LCMS (APCI+) m/z 430, 432, 434 [M+H]⁺; Rt=2.24 minutes.

Example 56

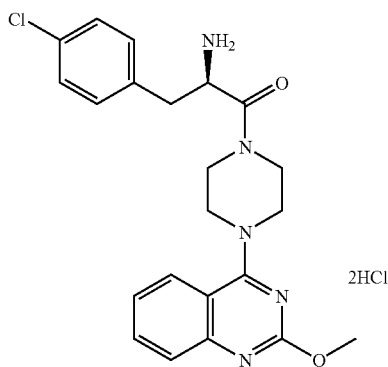 [SMILES: COc1nc(N2CCN(C(=O)[C@H](N)Cc3ccc(Cl)cc3)CC2)c2ccccc2n1 ; "2HCl"]

Preparation of (2R)-2-Amino-3-(4-chlorophenyl)-1-{4-(2-methoxyquinazolin-4-yl)-piperazin-1-one dihydrochloride To a solution of (2R)-{1-(4-chlorobenzyl)-2-[4-(2-chloroquinazolin-4-yl)-piperazin-1-yl]-2-oxo-ethyl}-carbamic acid tert-butyl ester (23 mg, 0.043 mmol) in MeOH (1 mL) was added 4N HCl in dioxane (1 mL). The mixture was stirred at room temperature for 2 days and then evaporated to give the title compound (14 mg, 65%) as a white solid. $^1$H NMR (CD$_3$OD, 400 MHz) δ 8.17 (d, J=7.2 Hz, 1H), 7.94 (t, J=7.2 Hz, 1H), 7.60 (d, J=8.0 Hz, 2H), 7.39 (m, 4H), 4.75 (m, 1H), 4.10-4.35 (m, 6H), 3.86 (m, 4H), 3.17 (m, 3H). LCMS (APCI+) m/z 426, 428 [M+H]⁺; Rt=1.86 minutes.

Example 57

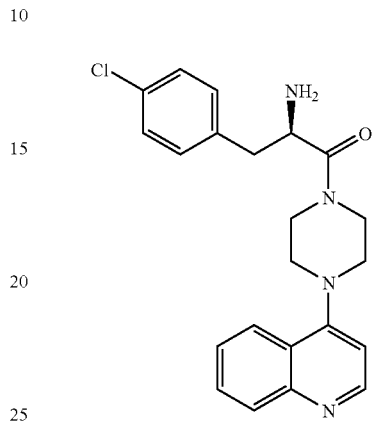

Preparation of (2R)-2-Amino-3-(4-chlorophenyl)-1-(4-quinolin-4-yl-piperazin-1-yl)-propan-1-one Step 1: To a solution of 4-chloroquinoline (2.0 g, 12.2 mmol) in toluene (100 mL) was added piperazine (7.98 g, 92.7 mmol). The reaction mixture was heated to reflux and stirred for 96 hours, after which it was cooled to room temperature and then further cooled to 0° C. The resulting mixture was filtered to remove the hydrochloride salts that had precipitated. After washing the salts with toluene, the combined filtrate was washed with 10% aqueous acetic acid (2×25 mL). The combined aqueous extracts were washed with diethyl ether (25 mL) and then basified to pH 8-10 by adding 1M NaOH. The resulting aqueous mixture was extracted with dichloromethane (3×25 mL). The combined organic extracts were dried (Na$_2$SO$_4$), filtered, and concentrated by rotary evaporation. The crude residue, 4-Piperazinylquinoline, was obtained as a yellow solid (2.54 g, 97%) and used without further purification. $^1$H NMR was consistent with that reported in the literature (Abel, M. D., et al., *Journal of Heterocyclic Chemistry* (1996), 33(2), 415-420).

Step 2: To a Jones tube containing PS-CDI (Argonaut, 1.04 mmol/g, 2.2 equivalents) suspended in a solution of 4-Piperazinylquinoline (1.0 equivalent) in CHCl$_3$ was added the solid Boc-protected amino acid (1.5 equivalents). The reaction mixture was shaken for 15 hours at room temperature, after which it was vacuum filtered, the resin rinsed with CHCl$_3$, and the filtrate concentrated by rotary evaporation. If necessary, the crude coupled product was purified on silica (DCM/EtOAc or DCM/MeOH). The resulting Boc-amino amide was dissolved in minimal dioxane, and 4M HCl/dioxane (10 equivalents) was added. The suspension was sonicated 5 minutes and stirred at room temperature for 12 hours, after which it as concentrated by rotary evaporation. The solids were dispersed in ether, isolated by filtration with nitrogen pressure, and dried under reduced pressure to give the corresponding amino amide as the hydrochloride salt, which was 90% pure by HPLC analysis. R$_t$ 2.36. MS (APCI+) [M+H]⁺395. R$_t$ 2.36. MS (APCI+) [M+H]⁺395.

Example 58

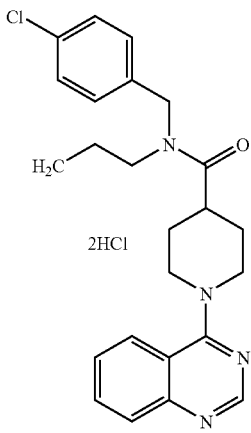 [SMILES: CCCN(Cc1ccc(Cl)cc1)C(=O)C1CCN(c2ncnc3ccccc23)CC1 ; "2HCl"]

Preparation of 1-Quinazolin-4-yl-piperidine-4-carboxylic acid (2-amino-ethyl)-(4-chlorobenzyl)-amide dihydrochloride Step 1: Triethylamine (12.7 mL, 91.1 mmol) was added to a solution of 4-chloro-quinazoline (5.00 g, 30.4 mmol) and ethyl isonipecotate (4.78 g, 30.4 mmol) in THF (80 mL) at ambient temperature. After being refluxed for 12 hours, the mixture was concentrated in vacuo, and the resulting residue was partitioned between DCM and aqueous 0.1 M NaOH. The separated DCM layer was dried ($Na_2SO_4$), filtered, and concentrated in vacuo. The resulting solids were suspended in $Et_2O$ and filtered to give 1-quinazolin-4-yl-piperidine-4-carboxylic acid ethyl ester (8.0 g, 28.0 mmol). This material was dissolved in EtOH (50 mL) and THF (50 mL) followed by the addition of NaOH (3.73 g, 93.4 mmol) in $H_2O$ (50 mL). After being stirred for 12 hours, the mixture was neutralized with 1.0N HCl (93.5 mL) and concentrated in vacuo. After the volatile organics are removed, a white precipitate forms in the resulting aqueous solution. The solid was filtered off and air-dried to give 1-quinazolin-4-yl-piperidine-4-carboxylic acid (6.5 g). $^1$H NMR (DMSO-$d_6$, 400 MHz) δ 12.28 (bs, 1H), 8.57 (s, 1H), 7.91 (m, 1H), 7.75 (m, 2H), 7.49 (m, 1H), 4.13 (m, 2H), 3.22 (m, 2H), 2.57 (m, 1H), 1.93 (m, 2H), 1.72 (m, 2H).

Step 2: Thionyl chloride (1.37 mL, 18.8 mmol) was added to a suspension of 1-quinazolin-4-yl-piperidine-4-carboxylic acid (2.20 g, 8.55 mmol) in DCM (40 mL), which results in a clear solution. After being stirred for 2 hours, a precipitate forms and was filtered off to give 1-quinazolin-4-yl-piperidine-4-carbonyl chloride hydrochloride as a white solid (2.0 g).

Step 3: A solution of tert-butyl N-(2-aminoethyl)carbamate (1.00 g, 6.24 mmol) and 4-chlorobenzaldehyde (0.90 g, 6.37 mmol) in DCE (10 mL) was stirred for 30 minutes, followed by the addition of NaBH(OAc)$_3$ (1.98 g, 9.36 mmol) in a single portion. After being stirred for 12 hours, the mixture was acidified to pH 2 with 0.2N HCl, and extracted with DCM (3 times, each discarded). The acidic aqueous layer was basified to pH 10 with 2.0 M NaOH, and extracted with DCM. The DCM extracts were dried ($Na_2SO_4$), filtered, and concentrated in vacuo to give [2-(4-chlorobenzylamino)-ethyl]-carbamic acid tert-butyl ester as an oil (1.0 g). LCMS (APCI+) m/z 285, 287 [M+H]$^+$.

Step 1-Quinazolin-4-yl-piperidine-4-carbonyl chloride hydrochloride (197 mg, 0.63 mmol) was added to a solution of [2-(4-chlorobenzylamino)-ethyl]-carbamic acid tert-butyl ester (180 mg, 0.63 mmol) and DMAP (154 mg, 1.26 mmol) in DCM (6.5 mL) cooled in an ice bath. After being stirred for 12 hours, the mixture was partitioned between DCM (50 mL) and $H_2O$ (80 mL) containing 1 mL of 1.0 M HCl. The DCM layer was drained off and the acidic aqueous layer was extracted 3 more times with DCM. The combined DCM extracts were dried ($Na_2SO_4$), filtered, and concentrated in vacuo. The crude material was chromatographed ($SiO_2$) using EtOAc as eluent to give {2-[(4-chlorobenzyl)-(1-quinazolin-4-yl-piperidine-4-carbonyl)-amino]-ethyl}-carbamic acid tert-butyl ester (190 mg).

Step 5: 1 {2-[(4-Chlorobenzyl)-(1-quinazolin-4-yl-piperidine-4-carbonyl)-amino]-ethyl}-carbamic acid tert-butyl ester (190 mg, 0.36 mmol) was dissolved in DCM (5 mL) followed by the addition of 2.0 M HCl in $Et_2O$ (2 mL). After being stirred for 12 hours, the mixture was diluted with DCE and concentrated in vacuo. The resulting white solid was then suspended in MeCN and concentrated in vacuo (repeated twice) to give 1-quinazolin-4-yl-piperidine-4-carboxylic acid (2-amino-ethyl)-(4-chlorobenzyl)-amide dihydrochloride as a white powder (120 mg). $^1$H NMR (DMSO-$d_6$, 400 MHz) δ 8.83 (m, 1H), 8.51 (bs, 2H), 8.20 (m, 2H), 8.01 (m, 2H), 7.71 (m, 1H), 7.48 (d, J=8.3 Hz, 1H), 7.39 (d, J=8.3 Hz, 1H), 7.31 (d, J=8.3 Hz, 1H), 7.25 (d, J=8.3 Hz, 1H), 4.79 (m, 2H), 4.55 (s, 1H), 3.59 (m, 7H), 3.03 (m, 1H), 2.90 (m, 1H), 1.92 (m, 4H). LCMS (APCI+) m/z 424, 426 [M+H]$^+$.

Example 59

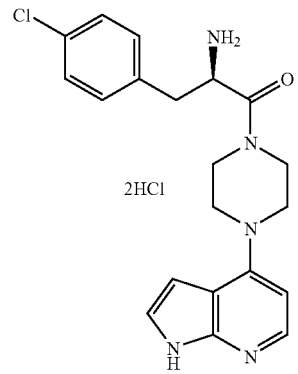 [SMILES: N[C@H](Cc1ccc(Cl)cc1)C(=O)N1CCN(c2ccnc3[nH]ccc23)CC1 ; "2HCl"]

Preparation of 2-(R)-Amino-3-(4-chlorophenyl)-1-[4-(1H-pyrrolo[2,3-b]pyridin-4-yl)-piperazin-1-yl]-propan-1-one dihydrochloride Step 1: A mixture of 4-chloro-1H-pyrrolo[2,3-b]pyridine (2.50 g, 16.4 mmol) and N-benzyl piperazine (3.18 g, 18.0 mmol) were melted at 175° C. for 3 hours in a sealed tube, resulting in the formation of a crystalline solid mass. A solution of 0.1 M aqueous NaOH (10 mL) was added and the solid was broken up to give a suspension. Filtration gave 4-(4-benzyl-piperazin-1-yl)-1H-pyrrolo[2,3-b]pyridine as a white solid (3.90 g). LCMS (APCI+) m/z 293 [M+H]$^+$.

Step 2: A solution of 4-(4-benzyl-piperazin-1-yl)-1H-pyrrolo[2,3-b]pyridine (3.90 g, 13.3 mmol) and Pd(OH)$_2$/C (937 mg, 1.33 mmol) in MeOH (60 mL) was stirred under 1 atmosphere of $H_2$ for 2 d. The mixture was diluted with MeOH, filtered through diatomaceous earth, and the filtrate was concentrated in vacuo to give 4-piperazin-1-yl-1H-pyrrolo[2,3-b]pyridine as a solid (100 mg kept as free base). The remaining material was suspended in MeOH and treated with 2.0 M HCl in Et$_2$O. This mixture was concentrated in vacuo to give 4-piperazin-1-yl-1H-pyrrolo[2,3-b]pyridine dihydrochloride (2.30 g). $^1$H NMR (DMSO-d$_6$, 400 MHz) δ 11.5 (bs, 1H), 9.43 (bs, 2H), 7.96 (d, J=5.4 Hz, 1H), 7.25 (d, J=3.3 Hz, 1H), 6.49 (d, J=3.4 Hz, 1H), 6.45 (d, J=5.4 Hz, 1H), 3.56 (bs, 4H), 3.21 (bs, 4H).

Step 3: PyBrop (407 mg, 0.87 mmol) was added in a single portion to a solution of (R)—N-Boc-4-chlorophenylalanine (458 mg, 1.53 mmol) and 4-piperazin-1-yl-1H-pyrrolo[2,3-b]pyridine (200 mg, 0.73 mmol) in DCM (5 mL) cooled in an ice bath. DIEA (0.66 mL, 3.78 mmol) was then dropped in, the ice bath was removed, and the mixture was stirred for 12 hours at ambient temperature. The mixture was diluted with DCM and washed with 0.1N HCl. The separated DCM layer was dried (Na$_2$SO$_4$), filtered, and concentrated in vacuo. This material was dissolved in MeOH (4 mL) followed by the addition of LiOH monohydrate (122 mg, 2.91 mmol) in H$_2$O (2 mL) and stirred for 12 hours. The mixture was concentrated in vacuo and chromatographed (SiO$_2$) using 2% MeOH/DCM followed by 5% MeOH/DCM as eluent. The resulting material was dissolved in DCM (4 mL) and 2.0 M HCl in Et$_2$O (2 mL), and then stirred for 12 hours. The mixture was concentrated in vacuo and chromatographed (SiO$_2$) using 10% MeOH/DCM followed by 10% (7N NH$_3$ in MeOH)/DCM as eluent. The purified material was dissolved in MeOH followed by the addition of 2.0N HCl in Et$_2$O, and then concentrated in vacuo. The resulting glass was suspended in Et$_2$O and concentrated in vacuo (repeat twice) to give 2-(R)-amino-3-(4-chlorophenyl)-1-[4-(1H-pyrrolo[2,3-b]pyridin-4-yl)-piperazin-1-yl]-propan-1-one dihydrochloride as an off-white powder (50 mg). $^1$H NMR (DMSO-d$_6$, 400 MHz) δ 12.6 (s, 1H), 8.56 (bs, 3H), 8.03 (d, J=7.1 Hz, 1H), 7.38 (m, 3H), 7.32 (m, 2H), 6.84 (s, 1H), 6.69 (d, J=7.1 Hz, 1H), 4.63 (bs, 1H), 3.88-3.58 (m, 7H), 3.33 (m, 1H), 3.14 (m, 1H), 3.05 (m, 1H). LCMS (APCI+) m/z 384, 386 [M+H]$^+$.

Example 60

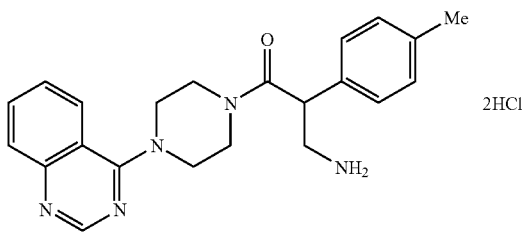 [SMILES: Cc1ccc(C(CN)C(=O)N2CCN(c3ncnc4ccccc34)CC2)cc1 ; "2HCl"]

Preparation of 3-Amino-1-(4-quinazolin-4-yl-piperazin-1-yl)-2-p-tolyl-propan-1-one dihydrochloride Step 1: n-BuLi (1.60M in hexanes, 40.7 mL, 65.1 mmol) was added to a 0° C. solution of diisopropylamine (9.4 mL, 67.0) in 280 mL THF. The mixture was allowed to stir at 0° C. for 30 minutes, then cooled to −78° C. A solution of p-tolyl-acetic acid methyl ester (10.48 g, 63.8 mmol; prepared from p-tolyl-acetic acid) in 10 mL of THF was added to the −78° C. LDA solution by syringe, which was then stirred for 45 minutes. Neat tert-butyl bromoacetate (28 mL) was added by syringe, and the reaction was stirred 15 minutes at −78° C. The bath was removed, and the reaction was allowed to warm to room temperature. After stirring an additional 5 hours, the reaction mixture was quenched with saturated NH$_4$Cl solution, and the organics were removed in vacuo. The oily mixture was extracted with ethyl acetate, and the organics were combined. The organic was dried over MgSO$_4$, filtered, and concentrated in vacuo. The crude oil was purified by on silica gel (25:1 hexanes:EtOAc) to afford the 2-p-tolyl-succinic acid 4-tert-butyl ester 1-methyl ester as a pale yellow oil (15.3 g, 86%). $^1$H NMR (CDCl$_3$, 400 MHz) δ 7.16 (d, J=8.0 Hz, 2H), 7.12 (d, J=8.0 Hz, 2H), 3.99 (dd, J=10.4, 5.6 Hz, 1H), 3.66 (s, 3H), 3.09 (dd, J=16.8, 10.4 Hz, 1H), 2.57 (dd, J=16.8, 5.6 Hz, 1H), 2.32 (s, 3H), 1.41 (m, 1H). HPLC R$_t$=3.71 min.

Step 2: A solution of 2-p-tolyl-succinic acid 4-tert-butyl ester 1-methyl ester (15.3 g, 54.8 mmol) in 110 ml of DCM was treated with neat TFA (63 mL) at room temperature. The mixture was stirred for five hours to completion, after which the reaction mixture was concentrated and dried in vacuo overnight to afford a white solid. The solid was suspended in 190 mL of toluene, cooled to 0° C., and treated successively with diphenylphosphoryl azide (13.4 mL, 62.1 mmol) and triethyl amine (19.7 mL, 141 mmol). The reaction mixture (homogeneous) was allowed to warm to room temperature and stirred for four hours to completion. The solution was quenched with 1% citric acid solution and extracted with EtOAc. The combined organic was washed with brine, dried over Na$_2$SO$_4$, filtered, and concentrated in vacuo to give a light brown oil. The crude azide was dissolved in 190 mL of tert-butanol, treated with neat SnCl$_4$ (0.25 mL, 2.82 mmol), and carefully heated to 90° C. with evolution of nitrogen. The mixture was stirred at 90° C. for 2.5 hours and cooled to room temperature. The solution was quenched with saturated NaHCO$_3$ solution and then concentrated. The oily mixture was extracted with EtOAc, and the combined organic was washed with brine, dried over MgSO$_4$, filtered, and concentrated in vacuo. The residue was purified by on silica gel (9:1 hexanes:EtOAc) to afford the 3-tert-butoxycarbonylamino-2-p-tolyl-propionic acid methyl ester as a pale yellow oil (12.3 g, 74%). $^1$H NMR (CDCl$_3$, 400 MHz) δ 7.14 (s, 4H), 4.86 (br s, 1H), 3.85 (m, 1H), 3.68 (s, 3H), 3.58 (m, 1H), 3.49 (m, 1H), 2.33 (s, 3H), 1.42 (s, 9H). HPLC R$_t$=3.31 min.

Step 3: The 3-tert-butoxycarbonylamino-2-p-tolyl-propionic acid methyl ester (12.3 g, 41.9 mmol) was dissolved in 200 mL 1:1 THF:water and treated with lithium hydroxide monohydrate (2.64 g, 62.9 mmol) at room temperature. The reaction was stirred at room temperature overnight to completion and concentrated in vacuo. The oily mixture was partitioned with water and washed with EtOAc (discarded). The aqueous was treated with solid KHSO$_4$ until pH<2, then extracted with EtOAc. The combined organic was dried over Na$_2$SO$_4$, filtered, and concentrated in vacuo to afford the 3-tert-butoxycarbonylamino-2-p-tolyl-propionic acid as a white solid (10.95 g, 93%). $^1$H NMR (ca. 1:1 mixture of rotamers) (CDCl$_3$, 400 MHz) δ 10.40-8.40 (br s, 1H), 7.16 (d, J=8.4 Hz, 2H), 7.13 (d, J=8.4 Hz, 2H), 6.80 or 4.91 (br s, 1H), 3.86 and 3.75 (m, 1H), 3.55 (m, 1H), 3.47 (m, 2H), 2.31 (s, 3H), 1.44 and 1.41 (s, 9H). LCMS (APCI−) m/z 557 [2M−H]$^−$. HPLC R$_2$=2.80 min.

Step 4: The 4-piperazin-1-yl-quinazoline dihydrochloride (50 mg, 0.174 mmol, free-based with 2N NaOH and extracted with DCM), HOBt monohydrate (27 mg, 0.174 mmol), and 3-tert-butoxycarbonylamino-2-p-tolyl-propionic acid (58 mg, 0.209 mmol) were dissolved in 1.3 mL of DCM/3-5 drops of THF. The reaction mixture was treated with DCC (43 mg, 0.209 mmol) and allowed to stir at room temperature for 2.5 hours to completion. The mixture was diluted with DCM, vacuum filtered through compressed Celite, and rinsed with DCM. The filtrate was stirred with 2N sodium hydroxide solution for five minutes, transferred to separatory funnel, and extracted with DCM. The combined organic was dried over Na$_2$SO$_4$, filtered, and concentrated. The residue was purified on silica gel (1:19 DCM:EtOAc) to afford 3-Boc-amino-1-(4-quinazolin-4-yl-piperazin-1-yl)-2-p-tolyl-propan-1-one. The material was dissolved in 1.0 mL of 1,4-dioxane and treated with 1.0 mL of 4M HCl in 1,4-dioxane (precipitation). The mixture was stirred at room temperature overnight to completion, then concentrated to dryness. The solid was dissolved in a minimal amount of MeOH, then triturated with diethyl ether. The resulting solid was isolated by filtration through a fritted funnel with nitrogen pressure, rinsed with ether, and dried in vacuo to afford the 3-amino-1-(4-quinazolin-4-yl-piperazin-1-yl)-2-p-tolyl-propan-1-one dihydrochloride as a pale yellow powder (60 mg, 77%). $^1$H NMR (DMSO-d$_6$, 400 MHz) δ 8.84 (s, 1H), 8.16 (d, J=8.4 Hz, 1H), 8.00 (m, 4H), 7.91 (d, J=8.0 Hz, 1H), 7.69 (t, J=8.0 Hz, 1H), 7.20 (s, 4H), 4.40 (m, 1H), 4.14 (m, 3H), 3.81 (m, 4H), 3.45 (m, 2H), 2.94 (m, 1H), 2.28 (s, 3H). LCMS (APCI+) m/z 376 [M+H]$^+$. HPLC R$_t$=1.67 min.

Example 61

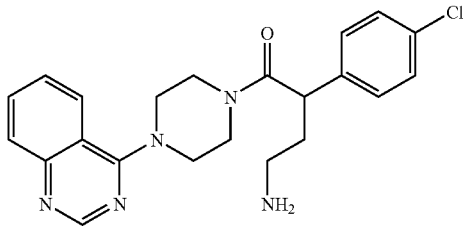 [SMILES: NCCC(C(=O)N1CCN(c2ncnc3ccccc23)CC1)c1ccc(Cl)cc1]

Preparation of 4-Amino-2-(4-chlorophenyl)-1-(4-quinazolin-4-yl-piperazin-1-yl)-butan-1-one Step 1: The (4-chlorophenyl)-acetic acid (20.0 g, 106 mmol) was dissolved in 220 mL of ethanol at ambient temperature. A catalytic amount of sulfuric acid (10 drops) was added to afford a light yellow solution. The reaction was allowed to stir overnight to completion and was concentrated to 30 mL. The concentrate was partitioned between ethyl acetate and half-saturated NaHCO$_3$ solution. The aqueous was extracted with ethyl acetate, and the organics were combined. The organic was washed with water, brine, separated, dried over MgSO$_4$, filtered, and concentrated in vacuo to afford the desired pure (4-chlorophenyl)-acetic acid ethyl ester as a pale yellow oil (21.0 g, 99%). $^1$H NMR (CDCl$_3$, 400 MHz) δ 7.29 (d, J=8.4 Hz, 2H), 7.22 (d, J=8.4 Hz, 2H), 4.15 (q, J=7.2 Hz, 2H), 3.58 (s, 2H), 1.25 (t, J=7.2 Hz, 3H).

Step 2: The (4-chlorophenyl)-acetic acid ethyl ester (9.52 g, 47.9 mmol) was dissolved in 80 mL of THF, cooled to 0° C., and treated with potassium tert-butoxide (538 mg, 4.79 mmol). The resulting orange solution was allowed to stir for 15 minutes at 0° C., then cooled to −78° C. The tert-butyl acrylate (7.72 mL, 52.7 mmol) was added in three equal portions over ten minutes. The solution was allowed to stir overnight warming slowly to room temperature. The reaction solution was concentrated in vacuo, and the residue was partitioned between ethyl acetate and saturated NH$_4$Cl solution. The aqueous was extracted with ethyl acetate, and the organics were combined. The organic was washed with brine, separated, dried over MgSO$_4$, filtered, and concentrated in vacuo. The residue was purified by chromatography (silica gel eluted with 9:1 hexanes:EtOAc) to afford the 2-(4-chlorophenyl)-pentanedioic acid 5-tert-butyl ester 1-ethyl ester in greater than 80% purity (9.00 g, 57%). $^1$H NMR (CDCl$_3$, 400 MHz) δ 7.31-7.21 (m, 4H), 4.13 (q, J=7.6 Hz, 2H), 3.58 (t, J=8.0 Hz, 1H), 2.27 (m, 1H), 2.16 (t, J=7.2 Hz, 2H), 2.04 (m, 1H), 1.43 (s, 9H), 1.21 (t, J=7.6 Hz, 3H).

Step 3: The 2-(4-chlorophenyl)-pentanedioic acid 5-tert-butyl ester 1-ethyl ester (9.00 g, 27.5 mmol) was dissolved in 40 mL of DCM at room temperature and treated slowly with 40 mL of TFA. The solution was allowed to stir for three hours to completion, then concentrated in vacuo. The residue was stored under vacuum overnight then dissolved in 80 mL of toluene. The solution was degassed under nitrogen, cooled to 0° C., treated with triethyl amine (8.44 mL, 60.6 mmol), and treated with diphenylphosphoryl azide (6.53 mL, 30.3 mmol), respectively. The reaction was allowed to warm to room temperature and stir for three hours, then concentrated in vacuo. The residue was re-dissolved in ethyl acetate and washed with 1 w/w % citric acid solution. The organic was dried over MgSO$_4$, filtered, and concentrated (<30° C.) to afford the intermediate azide as a yellow oil. The material was immediately dissolved in 80 mL of tert-butanol and treated with SnCl$_4$ (1.65 mL of a 1.0M sol'n in DCM, 1.65 mmol). The solution was heated to 80 C for one hour to give evolution of nitrogen gas. The reaction mixture was treated with saturated NaHCO$_3$ (20 mL), and concentrated in vacuo to give a gel. The residue was partitioned between ethyl acetate and water, and the aqueous was extracted with ethyl acetate. The organic was washed with brine, separated, dried over MgSO$_4$, filtered, and concentrated in vacuo. The residue was purified by chromatography (silica gel eluted with 4:1 hexanes:EtOAc, R$_f$=0.20) to give the pure 4-tert-butoxycarbonylamino-2-(4-chlorophenyl)-butyric acid ethyl ester as a colorless oil (5.61 g, 60%). $^1$H NMR (CDCl$_3$, 400 MHz) δ 7.29 (d, J=8.4 Hz, 2H), 7.23 (d, J=8.4 Hz, 2H), 4.51 (brs, 1H), 4.12 (m, 2H), 3.57 (t, J=7.6 Hz, 1H), 3.09 (m, 2H), 2.25 (m, 1H), 1.93 (m, 1H), 1.43 (s, 9H), 1.20 (t, J=7.2 Hz, 3H).

Step 4: The 4-tert-butoxycarbonylamino-2-(4-chlorophenyl)-butyric acid ethyl ester (5.61 g, 16.4 mmol) was dissolved in 40 mL of THF and 10 mL of water, then cooled to 0° C. The mixture was treated with lithium hydroxide monohydrate (1.38 g, 32.8 mmol) to afford a yellow solution. The ice-bath was removed, and the mixture was allowed to stir overnight to room temperature. The reaction mixture was concentrated to approximately 15 mL and diluted with water. The aqueous was washed with ethyl acetate (discarded) then treated with 3M HCl solution until acidic (pH=2-3). The resulting white precipitate was extracted with ethyl acetate, and the organics were combined. The organic was washed with brine, separated, dried over MgSO$_4$, filtered, and concentrated in vacuo to afford the 4-tert-butoxycarbonylamino-2-(4-chlorophenyl)-butyric acid as a colorless oil. The material was re-dissolved in a minimal amount of warm (60° C.) hexanes and re-concentrated to afford the pure desired product as a white foam. $^1$H NMR (CDCl$_3$, 400 MHz) δ 12.05-9.51 (brs, 1H), 7.31-7.25 (m, 4H), 4.59 (brs, 1H), 3.61 (d, J=7.6 Hz, 1H), 3.14 (brs, 2H), 2.28 (m, 1H), 1.92 (m, 1H), 1.43 (s, 9H).

Step 5: The 4-piperazin-1-yl-quinazoline (60 mg, 0.21 mmol) and 4-tert-butoxycarbonylamino-2-(4-chlorophenyl)-butyric acid (62 mg. 0.21 mmol) were dissolved in 1.5 mL of DCM and cooled to 0° C. The solution was treated with PyBrop (98 mg, 0.21 mmol) and DIEA (74 µL, 0.42 mmol), respectively. The mixture was allowed to warm to room temperature overnight, and the contents were partitioned between ethyl acetate and saturated NH$_4$Cl solution. The aqueous was extracted with ethyl acetate, and the organics were combined.

The organic was washed with NaHCO₃ solution, separated, dried over Na₂SO₄, filtered, and concentrated in vacuo. The residue was purified by chromatography (silica gel eluted with hexanes/EtOAc gradients) to afford the pure Boc-intermediate as a colorless oil. The material was dissolved in 1.0 mL of 1,4-dioxane and treated with 1.0 mL of 4M HCl in dioxane (2.79 mmol). The solution was allowed to stir at room temperature overnight to completion. The resulting suspension was diluted with diethyl ether and isolated by vacuum filtration. The pad of solid was allowed to dry under a stream of dry nitrogen to afford the pure 4-amino-2-(4-chlorophenyl)-1-(4-quinazolin-4-yl-piperazin-1-yl)-butan-1-one bis-hydrochloride as a white solid (32 mg, 37%). A small amount of the product was free-based for analytical purposes. $^1$H NMR (CDCl₃, 400 MHz) δ 8.73 (s, 1H), 7.91 (d, J=8.4 Hz, 1H), 7.81 (d, J=8.4 Hz, 1H), 7.75 (t, J=7.6 Hz, 1H), 7.47 (t, J=7.6 Hz, 1H), 7.32 (d, J=8.8 Hz, 2H), 7.25 (d, J=8.8 Hz, 2H), 4.01 (dd, J=7.2 Hz, 1H), 3.94 (m, 1H), 3.81 (m, 1H), 3.71 (m, 3H), 3.62 (m, 2H), 3.25 (m, 1H), 2.69 (t, J=6.8 Hz, 2H), 2.26 (m, 1H), 1.84 (m, 1H), 1.40 (brs, 2H). LCMS (APCI+) m/z 410 [M+H]⁺; Rt=1.64 min.

Example 62

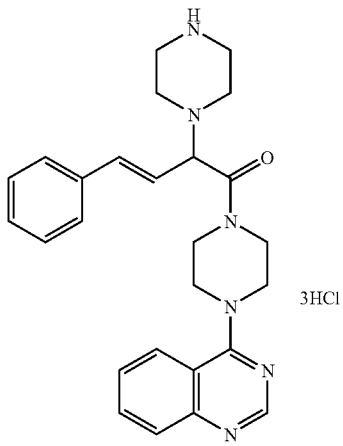 [SMILES: O=C(C(/C=C/c1ccccc1)N1CCNCC1)N1CCN(c2ncnc3ccccc23)CC1 ; "3HCl"]

Preparation of (3E)-4-phenyl-2-piperazin-1-yl-1-(4-quinazolin-4-yl-piperazin-1-yl)-but-3-en-1-one trihydrochloride (3E)-4-Phenyl-2-piperazin-1-yl-1-(4-quinazolin-4-yl-piperazin-1-yl)-but-3-en-1-one trihydrochloride (17 mg, 47%) was prepared by the procedures described for the preparation of Example 1A using (3E)-2-(4-Boc-piperazinyl)-4-phenyl-but-3-enoic acid. LCMS (APCI+) m/z 443 [M+H]⁺. HPLC Rt 2.31 min.

Example 63

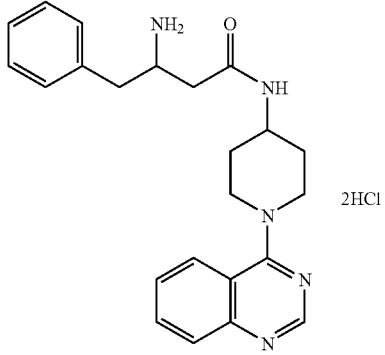 [SMILES: NC(CC(=O)NC1CCN(c2ncnc3ccccc23)CC1)Cc1ccccc1 ; "2HCl"]

Preparation 3-amino-4-phenyl-N-(1-quinazolin-4-yl-piperidin-4-yl)-butyramide dihydrochloride Step 1: To a solution of 4-chloroquinazoline (2.0 g, 12.2 mmol) in 45 mL IPA was added Boc-4-aminopiperidine (2.56 g, 12.8 mmol) and DIEA (3.2 mL, 18.2 mmol). The reaction mixture was heated to reflux and stirred 16 hours, after which the reaction mixture was cooled to room temperature and concentrated. The residue was dissolved in EtOAc and washed with water, 1N NaOH, brine, dried (Na₂SO₄), filtered, and concentrated to provide 4-(4-Boc-aminopiperidin-1-yl)quinazoline, which was used directly in the next step.

Step 2: To a solution of crude 4-(4-Boc-aminopiperidin-1-yl)quinazoline in 40 mL 1:1 dioxane:DCM was added 20 mL 4M HCl/dioxane. The resulting suspension was stirred at room temperature for 14 hours, after which it was concentrated to dryness. The residue was stirred in DCM and 1M NaOH, the phases were separated, and the aqueous phase was extracted with DCM. The combined organic phases were dried (Na₂SO₄), filtered and concentrated. The residue was purified on silica gel (8:1 EtOAc:MeOH to furnish 4-(4-aminopiperidin-1-yl)quinazoline (2.7 g, 96%) as a yellow oil. 1H NMR (CDCl₃, 400 MHz) δ 8.73 (s, 1H), 7.92-7.85 (m, 2H), 7.76-7.70 (m, 1H), 7.48-7.42 (m, 1H), 4.35-4.26 (m, 2H), 3.26-3.17 (m, 2H), 3.09-2.99 (m, 1H), 2.05-1.96 (m, 2H), 1.66-1.52 (m, 2H), 1.47 (br s, 2H). LCMS (APCI+) m/z 329 [M+H]⁺. HPLC Rt 1.57 min.

Step 3: 3-Amino-4-phenyl-N-(1-quinazolin-4-yl-piperidin-4-yl)-butyramide dihydrochloride (10 mg, 33%) was prepared from 4-(4-aminopiperidin-1-yl)quinazoline according to the procedure employed for Example 1A, Step 2, using Boc-β-homophenylalanine. LCMS (APCI+) m/z 390 [M+H]⁺. HPLC Rt 1.94 min.

Example 64

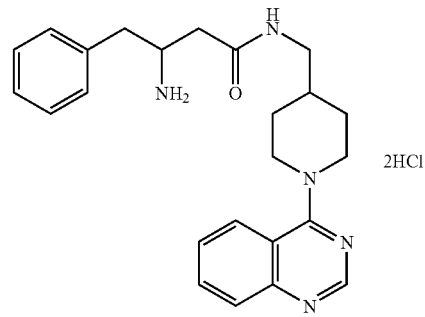 [SMILES: NC(CC(=O)NCC1CCN(c2ncnc3ccccc23)CC1)Cc1ccccc1 ; "2HCl"]

Preparation of 3-amino-4-phenyl-N-(1-quinazolin-4-yl-piperidin-4-ylmethyl)-butyramide dihydrochloride 3-Amino-4-phenyl-N-(1-quinazolin-4-yl-piperidin-4-ylmethyl)-butyramide dihydrochloride (13 mg, 42%) was prepared by the procedures described for the preparation of Example 63 using 4-Boc-aminomethylpiperidine in the S$_N$Ar step. LCMS (APCI+) m/z 404 [M+H]⁺. HPLC Rt 1.98 min.

Example 65

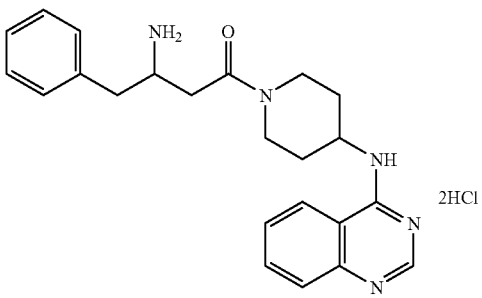 [SMILES: NC(CC(=O)N1CCC(Nc2ncnc3ccccc23)CC1)Cc1ccccc1 ; "2HCl"]

Preparation of 3-amino-4-phenyl-1-[4-(quinazolin-4-ylamino)-piperidin-1-yl]-butan-1-one dihydrochloride 3-Amino-4-phenyl-1-[4-(quinazolin-4-ylamino)-piperidin-1-yl]-butan-1-one dihydrochloride (19 mg, 59%) was prepared by the procedures described for the preparation of Example 63 using 4-amino-1-Boc-piperidine in the $S_NAr$ step. LCMS (APCI+) m/z 390 [M+H]$^+$. HPLC Rt 2.24 min.

Example 66

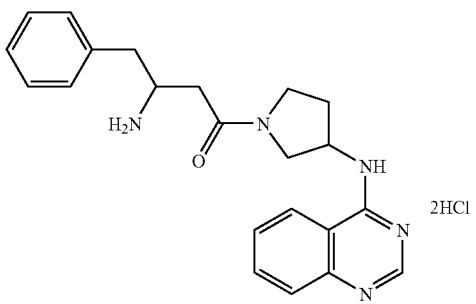 [SMILES: NC(CC(=O)N1CCC(Nc2ncnc3ccccc23)C1)Cc1ccccc1 ; "2HCl"]

Preparation of 3-amino-4-phenyl-1-[3-(quinazolin-4-ylamino)-pyrrolidin-1-yl]-butan-1-one dihydrochloride 3-Amino-4-phenyl-1-[3-(quinazolin-4-ylamino)-pyrrolidin-1-yl]-butan-1-one dihydrochloride (16 mg, 51%) was prepared by the procedures described for the preparation of Example 63 using 3-amino-Boc-pyrrolidine in the $S_NAr$ step. LCMS (APCI+) m/z 376 [M+H]$^+$. HPLC Rt 2.17 min.

Example 67

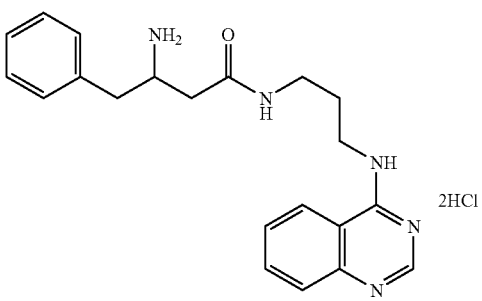 [SMILES: NC(CC(=O)NCCCNc1ncnc2ccccc12)Cc1ccccc1 ; "2HCl"]

Preparation of 3-amino-4-phenyl-N-[3-(quinazolin-4-ylamino)-propyl]-butyramide dihydrochloride 3-Amino-4-phenyl-N-[3-(quinazolin-4-ylamino)-propyl]-butyramide dihydrochloride (14 mg, 46%) was prepared by the procedures described for the preparation of Example 63 using Boc-propylenediamine in the $S_NAr$ step. LCMS (APCI+) m/z 364 [M+H]$^+$. HPLC Rt 2.14 min.

Example 68

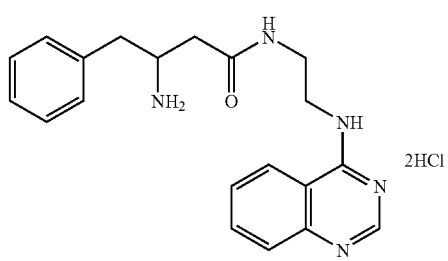 [SMILES: NC(CC(=O)NCCNc1ncnc2ccccc12)Cc1ccccc1 ; "2HCl"]

Preparation of 3-amino-4-phenyl-N-[3-(quinazolin-4-ylamino)-ethyl]-butyramide dihydrochloride 3-Amino-4-phenyl-N-[3-(quinazolin-4-ylamino)-ethyl]-butyramide dihydrochloride (11 mg, 37%) was prepared by the procedures described for the preparation of Example 63 using Boc-ethylenediamine in the $S_NAr$ step. LCMS (APCI+) m/z 350 [M+H]$^+$. HPLC Rt 2.07 min.

Example 69

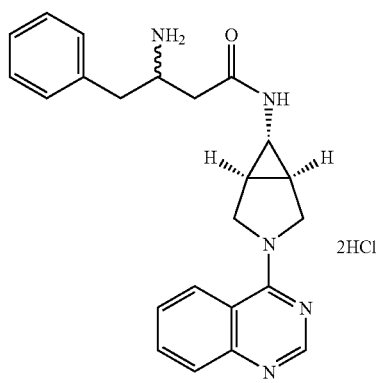 [SMILES: NC(CC(=O)N[C@H]1[C@@H]2CN(c3ncnc4ccccc34)C[C@@H]21)Cc1ccccc1 ; "2HCl"]

Preparation of 3-Amino-4-phenyl-N-(3-quinazolin-4-yl-3-aza-bicyclo[3.1.0]hex-6-yl)-butyramide dihydrochloride 3-Amino-4-phenyl-N-(3-quinazolin-4-yl-3-aza-bicyclo[3.1.0]hex-6-yl)-butyramide dihydrochloride (19 mg, 59%, mixture of diastereomers) was prepared by the procedures described for the preparation of Example 63 using (1α,5α,6α)-6-Boc-amino-3-azabicyclo[3.1.0]hexane (prepared according to the literature: Tamim F Braish et al. 1996, 1100-1102) in the $S_NAr$ step. LCMS (APCI+) m/z 388 [M+H]$^+$. HPLC Rt 2.13, 2.23 min.

Example 70

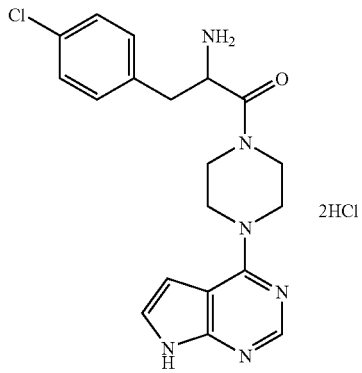 [SMILES: NC(Cc1ccc(Cl)cc1)C(=O)N1CCN(c2ncnc3[nH]ccc23)CC1 ; "2HCl"]

Preparation of (2R)-2-amino-3-(4-chlorophenyl)-1-[4-(7H-pyrrolo[2,3-d]pyrimidin-4-yl)-piperazin-1-yl]-propan-1-one dihydrochloride Step 1: A solution containing 4-chloro-7H-pyrrolo[2,3-d]pyrimidine (5.0 g, 32.6 mmol), Boc-piperazine (15 g, 81 mmol), and DIEA (19.8 mL, 114 mmol) in 130 mL IPA was stirred at 80 C for 18 hours, after which the reaction was concentrated. The crude was flashed on silica gel (20:1 DCM: MeOH) to give a yellow powder, which was recrystallized from MeOH/minimal DCM to give 4-Boc-piperazin-1-yl-7H-pyrrolo[2,3-d]pyrimidine as a white crystalline solid (3 crops). $^1$H NMR (CDCl$_3$, 400 MHz) δ 11.37 (br s, 1H), 8.34 (s, 1H), 7.12 (d, J=3.3 Hz, 1H), 6.49 (d, J=3.5 Hz, 1H), 4.01-3.94 (m, 4H), 3.64-3.56 (m, 4H), 1.48 (s, 9H). HPLC Rt 2.05 min.

Step 2: To a solution of 4-Boc-piperazin-1-yl-7H-pyrrolo[2,3-d]pyrimidine in 225 mL DCM was added dropwise by addition funnel 120 mL 4M HCl/dioxane, and the resulting suspension was stirred at room temperature 18 hours. The reaction mixture was then diluted with ether, and the solids were isolated by filtration through a fritted funnel with nitrogen pressure, rinsed with ether, and dried in vacuo to give 4-piperazin-1-yl-7H-pyrrolo[2,3-d]pyrimidine dihydrochloride (8.44 g, 94%) as a white powder. $^1$H NMR (DMSO-d6, 400 MHz) δ 12.75 (1H, s), 9.63 (2H, s), 8.44 (1H, s), 7.50 (1H, s), 6.95 (1H, s), 4.26-4.21 (4H, m), 3.33-3.26 (4H, m). LC/MS (APCI+) m/z 204 [M+H]$^+$.

Step 3: To a solution of 4-piperazin-1-yl-7H-pyrrolo[2,3-d]pyrimidine dihydrochloride (30 mg, 0.11 mmol), HOBt.H2O (17 mg, 0.11 mmol), TEA (45 µL, 0.33 mmol), and (D)-Boc-4-chlorophenylalanine (39 mg, 0.13 mmol) in 1.6 mL DMF was added DCC (27 mg, 0.13 mmol). The reaction mixture was stirred at room temperature for 4 hours, after which it was concentrated. The residue was suspended in DCM, and the solids were removed by vacuum filtration through cotton plug and rinsed with DCM. The filtrate was concentrated, and the crude purified on silica gel (1:1 to 1:4 DCM:EtOAc) to afford (2R)-2-Boc-amino-3-(4-chlorophenyl)-1-[4-(7H-pyrrolo[2,3-d]pyrimidin-4-yl)-piperazin-1-yl]-propan-1-one, which was used in the next step.

Step 4: To a solution of (2R)-2-Boc-amino-3-(4-chlorophenyl)-1-[4-(7H-pyrrolo[2,3-d]pyrimidin-4-yl)-piperazin-1-yl]-propan-1-one in 1 mL dioxane was added 1 mL 4M HCl/dioxane. The resulting suspension was stirred at room temperature overnight, after which it was concentrated to dryness. The solids were dissolved in minimal MeOH and then triturated with ether. The resulting solids were isolated by filtration through a fritted funnel with nitrogen pressure, rinsed with ether, and dried in vacuo to give (2R)-2-amino-3-(4-chlorophenyl)-1-[4-(7H-pyrrolo[2,3-d]pyrimidin-4-yl)-piperazin-1-yl]-propan-1-one dihydrochloride (19 mg, 38%) as a pink powder. $^1$H NMR (D$_2$O, 400 MHz) δ 8.16 (1H, s), 7.27 (1H, s), 7.18-7.11 (4H, m), 6.68 (1H, s), 4.60-4.56 (1H, m), 3.98-3.69 (4H, m), 3.61-3.52 (2H, m), 3.45-3.37 (1H, m), 3.20-3.12 (1H, m), 3.00-2.91 (2H, m). LCMS (APCI+) m/z 385 [M+H]$^+$. HPLC Rt 1.68 min.

Example 71

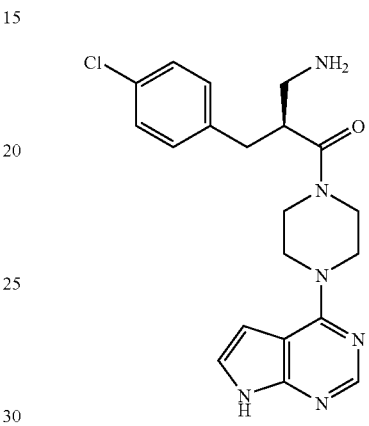

Preparation of (S)-2-Aminomethyl-3-(4-chlorophenyl)-1-[4-(7H-pyrrolo[2,3-d]pyrimidin-4-yl)-piperazin-1-yl]-propan-1-one dihydrochloride Step 1: nBuLi (1.6M in hexanes, 20 mL, 32 mmol) was added to a stirred solution of (4R,5S)-4-Methyl-5-phenyl-oxazolidin-2-one (5.2 g, 29 mmol) in THF (60 mL) at −78 C under N2. The solution was stirred at −78° C. for 10 mL and then 3-(4-Chlorophenyl)-propionyl chloride (6.0 g, 29 mmol) was added and the solution allowed to warm to room temperature over 1 hour. The solution was quenched with saturated aqueous NH4Cl, extracted into DCM (2×200 mL), dried over Na$_2$SO$_4$ and concentrated in vacuo. The product was purified by column chromatography on silica (50% EtOAc/hexanes) to give (4R,5S)-3-[3-(4-Chlorophenyl)-propionyl]-4-methyl-5-phenyl-oxazolidin-2-one (4.8 g, 48%.) $^1$H NMR (CDCl$_3$, 400 MHz) δ 7.44-7.35 (3H, m), 7.30-7.24 (4H, m), 7.19 (2H, d, J 8.0 Hz), 5.64 (1H, d, J 7.4 Hz), 4.77-4.71 (1H, m), 3.34-3.17 (2H, m), 2.98 (2H, t, J 7.7 Hz), 0.88 (3H, d, J 6.7 Hz.)

Step 2: NaHMDS (1.0M, 17 mL, 17 mmol) was added to a stirred solution of (4R,5S)-3-[3-(4-Chlorophenyl)-propionyl]-4-methyl-5-phenyl-oxazolidin-2-one (4.8 g, 14 mmol) in THF (200 mL) at −78° C. under N$_2$. Stirred at −78° C. for 45 minutes and then Bromo-acetic acid tert-butyl ester (2.5 mL, 17 mmol) was added dropwise over 10 minutes. The solution was allowed to warm to −20° C. over 4 hours and then quenched with saturated aqueous NH$_4$Cl. The product was extracted into EtOAc (2×300 mL), dried over Na$_2$SO$_4$, concentrated in vacuo and purified by column chromatography on silica (20% EtOAc/hexanes) to give (3S)-3-(4-Chlorobenzyl)-4-((4R,5S)-4-methyl-2-oxo-5-phenyl-oxazolidin-3-yl)-4-oxo-butyric acid tert-butyl ester (5.1 g, 80%.) $^1$H NMR (CDCl3, 400 MHz) δ 7.44-7.21 (9H, m), 5.45 (1H, d, J 7.3 Hz), 4.68-4.62 (1H, m), 4.51-4.42 (1H, m), 3.01 (1H, dd, J 13.0 and 6.2 Hz), 2.78 (1H, dd, J 16.7 and 10.6 Hz), 2.63 (1H, dd, J 13.2 and 9.0 Hz), 2.32 (1H, dd, J 6.7 and 4.3 Hz), 1.38 (9H, s), 0.89 (3H, d, J 6.6 Hz.)

Step 3: A solution of (3S)-3-(4-Chlorobenzyl)-4-((4R,5S)-4-methyl-2-oxo-5-phenyl-oxazolidin-3-yl)-4-oxo-butyric acid tert-butyl ester (5.1 g, 11 mmol) in DCM (100 mL) was treated with TFA (50 mL) and stirred at room temperature for 1 hour. The solution was concentrated in vacuo, taken up into toluene and then conc. in vacuo. Placed on high vacuum for 6 hours to give (3S)-3-(4-Chlorobenzyl)-4-((4R,5S)-4-methyl-2-oxo-5-phenyl-oxazolidin-3-yl)-4-oxo-butyric acid (4.5 g, 100%.) $^1$H NMR (CDCl3, 400 MHz) δ 7.44-7.37 (3H, m), 7.31-7.21 (6H, m), 5.48 (1H, d, J 6.9 Hz), 4.70-4.63 (1H, m), 4.50-4.42 (1H, m), 3.05 (1H, dd, J 13.3 and 6.2 Hz), 2.89 (1H, dd, J 17.7 and 10.6 Hz), 2.63 (1H, dd, J 13.2 and 9.0 Hz), 2.43 (1H, dd, J 17.6 and 4.4 Hz), 0.86 (3H, d, J 6.6 Hz.)

Step 4: NEt3 (700 uL, 5.0 mmol) was added to a stirred solution of (3S)-3-(4-Chlorobenzyl)-4-((4R,5S)-4-methyl-2-oxo-5-phenyl-oxazolidin-3-yl)-4-oxo-butyric acid (1.0 g, 2.5 mmol) in PhMe (50 mL) at 0° C. under N$_2$. This was followed by the addition of the diphenylphosphoryl azide (650 μL, 3.0 mmol.) The solution was stirred at 0° C. for 15 minutes and then stirred at room temperature overnight. The solution was washed with 1% citric acid, extracted into EtOAc and concentrated in vacuo. Taken up into tBuOH (50 mL), SnCl4 (1.0M in DCM, 0.1 mL) added and stirred and heated at 85° C. for 5 hours. Cooled to room temperature and quenched with saturated aqueous bicarbonate. Stirred at RT for 10 minutes and then concentrated in vacuo. The product was taken up into water (100 mL) and extracted into EtOAc (2×200 mL.) Dried over Na$_2$SO$_4$ and concentrated in vacuo. The product was purified by column chromatography on silica (10% EtOAc/hexanes) and then on the Biotage to give [(2S)-2-(4-Chlorobenzyl)-3-((4R,5S)-4-methyl-2-oxo-5-phenyl-oxazolidin-3-yl)-3-oxo-propyl]-carbamic acid tert-butyl ester (300 mg, 25%.) LCMS (APCI+) m/z 373 [M-Boc+H]$^+$; Rt: 3.92 min.

Step 5: To a solution of [(2S)-2-(4-Chlorobenzyl)-3-((4R,5S)-4-methyl-2-oxo-5-phenyl-oxazolidin-3-yl)-3-oxo-propyl]-carbamic acid tert-butyl ester (300 mg, 0.63 mmol) in THF/H2O (30/10 mL) at 0° C. was added LiOH (80 mg, 1.9 mmol) and H2O2 (30% by volume, 3.0 mL, 0.63 mmol) and stirred at 0° C. for 30 minutes. Then Na$_2$SO$_3$ (saturated solution, 10 mL) was added slowly & cautiously. Diluted with EtOAc (100 mL) and extracted into water (2×100 mL) The aq. layer was acidified (1N HCl) and extracted into EtOAc (3×100 mL) Dried over Na$_2$SO$_4$ and concentrated in vacuo to give (S)-2-(tert-Butoxycarbonylamino-methyl)-3-(4-chlorophenyl)-propionic acid (150 mg, 75%.) LCMS (APCI−) m/z 322 [M-Boc+H]$^−$; Rt: 2.23 min Step 6: NEt$_3$ (150 μL, 1.1 mmol) was added to a stirred suspension of 4-Piperazin-1-yl-7H-pyrrolo[2,3-d]pyrimidine dihydrochloride (100 mg, 0.36 mmol), (S)-2-(tert-Butoxycarbonylamino-methyl)-3-(4-chlorophenyl)-propionic acid (130 mg, 0.40 mmol), EDCI (83 mg, 0.44 mmol) and HOBt (59 mg, 0.44 mmol) in DMF (15 mL) at RT. Stirred at RT overnight. Poured into EtOAc (100 mL), washed with water (100 mL), 1N NaOH (50 mL), dried over Na2SO4, concentrated in vacuo, purified by column chromatography on silica (100% EtOAc) to give (S)-{2-(4-Chlorobenzyl)-3-oxo-3-[4-(7H-pyrrolo[2,3-d]pyrimidin-4-yl)-piperazin-1-yl]-propyl}-carbamic acid tert-butyl ester. LCMS (APCI+) m/z 499 [M+H]$^+$; Rt: 2.70 minutes. This was taken up into DCM (50 mL) and stirred with TFA (5 mL) overnight. Poured into EtOAc (100 mL) and washed with 1N NaOH (2×100 mL), dried over Na$_2$SO$_4$ and concentrated in vacuo. Formed HCl salt (Et$_2$O.HCl, 2M in diethyl ether) to give (S)-2-Aminomethyl-3-(4-chlorophenyl)-1-[4-(7H-pyrrolo[2,3-d]pyrimidin-4-yl)-piperazin-1-yl]-propan-1-one dihydrochloride (100 mg, 59%.) LCMS (APCI+) m/z 399 [M+H]$^+$; Rt: 1.82 min. [Free base: $^1$H NMR (CDCl3, 400 MHz) δ 9.97 (1H, br.s), 8.32 (1H, s), 7.24 (2H, d, J 7.4 Hz), 7.13 (2H, d, J 7.4 Hz), 7.09 (1H, d, J 2.4 Hz), 6.45 (1H, d, J 2.3 Hz), 4.00-3.68 (5H, m), 3.60-3.53 (1H, m), 3.46-3.40 (1H, m), 3.33-3.27 (1H, m), 3.16-3.05 (2H, m), 2.92-2.83 (2H, m), 2.77 (1H, dd, J 13.3 and 5.5 Hz.)]

Example 72

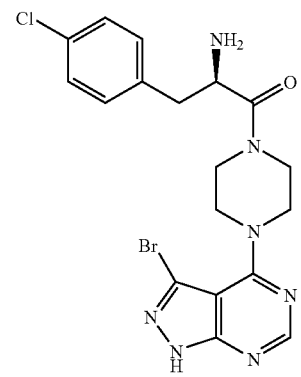 [SMILES: N[C@H](Cc1ccc(Cl)cc1)C(=O)N1CCN(c2ncnc3[nH]nc(Br)c23)CC1]

Preparation of (R)-2-Amino-1-[4-(3-bromo-1H-pyrazolo[3,4-d]pyrimidin-4-yl)-piperazin-1-yl]-3-(4-chlorophenyl)-propan-1-one, dihydrochloride Step 1: The 4-hydroxypyrazolopyrimidine (2.5 g, 18 mmol) was dissolved in POCl3 (34 mL, 0.37 mol) and N,N-dimethyl aniline (4.7 mL, 37 mmol.) This mixture was heated to reflux (120° C.) for 1.5 hours to afford a dark red solution. The mixture was concentrated to a viscous oil and cooled to 0° C. in an ice bath. The oil was poured into a mixture of ice-water and was stirred for 5 minutes. The acidic melt was extracted with ether (4×100 mL), and the organics were combined. The organic was washed with cold water, then cold half saturated NaHCO3 solution, then brine, separated, dried over MgSO$_4$, filtered, and concentrated in vacuo to afford 4-Chloro-1H-pyrazolo[3,4-d]pyrimidine (1.1 g, 39%) as a light yellow powder. $^1$H NMR (DMSO-d6, 400 MHz) δ 8.79 (1H, s), 8.41 (1H, s.)

Step 2: To a suspension of 4-Chloro-1H-pyrazolo[3,4-d]pyrimidine (1.1 g, 7.1 mmol) in CHCl$_3$ (50 mL) was added NBS (1.49 g, 8.4 mmol) The mixture was stirred at room temperature for 5 hours, cooled to 0 C and the solids were isolated by vacuum filtration, rinsed with cold CHCl$_3$, and air dried. The solid was purified by column chromatography on silica (50% EtOAc/hexanes) to give 3-Bromo-4-chloro-1H-pyrazolo[3,4-d]pyrimidine (1.3, 77%.)

Step 3: To a solution of 3-Bromo-4-chloro-1H-pyrazolo[3,4-d]pyrimidine (1.3 g, 5.5 mmol) in DMF (42 mL) at 0° C. was added NaH (180 mg, 7.7 mmol) in portions. The reaction mixture was stirred at 0° C. for 5 minutes, then stirred at room temperature for 1.5 hours, after which it was cooled back to 0° C. Neat PhSO$_2$Cl (0.7 mL, 5.6 mmol) was added and the reaction mixture was warmed to room temperature and stirred overnight. The reaction was quenched with saturated aqueous NH$_4$Cl and diluted further with H$_2$O. The resulting precipitate was isolated by vacuum filtration to give 1-Benzenesulfonyl-3-bromo-4-chloro-1H-pyrazolo[3,4-d]pyrimidine (1.8 g, 88%.) $^1$H NMR (DMSO-d6, 400 MHz) δ 9.11 (1H, s), 8.11 (2H, d, J 8.1 Hz), 7.84 (1H, t, J 7.5 Hz), 7.70 (2H, t, J 8.0 Hz.)

Step 4: A solution of 1-Benzenesulfonyl-3-bromo-4-chloro-1H-pyrazolo[3,4-d]pyrimidine (1.8 g, 4.8 mmol), Boc-piperazine (1.4 g, 7.2 mmol) and DIPEA (2.1 mL, 12 mmol) in IPA (40 mL) was stirred and heated at reflux overnight. The reaction mixture was cooled to −10° C., the solids isolated by vacuum filtration, rinsed with cold IPA and dried further on high vacuum line to give 4-(1-Benzenesulfonyl-3-bromo-1H-pyrazolo[3,4-d]pyrimidin-4-yl)-piperazine-1-carboxylic acid tert-butyl ester (1.7 g, 67%) as a white powder. LCMS (APCI+) m/z 523 and 525 [M+H]$^+$; Rt: 3.57 min. $^1$H NMR (CDCl$_3$, 400 MHz) δ 8.53 (1H, s), 8.23 (2H, d, J 8.5 Hz), 7.65 (1H, t, J 6.9 Hz), 7.54 (2H, t, J 7.8 Hz), 3.82-3.79 (4H, m), 3.60-3.57 (4H, m), 1.48 (9H, s.)

Step 5: Anhydrous HCl (4N in dioxane, 10 mL) was added to a stirred solution of 1-Benzenesulfonyl-3-bromo-4-piperazin-1-yl-1H-pyrazolo[3,4-d]pyrimidine (210 mg, 0.40 mmol) in MeOH (20 mL) and stirred at room temperature overnight. The suspension was concentrated in vacuo to give 1-Benzenesulfonyl-3-bromo-4-piperazin-1-yl-1H-pyrazolo[3,4-d]pyrimidine dihydrochloride (200 mg, 100%.) LCMS (APCI+) m/z 423 and 425 [M+H]$^+$; Rt: 1.98 min.

Step 6: DIPEA (84 ul, 0.48 mmol) was added to a suspension of 1-Benzenesulfonyl-3-bromo-4-piperazin-1-yl-1H-pyrazolo[3,4-d]pyrimidine dihydrochloride (40 mg, 0.081 mmol) and (D)-2-tert-Butoxycarbonylamino-3-(4-chlorophenyl)-propionic acid (27 mg, 0.089 mmol) in DCM (10 mL) at room temperature. Then, HBTU (34 mg, 0.089 mmol) was added and the reaction stirred at room temperature overnight. MeOH (5 mL) and 3M LiOH (3 mL) were added and the mixture stirred and heated at 50° C. for 2 hours. The mixture was diluted with saturated aqueous NaHCO$_3$ (10 mL), extracted into DCM, dried over Na$_2$SO$_4$ and concentrated in vacuo. The crude mixture was purified by column chromatography on silica (50% EtOAc/hexanes) to give (R)-[2-[4-(3-Bromo-1H-pyrazolo[3,4-d]pyrimidin-4-yl)-piperazin-1-yl]-1-(4-chlorobenzyl)-2-oxo-ethyl]-carbamic acid tert-butyl ester. LCMS (APCI+) m/z 564 and 566 [M+H]$^+$; Rt: 3.04 min. This was taken up into MeOH (10 mL) and treated with anhydrous HCl (4M in dioxane, 20 mL.) The solution was stirred at room temperature overnight and concentrated in vacuo to give (R)-2-Amino-1-[4-(3-bromo-1H-pyrazolo[3,4-d]pyrimidin-4-yl)-piperazin-1-yl]-3-(4-chlorophenyl)-propan-1-one, dihydrochloride (13 mg, 30%.) LCMS (APCI+) m/z 464 and 466 [M+H]$^+$; Rt: 2.00 min.

Example 73

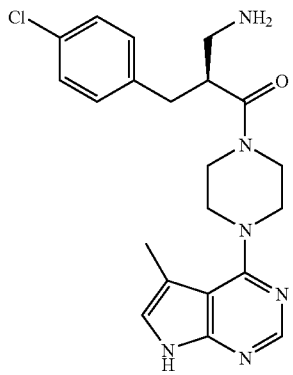 [SMILES: Cc1c[nH]c2ncnc(N3CCN(C(=O)[C@H](CN)Cc4ccc(Cl)cc4)CC3)c12]

Preparation of (S)-2-Aminomethyl-3-(4-chlorophenyl)-1-[4-(5-methyl-7H-pyrrolo[2,3-d]pyrimidin-4-yl)-piperazin-1-yl]-propan-1-one dihydrochloride Step 1: To a suspension of 4-Chloro-7H-pyrrolo[2,3-d]pyrimidine (2.5 g, 16 mmol) in CDCl$_3$ (65 mL) was added NBS (2.9 g, 16 mmol) and the reaction mixture stirred and heated at reflux for 2.5 hours. The mixture was cooled to room temperature, the solids isolated by vacuum filtration, rinsed with cold CHCl3 and air dried to give 5-Bromo-4-chloro-7H-pyrrolo[2,3-d]pyrimidine (3.0 g, 79%.) LCMS (APCI+) m/z 232 and 234 [M+H]$^+$; Rt: 2.32 min. $^1$H NMR (DMSO-d6, 400 MHz) δ 12.98 (1H, br. s), 8.63 (1H, s), 7.96 (1H, s.)

Step 2: To a solution of 5-Bromo-4-chloro-7H-pyrrolo[2,3-d]pyrimidine (3.0 g, 13 mmol) in DMF (40 mL) at 0° C. was added NaH (60% w/w in mineral oil, 720 mg, 18.1 mmol) and the mixture stirred at 0° C. under N$_2$ for 30 minutes. Then PhSO2Cl (1.7 g, 13 mmol) was added and the reaction stirred at room temperature for 2 hours, after which H2O (200 mL) was added, causing precipitation. The precipitate was collected by filtration and dried under vacuum to give 7-Benzenesulfonyl-5-bromo-4-chloro-7H-pyrrolo[2,3-d]pyrimidine (4.9 g, 100%.) $^1$H NMR (DMSO-d6, 400 MHz) δ 8.85 (1H, s), 8.45 (1H, s), 8.19 (2H, d, J 8.7 Hz), 7.81 (1H, t, J 7.4 Hz), 7.70 (2H, t, J 7.8 Hz.)

Step 3: A suspension of 7-Benzenesulfonyl-5-bromo-4-chloro-7H-pyrrolo[2,3-d]pyrimidine (4.9 g, 13 mmol), Piperazine-1-carboxylic acid tert-butyl ester (3.7 g, 20 mmol), and DIPEA (5.7 mL, 33 mmol) in IPA (30 mL) was stirred and heated at reflux for 6 hours. The mixture was cooled to −10° C., the solids collected by vacuum filtration, rinsed with cold IPA and dried under vacuum to give 4-(7-Benzenesulfonyl-5-bromo-7H-pyrrolo[2,3-d]pyrimidin-4-yl)-piperazine-1-carboxylic acid tert-butyl ester (5.9 g, 86%.) LCMS (APCI+) m/z 522 and 524 [M+H]$^+$; Rt: 3.92 min. $^1$H NMR (DMSO-d6, 400 MHz) δ 8.48 (1H, s), 8.21 (2H, d, J 8.2 Hz), 7.66-7.62 (2H, m), 7.54 (2H, t, J 7.8 Hz), 3.62-3.55 (8H, m), 1.48 (9H, s.)

Step 4: MeZnCl (2.0M in THF, 720 uL, 1.4 mmol) was added to a stirred solution 4-(7-Benzenesulfonyl-5-bromo-7H-pyrrolo[2,3-d]pyrimidin-4-yl)-piperazine-1-carboxylic acid tert-butyl ester (250 mg, 0.48 mmol) and tetrakis(triphenylphosphine)palladium(0) (140 mg, 0.12 mmol) in THF (10 mL) at room temperature under N$_2$. The solution was stirred and heated at reflux for 2 hours, cooled to room temperature, quenched with saturated aqueous NH4Cl, extracted into EtOAc (2×100 mL), dried over Na$_2$SO$_4$ and concentrated in vacuo. The product was purified on a Biotage (silica, 40% EtOAc/hexanes) to give 4-(7-Benzenesulfonyl-5-methyl-7H-pyrrolo[2,3-d]pyrimidin-4-yl)-piperazine-1-carboxylic acid tert-butyl ester (210 mg, 94%.) LCMS (APCI+) m/z 458 [M+H]$^+$; Rt: 3.73. $^1$H NMR (CDCl3, 400 MHz) δ 8.49 (1H, s), 8.18 (2H, d, J 8.2 Hz), 7.59 (1H, t, J 6.9 Hz), 7.50 (2H, t, J 7.8 Hz), 7.34 (1H, s), 3.59-3.54 (4H, m), 3.48-3.44 (4H, m), 2.35 (3H, s), 1.48 (9H, s.)

Step 5: A solution of 4-(7-Benzenesulfonyl-5-methyl-7H-pyrrolo[2,3-d]pyrimidin-4-yl)-piperazine-1-carboxylic acid tert-butyl ester (4.0 g, 13 mmol) in DCM (100 mL) was treated with anhydrous HCl (4M in dioxane, 100 mL) and stirred at room temperature overnight. The suspension was concentrated in vacuo to give 7-Benzenesulfonyl-5-methyl-4-piperazin-1-yl-7H-pyrrolo[2,3-d]pyrimidine dihydrochloride (5.4 g, 100%.) LCMS (APCI+) m/z 358 [M+H]$^+$; Rt: 1.79.

Step 6: DIPEA (120 μL, 0.70 mmol) was added to a suspension of 7-Benzenesulfonyl-5-methyl-4-piperazin-1-yl-7H-pyrrolo[2,3-d]pyrimidine dihydrochloride (50 mg, 0.12 mmol) and (S)-2-(tert-Butoxycarbonylamino-methyl)-3-(4-chlorophenyl)-propionic acid (40 mg, 0.13 mmol) in DCM (10 mL) at room temperature. Then, HBTU (48 mg, 0.13 mmol) was added and the reaction stirred at room temperature overnight. MeOH (5 mL) and 3M LiOH (1.2 mL) were added and the mixture stirred and heated at 50° C. for 2 hours. The mixture was diluted with saturated aqueous NaHCO$_3$ (10 mL), extracted into DCM, dried over Na$_2$SO$_4$ and concentrated in vacuo. The crude mixture was purified by column chromatography on silica (50% EtOAc/hexanes) to give (S)-{2-(4-Chlorobenzyl)-3-[4-(5-methyl-7H-pyrrolo[2,3-d]pyrimidin-4-yl)-piperazin-1-yl]-3-oxo-propyl}-carbamic acid tert-butyl ester. LCMS (APCI+) m/z 253 [M+H]$^+$; Rt: 2.85 min. This was taken up into MeOH (10 mL) and treated with anhydrous HCl (4M in dioxane, 20 mL.) The solution was stirred at room temperature overnight and concentrated in vacuo to give (S)-2-Aminomethyl-3-(4-chlorophenyl)-1-[4-(5-methyl-7H-pyrrolo[2,3-d]pyrimidin-4-yl)-piperazin-1-yl]-propan-1-one dihydrochloride (21 mg, 37%.) LCMS (APCI+) m/z 413 [M+H]$^+$; Rt: 1.82 min.

Example 73

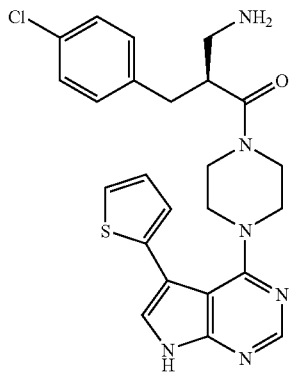 [SMILES: NC[C@H](Cc1ccc(Cl)cc1)C(=O)N1CCN(c2ncnc3[nH]cc(-c4cccs4)c23)CC1]

The preparation of (2S)-2-Aminomethyl-3-(4-chlorophenyl)-1-[4-(5-thiophen-2-yl-7H-pyrrolo[2,3-d]pyrimidin-4-yl)-piperazin-1-yl]-propan-1-one dihydrochloride Step 1: To a solution of 4-(7-Benzenesulfonyl-5-bromo-7H-pyrrolo[2,3-d]pyrimidin-4-yl)-piperazine-1-carboxylic acid tert-butyl ester (150 mg, 0.29 mmol) in 4 mL DME (degassed with nitrogen prior to use) was added 0.94M aqueous Na$_2$CO$_3$ (0.61 mL, 0.57 mmol) and Pd(PPh$_3$)$_4$ (66 mg, 0.057 mmol). The reaction mixture was stirred 5 minutes, then 2-thiophene boronic acid (55 mg, 0.43 mmol) was added. The reaction mixture heated to reflux and stirred 16 hours, after which it was cooled to room temperature and DME was removed by rotary evaporation. The reaction mixture was diluted with H$_2$O and extracted with DCM, and the combined extracts were dried (Na$_2$SO$_4$), filtered, and concentrated. The crude was purified on silica gel (8:1 to 4:1 hexanes:EtOAc) to furnish 4-(7-Benzenesulfonyl-5-thiophen-2-yl-7H-pyrrolo[2,3-d]pyrimidin-4-yl)-piperazine-1-carboxylic acid tert-butyl ester (120 mg, 79%) as a beige powder. LCMS (APCI+) m/z 526 [M+H]$^+$; Rt: 3.25 min.

Step 2: To a solution of 4-(7-Benzenesulfonyl-5-thiophen-2-yl-7H-pyrrolo[2,3-d]pyrimidin-4-yl)-piperazine-1-carboxylic acid tert-butyl ester (120 mg, 0.23 mmol) in 2 mL dioxane was added 1.5 mL 4M HCl/dioxane. The reaction mixture was stirred at room temperature 6 hours, after which it was diluted with ether, and the solids were isolated by filtration through a fritted funnel with nitrogen pressure, rinsed with ether, and dried in vacuo to give 7-Benzenesulfonyl-4-piperazin-1-yl-5-thiophen-2-yl-7H-pyrrolo[2,3-d]pyrimidine dihydrochloride (110 mg, 95%) as a yellow powder. LCMS (APCI+) m/z 426 [M+H]$^+$; Rt: 1.95 min.

Step 3: To a solution of 7-Benzenesulfonyl-4-piperazin-1-yl-5-thiophen-2-yl-7H-pyrrolo[2,3-d]pyrimidine dihydrochloride (50 mg, 0.10 mmol), DIEA (0.10 mL, 0.60 mmol), and (2S)-2-(Boc-aminomethyl)-3-(4-chlorophenyl)-propionic acid (38 mg, 0.12 mmol) in 2 mL DCM was added HBTU (44 mg, 0.12 mmol). The reaction mixture was stirred at room temperature 2 hours, after which 2 mL MeOH and 0.5 mL 3M LiOH were added. The reaction mixture was heated to 35° C. and stirred 2 hours, after which saturated NaHCO$_3$ was added, and the mixture was extracted with DCM. The combined extracts were dried (Na$_2$SO$_4$), filtered, and concentrated. The crude was purified on silica gel (flushed with 2:1 DCM:EtOAc, then gradient to 1:4 DCM:EtOAc) to give (2S)-2-Boc-aminomethyl-3-(4-chlorophenyl)-1-[4-(5-thiophen-2-yl-7H-pyrrolo[2,3-d]pyrimidin-4-yl)-pip-erazin-1-yl]-propan-1-one, which was used in the next step.

Step 4: To a solution of (2S)-2-Boc-aminomethyl-3-(4-chlorophenyl)-1-[4-(5-thiophen-2-yl-7H-pyrrolo[2,3-d]pyrimidin-4-yl)-pip-erazin-1-yl]-propan-1-one in 1.5 mL dioxane was added 1.5 mL 4M HCl/dioxane. The resulting suspension was stirred at room temperature 16 hours, after which it was concentrated to dryness. The solids were dissolved in minimal MeOH, and the product was triturated by the addition of ether. The solids were isolated by filtration through a fritted funnel with nitrogen pressure, rinsed with ether, and dried in vacuo to give (2S)-2-aminomethyl-3-(4-chlorophenyl)-1-[4-(5-thiophen-2-yl-7H-pyrrolo[2,3-d]pyrimidin-4-yl)-piperazin-1-yl]-propan-1-one dihydrochloride (37 mg, 67%) a pale yellow powder. $^1$H NMR (D$_2$O, 400 MHz) δ 8.18 (1H, s), 7.41 (1H, d, J 5.4 Hz), 7.30 (1H, s), 7.19 (2H, d, J 8.6 Hz), 7.06 (1H, dd, J 5.0 and 3.5 Hz), 7.01 (2H, d, J 8.0 Hz), 6.88 (1H, d, J 3.5 Hz), 3.47-3.14 (5H, m), 3.08-3.00 (3H, m), 2.86-2.77 (3H, m), 2.59 (1H, t, J 12.0 Hz), 2.13-2.06 (1H, m). LCMS (APCI+) m/z 481 [M+H]$^+$; Rt: 1.87 min.

Example 75

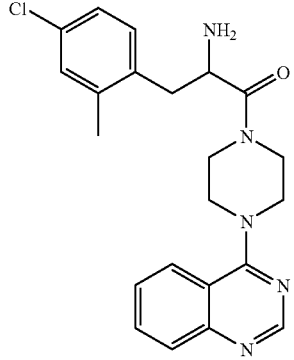 [SMILES: Cc1cc(Cl)ccc1CC(N)C(=O)N1CCN(c2ncnc3ccccc23)CC1]

Preparation of 2-Amino-3-(4-chloro-2-methyl-phenyl)-1-(4-quinazolin-4-yl-piperazin-1-yl)-propan-1-one, dihydrochloride Step 1: A mixture containing 4-Chloro-2-methyl-benzoic acid (4 g, 23 mmol) and LiAlH4 (890 mg, 23.5 mmol) in 250 mL of THF under a nitrogen atmosphere was allowed to stir at room temperature for 2 hours. The reaction was quenched with sodium sulfate decahydrate. The mixture was filtered through a pad of Celite and the filter cake washed with THF. The filtrate was concentrated under reduced pressure. Purification of the residue via biotage eluting with 30% ethyl acetate/hexanes gave (4-Chloro-2-methyl-phenyl)-methanol (3.70 g, 100%) as a colorless oil. $^1$H NMR (CDCl3, 400 MHz) δ 7.30-7.25 (1H, m), 7.18-7.14 (2H, m), 4.66 (2H, d, J 5.8 Hz), 2.32 (3H, s.)

Step 2: A solution containing gave (4-Chloro-2-methyl-phenyl)-methanol (2 g, 13 mmol) and PBr3 (1.3 mL, 14 mmol) in 150 mL of diethyl ether was allowed to stir at room temperature overnight. The reaction was diluted with ether and washed with water. The organic phase was dried over magnesium sulfate. Filtration, removal of solvent and purification of the residue via biotage eluting with 20% ethyl acetate/hexanes gave 1-Bromomethyl-4-chloro-2-methyl-benzene (1.89 g, 67%) as a colorless oil. $^1$H NMR (CDCl3, 400 MHz) δ 7.26-7.11 (3H, m), 4.67 (2H, s), 2.39 (3H, s.)

Step 3: To a solution containing (Benzhydrylidene-amino)-acetic acid ethyl ester (2.3 g, 8.6 mmol) in 50 mL of DMSO under a nitrogen atmosphere was added potassium t-butoxide (1.2 g, 11 mmol) After stirring for 20 minutes, 1-Bromomethyl-4-chloro-2-methyl-benzene (1.89 g, 8.6 mmol) was added and the reaction allowed to stir at room temperature overnight. The reaction was diluted with ethyl acetate and washed with brine. The organic phase was dried over magnesium sulfate. Filtration, removal of solvent and purification of the residue via biotage eluting with 20% ethyl acetate/hexanes gave 2-(Benzhydrylidene-amino)-3-(4-chloro-2-methyl-phenyl)-propionic acid ethyl ester (1.75 g, 50%) as a yellow oil. LCMS (APCI+) m/z 406 [M+H]$^+$; Rt: 4.16 min.

Step 4: A mixture containing 2-(Benzhydrylidene-amino)-3-(4-chloro-2-methyl-phenyl)-propionic acid ethyl ester (1.7 g, 4.2 mmol) and 90 mL of 3N HCl was heated at 75 C overnight. The reaction was cooled to room temperature and washed with ethyl acetate. The aqueous phase was concentrated under reduced pressure to afford 2-Amino-3-(4-chloro-2-methyl-phenyl)-propionic acid (640 mg, 72%) as white solid. LCMS (APCI+) m/z 214 [M+H]$^+$; Rt: 1.83 min. $^1$H NMR (D$_2$O, 400 MHz) δ 7.18 (1H, s), 7.11 (1H, d, J 8.7 Hz), 7.05 (1H, d, J 8.3 Hz), 4.05-4.00 (1H, m), 3.23 (1H, dd, J 14.3 and 6.1 Hz), 2.98 (1H, dd, J 14.4 and 8.5 Hz), 2.19 (3H, s.)

Step 5: To a solution containing 2-Amino-3-(4-chloro-2-methyl-phenyl)-propionic acid (640 mg, 3.0 mmol), 25 mL of dioxane and 9 mL of 1N sodium hydroxide was added boc anhydride (0.73 g, 3.3 mmol.) The reaction was allowed to stir at room temperature for 3 hours. The reaction was diluted with water and washed with DCM. The aqueous phase was acidified with 1N HCl and extracted with ethyl acetate. The organic phase was dried over magnesium sulfate. Filtration and removal of solvent gave 2-tert-Butoxycarbonylamino-3-(4-chloro-2-methylphenyl)-propionic acid (640 mg, 80%) as a white solid. $^1$H NMR (CDCl$_3$, 400 MHz) δ 7.13 (1H, s), 7.07 (2H, s), 5.14-5.08 (1H, m), 4.55-4.48 (1H, m), 3.24-3.16 (1H, m), 2.96-2.88 (1H, m), 2.33 (3H, s), 1.38 (9H, s.)

Step 6: To a solution containing 2-tert-Butoxycarbonylamino-3-(4-chloro-2-methyl-phenyl)-propionic acid (200 mg, 0.64 mmol) in 30 mL of DMF was added HOBT (0.12 g, 0.76 mmol), EDCI (0.15 g, 0.76 mmol) and NMM (0.19 g, 1.9 mmol) under a nitrogen atmosphere. After stirring for 10 minutes, 4-Piperazin-1-yl-quinazoline (200 mg, 0.93 mmol) was added and stirring continued overnight. The reaction was diluted with ethyl acetate and washed with water. The organic phase was dried over magnesium sulfate. Filtration, removal of solvent and purification of the residue via biotage eluting with 10% MeOH/DCM gave [1-(4-Chloro-2-methylbenzyl)-2-oxo-2-(4-quinazolin-4-yl-piperazin-1-yl)-ethyl]-carbamic acid tert-butyl ester (0.31 g, 95%.) LCMS (APCI+) m/z 510 [M+H]$^+$; Rt: 2.54 min.

Step 7: To a solution containing [1-(4-Chloro-2-methyl-benzyl)-2-oxo-2-(4-quinazolin-4-yl-piperazin-1-yl)-ethyl]-carbamic acid tert-butyl ester (0.30 g, 0.59 mmol) in 30 mL of DCM under a nitrogen atmosphere was added TFA (1.4 mL.) After stirring at room temperature overnight, the reaction was concentrated under reduced pressure. The residue was dissolved in DCM and 2N HCl in ether added. The solids were filtered and dried to afford 2-Amino-3-(4-chloro-2-methyl-phenyl)-1-(4-quinazolin-4-yl-piperazin-1-yl)-propan-1-one dihydrochloride (0.217 g) as an off-white solid. LCMS (APCI+) m/z 410 [M+H]$^+$; Rt: 1.87 min. $^1$H NMR (D2O, 400 MHz) δ 8.48 (1H, s), 7.91-7.86 (2H, m), 7.66-7.59 (2H, m), 7.08-7.02 (2H, m), 4.60-4.54 (1H,m), 4.20-4.12 (1H, m), 3.86-3.72 (3H, m), 3.61-3.38 (2H, m), 3.28-3.16 (2H, m), 3.01-2.94 (1H, m), 2.76-2.68 (1H, m), 2.19 (3H, s.)

Example 76

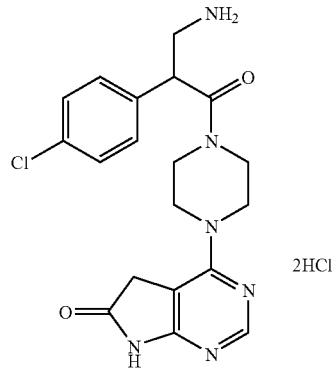 [SMILES: NCC(C(=O)N1CCN(c2ncnc3c2CC(=O)N3)CC1)c1ccc(Cl)cc1 ; "2HCl"]

Preparation of 4-{4-[3-amino-2-(4-chlorophenyl)-propionyl]-piperazin-1-yl)}-1,3-dihydropyrrolo[2,3-b]pyrimidin-2-one dihydrochloride Step 1: A solution of 4-chloro-5,7-dihydropyrrolo[2,3-d]pyrimidin-6-one (prepared according to the literature: Li Sun et al. *Bioorg. and Med. Chem. Lett.* 2002, 12, 2153-2157; 690 mg, 3.7 mmol), Boc-piperazine (630 mg, 3.7 mmol), and DIEA (0.96 mL, 5.5 mmol) in 20 mL IPA was heated to reflux and stirred 14 hours, after which the reaction mixture was concentrated. The crude was purified on silica gel (1:2 DCM:EtOAc to 1:4 DCM:EtOAc gradient) to give 4-Boc-piperazin-1-yl-5,7-dihydropyrrolo[2,3-d]pyrimidin-6-one, which was used in the next step.

Step 2: To a solution of 4-Boc-piperazin-1-yl-5,7-dihydro-pyrrolo[2,3-d]pyrimidin-6-one in 25 mL dioxane, was added 15 mL 4M HCl/dioxane. The resulting suspension was stirred at room temperature 15 hours, after which it was diluted with ether. The solids were isolated by filtration through a fritted funnel with nitrogen pressure, rinsed with ether, and dried in vacuo to furnish 4-piperazin-1-yl-5,7-dihydropyrrolo[2,3-d]pyrimidin-6-one dihydrochloride (350 mg, 100%) as a red powder. $^1$H NMR (DMSO-d6, 400 MHz) δ 11.12 (1H, s), 9.26 (2H, br. s), 8.25 (1H, s), 3.89-3.84 (4H, m), 3.77 (2H, s), 3.16-3.09 (4H, m). LCMS (APCI+) m/z 220 [M+H]$^+$; Rt: 0.68 min.

Step 3: To a solution of give 4-piperazin-1-yl-5,7-dihydropyrrolo[2,3-d]pyrimidin-6-one dihydrochloride (40 mg, 0.14 mmol), HOBt.H$_2$O (21 mg, 0.14 mmol), TEA (57 μL 0.41 mmol), and 3-Boc-amino-2-(4-chlorophenyl)-propionic acid (prepared from 4-chlorophenylacetic acid methyl ester using the procedures described for the preparation of A109; 49 mg, 0.16 mmol) in 1.2 mL 5:1 DCM:THF was added DCC (34 mg, 0.16 mmol). The reaction mixture was stirred at room temperature 4 hours, after which it was concentrated. The residue was suspended in DCM, and solids were removed by vacuum filtration through a cotton plug and rinsed with DCM. The filtrate was concentrated, and the crude was purified on silica gel (1:1 to 1:5 DCM:EtOAc gradient) to give 4-{4-[3-Boc-amino-2-(4-chlorophenyl)-propionyl]-piperazin-1-yl}-1,3-dihydropyrrolo[2,3-b]pyrimidin-2-one, which was used in the next step. LCMS (APCI+) m/z 401 [M-Boc+H]$^+$; Rt: 2.16 min.

Step 4: To a solution of 4-{4-[3-Boc-amino-2-(4-chlorophenyl)-propionyl]-piperazin-1-yl}-1,3-dihydropyrrolo[2,3-b]pyrimidin-2-one in 1.2 mL dioxane was added 1.2 mL 4M HCl/dioxane. The resulting suspension was stirred at room temperature 15 hours, after which it was concentrated to dryness. The solids were dissolved in minimal MeOH, and the product was triturated by the addition of ether. The resulting solids were isolated by filtration through a fritted funnel with nitrogen pressure, rinsed with ether, and dried in vacuo to give 4-{4-[3-amino-2-(4-chlorophenyl)-propionyl]-piperazin-1-yl}-1,3-dihydropyrrolo[2,3-b]pyridin-2-one dihydrochloride (28 mg, 43%) as a dark pink powder. $^1$H NMR (D$_2$O, 400 MHz) δ 8.10 (1H, s), 7.31-7.14 (4H, m), 4.28-4.22 (1H, m), 3.92-3.82 (1H, m), 3.73-2.94 (11H, m). LCMS (APCI+) m/z 401 [M+H]$^{3O}$; Rt: 1.98 min.

Example 77

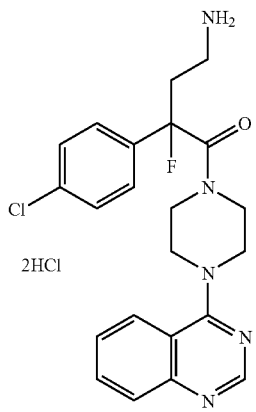 [SMILES: "2HCl" ; NCCC(F)(C(=O)N1CCN(c2ncnc3ccccc23)CC1)c1ccc(Cl)cc1]

Preparation of 4-Amino-2-(4-chlorophenyl)-2-fluoro-1-(4-quinazolin-4-yl-piperazin-1-yl)-butan-1-one dihydrochloride Step 1: A solution of 4-chloromandelic acid (12.3 g, 65.9 mmol) in toluene (50 mL), EtOH (16 mL), and concentrated H$_2$SO$_4$ (0.1 mL) was refluxed for 12 hours while removing water using a Dean-Stark trap. The mixture was concentrated in vacuo, diluted with DCM, and washed with dilute aqueous NaHCO$_3$. The separated DCM layer was dried (MgSO$_4$), filtered, and concentrated in vacuo to give (4-chlorophenyl)-hydroxy-acetic acid ethyl ester as a colorless oil (10.0 g) that crystallized upon standing.

Step 2: (4-Chlorophenyl)-hydroxy-acetic acid ethyl ester (10.0 g, 46.6 mmol) in DCM (35 mL) was cannulated into a solution of [bis(2-methoxyethyl)amino]sulfur trifluoride (9.45 mL, 51.3 mmol) in DCM (35 mL) cooled at −78° C. After being stirred for 12 hours and allowed to warm to ambient temperature, the mixture was poured into saturated aqueous NaHCO$_3$. The mixture was extracted with DCM and the organic extracts were dried (MgSO$_4$), filtered, and concentrated in vacuo. The crude material was chromatographed (SiO$_2$) using DCM as eluent to give (4-chlorophenyl)-fluoroacetic acid ethyl ester as a colorless oil (7.0 g).

Step 3: Potassium tert-butoxide (155 mg, 1.38 mmol) was added to a solution of (4-chlorophenyl)-fluoroacetic acid ethyl ester (3.00 g, 13.8 mmol) in THF (25 mL) at 0° C. to give an orange-red color. After 15 minutes, the mixture was cooled to −78° C. and t-butyl acrylate (2.23 mL, 15.2 mmol) was added neat. After being stirred and allowed to warm to ambient temperature for 12 hours, the mixture was quenched with saturated NH$_4$Cl, concentrated in vacuo, diluted with H$_2$O, and extracted with DCM. The DCM extracts were dried (MgSO$_4$), filtered, and concentrated in vacuo. The crude material was chromatographed (SiO$_2$) using DCM as eluent to give a colorless oil (1.20 g). A solution of the oil in DCM (6 mL) and TFA (4 mL) was stirred overnight. The mixture was diluted with toluene (40 mL) and concentrated in vacuo. The crude product was dissolved in dilute aqueous NaHCO$_3$ and extracted with DCM (twice, discarded). The aqueous layer was acidified to pH 1.0 with 1.0N HCl and extracted with DCM (twice). The organic extracts were dried (Na$_2$SO$_4$), filtered, and concentrated in vacuo to give 2-(4-chlorophenyl)-2-fluoro-pentanedioic acid 1-ethyl ester as an oil (1.0 g).

Step 4: Triethylamine (0.53 mL, 3.81 mmol) was added to a solution of 2-(4-chlorophenyl)-2-fluoro-pentanedioic acid 1-ethyl ester (1.00 g, 3.46 mmol) in t-BuOH (20 mL) followed by the addition of diphenylphosphoryl azide (0.82 mL, 3.81 mmol). The mixture was heated at 95° C. for 3 hours, concentrated in vacuo, and partitioned between dilute aqueous NaHCO$_3$ and DCM. The separated DCM layer was dried (Na$_2$SO$_4$), filtered, and concentrated in vacuo. The crude product was chromatographed (SiO$_2$) using DCM as eluent to give 4-tert-butoxycarbonylamino-2-(4-chlorophenyl)-2-fluoro-butyric acid ethyl ester (600 mg). $^1$H NMR (CDCl$_3$, 400 MHz) δ 7.42 (m, 2H), 7.35 (m, 2H), 5.25 (m, 0.4H), 4.61 (m, 0.6H), 4.19 (m, 2H), 3.35 (m, 0.6H), 3.23 (m, 1.4H), 2.59 (m, 1H), 2.34 (m, 1H), 1.40 (m, 9H), 1.24 (m, 3H). LCMS (APCI+) m/z 260 [M+H]$^+$(loss of Boc group).

Step 5: Lithium hydroxide monohydrate (0.27 g, 6.45 mmol) in H$_2$O (5 mL) was added to a solution of 4-tert-butoxycarbonylamino-2-(4-chlorophenyl)-2-fluoro-butyric acid ethyl ester (580 mg, 1.61 mmol) in THF (5 mL) and MeOH (5 mL). After being stirred for 12 hours, the mixture was concentrated in vacuo, diluted with H$_2$O, and extracted with DCM (3 times, discarded). The aqueous phase was then acidified to pH 1 and extracted with DCM (2 times). The organic extracts were dried (Na$_2$SO$_4$), filtered, and concentrated in vacuo to give 4-tert-butoxycarbonylamino-2-(4-chlorophenyl)-2-fluoro-butyric acid (400 mg). The material was used in the following step without further purification.

Step 6: PyBrop (562 mg, 1.21 mmol) was added in a single portion to a solution of 4-tert-butoxycarbonylamino-2-(4-chlorophenyl)-2-fluoro-butyric acid (400 mg, 1.21 mmol) and 4-piperazin-1-yl-quinazoline dihydrochloride (346 mg, 1.21 mmol) in DCM (12 mL) cooled in an ice bath. DIEA (0.84 mL, 4.82 mmol) was added and the mixture was allowed to warm to ambient temperature and stirred for 12 hours. The mixture was diluted with DCM and washed with 0.1N HCl. The separated DCM layer was dried (Na$_2$SO$_4$), filtered, and concentrated in vacuo. The crude material was chromatographed (SiO$_2$) using 2% MeOH/DCM followed by 5% MeOH/DCM as eluent to give [3-(4-chlorophenyl)-3-fluoro-4-oxo-4-(4-quinazolin-4-yl-piperazin-1-yl)-butyl]-carbamic acid tert-butyl ester (230 mg). LCMS (APCI+) m/z 528, 530 [M+H]$^+$.

Step 7: A solution of [3-(4-chlorophenyl)-3-fluoro-4-oxo-4-(4-quinazolin-4-yl-piperazin-1-yl)-butyl]-carbamic acid tert-butyl ester (226 mg, 0.43 mmol) in DCM (2 mL) and 2.0 M HCl in Et$_2$O (1 mL) was stirred for 12 hours. The mixture was concentrated in vacuo and chromatographed (SiO$_2$) using 10% MeOH/DCM followed by 10% (7N NH$_3$ in MeOH)/DCM as eluent. The purified material was dissolved in MeOH followed by the addition of 2.0N HCl in Et$_2$O, and then concentrated in vacuo. The resulting glass was heated at reflux in isopropyl alcohol and concentrated in vacuo. The resulting solid was suspended in acetonitrile and concentrated in vacuo (repeated twice) to give 4-amino-2-(4-chlorophenyl)-2-fluoro-1-(4-quinazolin-4-yl-piperazin-1-yl)-butan-1-one dihydrochloride as a white powder. $^1$H NMR (DMSO-d$_6$, 400 MHz) δ 8.86 (s, 1H), 8.18 (m, 4H), 8.01 (m, 2H), 7.69 (m, 1H), 7.58 (d, J=8.4 Hz, 2H), 7.40 (d, J=8.6 Hz, 2H), 4.23 (m, 2H), 4.09 (m, 1H), 3.80 (m, 4H), 3.47 (m, 1H), 2.86 (m, 1H), 2.67 (m, 2H), 2.41 (m, 1H). LCMS (APCI+) m/z 428, 430 [M+H]$^+$.

Example 78

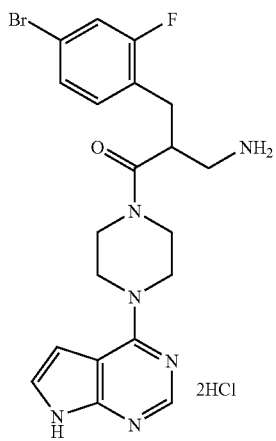 [SMILES: NCC(Cc1ccc(Br)cc1F)C(=O)N1CCN(c2ncnc3[nH]ccc23)CC1 ; "2HCl"]

Preparation of 3-Amino-2-(4-bromo-2-fluoro-benzyl)-1-[4-(7H-pyrrolo[2,3-d]pyrimidin-4-yl)-piperazin-1-yl]-propan-1-one dihydrochloride Step 1: To a stirred solution of diisopropyl amine (1.3 mL, 9.0 mmol) in THF (20 mL) was added n-BuLi (1.6 M solution in hexanes, 5.6 mL, 9.0 mmol) at 0° C. The reaction was stirred at 0° C. for 15 minutes and then cooled to −78° C. A solution of 3-tert-butoxycarbonylamino-propionic acid tert-butyl ester (1.0 g, 4.1 mmol) in THF (5 mL) was added dropwise. The mixture was stirred at −78° C. for 2 hours. A solution of 4-Bromo-1-bromomethyl-2-fluoro-benzene (1.3 g, 4.9 mmol) in THF (4 mL) was added dropwise. After completion, the dry-ice bath was removed and the reaction was warmed to 0° C. in an ice bath. After stirring at 0° C. for 30 minutes, the reaction was poured into saturated NH$_4$Cl aqueous solution. The organic layer was separated. The aqueous layer was extracted with EtOAc. The combined organic layers were washed with brine, dried and concentrated. The residue was purified by column chromatography (hexane: EtOAc, 20:1 to 5:1) to give 2-(4-Bromo-2-fluoro-benzyl)-3-tert-butoxycarbonylamino-propionic acid tert-butyl ester (1.35 g, 77%) as a colorless oil. $^1$H NMR (CDCl$_3$, 400 MHz) δ 7.20 (d, J=8.0 Hz, 2H), 7.08 (t, J=8.0 Hz, 1H), 4.86 (m, 1H), 3.28 (m, 2H), 2.92 (m, 3H), 1.43 (s, 9H), 1.36 (s, 9H).

Step 2: 2-(4-Bromo-2-fluoro-benzyl)-3-tert-butoxycarbonylamino-propionic acid tert-butyl ester (1.30 g, 3.01 mmol) was dissolved in THF (12 mL) and MeOH (12 mL). A solution of LiOH monohydrate (0.50 g, 12.0 mmol) in H$_2$O (12 mL) was added. The mixture was heated at reflux overnight. After cooling, the solvents were evaporated in vacuo. The residue was dissolved in water and extracted with ether (2x). The aqueous phase was acidified with 1N HCl and extracted with EtOAc. The combined organic layers were washed with brine, dried and concentrated to give 2-(4-Bromo-2-fluoro-benzyl)-3-tert-butoxycarbonylamino-propionic acid (1.00 g, 88%) as a white solid. $^1$H NMR (CD$_3$OD, 400 MHz) δ 7.26 (m, 2H), 7.19 (m, 1H), 3.27 (m, 2H), 2.86 (m, 3H), 1.43 (s, 9H).

Step 3: 3-Amino-2-(4-bromo-2-fluoro-benzyl)-1-[4-(7H-pyrrolo[2,3-d]pyrimidin-4-yl)-piperazin-1-yl]-propan-1-one dihydrochloride was prepared by substituting 5-piperazin-1-yl-1H-indazole with 4-Piperazin-1-yl-7H-pyrrolo[2,3-d]pyrimidine dihydrochloride and substituting (D)-Boc-4-chlorophenylalanine with 2-(4-Bromo-2-fluoro-benzyl)-3-tert-butoxycarbonylamino-propionic acid in Example 34, Step 2, then removing the Boc protecting group as described in Example 34, Step 3. $^1$H NMR (CD$_3$OD, 400 MHz) δ 8.37 (s, 1H), 7.40 (d, J=3.6 Hz, 1H), 7.36 (m, 1H), 7.31 (m, 1H), 7.24 (t, J=8.0 Hz, 1H), 6.95 (d, J=3.6 Hz, 1H), 4.14 (m, 2H), 4.02 (m, 1H), 3.87 (m, 4H), 3.55 (m, 2H), 3.34 (m, 1H), 3.11 (m, 1H), 2.98 (m, 2H). LCMS (APCI+) m/z 461, 463 [M+H]$^+$; Rt=1.79 min.

Example 79

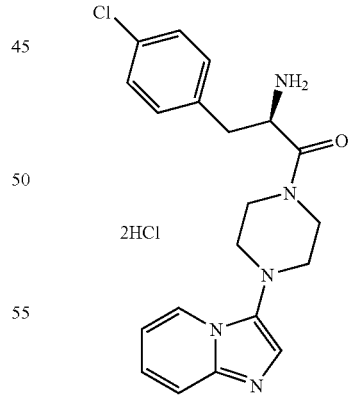

Preparation of 2-(R)-Amino-3-(4-chlorophenyl)-1-(4-imidazo r pyridin-3-yl-piperazin-1-yl)-propan-1-one dihydrochloride Step 1: A mixture of tert-butyl 1-piperazinecarboxylate (7.45 g, 40.0 mmol) and benzotriazole (4.76 g, 40.0 mmol) in H₂O (200 mL) was stirred for 1 hour. Glyoxal (40 wt. % in water, 2.90 g, 20 mmol) was then added and the mixture was stirred for 12 hours to produce a white precipitate. The precipitate was filtered off and washed with H₂O. The solids were dissolved in DCM, dried (Na₂SO₄), filtered, and concentrated in vacuo to give 1,2-(benzotriazol-1-yl)-1,2-(4-piperazine-1-carboxylic acid tert-butyl ester)ethane off-white solid (10.0 g).

Step 2: A mixture of 2-aminopyridine (282 mg, 3.00 mmol) and 1,2-(benzotriazol-1-yl)-1,2-(4-piperazine-1-carboxylic acid tert-butyl ester)ethane (1.90 g, 3.00 mmol) in dichloroethane (30 mL) was refluxed for 3 hours. Powdered KOH (555 mg, 9.90 mmol) was then added, and the mixture was stirred for 12 hours. The mixture was filtered and the filtrate was concentrated in vacuo. The resulting material was chromatographed (SiO₂) using DCM followed by 5% MeOH/DCM as eluent to give 4-imidazo[1,2-a]pyridin-3-yl-piperazine-1-carboxylic acid tert-butyl ester (900 mg). $^1$H NMR (CDCl₃, 400 MHz) δ 7.96 (m, 1H), 7.52 (m, 1H), 7.25 (m, 1H), 7.10 (m, 1H), 6.78 (m, 1H), 3.61 (m, 4H), 2.98 (m, 4H), 1.47 (s, 9H).

Step 3: A solution of 4-imidazo[1,2-a]pyridin-3-yl-piperazine-1-carboxylic acid tert-butyl ester (950 mg, 3.14 mmol) in DCM (10 mL) and 2.0N HCl in Et₂O (5 mL) was stirred for 12 hours. A precipitate formed and was filtered off to give 3-piperazin-1-yl-imidazo[1,2-a]pyridine dihydrochloride as a red solid (800 mg).

Step 4: Triethylamine (0.30 mL, 2.18 mmol) was added to a solution of (R)—N-Boc-4-chlorophenylalanine (392 mg, 1.31 mmol), 3-piperazin-1-yl-imidazo[1,2-a]pyridine dihydrochloride (300 mg, 1.09 mmol), and 1-hydroxybenzotriazole (177 mg, 1.31 mmol) in DMF (5 mL) followed by the addition of 1-[3-(dimethylamino)propyl]-3-ethylcarbodiimide hydrochloride (251 mg, 1.31 mmol) in a single portion. After being stirred for 12 hours, the mixture was diluted with H₂O, basified to pH 12 with 1.0 M NaOH, and extracted with DCM. The DCM extracts were dried (Na₂SO₄), filtered, and concentrated in vacuo. The residue was chromatographed (SiO₂) using DCM:Et₂O (1:1) followed by 10% MeOH/DCM as eluent to give (R)-[1-(4-chlorobenzyl)-2-(4-imidazo[1,2-a]pyridin-3-yl-piperazin-1-yl)-2-oxo-ethyl]-carbamic acid tert-butyl ester (350 mg).

Step 5: A solution of (R)-[1-(4-chlorobenzyl)-2-(4-imidazo[1,2-a]pyridin-3-yl-piperazin-1-yl)-2-oxo-ethyl]-carbamic acid tert-butyl ester (350 mg, 0.72 mmol) in DCM (3 mL) and 2.0N HCl in Et₂O (2 mL) was stirred for 12 hours. The mixture was concentrated in vacuo and the resulting material was chromatographed (SiO₂) using 10% MeOH/DCM followed by 10% (7N NH₃ in MeOH)/DCM as eluent. This material was dissolved in MeOH followed by the addition of 2.0N HCl in Et₂O, and then concentrated in vacuo. The resulting gum was tripped from isopropyl alcohol, and then from acetonitrile to give 2-(R)-amino-3-(4-chlorophenyl)-1-(4-imidazo[1,2-a]pyridin-3-yl-piperazin-1-yl)-propan-1-one dihydrochloride as a white solid (100 mg). $^1$H NMR (DMSO-d₆, 400 MHz) δ 8.66 (d, J=6.8 Hz, 1H), 8.49 (bs, 3H), 7.89 (m, 3H), 7.45 (m, 1H), 7.38 (d, J=8.3 Hz, 2H), 7.26 (d, J=8.3 Hz, 2H), 4.69 (bs, 1H), 3.49 (m, 6H), 3.08 (m, 1H), 2.94 (m, 3H), 2.85 (m, 1H). LCMS (APCI+) m/z 384, 386 [m+H]+.

Example 80

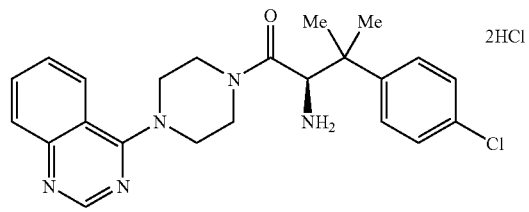 [SMILES: CC(C)(c1ccc(Cl)cc1)[C@@H](N)C(=O)N1CCN(c2ncnc3ccccc23)CC1 ; "2HCl"]

Preparation of 2(R)-Amino-3-(4-chlorophenyl)-3-methyl-1-(4-quinazolin-4-yl-piperazin-1-yl)-butan-1-one Step 1: The 2-(4-chlorophenyl)-2-methyl-propionic acid (6.10 g, 30.7 mmol) was dissolved in 120 mL of dry THF at room temperature. A 70% w/w solution of Red-Al (28.25 mL, 0.101 mol) was added dropwise via syringe over 5 minutes (vigorous bubbling). The mixture was heated to reflux for three hours. The solution was cooled to 0 C and carefully quenched with the addition of saturated sodium tartrate solution (100 mL, violent hydrogen evolution) and 100 mL of water. The aqueous mixture was extracted with ethyl acetate, and the combined organic was washed with diluted NaHCO₃ solution, then brine, separated, dried over MgSO₄, filtered, and concentrated in vacuo to afford 2-(4-chlorophenyl)-2-methyl-propan-1-ol as a colorless oil (5.70 g, 99%). The material was used without purification. $^1$H NMR (CDCl₃, 400 MHz) δ 7.32 (s, 5H), 3.62 (d, J=4.4 Hz, 2H), 1.33 (s, 6H), 1.23 (t, J=4.4 Hz, 1H).

Step 2: The DMSO (436 mL, 61.4 mmol) was dissolved in 100 mL of DCM and treated with oxalyl chloride (4.02 μL, 46.6 mmol) at −78° C. The solution stirred for 30 minutes at −78° C. before the 2-(4-chlorophenyl)-2-methyl-propan-1-ol (5.67 g, 30.7 mmol) was added dropwise as a solution in 10 mL of DCM. After addition was complete, the solution was stirred for two hours at −78° C., and then treated with triethyl amine (25.7 mL, 184 mmol). The solution was allowed to warm to ambient temperature and stir for three hours. The solution was quenched with the addition of water and partitioned with more DCM. The aqueous was extracted with DCM, and the combined organics were dried over MgSO₄, filtered, and concentrated in vacuo. The residue was purified by chromatography (silica, hexanes/ethyl acetate gradients) to afford 2-(4-chlorophenyl)-2-methylpropionaldehyde as a yellow oil (5.60 g, 99%). $^1$H NMR (CDCl₃, 400 MHz) δ 9.48 (s, 1H), 7.35 (d, J=8.8 Hz, 2H), 7.21 (d, J=8.8 Hz, 1H), 1.45 (s, 6H).

Step 3: The 2-(4-chlorophenyl)-2-methylpropionaldehyde (5.60 g, 30.7 mmol) and (S)-4-methyl-benzenesulfinic acid amide (5.00 g, 32.2 mmol) were dissolved in 300 mL of DCM and treated with Ti(OEt)₄ (32.1 mL, 153 mmol). The mixture was heated to reflux under nitrogen for four hours. The solution was cooled in an ice bath and quenched with the dropwise-addition of 200 mL of water. The resulting precipitate (Ti salts) were removed by filtration through a plug of celite and washed with DCM. The resulting filtrate was separated, and the aqueous was extracted with more DCM. The combined organic was dried over MgSO₄, filtered, and concentrated in vacuo. The residue was purified by filtration through a plug of silica gel (hexanes:ethyl acetate, 1:1) to afford the (R)-4-methylbenzenesulfinic acid [2-(4-chlorophenyl)-2-methylpropyliden]-amide as a colorless oil, which solidified upon standing to give a white solid (9.28 g, 95%). $^1$H NMR (CDCl$_3$, 400 MHz) δ 8.14 (s, 1H), 7.54 (d, J=8.4 Hz, 2H), 7.31 (d, J=8.8 Hz, 2H), 7.27 (d, J=8.8 Hz, 2H), 7.14 (m, 2H), 2.42 (s, 3H), 1.52 (s, 3H), 1.47 (s, 3H).

Step 4: The diethyl aluminum cyanide (43.5 mL of a 1.0M solution in toluene, 43.5 mmol) was added to isopropanol (28.9 mL, 377 mmol) and stirred at 10° C. for 15 minutes. This solution was cannulated into the (R)-4-methylbenzene-sulfinic acid [2-(4-chlorophenyl)-2-methyl-propylidene]-amide (9.28 g, 29.0 mmol) as a solution in 290 mL of THF at −78° C. This solution was allowed to stir for 15 minutes at −78° C. then allowed to warm slowly to room temperature overnight. The solution was quenched with the addition of diluted NaHCO$_3$ solution and extracted with ethyl acetate. The combined organic was washed with brine, separated, dried over Na$_2$SO$_4$, filtered, and concentrated in vacuo to afford the 4-methyl-benzenesulfinic acid [2-(4-chlorophenyl)-1-cyano-2-methyl-propyl]-amide as a colorless oil (9.55 g, 95% yield). The material was heated to 110° C. (reflux) in concentrated HCl solution over the weekend. The solution was cooled to room temperature, washed with ether, then concentrated in vacuo to give the (S)-2-amino-3-(4-chlorophenyl)-3-methyl-butyric acid hydrochloride salt a white solid (1.61 g, 21%). $^1$H NMR (DMSO-d$_6$, 400 MHz) δ 8.19 (brs, 1H), 7.48 (d, J=8.0 Hz, 2H), 7.41 (d, J=8.0 Hz, 2H), 7.13 (s, 3H), 4.15 (s, 1H), 1.42 (s, 3H), 1.40 (s, 3H). LCMS (APCI+) m/z 228 [M+H]$^+$; Rt=1.81 min.

Step 5: The (S)-2-amino-3-(4-chlorophenyl)-3-methyl-butyric acid hydrochloride salt (1.00 g, 3.79 mmol) was dissolved in 6 mL of 2M NaOH solution at room temperature and treated with di-tert-butyl di-carbonate (957 μL, 4.16 mmol). The solution was allowed to stir for four hours to completion, and the aqueous solution was acidified with the addition of 1M HCl solution (pH=2-3). The aqueous was extracted with ethyl acetate, and the organics were combined. The organic was washed with brine, separated, dried over MgSO$_4$, filtered, and concentrated in vacuo to give a colorless oil. The residue was purified by chromatography (silica, hexanes/ethyl acetate gradients) to afford the (S)-2-tert-butoxycarbonylamino-3-(4-chlorophenyl)-3-methyl-butyric acid (636 mg, 51%). $^1$H NMR (CDCl$_3$, 400 MHz) δ 12.67-10.55 (brs, 1H), 7.29 (m, 4H), 4.97 (d, J=8.4 Hz, 1H), 4.55 (d, J=8.4 Hz, 1H), 1.45 (s, 9H), 1.38 (s, 6H). LCMS (APCI+) m/z 228 [M-Boc+H]$^+$; Rt=3.20 min.

Step 6: The 4-piperazin-1-yl-quinazoline bis-hydrochloride (220 mg, 0.766 mmol), (S)-2-tert-butoxycarbonylamino-3-(4-chlorophenyl)-3-methyl-butyric acid (251 mg, 0.766 mmol, 1.0 equiv), 1-hydroxybenzotriazole (109 mg, 0.804 mmol, 1.05 equiv), and EDCI (154 mg, 0.804 mmol, 1.05 equiv) were dissolved/suspended in 6.0 mL of DMF. The mixture was treated with triethylamine (427 μL, 3.06 mmol) and allowed to stir overnight to completion. The reaction was partitioned between ethyl acetate and diluted NaHCO$_3$ solution. The aqueous was extracted with ethyl acetate, and the organics were combined. The organic was washed with water, then brine, separated, dried over MgSO$_4$, filtered, and concentrated in vacuo. The residue was eluted through a small plug of silica gel with ethyl acetate and concentrated in vacuo. The protected intermediate was immediately dissolved in 1 mL of dioxane and treated with 4M HCl in dioxane (1.92 mL, 7.66 mmol) at room temperature for four hours. The resulting precipitate was triturated with ether, then filtered to afford the (R)-2-amino-3-(4-chlorophenyl)-3-methyl-1-(4-quinazolin-4-yl-piperazin-1-yl)-butan-1-one bis-hydrochloride as a light-yellow solid (277 mg, 73%) upon drying under vacuum. $^1$H NMR (DMSO-d$_6$, 400 MHz) δ 8.89 (s, 1H), 8.46 (brs, 3H), 8.17 (d, J=8.4 Hz, 1H), 8.06 (t, J=7.6 Hz, 1H), 7.97 (d, J=8.4 Hz, 1H), 7.74 (d, J=8.0 Hz, 1H), 7.50 (d, J=8.0 Hz, 2H), 7.42 (d, J=8.0 Hz, 2H), 4.53 (brs, 1H), 4.09 (m, 3H), 3.90 (m, 3H), 3.32 (m, 1H), 3.04 (t, J=9.2 Hz, 1H), 1.51 (s, 3H), 1.43 (s, 3H). LCMS (APCI+) m/z 424 [M+H]$^+$; Rt=1.90 min.

Example 81

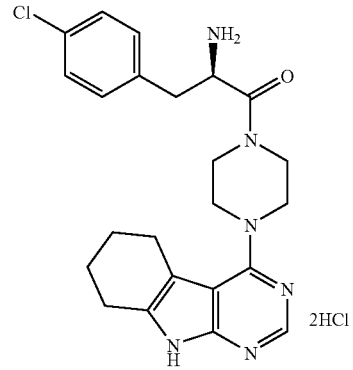 [SMILES: N[C@H](Cc1ccc(Cl)cc1)C(=O)N1CCN(c2ncnc3[nH]c4c(c23)CCCC4)CC1 ; "2HCl"]

Preparation of (2R)-2-Amino-3-(4-chlorophenyl)-1-[4-(6,7,8,9-tetrahydro-5H-1,3,9-triaza-fluoren-4-yl)-piperazin-1-yl]propan-1-one dihydrochloride Step 1: 4-(6,7,8,9-Tetrahydro-5H-1,3,9-triaza-fluoren-4-yl)-piperazine-1-carboxylic acid tert-butyl ester was prepared by the procedures described in Example 40, Step 1, substituting 4-chloro-5-iodopyrimidine with 4-Chloro-6,7,8,9-tetrahydro-5H-1,3,9-triaza-fluorene (prepared from 2-Amino-1-(4-methoxy-benzyl)-4,5,6,7-tetrahydro-1H-indole-3-carbonitrile according to the literature: Traxler, P. M. et. al. (1996), J. Med. Chem., 39, 2285-2292). $^1$H NMR (CDCl$_3$, 400 MHz) δ 10.24 (s, 1H), 8.32 (s, 1H), 3.59 (m, 4H), 3.55 (m, 4H), 2.78 (m, 4H), 1.92 (m, 2H), 1.82 (m, 2H), 1.43 (s, 9H). LCMS (APCI+) m/z 358 [M+H]$^+$; Rt=3.12 min.

Step 2: 4-Piperazin-1-yl-6,7,8,9-tetrahydro-5H-1,3,9-triaza-fluorene dihydrochloride was prepared by the procedures described in Example 34, Step 3, substituting (2R)-{1-(4-Chlorobenzyl)-2-[4-(1H-indazol-5-yl)-piperazin-1-yl]-2-oxo-ethyl}-carbamic acid tert-butyl ester with 4-(6,7,8,9-Tetrahydro-5H-1,3,9-triaza-fluoren-4-yl)-piperazine-1-carboxylic acid tert-butyl ester. $^1$H NMR (CD$_3$OD, 400 MHz) δ 8.42 (s, 1H), 4.14 (m, 4H), 3.48 (m, 4H), 2.83 (m, 4H), 1.96 (m, 2H), 1.86 (m, 2H). LCMS (APCI+) m/z 258 [M+H]$^+$; Rt=1.52 min.

Step 3: To a suspension of 4-Piperazin-1-yl-6,7,8,9-tetrahydro-5H-1,3,9-triaza-fluorene dihydrochloride (20 mg, 0.061 mmol) and (D)-Boc-4-chlorophenylalanine (20 mg, 0.067 mmol) were added DIEA (63 μL, 0.36 mmol) and HBTU (25 mg, 0.067 mmol). The reaction was stirred at room temperature for 2 hours. The mixture was partitioned between water and EtOAc. The organic layer was washed with aqueous NaHCO$_3$ and brine, dried and concentrated. The residue was purified by column chromatography (DCM:MeOH, 40:1 to 20:1) to give (2R)-{1-(4-Chlorobenzyl)-2-oxo-2-[4-(6,7,8,9-tetrahydro-5H-1,3,9-triaza-fluoren-4-yl)-piperazin-1-yl]-ethyl}-carbamic acid tert-butyl ester as a colorless oil.

Removal of the Boc protecting group by procedures described in Example 34, Step 3 afforded (2R)-2-Amino-3-(4-chlorophenyl)-1-[4-(6,7,8,9-tetrahydro-5H-1,3,9-triaza-fluoren-4-yl)-piperazin-1-yl]-propan-1-one dihydrochloride (28 mg, 90%) as a white solid. $^1$H NMR (CD$_3$OD, 400 MHz) δ 8.29 (s, 1H), 7.42 (d, J=8.0 Hz, 2H), 7.33 (d, J=8.0 Hz, 2H), 4.74 (m, 1H), 3.75 (m, 6H), 3.38 (m, 1H), 3.16 (m, 3H), 2.77 (m, 4H), 1.92 (m, 4H) LCMS (APCI+) m/z 439, 441 [M+H]$^+$; Rt=2.16 min.

Example 82

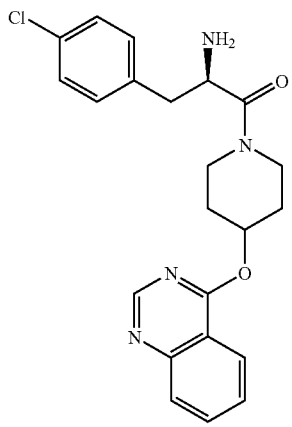 [SMILES: N[C@H](Cc1ccc(Cl)cc1)C(=O)N1CCC(Oc2ncnc3ccccc23)CC1]

Preparation of (2R)-2-Amino-3-(4-chlorophenyl)-1-[4-(quinazolin-4-yloxy)-piperidin-1-yl]-propan-1-one Step 1: To a stirred suspension of NaH (60%, 0.146 g, 3.65 mmol) in DMF (15 mL) was added dropwise a solution of 4-Hydroxypiperidine-1-carboxylic acid tert-butyl ester (0.611 g, 3.04 mmol) in DMF (5 mL) at 0° C. The reaction was stirred for 1 hour and then 4-chloroquinazoline (0.500 g, 3.04 mmol) was added. The mixture was allowed to warm to room temperature and stirred overnight. The mixture was partitioned between H$_2$O and EtOAc. The aqueous phase was extracted with EtOAc. The combined organic layers were washed with brine, dried and concentrated. The residue was purified by column chromatography (hexanes:EtOAc, 2:1) to give 4-(Quinazolin-4-yloxy)-piperidine-1-carboxylic acid tert-butyl ester (0.76 g, 76%) as a colorless oil. Removal of the Boc group by the procedures described in Example 34, Step 3 afforded 4-(Piperidin-4-yloxy)-quinazoline dihydrochloride as a white solid. $^1$H NMR (CD$_3$OD, 400 MHz) δ 9.35 (s, 1H), 8.59 (d, J=8.4 Hz, 1H), 8.31 (td, J=7.2 Hz, J=1.2 Hz 1H), 8.11 (d, J=8.4 Hz, 1H), 8.04 (t, J=7.2 Hz, 1H), 6.00 (m, 1H), 3.55 (m, 2H), 3.40 (m, 2H), 2.42 (m, 4H). LCMS (APCI+) m/z 230 [M+H]$^+$; Rt=1.67 min.

Step 2: (2R)-{1-(4-Chlorobenzyl)-2-oxo-2-[4-(quinazolin-4-yloxy)-piperidin-1-yl]-ethyl}-carbamic acid 9H-fluoren-9-ylmethyl ester was prepared by the procedures described in Example 34, Step 2, substituting 5-Piperazin-1-yl-1H-indazole with 4-(Piperidin-4-yloxy)-quinazoline dihydrochloride and substituting (D)-Boc-4-chlorophenylalanine with (D)-Fmoc-4-chlorophenylalanine. $^1$H NMR (CDCl$_3$, 400 MHz) δ 8.77 (s, 1H), 8.12 (m, 1H), 8.02 (s, 1H), 7.94 (m, 1H), 7.84 (m, 1H), 7.77 (m, 2H), 7.59 (m, 4H), 7.41 (m, 2H), 7.30 (m, 4H), 7.15 (m, 2H), 5.71 (d, J=8.4 Hz, 1H), 5.55 (m, 1H), 4.94 (m, 1H), 4.40 (m, 2H), 4.21 (m, 1H), 3.85 (m, 1H), 3.61 (m, 1H), 3.38 (m, 1H), 3.02 (m, 2H), 1.94 (m, 5H). LCMS (APCI+) m/z 633, 635 [M+H]$^+$; Rt=3.98 min.

Step 3: To a stirred solution of (2R)-{1-(4-Chlorobenzyl)-2-oxo-2-[4-(quinazolin-4-yloxy)-piperidin-1-yl]-ethyl}-carbamic acid 9H-fluoren-9-ylmethyl ester (0.166 g, 0.262 mmol) in DCM (5 mL) was added piperidine (1 mL). The reaction was stirred at room temperature for 4 hours. The volatiles were evaporated. The residue was purified by column chromatography (DCM:MeOH, 50:1 to 10:1) to give (2R)-2-Amino-3-(4-chlorophenyl)-1-[4-(quinazolin-4-yloxy)-piperidin-1-yl]-propan-1-one (0.099 g, 92%) as a colorless oil. $^1$H NMR (CDCl$_3$, 400 MHz) δ 8.77 (s, 1H), 8.15 (m, 1H), 7.94 (d, J=8.4 Hz, 1H), 7.85 (m, 1H), 7.59 (m, 1H), 7.30 (d, J=8.0 Hz, 2H), 7.17 (d, J=8.0 Hz, 2H), 5.57 (m, 1H), 3.95 (m, 2H), 3.10-3.70 (m, 3H), 2.95 (m, 1H), 2.82 (m, 1H), 1.30-2.10 (m, 4H). LCMS (APCI+) m/z 411, 413 [M+H]$^+$; Rt=2.19 min.

Example 83

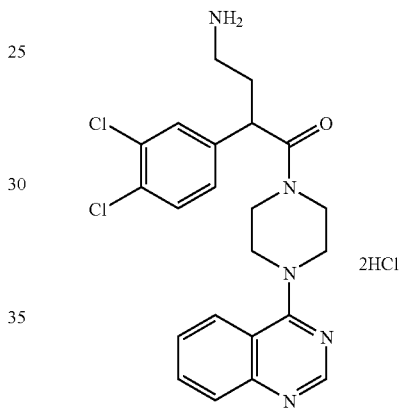

Preparation of 4-Amino-2-(3,4-dichlorophenyl)-1-(4-quinazolin-4-yl-piperazin-1-yl)-butan-1-one dihydrochloride Step 1: An analogous reaction to that described in example 61Steps 1-3, but starting with (3,4-dichlorophenyl)-acetic acid methyl ester yielded 4-tert-butoxycarbonylamino-2-(3,4-dichlorophenyl)-butyric acid. $^1$H NMR (CDCl$_3$, 400 MHz) δ 7.41 (m, 2H), 7.17 (d, J=8 Hz, 1H), 4.61 (brs, 1H), 3.58 (m, 1H), 3.16 (m, 2H), 2.28 (m, 1H), 1.92 (m, 1H), 1.44 (s, 9H).

Step 2: The 4-piperazin-1-yl-quinazoline (20 mg, 0.070 mmol) was dissolved in 1 mL CHCl$_3$ and 4-tert-butoxycarbonylamino-2-(3,4-dichlorophenyl)-butyric acid (36 mg, 0.10 mmol) was added. PS-carbodiimide resin (0.21 mmol) was added and the mixture was shaken overnight. The reaction mixture was filtered and the filtrate was concentrated in vacuo. The residue was purified by column chromatography (silica gel eluted with 1:4 DCM/EtOAc) to afford the pure Boc-protected intermediate. The material was dissolved in 1.0 mL of 1,4-dioxane and treated with 1.0 mL of 4M HCl in dioxane (4 mmol). The solution was allowed to stir at room temperature overnight to completion. The reaction mixture was concentrated to dryness and the residue was triturated with 2 mL diethyl ether. The solid was filtered under a nitrogen atmosphere and was allowed to dry under vacuum for 2 hours to afford 4-amino-2-(3,4-dichlorophenyl)-1-(4-quinazolin-4-yl-piperazin-1-yl)-butan-1-one dihydrochloride (15 mg, 42%). ¹H NMR (CD₃OD, 400 MHz) δ 8.69 (s, 1H), 8.22 (d, J=9 Hz, 1H), 8.04 (t, J=8 Hz, 1H), 7.77 (m, 2H), 7.54 (m, 2H), 7.31 (d, J=8.6 MHz, 1H), 4.30 (m, 4H), 3.98 (m, 4H), 3.60 (m, 1H), 2.98 (m, 1H), 2.86 (m, 1H), 2.36 (m, 1H), 2.02 (m, 1H).

Example 84

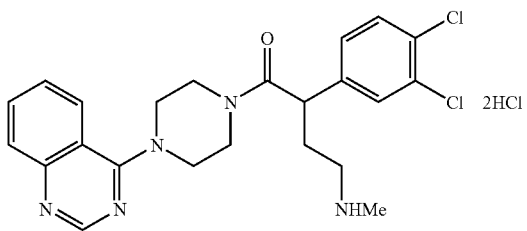 [SMILES: CNCCC(C(=O)N1CCN(c2ncnc3ccccc23)CC1)c1ccc(Cl)c(Cl)c1 ; "2HCl"]

Preparation of 2-(3,4-Dichlorophenyl)-4-methylamino-1-(4-quinazolin-4-yl-piperazin-1-yl)-butan-1-one dihydrochloride 2-(3,4-dichlorophenyl)-4-Boc-amino-1-(4-quinazolin-4-yl-piperazin-1-yl)-butan-1-one was N-methylated following a literature procedure (Mahavir Prashad et al. *Org. Lett.* 2003, 5(2), 125-128) to give [3-(3,4-Dichlorophenyl)-4-oxo-4-(4-quinazolin-4-yl-piperazin-1-yl)-butyl]-methyl-carbamic acid tert-butyl ester, which was treated with excess HCl/dioxane to furnish 2-(3,4-dichlorophenyl)-4-methylamino-1-(4-quinazolin-4-yl-piperazin-1-yl)-butan-1-one dihydrochloride (7 mg, 31%). ¹H NMR (DMSO-d₆, 400 MHz) δ 8.85 (br s, 2H), 8.84 (s, 1H), 8.17 (d, J=7.6 Hz, 1H), 8.01 (m, 1H), 7.89 (d, J=7.6 Hz, 1H), 7.69-7.61 (m, 3H), 7.33 (d, J=7.6 Hz, 1H), 4.40 (m, 1H), 4.11 (br s, 3H), 3.95 (m, 2H), 3.78 (m, 1H), 3.73 (m, 2H), 3.45 (m, 3H), 2.80 (m, 1H), 2.71 (m, 1H), 2.25 (m, 1H), 1.97 (m, 1H). LCMS (APCI+) m/z 458 [M+H]⁺. HPLC R_f=1.78 min.

Example 85

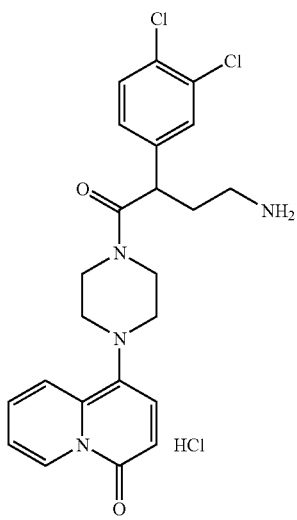 [SMILES: NCCC(C(=O)N1CCN(c2ccc(=O)n3ccccc23)CC1)c1ccc(Cl)c(Cl)c1 ; Cl]

Preparation of 1-{4-[4-Amino-2-(3,4-dichlorophenyl)-butyryl]-piperazin-1-yl}-quinolizin-4-one hydrochloride Step 1: To a solution of 4-Pyridin-2-ylmethyl-piperazine-1-carboxylic acid tert-butyl ester (prepared from 1-Pyridin-2-ylmethyl-piperazine according to the literature: *J. Med. Chem.* (1993), 36, 2984) (2.00 g, 7.21 mmol) in THF (15 mL) was added n-BuLi (1.6 M in hexanes, 5.0 mL, 7.9 mmol) at −78° C. The mixture was allowed to warm to room temperature and stirred for 30 minutes. The solution was then cooled to −78° C. and a solution of diethyl ethoxymethylenemalonate (1.72 g, 7.93 mmol) in THF (2 mL) was added dropwise. The reaction mixture was allowed to warm to 0° C. over 1 hour and stirred at 0° C. for 1 hour. The reaction was poured into water and extracted with EtOAc. The combined organic layers were washed with brine, dried and concentrated. The residue was purified by column chromatography (hexanes:EtOAc, 8:1 to 1; 1) to give 2-[2-(4-tert-Butoxycarbonyl-piperazin-1-yl)-1-ethoxy-2-pyridin-2-yl-ethyl]-malonic acid diethyl ester (2.40 g, 67%) as a mixture of diastereomers. Diastereomer 1: ¹H NMR (CDCl₃, 400 MHz) δ 8.55 (d, J=4.4 Hz, 1H), 7.63 (td, J=7.6 Hz, J=1.6 Hz, 1H), 7.21 (d, J=7.6 Hz, 1H), 7.16 (dd, J=7.6 Hz, J=1.6 Hz, 1H), 4.74 (m, 1H), 4.16 (m, 5H), 3.75 (q, J=7.2 Hz, 2H), 3.52 (d, J=4.4 Hz, 1H), 3.38 (m, 4H), 2.67 (m, 2H), 2.44 (m, 2H), 1.40 (s, 9H), 1.22 (m, 6H), 1.44 (t, J=7.2 Hz, 3H). LCMS (APCI+) m/z 494 [M+H]⁺; Rt=3.61 min. Diastereomer 2: ¹H NMR (CDCl₃, 400 MHz) δ 8.58 (d, J=4.8 Hz, 1H), 7.59 (td, J=7.6 Hz, J=1.6 Hz, 1H), 7.15 (dd, J=7.6 Hz, J=1.6 Hz, 1H), 7.08 (d, J=8.0 Hz, 1H), 4.91 (m, 1H), 4.16 (m, 5H), 3.53 (m, 1H), 3.22 (m, 6H), 2.50 (m, 2H), 2.19 (m, 2H), 1.34 (s, 9H), 1.24 (m, 6H), 0.69 (t, J=7.2 Hz, 3H). LCMS (APCI+) m/z 494 [M+H]⁺; Rt=3.62 min.

Step 2: 2-[2-(4-tert-Butoxycarbonyl-piperazin-1-yl)-1-ethoxy-2-pyridin-2-yl-ethyl]-malonic acid diethyl ester (2.40 g, 4.86 mmol) was dissolved in xylene (20 mL) and heated at 140° C. for 12 hours. After cooling, the volatiles were evaporated and the residue was purified by column chromatography (EtOAc) to give 1-(4-tert-Butoxycarbonyl-piperazin-1-yl)-4-oxo-1,9a-dihydro-4H-quinolizine-3-carboxylic acid ethyl ester (1.39 g, 71%) as an orange solid. ¹H NMR (CDCl₃, 400 MHz) δ 9.48 (d, J=7.2 Hz, 1H), 8.34 (s, 1H), 7.69 (td, J=7.2 Hz, J=1.2 Hz, 1H), 7.23 (m, 1H), 4.44 (q, J=7.2 Hz, 2H), 4.14 (m, 2H), 3.10 (m, 2H), 2.88 (m, 4H), 1.51 (s, 9H), 1.43 (t, J=7.2 Hz, 3H). LCMS (APCI+) m/z 402 [M+H]⁺; Rt=2.85 min.

Step 3: A mixture of 1-(4-tert-Butoxycarbonyl-piperazin-1-yl)-4-oxo-1,9a-dihydro-4H-quinolizine-3-carboxylic acid ethyl ester (0.320 g, 0.797 mmol) in concentrated HCl (5 mL) was refluxed for 30 minutes. After cooling, the reaction was basified with aqueous NaHCO₃ solution and thoroughly extracted with DCM. The combined organic layers were washed with brine, dried and concentrated to give 1-Piperazin-1-yl-1,9a-dihydro-quinolizin-4-one (0.075 g, 41%) as a yellow oil. ¹H NMR (CDCl₃, 400 MHz) δ 9.16 (d, J=7.2 Hz, 1H), 8.20 (d, J=9.2 Hz, 1H), 7.71 (d, J=9.6 Hz, 1H), 7.37 (t, J=7.2 Hz, 1H), 7.03 (t, J=6.4 Hz, 1H), 6.61 (d, J=9.2 Hz, 1H), 3.07 (m, 4H), 2.87 (m, 4H). LCMS (APCI+) m/z 230 [M+H]⁺; Rt=0.29 min.

Step 4: 1-{4-[4-Amino-2-(3,4-dichlorophenyl)-butyryl]-piperazin-1-yl}-quinolizin-4-one hydrochloride was prepared by substituting 5-piperazin-1-yl-1H-indazole with 1-Piperazin-1-yl-1,9a-dihydro-quinolizin-4-one and substituting (D)-Boc-4-chlorophenylalanine with 4-tert-Butoxycarbonylamino-2-(3,4-dichlorophenyl)-butyric acid in Example 34, Step 2, then removing the Boc protecting group as described in Example 34, Step 3. ¹H NMR (CD₃OD, 400 MHz) δ 9.25 (d, J=7.2 Hz, 1H), 9.57 (d, J=8.8 Hz, 1H), 8.00 (m, 2H), 7.71 (d, J=7.2 Hz, 1H), 7.58 (m, 2H), 7.33 (d, J=8.0 Hz, 1H), 7.02 (d, J=8.4 Hz, 1H), 4.31 (m, 1H), 3.82 (m, 5H), 3.65 (m, 2H), 3.34 (m, 1H), 2.98 (m, 1H), 2.86 (m, 1H), 2.36 (m, 1H), 2.03 (m, 1H). LCMS (APCI+) m/z 459, 461, 463 [M+H]⁺; Rt=2.02 min.

Example 86

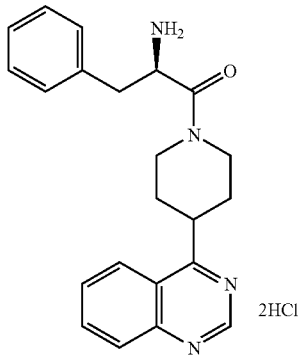 [SMILES: N[C@H](Cc1ccccc1)C(=O)N1CCC(c2ncnc3ccccc23)CC1 ; "2HCl"]

Preparation of (2R)-2-Amino-3-phenyl-1-(4-quinazolin-4-yl-piperidin-1-yl)-propan-1-one dihydrochloride Step 1: To a 25 mL flask was charged 4-Trifluoromethanesulfonyloxy-3,6-dihydro-2H-pyridine-1-carboxylic acid benzyl ester (prepared from 4-Oxo-piperidine-1-carboxylic acid benzyl ester according to the literature: Wustrow, D. J. et. al. (1991), *Synthesis*, 993-995. 1.14 g, 3.12 mmol), 4-chloroquinazoline (0.512 g, 3.12 mmol), lithium chloride (0.397 g, 9.36 mmol), Pd(PPh₃)₄ (0.180 g, 0.156 mmol) and hexamethyl ditin (1.02 g, 3.12 mmol). 1,4-Dioxane (20 mL) was added and the reaction was degassed with N₂ for 15 minutes. The mixture was stirred at reflux overnight. After cooling, the black suspension was poured into saturated aqueous potassium fluoride solution. The mixture was diluted with EtOAc and stirred for 2 hours. The organic phase was separated. The aqueous phase was extracted with EtOAc. The combined organic layers were washed with brine, dried and concentrated. The residue was purified by column chromatography (hexanes:EtOAc, 2:3) to give 4-Quinazolin-4-yl-3,6-dihydro-2H-pyridine-1-carboxylic acid benzyl ester (0.790 g, 73%) as a colorless oil. ¹H NMR (CDCl₃, 400 MHz) δ 9.27 (s, 1H), 8.19 (d, J=7.2 Hz, 1H), 8.07 (d, J=8.8 Hz, 1H), 7.91 (m, 1H), 7.62 (t, J=7.2 Hz, 1H), 7.41 (m, 6H), 6.18 (m, 1H), 5.23 (s, 2H), 4.32 (s, 2H), 3.85 (t, J=5.6 Hz, 1H), 2.80 (br s, 2H). LCMS (APCI+) m/z 346 [M+H]⁺; Rt=3.16 min.

Step 2: To a stirred solution of 4-Quinazolin-4-yl-3,6-dihydro-2H-pyridine-1-carboxylic acid benzyl ester (0.907 g, 2.63 mmol) in MeOH (30 mL) under N₂ was cautiously added 10% Pd on carbon (100 mg). The reaction was hydrogenated at 50 psi using a parr shaker for 3 days. The catalyst was removed by filtration. The filtrate was evaporated under vacuum. The resulting residue was purified by column chromatography (DCM:MeOH, 20:1 to DCM:MeOH:Et₃N, 100:10:1) to give 4-(1,2,3,6-Tetrahydro-pyridin-4-yl)-quinazoline (0.358 g, 64%) as a white waxy solid. ¹H NMR (CDCl₃, 400 MHz) δ 9.27 (s, 1H), 8.19 (d, J=8.4 Hz, 1H), 8.06 (d, J=8.4 Hz, 1H), 7.88 (t, J=8.4 Hz, 1H), 7.65 (t, J=8.4 Hz, 1H), 3.71 (m, 1H), 3.31 (m, 2H), 2.90 (m, 2H), 1.99 (m, 4H). LCMS (APCI+) m/z 214 [M+H]⁺; Rt=1.60 min.

Step 3: (2R)-[1-Benzyl-2-oxo-2-(4-quinazolin-4-yl-piperidin-1-yl)-ethyl]-carbamic acid tert-butyl ester was prepared by substituting 5-Piperazin-1-yl-1H-indazole with 4-(1,2,3,6-Tetrahydro-pyridin-4-yl)-quinazoline and substituting (D)-Boc-4-chlorophenylalanine with (D)-Boc-phenylalanine in Example 34, Step 2. ¹H NMR (CDCl₃, 400 MHz) (1:1 mixture of rotamers) δ 9.26, 9.21 (2s, 1H, rotamers), 8.08 (m, 2H), 7.89 (m, 1H), 7.65 (m, 1H), 7.28 (m, 5H), 5.51, 5.43 (2d, J=8.4 Hz, 1H, rotamers), 4.92 (m, 1H), 4.72 (m, 1H), 3.95, 3.83 (2d, J=13.2 Hz, 1H, rotamers), 3.65 (m, 1H), 2.20-3.30 (m, 4H), 1.20-2.10 (m, 4H), 1.44, 1.42 (2s, 9H, rotamers). LCMS (APCI+) m/z 461 [M+H]⁺; Rt=3.23 min.

Step 4: (2R)-2-Amino-3-phenyl-1-(4-quinazolin-4-yl-piperidin-1-yl)-propan-1-one dihydrochloride was prepared by the procedures described in Example 34, Step 3, substituting (2R)-{1-(4-Chlorobenzyl)-2-[4-(1H-indazol-5-yl)-piperazin-1-yl]-2-oxo-ethyl}-carbamic acid tert-butyl ester with (2R)-[1-Benzyl-2-oxo-2-(4-quinazolin-4-yl-piperidin-1-yl)-ethyl]-carbamic acid tert-butyl ester. LCMS (APCI+) m/z 361 [M+H]⁺; Rt=2.38 min.

Example 87

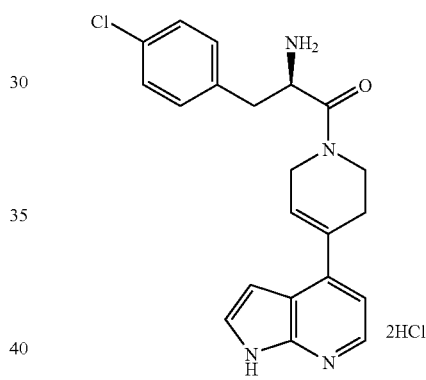

Preparation of (2R)-2-Amino-3-(4-chlorophenyl)-1-[4-(1H-pyrrolo[2,3-b]pyridin-4-yl)-3,6-dihydro-2H-pyridin-1-yl]-propan-1-one dihydrochloride Step 1: To a nitrogen flushed flask containing 4-(4,4,5,5-Tetramethyl-[1,3,2]dioxaborolan-2-yl)-3,6-dihydro-2H-pyridine-1-carboxylic acid tert-butyl ester (prepared from tert-butyl-4-oxopiperidine-1-carboxylate according to the literature: Eastwood, P. R. (2000), *Tetrahedron Lett.*, 3705-3708. 127 mg, 0.410 mmol), K₂CO₃ (142 mg, 1.02 mmol) and dichloro[1,1'-bis(diphenylphosphino)-ferrocene]palladium(II)dichloromethane adduct (17 mg, 0.020 mmol) was added a solution of 1-Benzenesulfonyl-4-chloro-1H-pyrrolo[2,3-b]pyridine (100 mg, 0.342 mmol) in DMF (3 mL). The mixture was heated at 80° C. for 36 hours. The mixture was cooled to room temperature and partitioned between EtOAc and water. The combined organic layers were washed with saturated aqueous NaHCO₃ and brine, dried and concentrated. The residue was purified by flash chromatography on silica gel, eluting with hexanes:EtOAc (2:1) to give 4-(1-Benzenesulfonyl-1H-pyrrolo[2,3-b]pyridin-4-yl)-3,6-dihydro-2H-pyridine-1-carboxylic acid tert-butyl ester (0.068 g, 45%) as a colorless oil. ¹H NMR (CDCl₃, 400 MHz) δ 8.37 (d, J=5.2 Hz, 1H), 8.20 (d, J=8.0 Hz, 2H), 7.73 (d, J=4.0 Hz, 1H), 7.56 (m, 1H), 7.49 (m, 2H), 7.03 (d, J=5.2 Hz, 1H), 6.73 (d, J=4.0 Hz, 1H), 6.14 (br s, 1H), 4.12 (m, 2H), 3.65 (m, 2H), 2.55 (m, 2H), 1.50 (s, 9H). LCMS (APCI+) m/z 440 [M+H]+; Rt=3.84 min.

Step 2: 1-Benzenesulfonyl-4-(1,2,3,6-tetrahydro-pyridin-4-yl)-1H-pyrrolo[2,3-b]pyridine dihydrochloride was prepared by the procedures described in Example 34, Step 3, substituting (2R)-{1-(4-Chlorobenzyl)-2-[4-(1H-indazol-5-yl)-piperazin-1-yl]-2-oxo-ethyl}-carbamic acid tert-butyl ester with 4-(1-Benzenesulfonyl-1H-pyrrolo[2,3-b]pyridin-4-yl)-3,6-dihydro-2H-pyridine-1-carboxylic acid tert-butyl ester. 1H NMR (CD3OD, 400 MHz) δ 8.36 (d, J=5.2 Hz, 1H), 8.15 (d, J=8.0 Hz, 2H), 7.93 (d, J=4.0 Hz, 1H), 7.76 (m, 1H), 7.56 (m, 2H), 7.29 (d, J=5.2 Hz, 1H), 6.97 (d, J=4.0 Hz, 1H), 6.29 (br s, 1H), 3.93 (m, 2H), 3.60 (m, 2H), 2.85 (m, 2H). LCMS (APCI+) m/z 340 [M+H]+; Rt=1.87 min.

Step 3: To a solution of 1-Benzenesulfonyl-4-(1,2,3,6-tetrahydro-pyridin-4-yl)-1H-pyrrolo[2,3-b]pyridine dihydrochloride (25 mg, 0.061 mmol) and (D)-Boc-4-chlorophenylalanine (20 mg, 0.067 mmol) in DMF (2 mL) were added DIEA (63 µL, 0.36 mmol) and HBTU (25 mg, 0.067 mmol). The reaction was stirred at room temperature for 2 hours. The mixture was partitioned between water and EtOAc. The organic layer was washed with aqueous NaHCO3 and brine, dried and concentrated. The residue was dissolved in THF (0.3 mL) and MeOH (0.3 mL). A solution of lithium hydroxide monohydrate (10 mg, 0.24 mmol) in H2O (0.3 mL) was added. The mixture was heated at 50° C. overnight. After cooling, the reaction was partitioned between EtOAc and water. The organic layer was washed with brine, dried and concentrated. The residue was purified by column chromatography (hexanes:EtOAc, 1:1 to 3:1) to give (2R)-{1-(4-Chlorobenzyl)-2-oxo-2-[4-(1H-pyrrolo[2,3-b]pyridin-4-yl)-3,6-dihydro-2H-pyridin-1-yl]-ethyl}-carbamic acid tert-butyl ester as a colorless oil. Removal of the Boc group by the procedures described in Example 34, Step 3 afforded (2R)-2-Amino-3-(4-chlorophenyl)-1-[4-(1H-pyrrolo[2,3-b]pyridin-4-yl)-3,6-dihydro-2H-pyridin-1-yl]-propan-1-one dihydrochloride (9 mg, 33%) as a white solid. 1H NMR (CD3OD, 400 MHz) (1:1 mixture of rotamers) δ 8.37 (m, 1H), 7.73 (s, 1H), 7.47, 7.40 (2d, J=6.0 Hz, rotamers), 7.33 (m, 3H), 7.23 (d, J=8.0 Hz, 2H), 6.99 (m, 1H), 6.33, 6.31 (2s, 1H, rotamers), 4.74 (m, 1H), 4.36 (m, 1H), 4.21 (m, 1H), 3.45-3.90 (m, 2H), 3.05-3.30 (m, 2H), 1.90-2.70 (m, 2H). LCMS (APCI+) m/z 381, 383 [M+H]+; Rt=1.95 min.

Example 88

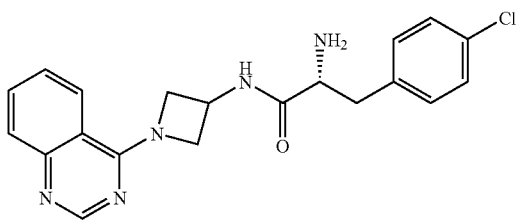 [SMILES: N[C@H](Cc1ccc(Cl)cc1)C(=O)NC1CN(c2ncnc3ccccc23)C1]

Preparation of 2(R)-Amino-3-(4-chlorophenyl)-N-(1-quinazolin-4-yl-azetidin-3-yl-propionamide Step 1: The (1-benzhydrylazetidin-3-yl)-carbamic acid tert-butyl ester (500 mg, 1.48 mmol), Pd/C (10% w/w, 157 mg, 0.07 mmol), and ammonium formate (932 mg, 14.8 mmol) were weighed into a 25 RBF equipped with a condenser, degassed 3 times, and suspended/dissolved in 6 mL of methanol. The mixture was heated to 60 C for 4 hours to completion and was allowed to cool to room temperature. The mixture was filtered through a plug of celite washed with ethanol, and the filtrate was concentrated in vacuo. The residue was re-dissolved in 30 mL of DCM, dried over Na2SO4, filtered, and concentrated in vacuo to afford the crude intermediate. The intermediate and 4-chloroquinazoline (268 mg, 1.63 mmol) were dissolved in 6 mL of NMP, then treated with diisopropylethyl amine (515 µL, 2.96 mmol). The solution was heated to 80° C. overnight to completion affording an orange mixture. After cooling to room temperature, the solution was diluted with ethyl acetate and poured into diluted NaHCO3 solution. The aqueous was extracted with ethyl acetate, and the organics were combined. The organic was washed with water, brine, separated, dried over MgSO4, filtered, and concentrated in vacuo. The residue was purified by chromatography (silica gel eluted with 9:1 MeOH:EtAc) to afford the pure (1-quinazolin-4-yl-azetidin-3-yl)-carbamic acid tert-butyl ester as a tan solid (390 mg, 88%). 1H NMR (DMSO-d6, 400 MHz) δ 8.47 (s, 1H), 7.94 (d, J=8.4 Hz, 1H), 7.78 (t, J=7.6 Hz, 1H), 7.72 (d, J=8.4 Hz, 1H), 7.67 (m, 1H), 7.48 (t, J=7.6 Hz, 1H), 4.73 (m, 2H), 4.50 (m, 1H), 4.30 (m, 2H), 1.41 (s, 9H). LCMS (APCI+) m/z 301 [M+H]+; Rt=2.26 min.

Step 2: The (1-quinazolin-4-yl-azetidin-3-yl)-carbamic acid tert-butyl ester (390 mg, 1.30 mmol) was dissolved in 7 mL, of 4M HCl and allowed to stir at 80° C. to completion after three hours. The aqueous solution was washed with ether (discarded), and the aqueous layer was concentrated in vacuo to afford the de-protected intermediate as a white solid. The flask containing this solid was charged with HOBt (193 mg, 1.43 mmol), EDCI (274 mg, 1.43 mmol), and the 2(S)-tert-butoxycarbonylamino-3-(4-chlorophenyl)-propionic acid (389 mg. 1.30 mmol). The mixture was suspended/dissolved in 12.0 mL of DMF and treated with TEA (905 µL, 6.49 mmol). The mixture was allowed to stir for four hours to completion. The contents were partitioned between ethyl acetate and diluted NaHCO3 solution. The aqueous was extracted with ethyl acetate, and the organics were combined. The organic was washed with water, brine, separated, dried over MgSO4, filtered, and concentrated in vacuo to afford the crude Boc-intermediate as a white solid. The material was dissolved in 7 mL of DCM and treated with 4.0 mL of TFA. After two hours, the reaction solution was concentrated in vacuo to afford a pale yellow oil. The contents were partitioned between ethyl acetate and diluted NaHCO3 solution. The aqueous was extracted with ethyl acetate, and the organics were combined. The organic was washed with brine, separated, dried over Na2SO4, filtered, and concentrated in vacuo. The residue was purified by chromatography (silica gel eluted with 9:1 MeOH:DCM) to afford the pure 2(R)-amino-3-(4-chlorophenyl)-N-(1-quinazolin-4-yl-azetidin-3-yl)-propionamide as a colorless oil (177 mg, 30%). 1H NMR (CDCl3, 400 MHz) δ 8.60 (s, 1H), 8.02 (brs, 1H), 7.82 (d, J=8.4 Hz, 1H), 7.75 (d, J=8.8 Hz, 1H), 7.72 (t, J=8.4 Hz, 1H), 7.40 (t, J=7.6 Hz, 1H), 7.29 (d, J=8.4 Hz, 1H), 7.15 (d, J=8.4 Hz, 1H), 4.85 (m, 3H), 4.29 (dd, J=15.6, 5.6 Hz, 2H), 3.64 (dd, J=8.8, 4.0 Hz, 1H), 3.22 (dd, J=13.6, 4.0 Hz, 1H), 2.78 (dd, J=14.0, 8.8 Hz, 1H). LCMS (APCI+) m/z 382 [M+H]+; Rt=0.76 min.

Example 89

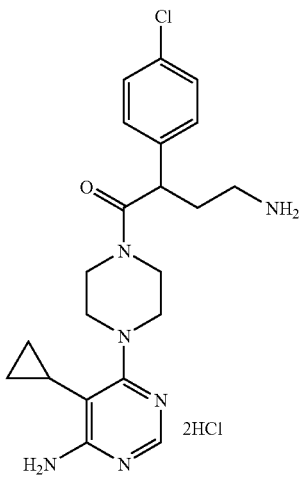 [SMILES: NCCC(C(=O)N1CCN(c2ncnc(N)c2C2CC2)CC1)c1ccc(Cl)cc1 ; "2HCl"]

Preparation of 4-Amino-1-[4-(6-amino-5-cyclopropyl-pyrimidin-4-yl)-piperazin-1-yl]-2-(4-dichlorophenyl)-butan-1-one dihydrochloride Step 1: To a stirred solution of 5-cyclopropyl-pyrimidine-4,6-diol (1.35 g, 8.87 mmol) in DCE (35 mL) was added slowly POCl₃ (4.14 mL, 44.4 mmol) followed by DIEA (1.72 g, 13.3 mmol). The reaction mixture was heated to reflux for 2 days. After cooling, the solvent was evaporated in vacuo. The residue was partitioned between 5% NaHCO₃ and EtOAc. The organic phase was washed with brine, dried, and passed through a Silica gel pad to give 4,6-dichloro-5-cyclopropyl-pyrimidine (1.30 g, 78%) as a yellow oil. ¹H NMR (CDCl₃, 400 MHz) δ (s, 1H), 1.65 (m, 1H), 1.03 (m, 2H), 1.58 (m, 2H).

Step 2: 4-(5-Cyclopropyl-6-chloro-pyrimidin-4-yl)-piperazine-1-carboxylic acid tert-butyl ester was prepared by the procedures described in Example 40, Step 1, substituting 4-chloro-5-iodopyrimidine with 5-cyclopropyl-4,6-dichloropyrimidine. ¹H NMR (CDCl₃, 400 MHz) δ 8.31 (s, 1H), 3.64 (m, 4H), 3.54 (m, 4H), 1.73 (m, 1H), 1.46 (s, 9H), 1.14 (m, 2H), 0.65 (m, 2H). LCMS (APCI+) m/z 339, 341 [M+H]+; Rt=2.38 min.

Step 3: A round bottom flask was charged with Pd(OAc)₂ (84 mg, 0.37 mmol) and rac-BINAP (234 mg, 0.37 mmol) and purged with N₂. To the flask was added 4-(5-cyclopropyl-6-chloro-pyrimidin-4-yl)-piperazine-1-carboxylic acid tert-butyl ester (1.27 g, 3.75 mmol), benzophenone imine (815 mg, 4.50 mmol), NaOBuᵗ (793 mg, 8.25 mmol) and toluene (24 mL). The mixture was heated to 95° C. for 1 hour. After cooling to room temperature, the reaction was diluted with EtOAc, filtered through Celite, and concentrated. The crude product was purified by column chromatography (hexanes:EtOAc, 2:1) to give 4-[6-(Benzhydrylidene-amino)-5-cyclopropyl-pyrimidin-4-yl]-piperazine-1-carboxylic acid tert-butyl ester (1.62 g, 89%) as a colorless oil. ¹H NMR (CDCl₃, 400 MHz) δ 8.38 (s, 1H), 7.41 (m, 10H), 3.40 (m, 4H), 3.32 (m, 4H), 1.46 (s, 9H), 0.93 (m, 1H), 0.86 (m, 2H), 0.59 (m, 2H). LCMS (APCI+) m/z 484 [M+H]+; Rt=3.94 min.

Step 4: To a stirred solution of 4-[6-(Benzhydrylidene-amino)-5-cyclopropyl-pyrimidin-4-yl]-piperazine-1-carboxylic acid tert-butyl ester (1.60 g, 3.31 mmol) in MeOH (70 mL) was added hydroxylamine hydrochloride (0.41 g, 6.0 mmol) and NaOAc (0.65 g, 7.9 mmol). After stirring at room temperature overnight, the reaction mixture was partitioned between 0.1N NaOH and DCM. The organic layer was dried and concentrated. The residue was purified by column (DCM:MeOH, 20:1) to give 4-(6-Amino-5-cyclopropyl-pyrimidin-4-yl)-piperazine-1-carboxylic acid tert-butyl ester (1.00 g, 95%) as a colorless syrup. ¹H NMR (CDCl₃, 400 MHz) δ 8.12 (s, 1H), 4.97 (s, 2H), 3.52 (m, 4H), 3.50 (m, 4H), 1.48 (s, 9H), 1.44 (m, 1H), 1.02 (m, 2H), 0.64 (m, 2H). LCMS (APCI+) m/z 320 [M+H]+; Rt=2.51 min.

Step 5: 5-Cyclopropyl-6-piperazin-1-yl-pyrimidin-4-ylamine dihydrochloride was prepared by the procedures described in Example 34, Step 3, substituting (2R)-{1-(4-Chlorobenzyl)-2-[4-(1H-indazol-5-yl)-piperazin-1-yl]-2-oxo-ethyl}-carbamic acid tert-butyl ester with 4-(6-Amino-5-cyclopropyl-pyrimidin-4-yl)-piperazine-1-carboxylic acid tert-butyl ester. ¹H NMR (CD₃OD, 400 MHz) δ 8.18 (s, 1H), 4.12 (m, 4H), 3.31 (m, 4H), 1.66 (m, 1H), 1.18 (m, 2H), 0.58 (m, 2H). LCMS (APCI+) m/z 220 [M+H]+; Rt=0.74 min.

Step 6: 4-Amino-1-[4-(6-amino-5-cyclopropyl-pyrimidin-4-yl)-piperazin-1-yl]-2-(4-chlorophenyl)-butan-1-one dihydrochloride was prepared by substituting 5-piperazin-1-yl-1H-indazole with 5-Cyclopropyl-6-piperazin-1-yl-pyrimidin-4-ylamine dihydrochloride and substituting (D)-Boc-4-chlorophenylalanine with 4-tert-Butoxycarbonylamino-2-(4-chlorophenyl)-butyric acid in Example 34, Step 2, then removing the Boc protecting group as described in Example 34, Step 3. ¹H NMR (CD₃OD, 400 MHz) δ 8.04 (s, 1H), 7.41 (d, J=8.4 Hz, 2H), 7.33 (d, J=8.4 Hz, 2H), 4.19 (m, 1H), 3.95 (m, 1H), 3.85 (m, 2H), 3.61 (m, 3H), 3.22 (m, 2H), 2.95 (m, 1H), 2.82 (m, 1H), 2.31 (m, 1H), 2.01 (m, 1H), 1.56 (m, 1H), 1.08 (m, 2H), 0.47 (m, 2H). LCMS (APCI+) m/z 415, 417 [M+H]+; Rt=1.87 min.

Example 90

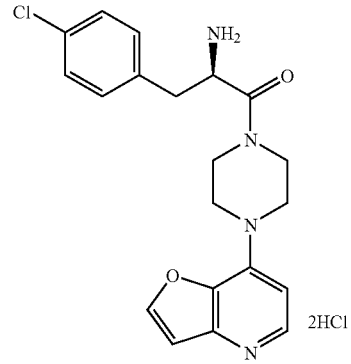

Preparation of (2R)-2-Amino-3-(4-chlorophenyl)-1-(4-furo[3,2-b]pyridin-7-yl-piperazin-1-yl)-propan-1-one dihydrochloride Step 1: A solution of 3-hydroxy-2-bromopyridine (21.4 g, 123 mmol) in acetic anhydride (25 g, 245 mmol) was refluxed for 1 hour. After cooling, the mixture was poured into ice water, neutralized with Na₂CO₃ and extracted with ether. The organic phase was dried and concentrated. The residue was subject to column chromatography, eluted by ether to afford Acetic acid 2-bromo-pyridin-3-yl ester (26.2 g, 99%). ¹H NMR (CDCl₃, 400 mHz) δ 8.28 (m, 1H), 7.46 (m, 1H), 7.30 (m, 1H), 2.38 (s, 3H).

Step 2: To a solution of PdCl₂(PPh₃)₂ (1.4 g, 2.0 mmol) and CuI (0.4 g, 2.1 mmol) in TEA (100 mL) and THF (200 mL) under nitrogen was added a mixture of 2-bromo-3-acetoxy-pyridine (13.1 g, 60.6 mmol) and TMS-acetylene (7.0 g, 71 mmol) in THF (100 mL) in one portion. The mixture was stirred at room temperature for 1 hour. Then quenched with saturated NaHCO₃ (50 mL) and MeOH (50 mL). The mixture was stirred at 80° C. for 2 hours. After cooling, the mixture was extracted with ether. The organic phase was dried and concentrated. The residue was subject to column chromatography to afford Furo[3,2-b]pyridine (1.54 g, 21%). ¹H NMR (CDCl₃, 400 MHz) δ 8.55 (m, 1H), 7.84 (m, 1H), 7.75 (m, 1H), 7.72 (m, 1H), 6.99 (m, 1H).

Step 3: To a solution of Furo[3,2-b]pyridine (1.5 g, 13.0 mmol) in CHCl₃ (30 mL) was added MCPBA (2.9 g, 17.0 mmol). The mixture was stirred at room temperature for 16 hours. Then the mixture was filtered through a alumina (140 g, basic) and washed with ethyl acetate/hexane (1:1) and DCM/MeOH (20:1) to give Furo[3,2-b]pyridine 4-oxide (1.49 g, 88%). ¹H NMR (CDCl₃, 400 MHz) δ 8.25 (m, 1H), 7.81 (m, 1H), 7.51 (m, 1H), 7.23 (m, 1H).

Step 4: To a solution of Furo[3,2-b]pyridine 4-oxide in CHCl₃ (5 mL) was added POCl₃ (5 g, 33 mmol). The mixture was refluxed for 2 hours. After cooling, the mixture was quenched with ice water and neutralized with NaHCO₃. Extracted with CHCl₃ (3×100 mL). The organic phase was dried and concentrated. The residue was subject to column chromatography to afford 7-Chloro-furo[3,2-b]pyridine (0.74 g, 50%). ¹H NMR (CDCl₃, 400 MHz) δ 8.46 (m, 1H), 7.92 (m, 1H), 7.28 (m, 1H), 7.04 (m, 1H).

Step 5: A mixture of 7-Chloro-furo[3,2-b]pyridine (0.73 g, 4.75 mmol) and piperazine (1.2 g, 14 mmol) in a sealed tube was heated to 130° C. for 4 hours. After cooling, the solid was dissolved in MeOH and DCM, concentrated and subject to column chromatography, eluted by DCM/MeOH (10:1-1:1) to give 7-Piperazin-1-yl-furo[3,2-b]pyridine (0.21 g, 22%). MS (APCI+) [M+H]⁺204.

Step 6: To a solution of 7-Piperazin-1-yl-furo[3,2-b]pyridine (0.21 g, 1.03 mmol) and (2R)-2-tert-Butoxycarbonylamino-3-(4-chlorophenyl)-propionic acid (0.6 g, 2.0 mmol) in DMF (10 mL) and TEA (2 mL) was added HOBT (0.3 g, 2.2 mmol) and EDCI (0.42 g, 2.2 mmol). The mixture was stirred at room temperature for 4 hours. The solvent was removed and the residue was subject to column chromatography to afford (2R)-[1-(4-Chlorobenzyl)-2-(4-furo[3,2-b]pyridin-7-yl-piperazin-1-yl)-2-oxo-ethyl]-carbamic acid tert-butyl ester (7 mg, 1.4%). MS (APCI+) [M+H]⁺ 486.

Step 7: To a solution of (2R)-[1-(4-Chlorobenzyl)-2-(4-furo[3,2-b]pyridin-7-yl-piperazin-1-yl)-2-oxo-ethyl]-carbamic acid tert-butyl ester (7 mg, 0.014 mmol) in DCM (4 mL) was added HCl in dioxane (4M, 1 mL). The mixture was stirred at room temperature for 4 hours. The solvent was removed to give (2R)-2-Amino-3-(4-chlorophenyl)-1-(4-furo[3,2-b]pyridin-7-yl-piperazin-1-yl)-propan-1-one as HCl salt (6 mg, 99%). MS (APCI+) [M+H]⁺ 386.

Example 91

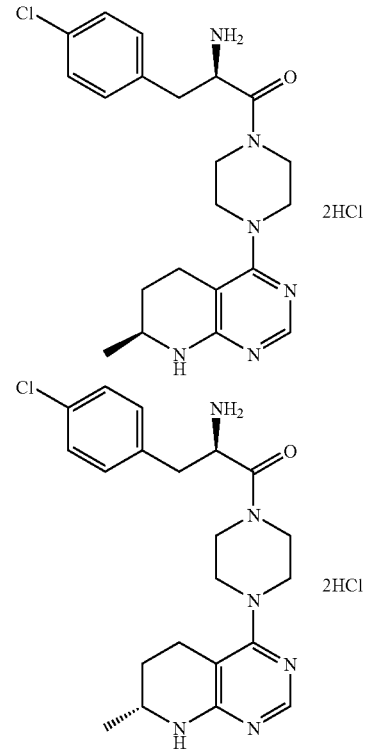

Preparation of (7S,2R)-2-Amino-3-(4-chlorophenyl)-1-[4-(7-methyl-5,6,7,8-tetrahydro-pyrido[2,3-d]pyrimidin-4-yl)-piperazin-1-yl]-propan-1-one dihydrochloride and (7R,2R)-2-Amino-3-(4-chlorophenyl)-1-[4-(7-methyl-5,6,7,8-tetrahydro-pyrido[2,3-d]pyrimidin-4-yl)-piperazin-1-yl]-propan-1-one dihydrochloride Step 1: A solution of 2-Chloro-6-methyl-nicotinic acid (3.00 g, 17.5 mmol) in ammonia in MeOH (7M, 60 mL) in a bomb was heated to 120° C. overnight. After cooling, the solvent was removed and the residue was neutralized with 2N HCl. The precipitate was filtered, washed with water and dried to afford 2-Amino-6-methyl-nicotinic acid (1.44 g, 54%). ¹H NMR (CD₃OD, 400 MHz) δ 8.21 (d, J=7.6 Hz, 1H), 6.60 (d, J=7.6 Hz, 1H), 2.41 (s, 3H). MS (APCI+) [M+H]⁺ 153.

Step 2: A mixture of 2-Amino-6-methyl-nicotinic acid (1.44 g, 9.46 mmol) and formamide (8.0 g, 178 mmol) was stirred at 170° C. for 2 hours. After cooling, the mixture was quenched with water (4 mL). The precipitate was filtered, washed with water and dried to afford 7-Methyl-pyrido[2,3-d]pyrimidin-4-ol (0.79 g, 51%). ¹H NMR (CDCl₃, 400 MHz) δ 8.49 (d, J=8.4 Hz, 1H), 8.22 (s, 1H), 7.35 (d, J=8.0 Hz, 1H), 2.75 (s, 3H). MS (APCI+) [M+H]⁺162.

Step 3: To a solution of 7-Methyl-pyrido[2,3-d]pyrimidin-4-ol (0.78 g, 4.84 mmol) in DCE (30 mL) was added DIEA (1.0 mL, 1.19 mmol), followed by POCl₃ (2.4 mL, 26.1 mmol). The mixture was refluxed overnight. After cooling, the solvent was removed and the residue was dissolved in water (50 mL) and extracted with ethyl acetate (3×100 mL). The organic phase was dried and concentrated. The residue was subject to column chromatography, eluted by hexane/ethyl acetate (2:1) to give 4-Chloro-7-methyl-pyrido[2,3-d]pyrimidine (0.66 g, 76%). $^1$H NMR (CDCl$_3$, 400 MHz) δ 9.22 (s, 1H), 8.49 (d, J=8.8 Hz, 1H), 7.57 (d, J=8.4 Hz, 1H), 2.88 (s, 3H). MS (APCI+) [M+H]$^+$180.

Step 4: The mixture of 4-Chloro-7-methyl-pyrido[2,3-d]pyrimidine (0.66 g, 3.67 mmol) and 1-Boc-piperazine (0.75 g, 4.03 mmol) in DCE (40 mL) and TEA (5 mL) was refluxed for 1 hour. After cooling, the solvent was removed and the residue was subject to column chromatography, eluted by ethyl acetate-DCM/MeOH (10:1) to give 4-(7-Methyl-pyrido[2,3-d]pyrimidin-4-yl)-piperazine-1-carboxylic acid tert-butyl ester (1.2 g, 99%). $^1$H NMR (CDCl$_3$, 400 MHz) δ 8.82 (s, 1H), 8.11 (d, J=8.4 Hz, 1H), 7.28 (d, J=8.8 Hz, 1H), 3.79 (m, 4H), 3.65 (m, 4H), 2.75 (s, 3H), 1.50 (s, 9H). MS (APCI+) [M+H]$^+$330.

Step 5: A solution of 4-(7-Methyl-pyrido[2,3-d]pyrimidin-4-yl)-piperazine-1-carboxylic acid tert-butyl ester (1.2 g, 3.64 mmol), PtO$_2$ (42 mg, 0.18 mmol) in MeOH (40 mL) and TFA (2 mL) was stirred under H$_2$ (1 atm) at room temperature for 4 hours. The catalyst was filtered and the solvent was removed. The residue was subject to column chromatography, eluted by DCM/MeOH (20:1) to give 4-(7-Methyl-5,6,7,8-tetrahydro-pyrido[2,3-d]pyrimidin-4-yl)-piperazine-1-carboxylic acid tert-butyl ester as TFA salt (0.43 g, 27%). $^1$H NMR (CDCl$_3$, 400 MHz) δ 9.75 (s, 1H), 7.97 (s, 1H), 3.60 (m, 10H), 2.60 (m, 2H), 2.00 (m, 1H), 1.48 (s, 9H), 1.35 (d, J=6.4 Hz, 3H). MS (APCI+) [M+H]$^+$334.

Step 6: To a solution of 4-(7-Methyl-5,6,7,8-tetrahydro-pyrido[2,3-d]pyrimidin-4-yl)-piperazine-1-carboxylic acid tert-butyl ester TFA salt (0.19 g, 0.44 mmol) in DCM (20 mL) and TEA (1 mL) was added (S)-Mosher's acid chloride (0.14 g, 0.55 mmol). The mixture was stirred at room temperature for 20 minutes. The solvent was removed and the residue was subject to column chromatography, eluted by hexane/ethyl acetate (4:1-3:1-2:1). The first spot gave (7S)-4-[7-Methyl-8-(3,3,3-trifluoro-2-methoxy-2-phenyl-propionyl)-5,6,7,8-tetrahydro-pyrido[2,3-d]pyrimidin-4-yl]-piperazine-1-carboxylic acid tert-butyl ester (84 mg, 34%). $^1$H NMR (CDCl$_3$, 400 MHz) δ 8.27 (s, 1H), 7.28 (m, 2H), 7.12 (m, 3H), 4.74 (m, 1H), 3.90 (s, 3H), 3.40 (m, 4H), 3.08 (m, 4H), 2.32 (m, 1H), 2.20 (m, 1H), 1.94 (m, 1H), 1.49 (s, 9H), 1.27 (m, 1H), 1.11 (d, J=6.4 Hz, 3H). MS (ESI+) [M+H]$^+$550 The second spot gave (7R)-4-[7-Methyl-8-(3,3,3-trifluoro-2-methoxy-2-phenyl-propionyl)-5,6,7,8-tetrahydro-pyrido[2,3-d]pyrimidin-4-yl]-piperazine-1-carboxylic acid tert-butyl ester (85 mg, 35%). $^1$H NMR (CDCl$_3$, 400 MHz) δ 8.20 (s, 1H), 7.57 (m, 2H), 7.40 (m, 3H), 4.54 (m, 1H), 3.52 (s, 3H), 3.50 (m, 4H), 3.31 (m, 4H), 2.55 (m, 1H), 2.42 (m, 1H), 1.91 (m, 1H), 1.48 (s, 9H), 1.27 (m, 1H), 1.19 (d, J=6.4 Hz, 3H). MS (APCI+) [M+H]$^+$550.

Step 7: To a solution of (7S)-4-[7-Methyl-8-(3,3,3-trifluoro-2-methoxy-2-phenyl-propionyl)-5,6,7,8-tetrahydro-pyrido[2,3-d]pyrimidin-4-yl]-piperazine-1-carboxylic acid tert-butyl ester (84 mg, 0.153 mmol) in MeOH (5 mL) was added LiOH (3M, 4 mL). The mixture was stirred at room temperature for 4 days and then neutralized with 2N HCl. The solvent was removed and the residue was subject to column chromatography, eluted by ethyl acetate—DCM/MeOH (20:1) to afford (7S)-4-(7-Methyl-5,6,7,8-tetrahydro-pyrido[2,3-d]pyrimidin-4-yl)-piperazine-1-carboxylic acid tert-butyl ester (32 mg, 63%). $^1$H NMR (CDCl$_3$, 400 MHz) δ 8.11 (s, 1H), 5.20 (s, 1H), 3.54 (m, 5H), 3.30 (m, 4H), 2.57 (m, 2H), 1.95 (m, 1H), 1.48 (s, 9H), 1.40 (m, 1H), 1.27 (d, J=6.4 Hz, 3H). MS (APCI+) [M+H]$^+$334.

Step 8: To a solution of (7S)-4-(7-Methyl-5,6,7,8-tetrahydro-pyrido[2,3-d]pyrimidin-4-yl)-piperazine-1-carboxylic acid tert-butyl ester (32 mg, 0.096 mmol) in DCM (2 mL) was added HCl in dioxane (4M, 2 mL). The mixture was stirred at room temperature for 3 hours. The solvent was removed to give (7S)-7-Methyl-4-piperazin-1-yl-5,6,7,8-tetrahydro-pyrido[2,3-d]pyrimidine as HCl salt (22 mg, 99%). MS (APCI+) [M+H]$^+$234.

Step 9: To a solution of (7S)-7-Methyl-4-piperazin-1-yl-5,6,7,8-tetrahydro-pyrido[2,3-d]pyrimidine (7.5 mg, 0.032 mmol) in DCM (4 mL) and DIEA (0.5 mL) was added D-2-tert-Butoxycarbonylamino-3-(4-chlorophenyl)-propionic acid (10 mg, 0.033 mmol) and HBTU (13 mg, 0.034 mmol). The mixture was stirred at room temperature for 1 hour. The solvent was removed and the residue was subject to column chromatography, eluted by hexane/ethyl acetate (2:1) to give (7S,2R)-{1-(4-Chlorobenzyl)-2-[4-(7-methyl-5,6,7,8-tetrahydro-pyrido[2,3-d]pyrimidin-4-yl)-piperazin-1-yl]-2-oxo-ethyl}-carbamic acid tert-butyl ester (16 mg, 96%). $^1$H NMR (CDCl$_3$, 400 MHz) δ 8.10 (s, 1H), 7.26 (d, J=6.8 Hz, 2H), 7.12 (d, J=8.0 Hz, 2H), 5.45 (d, J=8.4 Hz, 1H), 5.10 (s, 1H), 4.84 (m, 1H), 3.60 (m, 4H), 3.30 (m, 2H), 3.00 (m, 4H), 2.50 (m, 2H), 1.96 (m, 1H), 1.80 (m, 1H), 1.44 (m, 1H), 1.41 (s, 9H), 1.27 (d, J=6.4 Hz, 3H). MS (APCI+) [M+H]$^+$516.

Step 10: To a solution of (7S,2R)-{1-(4-Chlorobenzyl)-2-[4-(7-methyl-5,6,7,8-tetrahydro-pyrido[2,3-d]pyrimidin-4-yl)-piperazin-1-yl]-2-oxo-ethyl}-carbamic acid tert-butyl ester (16 mg, 0.031 mmol) in DCM (5 mL) was added HCl in dioxane (4M, 2 mL). The mixture was stirred at room temperature for 4 hours. The solvent was removed to give (7S, 2R)-2-Amino-3-(4-chlorophenyl)-1-[4-(7-methyl-5,6,7,8-tetrahydro-pyrido[2,3-d]pyrimidin-4-yl)-piperazin-1-yl]-propan-1-one dihydrochloride (13 mg, 99%). MS (APCI+) [M+H]$^+$416. (7R, 2R)-2-Amino-3-(4-chlorophenyl)-1-[4-(7-methyl-5,6,7,8-tetrahydro-pyrido[2,3-d]pyrimidin-4-yl)-piperazin-1-yl]-propan-1-one dihydrochloride was prepared in a similar manner from (7R)-4-[7-Methyl-8-(3,3,3-trifluoro-2-methoxy-2-phenyl-propionyl)-5,6,7,8-tetrahydro-pyrido[2,3-]pyrimidin-4-yl]-piperazine-1-carboxylic acid tert-butyl ester.

Example 92

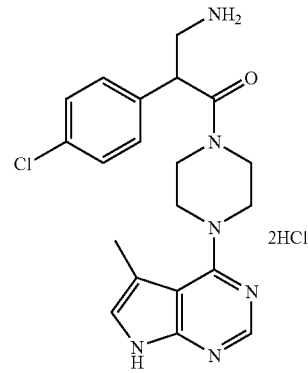 [SMILES: Cc1c[nH]c2ncnc(N3CCN(C(=O)C(CN)c4ccc(Cl)cc4)CC3)c12 ; "2HCl"]

Preparation of 3-amino-2-(4-chlorophenyl)-1-[4-(5-methyl-7H-pyrrolo[2,3-d]pyrimidin-4-yl)-piperazin-1-yl]-propan-1-one dihydrochloride Step 1: To a solution of 7-benzenesulfonyl-5-methyl-4-piperazin-1-yl-7H-pyrrolo[2,3-d]pyrimidine dihydrochloride (35 mg. 0.081 mmol), 3-Boc-amino-2-(4-chlorophenyl)-propionic acid (27 mg, 0.089 mmol), and TEA (0.11 mL, 0.81 mmol) 1.2 mL DCM was added HBTU (34 mg, 0.089 mmol). The reaction mixture was stirred at room temperature 2 hours, after which 0.15 mL 3M LiOH and 1.0 mL MeOH were added. The reaction mixture was stirred at 35° C. for 3.5 hours, after which saturated NaHCO$_3$ was added. The mixture was extracted with DCM, and the combined extracts were dried (Na$_2$SO$_4$), filtered, and concentrated. The crude was purified on silica gel (flushed with 1:1 DCM:EtOAc, then gradient to 1:4 DCM:EtOAc) to give 3-Boc-amino-2-(4-chlorophenyl)-1-[4-(5-methyl-7H-pyrrolo[2,3-d]pyrimidin-4-yl)-piperazin-1-yl]-propan-1-one, which was used in the next step.

Step 2: To a solution of 3-Boc-amino-2-(4-chlorophenyl)-1-[4-(5-methyl-7H-pyrrolo[2,3-d]pyrimidin-4-yl)-piperazin-1-yl]-propan-1-one in 1 mL dioxane was added 1.5 mL 4M HCl/dioxane. The resulting suspension was stirred at room temperature 7 hours, after which it was concentrated to dryness. The solids were then dissolved in minimal MeOH, and the product was triturated by the addition of ether. The solids were isolated by filtration through a flitted funnel with nitrogen pressure, rinsed with ether, and dried in vacuo to afford 3-amino-2-(4-chlorophenyl)-1-[4-(5-methyl-7H-pyrrolo[2,3-d]pyrimidin-4-yl)-piperazin-1-yl]-propan-1-one dihydrochloride (21 mg, 55%) as a beige powder. $^1$H NMR (D$_2$O, 400 MHz) δ 8.08 (s, 1H), 7.29 (d, J=8.4 Hz, 2H), 7.17 (d, J=8.4 Hz, 2H), 7.07 (s, 1H), 4.30 (t, J=6.5 Hz, 1H), 4.03-3.94 (m, 1H), 3.82-3.73 (m, 1H), 3.68-3.46 (m, 5H), 3.28 (dd, J=12.9, 7.4 Hz, 1H), 3.23 (dd, J=12.9, 5.7 Hz, 1H), 3.04-2.94 (m, 1H), 2.13 (s, 3H). LCMS (APCI+) m/z 399 [M+H]$^+$; Rt: 2.11 min.

Example 93

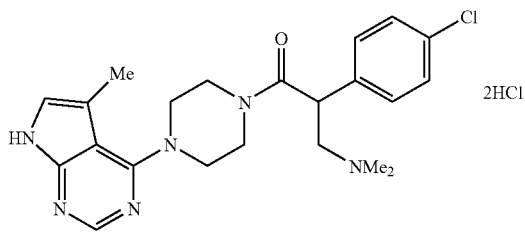 [SMILES: Cc1c[nH]c2ncnc(N3CCN(C(=O)C(CN(C)C)c4ccc(Cl)cc4)CC3)c12 ; "2HCl"]

The preparation of 2-(4-Chlorophenyl)-3-dimethylamino-1-[4-(5-methyl-7H-pyrrolo[2,3-d]pyrimidin-4-yl)-piperazin-1-yl]-propan-1-one bis-hydrochloride salt Step 1: The 7-benzenesulfonyl-5-methyl-4-piperazin-1-yl-7H-pyrrolo[2,3-d]pyrimidine bis-hydrochloride (200 mg, 0.465 mmol) and 3-tert-butoxycarbonylamino-2-(4-chlorophenyl)-propionic acid (146 mg, 0.488 mmol) were dissolved/suspended in 2.0 mL of DMF at room temperature and treated with TEA (259 µL, 1.86 mmol). The HBTU (194 mg, 0.511 mmol) was added in one sum, and the reaction was allowed to stir overnight at room temperature to completion. The reaction was partitioned between ethyl acetate and diluted NaHCO$_3$ solution. The aqueous was extracted with ethyl acetate, and the organics were combined. The organic was washed with water, then brine, separated, dried over MgSO$_4$, filtered, and concentrated in vacuo. The residue was purified by chromatography (silica gel eluted with 70:30 ethyl acetate:hexanes) to afford the pure [3-[4-(7-benzenesulfonyl-5-methyl-7H-pyrrolo[2,3-d]pyrimidin-4-yl)-piperazin-1-yl]-2-(4-chlorophenyl)-3-oxo-propyl]-carbamic acid tert-butyl ester as colorless gel (295 mg, 99%). $^1$H NMR (CDCl$_3$, 400 MHz) δ 8.44 (s, 1H), 8.16 (d, J=8.4 Hz, 2H), 7.59 (t, J=7.2 Hz, 1H), 7.49 (appt, J=7.6 Hz, 2H), 7.31 (m, 3H), 7.20 (d, J=8.0 Hz, 2H), 5.12 (m, 1H), 4.09 (m, 1H), 3.92 (m, 1H), 3.60 (m, 1H), 3.56-3.46 (m, 4H), 3.38 (d, J=10.4 Hz, 2H), 3.32 (m, 1H), 2.90 (m, 1H), 2.29 (s, 3H), 1.41 (s, 9H). LCMS (APCI+) m/z 639 [M+H]$^+$; Rt=3.70 min.

Step 2: The [3-[4-(7-benzenesulfonyl-5-methyl-7H-pyrrolo[2,3-d]pyrimidin-4-yl)-piperazin-1-yl]-2-(4-chlorophenyl)-3-oxo-propyl]-carbamic acid tert-butyl ester (295 mg, 0.464 mmol) was dissolved in 2.3 mL of 1,4-dioxane and treated with 4M HCl in 1,4-dioxane (2.3 mL, 9.29 mmol). The mixture was allowed to stir for 4 hours to completion affording a yellow precipitate. The suspension was diluted with diethyl ether and poured into water. More diethyl ether was added, and the layers were shaken. The ether wash was discarded, and the aqueous was treated with saturated NaHCO$_3$ solution until basic to pH paper (about 10) to afford a white precipitate. The aqueous was extracted with ethyl acetate, and the organics were combined. The organic was washed with water, then brine, separated, dried over MgSO4, filtered, and concentrated in vacuo to afford the near-pure 3-amino-1-[4-(7-benzenesulfonyl-5-methyl-7H-pyrrolo[2,3-d]pyrimidin-4-yl)-piperazin-1-yl]-2-(4-chlorophenyl)-propan-1-one as a colorless oil (194 mg, 77%). $^1$H NMR (free-base, CDCl$_3$, 400 MHz) δ 8.44 (s, 1H), 8.16 (d, J=8.4 Hz, 2H), 7.59 (t, J=7.2 Hz, 1H), 7.49 (appt, J=7.6 Hz, 2H), 7.31 (m, 3H), 7.19 (d, J=8.0 Hz, 2H), 3.92 (m, 1H), 3.85 (dd, J=8.4, 5.2 Hz, 1H), 3.61 (m, 1H), 3.56-3.50 (m, 4H), 3.43 (m, 2H), 3.32 (m, 2H), 2.90 (m, 2H), 2.29 (s, 3H). LCMS (APCI+) m/z 539 [M+H]$^+$; Rt=2.40 min.

Step 3: The 3-amino-1-[4-(7-benzenesulfonyl-5-methyl-7H-pyrrolo[2,3-d]pyrimidin-4-yl)-piperazin-1-yl]-2-(4-chlorophenyl)-propan-1-one (75 mg, 0.139 mmol) was dissolved in 1.0 mL of 1,2-dichloroethane and treated with 37% aqueous formaldehyde (31 µL, 0.417 mmol). The solution was allowed to stir at room temperature for 15 minutes before the sodium triacetoxyborohydride (118 mg, 0.557 mmol) was added in one sum. The reaction was complete in one hour, and the contents were poured into diluted NaHCO$_3$ solution. The aqueous was extracted with ethyl acetate, and the organics were combined. The organic was washed with water, then brine, separated, dried over MgSO$_4$, filtered, and concentrated in vacuo. The residue was purified by chromatography (silica gel eluted with 1% TEA in 9:1 ethyl acetate:methanol) to afford the pure 1-[4-(7-benzenesulfonyl-5-methyl-7H-pyrrolo[2,3-d]pyrimidin-4-yl)-piperazin-1-yl]-2-(4-chlorophenyl)-3-dimethylamino-propan-1-one intermediate as a colorless oil. The oil was dissolved in 0.5 mL of each: THF, methanol, and water. The solution was treated with lithium hydroxide-monohydrate (29 mg, 0.696 mmol) to afford an opaque solution, which stirred overnight to completion. The solution was partitioned between ethyl acetate and water, and the aqueous was extracted with more ethyl acetate. The combined organic was washed with water, then brine, separated, dried over Na$_2$SO$_4$, filtered, and concentrated in vacuo to afford the crude product as a yellow oil. The residue was purified by chromatography (silica gel eluted with 1% TEA in 4:1 ethyl acetate:methanol) to afford the titled free base as a colorless oil. The material was dissolved in a minimal amount of THF (>1 mL) and treated with 2.0M HCl in ether. The resulting white precipitate was filtered, washed with diethyl ether, and dried under reduced pressure to afford the 2-(4-chlorophenyl)-3-dimethylamino-1-[4-(5-methyl-7H-pyrrolo

[2,3-d]pyrimidin-4-yl)-piperazin-1-yl]-propan-1-one bis-hydrochloride salt as a white solid (24 mg, 35%). $^1$H NMR (Free-Base, CDCl$_3$, 400 MHz) δ 10.72 (brs, 1H), 8.34 (s, 1H), 7.30 (d, J=8.4 Hz, 2H), 7.24 (d, J=8.4 Hz, 2H), 6.93 (s, 1H), 4.11 (m, 1H), 3.95 (m, 1H), 3.65 (m, 2H), 3.55 (m, 3H), 3.33 (m, 2H), 3.05 (m, 1H), 2.48 (dd, J=12.4, 4.8 Hz, 1H), 2.36 (s, 3H), 2.32 (s, 6H). LCMS (APCI+) m/z 427 [M+H]$^+$; Rt=1.97 min.

Example 94

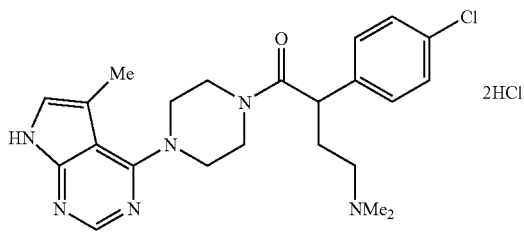 [SMILES: Cc1c[nH]c2ncnc(N3CCN(C(=O)C(CCN(C)C)c4ccc(Cl)cc4)CC3)c12 ; "2HCl"]

Predation of 2-(4-Chlorophenyl)-4-dimethylamino-1-[4-(5-methyl-7H-pyrrolo[2,3-d]pyrimidin-4-yl)-piperazin-1-yl]-butan-1-one bis-hydrochloride salt The 2-(4-chlorophenyl)-4-dimethylamino-1-[4-(5-methyl-7H-pyrrolo[2,3-d]pyrimidin-4-yl)-piperazin-1-yl]-butan-1-one bis-hydrochloride salt (21 mg, 30%) was prepared by procedures described in Example 93, Steps 1-3 [substituting 3-tert-butoxycarbonylamino-2-(4-chlorophenyl)-propionic acid with 4-tert-butoxycarbonylamino-2-(4-chlorophenyl)-butyric acid in Step 1]. $^1$H NMR (CD$_3$OD, 400 MHz) δ 8.29 (s, 1H), 7.41 (d, J=8.4 Hz, 2H), 7.36 (d, J=8.4 Hz, 2H), 7.25 (s, 1H), 4.25 (t, J=6.8 Hz, 1H), 3.97 (appd, J=8.8 Hz, 2H), 3.85-3.72 (m, 4H), 3.63 (m, 1H), 3.32 (m, 1H), 3.17 (m, 1H), 3.07 (m, 1H), 2.89 (s, 3H), 2.88 (s, 3H), 2.41 (m, 1H), 2.39 (s, 3H), 2.10 (m, 1H). LCMS (APCI+) m/z 441 [M+H]$^+$; Rt=1.87 min.

Example 95

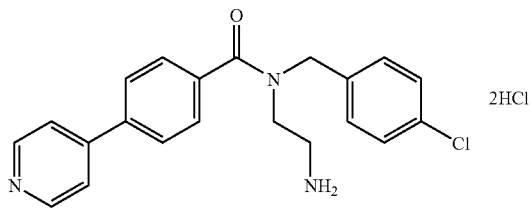 [SMILES: NCCN(Cc1ccc(Cl)cc1)C(=O)c1ccc(-c2ccncc2)cc1 ; "2HCl"]

Preparation of N-(2-Amino-ethyl)-N-(4-chlorobenzyl)-4-pyridin-4-yl-benzamide bis-hydrochloride salt Step 1: The (2-amino-ethyl)-carbamic acid tert-butyl ester (5.00 g, 31.2 mmol) and 4-chloro-benzaldehyde (4.61 g, 32.77 mmol) were dissolved in 60 mL of 1,2-dichloroethane at room temperature. The reaction mixture was allowed to stir for 40 minutes prior to treatment with sodium triacetoxyborohydride (9.90 g, 46.8 mmol). The mixture was allowed to stir overnight to completion and quenched with a saturated NaHCO$_3$ solution. The aqueous was extracted with DCM, separated, dried over MgSO$_4$, and concentrated in vacuo. The residue was purified by chromatography (silica gel eluted with hexanes/EtOAc plus 2% triethyl amine) to afford the pure [2-(4-chlorobenzylamino)-ethyl]-carbamic acid tert-butyl ester as a viscous yellow oil (5.38 g, 61%). $^1$H NMR (CDCl$_3$, 400 MHz) δ 7.29 (d, J=8.0 Hz, 2H), 7.25 (d, J=8.0 Hz, 2H), 4.92 (brs, 1H), 3.75 (s, 2H), 3.23 (appd, J=5.6 Hz, 2H), 2.73 (appt, J=6.0 Hz, 2H), 1.44 (s, 9H), 1.36 (brs, 1H). LCMS (APCI+) m/z 285 [M+H]$^+$; Rt=2.30 min.

Step 2: The 4-bromo-benzoic acid ethyl ester (1.00 g, 4.37 mmol), pyridine-4-boronic acid (537 mg, 4.37 mmol), and tetrakis(triphenylphosphine)palladium(0) (757 mg, 0.655 mmol) were degassed under nitrogen. The solids were dissolved in 15 mL of 1,4-dioxane and 2.6 mL of 2M sodium carbonate solution. The mixture was heated to 80° C. overnight completion and allowed to cool to room temperature. The contents were partitioned between ethyl acetate and water, and the aqueous was extracted with ethyl acetate. The combined organic was washed with water, brine, dried over MgSO$_4$, filtered, and concentrated in vacuo. The residue was purified by chromatography (silica gel eluted with 1:1 hexanes:EtOAc, Rf=0.2) to afford the pure 4-pyridin-4-yl-benzoic acid ethyl ester as a pale yellow solid (350 mg, 35%). $^1$H NMR (CDCl$_3$, 400 MHz) δ 8.71 (d, J=4.4 Hz, 2H), 8.16 (d, J=8.0 Hz, 2H), 7.71 (d, J=8.0 Hz, 2H), 7.53 (d, J=4.4 Hz, 2H), 4.42 (q, J=7.2 Hz, 2H), 1.43 (t, J=7.2 Hz, 3H). LCMS (APCI+) m/z 228 [M+H]$^+$; Rt=2.81 min.

Step 3: The 4-pyridin-4-yl-benzoic acid ethyl ester (430 mg, 1.89 mmol) was heated to 100° C. in 6.5 mL of 3M HCl solution overnight to completion. The mixture was cooled to room temperature and diluted with water (dissolves precipitate). The solution was filtered and concentrated in vacuo to afford the 4-pyridin-4-yl-benzoic acid hydrochloride salt as a pale yellow solid (380 mg, 85%). $^1$H NMR (DMSO-d$_6$, 400 MHz) δ 8.93 (d, J=5.6 Hz, 2H), 8.27 (d, J=5.6 Hz, 2H), 8.13 (d, J=8.0 Hz, 2H), 8.09 (d, J=8.0 Hz, 2H), —CO$_2$H or —NH$^+$ not observed. LCMS (APCI+) m/z 200 [M+H]$^+$; Rt=1.05 min.

Step 4: The 4-pyridin-4-yl-benzoic acid hydrochloride salt (100 mg, 0.502 mmol), [2-(4-chlorobenzylamino)-ethyl]-carbamic acid tert-butyl ester (143 mg, 0.502 mmol), HOBt (77 mg, 0.502 mmol), and EDCI (56 mg, 0.552 mmol) were dissolved in 1.7 mL DMF, then treated with triethyl amine (77 µL, 0.552 mmol) to room temperature. The reaction was allowed to stir overnight to completion and partitioned between ethyl acetate and diluted NaHCO$_3$ solution. The aqueous was extracted with ethyl acetate, and the organics were combined. The organic was washed with water, brine, dried over MgSO$_4$, filtered, and concentrated in vacuo. The residue was purified by chromatography (silica gel eluted with hexanes/ethyl acetate gradients plus 2% triethylamine) to afford the {2-[(4-chlorobenzyl)-(4-pyridin-4-yl-benzoyl)-amino]-ethyl}-carbamic acid tert-butyl ester as a colorless oil (184 mg, 93%). $^1$H NMR (CDCl$_3$, 400 MHz) δ 8.68 (d, J=4.8 Hz, 2H), 7.65 (m, 2H), 7.54 (d, J=8.4 Hz, 2H), 7.48 (d, J=4.4 Hz, 2H), 7.34 (m, 2H), 7.13 (m, 2H), 4.91 (m, 1H), 4.59 (brs, 2H), 3.62 (m, 2H), 3.44 (m, 2H), 1.46 (s, 9H). LCMS (APCI+) m/z 466 [M+H]$^+$; Rt=3.19 min.

Step 5: The {2-[(4-chlorobenzyl)-(4-pyridin-4-yl-benzoyl)-amino]-ethyl}-carbamic acid tert-butyl ester (184 mg, 0.395 mmol) was dissolved in 2.0 mL of 1,4-dioxane and treated with 2.0 mL of 4M HCl in 1,4-dioxane. The reaction was allowed to stir for one hour to completion and diluted with diethyl ether. The product was isolated by vacuum filtration to afford the N-(2-amino-ethyl)-N-(4-chlorobenzyl)-4-pyridin-4-yl-benzamide bis-hydrochloride salt as a fine pale-yellow powder (166 mg, 96%). $^1$H NMR (DMSO-d$_6$, 400 MHz) δ 8.91 (d, J=6.0 Hz, 2H), 8.26 (d, J=6.0 Hz, 2H), 8.13 (brs, 3H), 8.05 (d, J=8.0 Hz, 2H), 7.76 (d, J=7.6 Hz, 2H), 7.45 (brs, 1H), 7.44 (d, J=8.0 Hz, 2H), 7.26 (d, J=7.6 Hz, 2H), 4.57 (brs, 2H), 3.61 (m, 2H), 3.08 (m, 2H). LCMS (APCI+) m/z 366 [M+H]$^+$; Rt=2.13 min.

Example 96

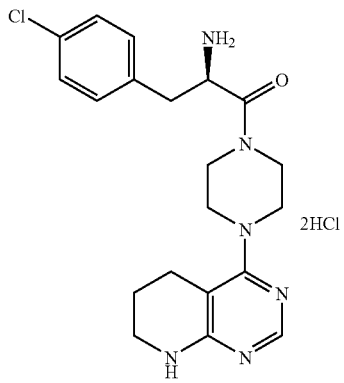 [SMILES: N[C@H](Cc1ccc(Cl)cc1)C(=O)N1CCN(c2ncnc3c2CCCN3)CC1 ; "2HCl"]

Preparation of (2R)-2-Amino-3-(4-chlorophenyl)-1-[4-(5,6,7,8-tetrahydro-pyrido[2,3-d]pyrimidin-4-yl)-piperazin-1-yl]-propan-1-one dihydrochloride Step 1: A mixture of 2-aminonicotinic acid (7.00 g, 50.7 mmol) and formamide (22.8 g, 506 mmol) was heated to 167° C. for 2.5 hours. After cooling, the solid was recrystallized from hot water (100 mL) to afford the pure product (4.80 g, 64%). $^1$H NMR (CDCl$_3$, 400 MHz) δ 8.94 (m, 1H), 8.64 (d, 1H, J=7.6 Hz), 8.30 (s, 1H), 7.59 (m, 1H). MS (APCI+) [M+H]$^+$148.

Step 2: The solution of 4-hydroxypyrido[2,3-d]pyrimidine (2.00 g, 13.6 mmol) in POCl$_3$ (40 mL) was refluxed for 2 hours. After cooling, the excess POCl$_3$ was removed under vacuum. The residue was quenched with saturated NaHCO$_3$ and extracted with ethyl acetate (3×100 mL). The organic phase was dried and concentrated. The residue was subject to column chromatography, eluted by hexane/ethyl acetate (1:1) to give 4-chloropyrido[2,3-d]pyrimidine (0.72 g, 32%). $^1$H NMR (CDCl$_3$, 400 MHz) δ 9.35 (m, 1H), 9.30 (s, 1H), 8.66 (m, 1H), 7.73 (m, 1H). MS (APCI+) [M+H]$^+$166.

Step 3: To a solution of 4-chloropyrido[2,3-d]pyrimidine (0.72 g, 4.4 mmol) and 1-Boc piperazine (0.84 g, 4.5 mmol) in DCE (10 mL) and IPA (10 mL) was added triethylamine (4 mL). The mixture was refluxed for 4 hours. After cooling, the solvent was removed. The residue was subject to column chromatography by ethyl acetate to give 4-pyrido[2,3-d]pyrimidin-4-yl-piperazine-1-carboxylic acid tert-butyl ester (1.26 g, 92%). $^1$H NMR (CDCl$_3$, 400 MHz) δ 9.07 (dd, J=4.30 Hz, J=1.98 Hz, 1H), 8.88 (s, 1H), 8.25 (dd, J=7.99 Hz, J=1.98 Hz, 1H), 7.41 (dd, J=8.18 Hz, J=3.74 Hz, 1H), 3.82 (m, 4H), 3.65 (m, 4H), 1.50 (s, 9H). MS (APCI+) [M+H]$^+$ 316.

Step 4: To a solution of 4-pyrido[2,3-d]pyrimidin-4-yl-piperazine-1-carboxylic acid tert-butyl ester (0.24 g, 0.76 mmol) in MeOH (10 mL) and TFA (1 mL) was added PtO$_2$ (10 mg). The mixture was stirred under H$_2$ (1 atm) at room temperature overnight. The catalyst was filtered off and the solvent was removed. The residue was subject to column chromatography, eluted by DCM/MeOH (20:1) to afford 4-(5,6,7,8-Tetrahydro-pyrido[2,3-d]pyrimidin-4-yl)-piperazine-1-carboxylic acid tert-butyl ester (0.15 g, 62%). $^1$H NMR (CDCl$_3$, 400 MHz) δ 8.10 (s, 1H), 5.92 (s, 1H), 3.50 (m, 4H), 3.40 (m, 2H), 3.25 (m, 4H), 2.55 (m, 2H), 1.85 (m, 2H), 1.48 (s, 9H). MS (APCI+) [M+H]$^+$320.

Step 5: To a solution of 4-(5,6,7,8-Tetrahydro-pyrido[2,3-d]pyrimidin-4-yl)-piperazine-1-carboxylic acid tert-butyl ester (0.88 g, 2.75 mmol) in DCM (10 mL) was added HCl in dioxane (4M, 5 mL). The mixture was stirred at RT for 4 hours. The solvent was removed to give 4-Piperazin-1-yl-5,6,7,8-tetrahydro-pyrido[2,3-d]pyrimidine as HCl salt (0.80 g, 99%). MS (APCI+) [M+H]$^+$220.

Step 6: To a solution of 4-Piperazin-1-yl-5,6,7,8-tetrahydro-pyrido[2,3-d]pyrimidine dihydrochloride (20 mg, 0.068 mmol) and (2R)-2-tert-Butoxycarbonylamino-3-(4-chlorophenyl)-propionic acid (21 mg, 0.070 mmol) in DCM (5 mL) and TEA (1 mL) was added HBTU (30 mg, 0.079 mmol). The mixture was stirred at room temperature for 4 hours. The solvent was removed and the residue was subject to column chromatography, eluted with ethyl acetate/DCM/MeOH (20:1) to give (2R)-{1-(4-Chlorobenzyl)-2-oxo-2-[4-(5,6,7,8-tetrahydro-pyrido[2,3-d]pyrimidin-4-yl)-piperazin-1-yl]-ethyl}-carbamic acid tert-butyl ester (18 mg, 53%). $^1$H NMR (CDCl$_3$, 400 MHz) δ 8.10 (s, 1H), 7.25 (m, 3H), 7.12 (m, 2H), 5.42 (d, J=8.8 Hz, 1H), 5.14 (s, 1H), 4.84 (m, 1H), 3.67 (m, 3H), 3.50 (m, 1H), 3.40 (m, 2H), 3.23 (m, 5H), 2.95 (m, 4H), 2.50 (m, 2H), 1.86 (m, 2H), 1.67 (s, 1H), 1.42 (s, 9H). MS (APCI+) [M+H]$^+$502.

Step 7: To a solution of (2R)-{1-(4-Chlorobenzyl)-2-oxo-2-[4-(5,6,7,8-tetrahydro-pyrido[2,3-d]pyrimidin-4-yl)-piperazin-1-yl]-ethyl}-carbamic acid tert-butyl ester (18 mg, 0.036 mmol) in DCM (4 mL) was added HCl in dioxane (4M, 2 mL). The mixture was stirred at room temperature for 4 hours. The solvent was removed to give (2R)-2-Amino-3-(4-chlorophenyl)-1-[4-(5,6,7,8-tetrahydro-pyrido[2,3-d]pyrimidin-4-yl)-piperazin-1-yl]-propan-1-one dihydrochloride (14 mg, 99%). MS (APCI+) [M+H]$^+$401.

Example 97

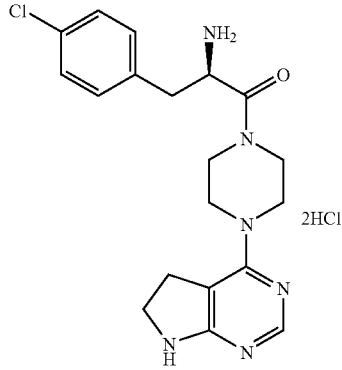 [SMILES: N[C@H](Cc1ccc(Cl)cc1)C(=O)N1CCN(c2ncnc3c2CCN3)CC1 ; "2HCl"]

Preparation of (2R)-2-Amino-3-(4-chlorophenyl)-1-[4-(6,7-dihydro-5H-pyrrolo[2,3-d]pyrimidin-4-yl)-piperazin-1-yl]-propan-1-one dihydrochloride Step 1: To a solution of formamide HCl salt (21.6 g, 268 mmol) in MeOH (300 mL) was added NaOMe (25%, in MeOH, 120 mL, 555 mmol). The mixture was stirred at room temperature for 1 hour. Then triethyl 1,1,2-ethanetricarboxylate (64.4 g, 60 mL, 262 mmol) in MeOH (90 mL) was added slowly. After addition, the mixture was stirred at room temperature for 20 hours. The solvent was removed and the residue was dissolved in ice water (200 mL) and neutralized with 2N HCl (140 mL) until pH=1-2. The solid formed was filtered, washed with water (50 mL) and dried under vacuum to afford (4,6-Dihydroxy-pyrimidin-5-yl)-acetic acid methyl ester (45 g, 93%). $^1$H NMR (CDCl$_3$, 400 MHz) δ 8.03 (s, 1H), 3.67 (s, 3H), 3.42 (s, 2H). MS (APCI+) [M+H]$^+$185.

Step 2: To a solution of (4,6-Dihydroxy-pyrimidin-5-yl)-acetic acid methyl ester (45 g, 244 mmol) in DCE (800 mL) was added DIEA (72 mL, 413 mmol), followed by POCl$_3$ (80 mL, 874 mmol) slowly. After addition, the mixture was stirred at room temperature for 2 hours and then refluxed overnight. After cooling, the solvent was removed and the residue was dissolved in ice water (400 mL), neutralized with 10N NaOH until pH 6. Extracted with ethyl acetate (3×500 mL). The organic phase was dried and concentrated. The residue was subject to column chromatography, eluted by hexane/ethyl acetate (4:1) to afford (4,6-Dichloro-pyrimidin-5-yl)-acetic acid methyl ester (38 g, 70%). $^1$H NMR (CDCl$_3$, 400 MHz) δ 8.73 (s, 1H), 4.00 (s, 2H), 3.77 (s, 3H). MS (APCI+) [M+H]$^+$ 222.

Step 3: To a solution of (4,6-Dichloro-pyrimidin-5-yl)-acetic acid methyl ester (0.52 g, 2.35 mmol) in ether (40 mL) at −78° C. was added DIBAL-H (1.5M, 4 mL, 6.05 mmol) dropwise. After addition, the mixture was allowed to warm up to room temperature and stirred for 3 hours. Then quenched with 2N HCl (10 mL) at −78° C. Extracted with ethyl acetate (3×50 mL). The organic phase was dried and concentrated to give fairly pure 2-(4,6-Dichloro-pyrimidin-5-yl)-ethanol (0.44 g, 97%). $^1$H NMR (CDCl$_3$, 400 MHz) δ 8.66 (s, 1H), 3.96 (t, J=6.8 Hz, 2H), 3.23 (t, J=6.8 Hz, 2H). 1.65 (s, 1H). MS (APCI+) [M+H]$^+$194.

Step 4: To a solution of 2-(4,6-Dichloro-pyrimidin-5-yl)-ethanol (0.46 g, 2.4 mmol) in DCM (40 mL) and was added MsCl (0.50 g, 4.36 mmol), triethylamine (1 mL) and cat. amount of DMAP. After stirring at room temperature overnight, the solvent was removed and the residue was subject to column chromatography, eluted by hexane/ethyl acetate (4:1) to afford methanesulfonic acid 2-(4,6-dichloro-pyrimidin-5-yl)-ethyl ester (0.52 g, 80%). $^1$H NMR (CDCl$_3$, 400 MHz) δ 8.71 (s, 1H), 4.50 (t, J=6.4 Hz, 2H), 3.42 (t, J=6.8 Hz, 2H), 3.02 (s, 3H).

Step 5: A solution of methanesulfonic acid 2-(4,6-dichloro-pyrimidin-5-yl)-ethyl ester (0.50 g, 1.84 mmol) and 4-methoxybenzylamine (0.60 g, 4.37 mmol) in DCE (30 mL) and TEA (4 mL) was refluxed overnight. After cooling, the solvent was removed and the residue was subject to column chromatography, eluted by hexane/ethyl acetate (4:1) to give 4-Chloro-7-(4-methoxy-benzyl)-6,7-dihydro-5H-pyrrolo[2,3-d]pyrimidine (0.36 g, 71%). $^1$H NMR (CDCl$_3$, 400 MHz) δ 8.35 (s, 1H), 7.26 (dd, J=2.8 Hz, J=1.6 Hz, 2H), 6.88 (d, J=4.4 Hz, 2H), 5.33 (s, 1H), 4.62 (d, J=5.6 Hz, 2H), 3.81 (s, 3H), 3.73 (t, J=7.2 Hz, 2H), 3.04 (t, J=6.8 Hz, 2H). MS (APCI+) [M+H]$^+$276.

Step 6: A solution of 4-Chloro-7-(4-methoxy-benzyl)-6,7-dihydro-5H-pyrrolo[2,3-d]pyrimidine (0.36 g, 1.31 mmol), 1-Boc-piperazine (1.0 g, 5.37 mmol) and $^t$BuOK (0.18 g, 1.60 mmol) in NMP (20 mL) was heated to 128° C. for 20 hours. After cooling, the mixture was diluted with ethyl acetate (500 mL) and washed with water (5×150 mL). The organic phase was dried and concentrated. The residue was subject to column chromatography, eluted by hexane/ethyl acetate (1:1) to give 4-[7-(4-Methoxy-benzyl)-6,7-dihydro-5H-pyrrolo[2,3-d]pyrimidin-4-yl]-piperazine-1-carboxylic acid tert-butyl ester (0.32 g, 57%). $^1$H NMR (CDCl$_3$, 400 MHz) δ 8.17 (s, 1H), 7.20 (d, J=8.4 Hz, 2H), 6.84 (d, J=8.4 Hz, 2H), 4.50 (s, 2H), 3.79 (s, 3H), 3.59 (m, 4H), 3.48 (m, 4H), 3.35 (m, 2H), 3.30 (m, 2H), 1.49 (s, 9H). MS (APCI+) [M+H]$^+$426.

Step 7: A solution of 4-[7-(4-Methoxy-benzyl)-6,7-dihydro-5H-pyrrolo[2,3-d]pyrimidin-4-yl]-piperazine-1-carboxylic acid tert-butyl ester (0.32 g, 0.74 mmol) in TFA (20 mL) was stirred at 65° C. for 20 hours. After cooling, the TFA was evaporated under vacuum to afford 4-Piperazin-1-yl-6,7-dihydro-5H-pyrrolo[2,3-d]pyrimidine bis-trifluoroacetate (0.15 g, 99%). MS (APCI+) [M+H]$^+$206.

Step 8: To a solution of 4-Piperazin-1-yl-6,7-dihydro-5H-pyrrolo[2,3-d]pyrimidine bis-trifluoroacetate (20 mg, 0.097 mmol) in DCM (10 mL) and TEA (2 mL) were added (2R)-2-tert-Butoxycarbonylamino-3-(4-chlorophenyl)-propionic acid (30 mg, 0.10 mmol) and HBTU (30 mg, 0.079 mmol). The mixture was stirred at room temperature for 2 hours. The solvent was removed and the residue was subject to column chromatography to afford (2R)-{1-(4-Chlorobenzyl)-2-[4-(6,7-dihydro-5H-pyrrolo[2,3-d]pyrimidin-4-yl)-piperazin-1-yl]-2-oxo-ethyl}-carbamic acid tert-butyl ester (19 mg, 40%). $^1$H NMR (CDCl$_3$, 400 MHz) δ 8.03 (s, 1H), 7.25 (m, 2H), 7.12 (m, 2H), 5.40 (m, 1H), 4.83 (m, 2H), 3.50 (m, 10H), 3.20 (m, 5H), 2.96 (m, 2H), 2.28 (m, 3H), 1.42 (s, 9H). MS (APCI+) [M+H]$^+$488.

Step 9: To a solution of (2R)-{1-(4-Chlorobenzyl)-2-[4-(6,7-dihydro-5H-pyrrolo[2,3-d]pyrimidin-4-yl)-piperazin-1-yl]-2-oxo-ethyl}-carbamic acid tert-butyl ester (19 mg, 0.039 mmol) in DCM (4 mL) was added HCl in dioxane (4M, 2 mL). The mixture was stirred at room temperature for 6 hours. The solvent was removed to afford (2R)-2-Amino-3-(4-chlorophenyl)-1-[4-(6,7-dihydro-5H-pyrrolo[2,3-d]pyrimidin-4-yl)-piperazin-1-yl]-propan-1-one dihydrochloride (15 mg, 99%). MS (APCI+) [M+H]$^+$388.

Example 98

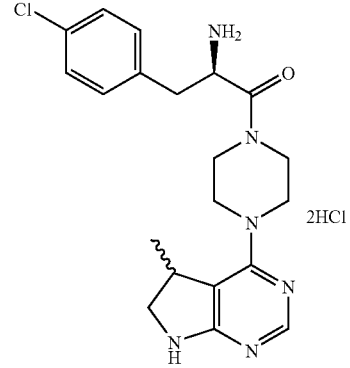 [SMILES: CC1CNc2ncnc(N3CCN(C(=O)[C@H](N)Cc4ccc(Cl)cc4)CC3)c21 ; "2HCl"]

Preparation of (2R)-2-Amino-3-(4-chlorophenyl)-1-[4-(5-methyl-6,7-dihydro-5H-pyrrolo[2,3-d]pyrimidin-4-yl)-piperazin-1-yl]-propan-1-one dihydrochloride Step 1: To a solution of KH (30%, 13.3 g, 125 mmol) in THF (200 mL) at 0° C. was added (4,6-Dichloro-pyrimidin-5-yl)-acetic acid methyl ester (20.0 g, 90.0 mmol) and MeI (290.0 g, 8.8 mL, 141.0 mmol) in THF (200 mL) slowly. After addition, the mixture was stirred at room temperature for 30 min, and then heated to reflux for 1 hour. After cooling to 0° C., the mixture was quenched with saturated aqueous NH$_4$Cl.

The organic phase was separated and the aqueous phase was extracted with ethyl acetate (3×200 mL). The organic phase was combined and dried. After removal of the solvent, the residue was subject to column chromatography, eluted by hexane/ethyl acetate (5:1) to give 2-(4,6-Dichloro-pyrimidin-5-yl)-propionic acid methyl ester (17.6 g, 83%). $^1$H NMR (CDCl$_3$, 400 MHz) δ 8.69 (s, 1H), 4.39 (dd, J=14.4 Hz, J=7.2 Hz, 1H), 3.73 (s, 3H), 1.57 (d, J=7.21 Hz, 3H).

Step 2: To a solution of 2-(4,6-Dichloro-pyrimidin-5-yl)-propionic acid methyl ester (0.5 g, 2.13 mmol) in ether (40 mL) at −78° C. was added DIBAL-H (1.5M, 4 mL, 6.0 mmol) dropwise. The mixture was allowed to warm up to room temperature and stirred for 3 hours. Then quenched with 2N HCl (10 mL) at −78° C. The aqueous phase was extracted with ethyl acetate (3×50 mL). The organic phase was dried and concentrated. The residue was subject to column chromatography, eluted by hexane/ethyl acetate (4:1) to give 2-(4,6-Dichloro-pyrimidin-5-yl)-propan-1-ol (0.40 g, 91%). $^1$H NMR (CDCl$_3$, 400 MHz) δ 8.62 (s, 1H), 4.16 (m, 1H), 3.90 (m, 2H), 1.93 (s, 1H), 1.40 (d, J=7.2 Hz, 3H).

Step 3: To a solution of 2-(4,6-Dichloro-pyrimidin-5-yl)-propan-1-ol (0.40 g, 1.93 mmol) in DCM (40 mL) were added MsCl (0.50 g, 4.36 mmol), TEA (1 mL) and catalytic amount of DMAP. The mixture was stirred at room temperature for 2 hours. The solvent was removed and the residue was subject to column chromatography, eluted by hexane/ethyl acetate (4:1) to give methanesulfonic acid 2-(4,6-dichloro-pyrimidin-5-yl)-propyl ester (0.54 g, 98%). $^1$H NMR (CDCl$_3$, 400 MHz) δ 8.68 (s, 1H), 4.74 (m, 1H), 4.55 (m, 1H), 4.14 (m, 1H), 2.99 (s, 3H), 1.49 (dd, J=7.2 Hz, J=1.2 Hz, 3H).

Step 4: To a solution of methanesulfonic acid 2-(4,6-dichloro-pyrimidin-5-yl)-propyl ester (0.54 g, 1.89 mmol) in DCM (30 mL) and TEA (4 mL) was added 4-methoxybenzyl amine (0.80 g, 5.83 mmol). The mixture was refluxed overnight. After cooling, the solvent was removed and the residue was subject to column chromatography, eluted by hexane/ethyl acetate (4:1) to give 4-Chloro-7-(4-methoxy-benzyl)-5-methyl-6,7-dihydro-5H-pyrrolo[2,3-d]pyrimidine (0.55 g, 99%). $^1$H NMR (CDCl$_3$, 400 MHz) δ 8.24 (s, 1H), 7.17 (d, J=7.6 Hz, 2H), 6.86 (d, J=7.6 Hz, 2H), 4.55 (s, 2H), 3.80 (s, 3H), 3.66 (m, 1H), 3.37 (m, 1H), 3.07 (m, 1H), 1.31 (dd, J=7.2 Hz, J=1.2 Hz, 3H). MS (APCI+) [M+H]$^+$291.

Step 5: To a solution of 4-Chloro-7-(4-methoxy-benzyl)-5-methyl-6,7-dihydro-5H-pyrrolo[2,3-d]pyrimidine (0.55 g, 1.88 mmol) in NMP (20 mL) were added 1-Boc-piperazine (1.0 g, 5.40 mmol) and $^t$BuOK (0.21 g, 1.88 mmol). The mixture was heated to 128° C. for 30 hours. After cooling, the mixture was diluted by ethyl acetate (500 mL) and washed with water (5×150 mL). The organic phase was dried and concentrated. The residue was subject to column chromatography, eluted by hexane/ethyl acetate (1:1) to give 4-(5-Methyl-6,7-dihydro-5H-pyrrolo[2,3-d]pyrimidin-4-yl)-piperazine-1-carboxylic acid tert-butyl ester (0.30 g, 36%). $^1$H NMR (CDCl$_3$, 400 MHz) δ 8.19 (s, 1H), 7.18 (d, J=8.4 Hz, 2H), 6.84 (d, J=8.4 Hz, 2H), 4.52 (dd, J=27.6 Hz, J=14.8 Hz, 2H), 3.79 (s, 3H), 3.58 (m, 12H), 3.34 (m 1H), 2.95 (m, 1H), 1.48 (s, 9H), 1.15 (d, J=6.8 Hz, 3H). MS (APCI+) [M+H]$^+$ 440.

Step 6: A solution of 4-(5-Methyl-6,7-dihydro-5H-pyrrolo[2,3-d]pyrimidin-4-yl)-piperazine-1-carboxylic acid tert-butyl ester (0.30 g, 0.68 mmol) in TFA (20 mL) was heated to 65° C. overnight. After cooling, the excess TFA was evaporated under vacuum to give 5-Methyl-4-piperazin-1-yl-6,7-dihydro-5H-pyrrolo[2,3-d]pyrimidine as TFA salt (0.15 g, 99%). MS (APCI+) [M+H]$^+$220.

Step 7: To a solution of 5-Methyl-4-piperazin-1-yl-6,7-dihydro-5H-pyrrolo[2,3-d]pyrimidine (18 mg, 0.082 mmol) in DCM (10 mL) and TEA (2 mL) were added (2R)-2-tert-Butoxycarbonylamino-3-(4-chlorophenyl)-propionic acid (25 mg, 0.082 mmol) and HBTU (31 mg, 0.082 mmol). The mixture was stirred at room temperature for 2 hours. The solvent was removed and the residue was subject to column chromatography, eluted by ethyl acetate-DCM/MeOH (30:1) to give (2R)-{1-(4-Chlorobenzyl)-2-[4-(5-methyl-6,7-dihydro-5H-pyrrolo[2,3-d]pyrimidin-4-yl)-piperazin-1-yl]-2-oxo-ethyl}-carbamic acid tert-butyl ester (32 mg, 78%). $^1$H NMR (CDCl$_3$, 400 MHz) δ 8.06 (s, 1H), 7.26 (d, J=6.0 Hz, 2 hours), 7.14 (d, J=8.0 Hz, 2H), 5.39 (d, J=8.0 Hz, 1H), 4.82 (m, 2H), 3.45 (m, 10H), 3.18 (m, 4H), 3.00 (m, 2H), 1.83 (m, 4H), 1.42 (s, 9H), 1.19 (m, 3H). MS (APCI+) [M+H]$^+$502.

Step 8: To a solution of (2R)-{1-(4-Chlorobenzyl)-2-[4-(5-methyl-6,7-dihydro-5H-pyrrolo[2,3-d]pyrimidin-4-yl)-piperazin-1-yl]-2-oxo-ethyl}-carbamic acid tert-butyl ester (32 mg, 0.064 mmol) in DCM/MeOH (5:1, 6 mL) was added HCl in dioxane (4M, 2 mL). The mixture was stirred at room temperature for 6 hours. The solvent was removed to afford (2R)-2-Amino-3-(4-chlorophenyl)-1-[4-(5-methyl-6,7-dihydro-5H-pyrrolo[2,3-d]pyrimidin-4-yl)-piperazin-1-yl]-propan-1-one dihydrochloride (26 mg, 99%). MS (APCI+) [M+H]$^+$402.

Example 99

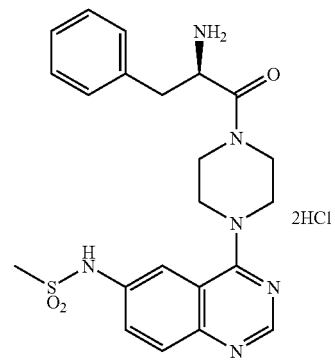 [SMILES: CS(=O)(=O)Nc1ccc2ncnc(N3CCN(C(=O)[C@H](N)Cc4ccccc4)CC3)c2c1 ; "2HCl"]

Preparation of (2R)—N-{4-[4-(2-amino-3-phenyl-propionyl)-piperazin-1-yl]-quinazolin-6-yl}-methanesulfonamide dihydrochloride Step 1: To a solution of 4-chloro-6-nitroquinazoline (prepared according to the literature: Alexander J. Bridges et al. *J. Med. Chem.* 1996, 39, 267-276, and references therein; 12 g, 57.5 mmol) and DIEA (10 mL, 57.5 mmol) in 230 mL IPA was added Boc-piperazine (10.7 g, 57.5 mmol). The reaction mixture was heated to 60° C. and stirred for 13 hours, after which it was cooled to room temperature and concentrated by rotary evaporation. The residue was dissolved in dichloromethane (DCM) and washed with 1N NaOH. The organic layer was dried (Na$_2$SO$_4$), filtered, and concentrated by rotary evaporation. The resulting oil was purified on silica gel (1:1 to 1:4 DCM:EtOAc gradient) to furnish 4-(6-nitro-quinazolin-4-yl)-1-Boc-piperazine as a pale yellow oil (18.3 g, 89%). LCMS (APCI+) m/z 360 [M+H]$^+$. HPLC Rt 3.06 min.

Step 2: To a suspension of Pd/C (5% w/w, 800 mg, 0.38 mmol) in 100 mL 2-methoxyethanol (degassed with nitrogen prior to use) was added a solution of 4-(6-nitro-quinazolin-4-yl)-1-Boc-piperazine (4.0 g, 11.1 mmol) in 10 mL 2-methoxyethanol. A balloon of H$_2$ was bubbled through the reaction mixture, and the reaction mixture was stirred at room temperature under an atmosphere of H₂ for 13 hours. Celite was then added, and the reaction mixture was filtered through a pad of celite and rinsed with MeOH. The filtrate was concentrated, and the resulting oil was filtered through a short plug of silica gel with EtOAc. The resulting filtrate was concentrated to give 4-(6-amino-quinazolin-4-yl)-1-Boc-piperazine (3.47 g, 95%). LCMS (APCI+) m/z 330 [M+H]⁺. HPLC Rt 2.31 min.

Step 3: To a 0° C. solution of (6-aminoquinazolin-4-yl)1-Boc-piperazine (1.0 g, 3.04 mmol), triethylamine (1.7 mL, 12.2 mmol) and DMAP (93 mg, 0.76 mmol) in 20 mL DCM was added dropwise by addition funnel a solution of methanesulfonyl chloride (0.59 mL, 7.6 mmol) in 6 mL DCM. The reaction mixture was stirred 5 minutes, warmed to room temperature, and stirred an additional 1.5 hours, after which the reaction mixture was cooled to 0° C., and NaOMe (5.4M in MeOH, 5.6 mL, 30.4 mmol) was added slowly by syringe. The reaction mixture was stirred 10 minutes, warmed to room temperature, and stirred another 2 hours, after which saturated NH₄Cl was added. The reaction mixture was extracted with DCM, and the combined extracts were washed with brine, dried (Na₂SO₄), filtered, and concentrated. The resulting residue was purified on silica gel (20:1 DCM:MeOH) to give N-(4-Boc-piperazin-1-yl-quinazolin-6-yl)-methanesulfonamide (1.05 g, 85%) as a beige powder. LCMS (APCI+) m/z 408 [M+H]⁺. HPLC Rt 2.64 min.

Step 4: To a solution of N-(4-Boc-piperazin-1-yl-quinazolin-6-yl)-methanesulfonamide (1.05 g, 2.58 mmol) in 15 mL dioxane was added 10 mL 4M HCl/dioxane. The resulting suspension was stirred at room temperature 17 hours, after which it was diluted with ether, and the solids were isolated by filtration through a fritted funnel with nitrogen pressure, rinsed with ether, and dried in vacuo to furnish N-(4-piperazin-1-yl-quinazolin-6-yl)-methanesulfonamide dihydrochloride (969 mg, 99%) as a white powder. ¹H NMR (CD₃OD, 400 MHz) δ 8.80 (s, 1H), 8.12 (s, 1H), 7.87-7.84 (m, 2H), 4.50 (dd, J=5.2, 5.2 Hz, 4H), 3.57 (dd, J=5.2, 5.2 Hz, 4H), 3.13 (s, 3H). LCMS (APCI+) m/z 308 [M+H]⁺. HPLC Rt 1.55 min.

Step 5: To a Jones tube containing PS-CDI (Argonaut, 1.04 mmol/g, 56 mg, 2.0 equiv) suspended in a solution of N-(4-piperazin-1-yl-quinazolin-6-yl)-mathanesulfonamide dihydrochloride (11 mg, 0.029 mmol, 1.0 equiv) and DIEA (25 μL, 0.15 mmol, 5.0 equiv) in 1.6 mL 9:1 CHCl₃:THF were added successively HOBt.H₂O (6 mg, 0.038 mmol, 1.3 equiv) and (D)-Boc-phenylalanine (8 mg, 0.032 mmol, 1.1 equiv.). The reaction mixture was shaken for 15 hours at room temperature, after which Si-trisamine (Silicycle, 1.21 mmol/g, 48 mg, 2.0 equiv) was added. The reaction mixture was shaken an additional 1 hour, after which it was vacuum filtered, the resins rinsed with CHCl₃, and the filtrate concentrated by rotary evaporation. The crude was purified on silica gel (19:1 DCM:MeOH) to afford (2R)—N-{4-[4-(2-Boc-amino-3-phenyl-propionyl)-piperazin-1-yl]-quinazolin-6-yl}-methanesulfonamide as a clear, colorless residue.

Step 6: To a solution of (2R)—N-{4-[4-(2-Boc-amino-3-phenyl-propionyl)-piperazin-1-yl]-quinazolin-6-yl}-methanesulfonamide in 1.0 mL dioxane was added 1.2 mL 4M HCl/dioxane. The resulting suspension was stirred at room temperature another 13 hours, after which it was concentrated to dryness. The resulting solids were dissolved in minimal MeOH, and the product was triturated by the addition of ether. The resulting suspension was diluted with ether, and the solids were isolated by filtration through a fritted funnel with nitrogen pressure, rinsed with ether, and dried further in vacuo to afford (2R)—N-{4-[4-(2-amino-3-phenyl-propionyl)-piperazin-1-yl]-quinazolin-6-yl}-methanesulfonamide dihydrochloride (13 mg, 84%) as a yellow powder. LCMS (APCI+) m/z 455 [M+H]⁺. HPLC Rt 2.18 min.

Example 100

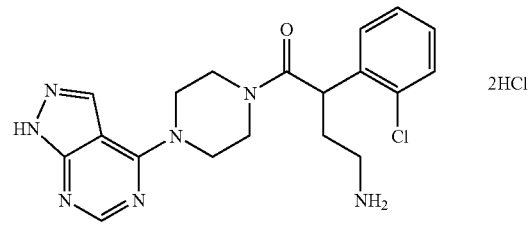 [SMILES: NCCC(C(=O)N1CCN(c2ncnc3[nH]ncc23)CC1)c1ccccc1Cl ; "2HCl"]

Preparation of 4-Amino-2-(2-chlorophenyl)-1-[4-(1H-pyrazolo[3,4-d]pyrimidin-4-yl)-piperazin-1-yl]-butan-1-one bis-hydrochloride salt Step 1: The 1H-Pyrazolo[3,4-d]pyrimidin-4-ol (5.00 g, 36.73 mmol) was dissolved in 68.5 mL of phosphorous oxychloride and 9.31 mL of N,N-dimethyl aniline (73.47 mmol). This mixture was heated to reflux (120 C) for 90 minutes to completion affording a dark red solution. The mixture was concentrated in vacuo and cooled to 0° C. in an ice bath. The residue was poured into ice water and stirred for three minutes. The acidic melt was extracted with ether, and the organics were combined. The organic was washed with cold water, cold half saturated NaHCO₃ solution, brine, separated, dried over MgSO₄, filtered, and concentrated in vacuo to afford the 4-chloro-1H-pyrazolo[3,4-d]pyrimidine as a light yellow powder (2.30 g, 41%). ¹H NMR (DMSO-d₆, 400 MHz) δ 8.84 (s, 1H), 8.46 (s, 1H), NH not observed.

Step 2: The 4-chloro-1H-pyrazolo[3,4-d]pyrimidine (500 mg, 3.24 mmol) and piperazine-1-carboxylic acid tert-butyl ester (603 mg, 3.24 mmol) were dissolved in 11.0 mL of NMP then treated with diisopropylethyl amine (845 μL, 4.85 mmol). The yellow solution was heated to 80 C overnight to completion and was allowed to cool to room temperature. The solution was diluted with ethyl acetate, poured into diluted NaHCO₃ solution, and extracted with ethyl acetate. The combined organic was washed with water, brine, separated, dried over MgSO₄, filtered, and concentrated in vacuo to afford the crude material as a tan solid. The material was triturated with DCM/hexanes to afford the 4-(1H-pyrazolo[3,4-d]pyrimidin-4-yl)-piperazine-1-carboxylic acid tert-butyl ester as a cream-colored solid (824 mg, 84%). ¹H NMR (CDCl₃, 400 MHz) δ 8.48 (s, 1H), 8.06 (s, 1H), 4.05 (m, 4H), 3.67 (m, 4H). LCMS (APCI+) m/z 305 [M+H]⁺; Rt=2.14 min.

Step 3: The 4-(1H-pyrazolo[3,4-d]pyrimidin-4-yl)-piperazine-1-carboxylic acid tert-butyl ester (600 mg, 1.97 mmol) was dissolved in 4 mL of 1,4-dioxane and treated with 10 mL of 4M HCl in 1,4-dioxane at room temperature. The solution was allowed to stir for two hours to afford a light-yellow suspension of product. The solvent was diluted with diethyl ether, stirred for ten minutes, and filtered. The pad of product was washed with diethyl ether and allowed to dry under a stream of nitrogen to give the 4-piperazin-1-yl-1H-pyrazolo[3,4-d]pyrimidine bis-hydrochloride salt as a light-yellow solid (539 mg, 99%). ¹H NMR (D₆O, 400 MHz) δ 8.59 (s, 1H), 8.42 (s, 1H), 4.29 (appt, J=5.6 Hz, 4H), 3.42 (appt, J=5.6 Hz, 4H). LCMS (APCI+) m/z 205 [M+H]⁺; Rt=0.34 min.

Step 4: The 4-piperazin-1-yl-1H-pyrazolo[3,4-d]pyrimidine bis-hydrochloride salt (60 mg, 0.22 mmol), HOBt (29 mg, 0.22 mmol), EDCI (46 mg, 0.24 mmol), and 4-tert-butoxycarbonylamino-2-(2-chlorophenyl)-butyric acid [prepared by procedures described in Example 61 (68 mg. 0.22 mmol)] were suspended/dissolved in 1.5 mL of DMF then treated with triethylamine (121 μL, 0.87 mmol). The mixture was allowed to stir for four hours to completion then partitioned between ethyl acetate and diluted NaHCO$_3$ solution. The aqueous was extracted with ethyl acetate, and the organics were combined. The organic was washed with water, brine, separated, dried over MgSO$_4$, filtered, and concentrated in vacuo. The residue was dissolved in 1 mL of 1,4-dioxane and treated with 1 mL of 4M HCl in 1,4-dioxane. The solution stirred overnight to completion at room temperature and diluted with diethyl ether to afford a precipitate. This material was broken up to afford a suspended granular solid which was stirred for 30 minutes. The suspension was filtered, washed with diethyl ether, and dried over a stream of nitrogen to afford the 4-amino-2-(2-chlorophenyl)-1-[4-(1H-pyrazolo[3,4-d]pyrimidin-4-yl)-piperazin-1-yl]-butan-1-one bis-hydrochloride salt as a tan solid (69.2 mg, 67%). $^1$H NMR (D$_6$O, 400 MHz) δ 8.52 (brs, 1H), 8.31 (s, 1H), 7.40 (d, J=7.2 Hz, 1H), 7.12 (m, 3H), 4.42 (t, J=6.8 Hz, 1H), 4.11 (m, 1H), 3.98 (m, 3H), 3.70 (m, 2H), 3.61 (m, 1H), 3.41 (m, 1H), 2.96 (m, 1H), 2.80 (m, 1H), 2.21 (m, 1H), 1.94 (m, 1H). LCMS (APCI+) m/z 400 [M+H]$^+$; Rt=1.52 min.

Example 101

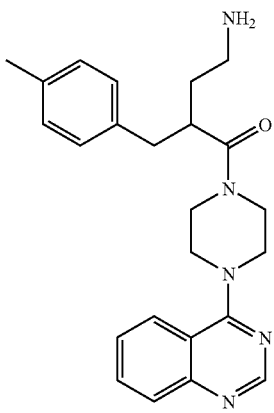 [SMILES: Cc1ccc(CC(CCN)C(=O)N2CCN(c3ncnc4ccccc34)CC2)cc1]

Preparation of 4-Amino-2-(4-methylbenzyl)-1-(4-quinazolin-4-yl-piperazin-1-yl)-butan-1-one, dihydrochloride Step 1: To a solution containing LiHMDS (1.0M, 11.3 mL, 11 mmol) in 40 mL of THF under a nitrogen atmosphere at −78C was added a solution of 2-Oxo-pyrrolidine-1-carboxylic acid tert-butyl ester (2.gg, 11 mmol) in 15 mL of THF dropwise over 5 minutes. After complete addition, the reaction was allowed to stir at −78° C. for 45 minutes, followed by the addition of a solution containing 4-methyl benzyl bromide (2.1 g, 11 mmol) in 15 mL of THF dropwise over 5 minutes. The reaction was allowed to stir at −78C for 1 hour then warmed to 0 C and stirred for 1 hour. The mixture was quenched with 36 mL of 3M LiOH and allowed to stir at room temperature overnight. The reaction was diluted with water and washed with ether. The aqueous phase was acidified with 1N HCl and extracted with DCM. The organic phase was dried over magnesium sulfate. Filtration and removal of solvent gave 4-tert-Butoxycarbonylamino-2-(4-methylbenzyl)-butyric acid (1.61 g, 49%.) LCMS (APCI−) m/z 306 [M-Boc-H]$^-$; Rt: 2.14 min.

Step 2: To a solution containing 4-tert-Butoxycarbonylamino-2-(4-methylbenzyl)-butyric acid (0.24 g, 0.77 mmol) in 25 mL of DMF under a nitrogen atmosphere was added EDCI (0.16 g, 0.84 mmol), HOBT (130 mg, 0.84 mmol) and NMM (0.28 g, 2.8 mmol.) After stirring at room temperature for 15 minutes, 4-Piperazin-1-yl-quinazoline (200 mg, 0.93 mmol) was added and the reaction allowed to stir at room temperature. The reaction was diluted with ethyl acetate and washed with water, saturated sodium bicarbonate and water. The organic phase was dried over magnesium sulfate. Filtration, removal of solvent and purification of the residue via biotage eluting with 10% MeOH/DCM gave [3-(4-Methyl-benzyl)-4-oxo-4-(4-quinazolin-4-yl-piperazin-1-yl)-butyl]-carbamic acid tert-butyl ester (0.225 g, 64%) as a white solid. LCMS (APCI+) m/z 504 [M+H]$^+$; Rt: 3.03 min. $^1$H NMR (CDCl3, 400 MHz) δ 3.8.69 (1H, s), 7.92 (1H, d, J 8.3 Hz), 7.76-7.71 (2H, m), 7.45 (1H, t, J 7.8 Hz), 7.06 (4H, m), 4.53 (1H, br. s), 3.96-3.76 (2H, m), 3.63-3.54 (2H, m), 3.47-3.40 (2H, m), 3.24-2.84 (6H, m), 2.76-2.70 (1H, m), 2.27 (3H, s), 2.09-2.00 (1H, m), 1.73-1.65 (1H, m), 1.40 (9H, s.)

Step 3: A mixture containing [3-(4-Methyl-benzyl)-4-oxo-4-(4-quinazolin-4-yl-piperazin-1-yl)-butyl]-carbamic acid tert-butyl ester (0.22 g, 0.44 mmol) in 10 mL of DCM and 5 mL of 4N HCl in dioxane was allowed to stir at room temperature under a nitrogen atmosphere overnight. The reaction was concentrated under reduced pressure. The residue was dissolved in methanol and ether added to precipitate the product. The solids were filtered and dried to afford 4-Amino-2-(4-methylbenzyl)-1-(4-quinazolin-4-yl-piperazin-1-yl)-butan-1-one dihydrochloride (167 mg.) LCMS (APCI+) m/z 404 [M+H]$^+$; Rt: 1.87 min. $^1$H NMR (D2O, 400 MHz) δ 8.45 (1H, s), 7.87 (2H, t, J 8.1 Hz), 7.65-7.57 (2H, m), 7.01 (4H, s), 4.18-4.12 (1H, m), 3.98-3.92 (1H, m), 3.82-3.71 (2H, m), 3.52-3.37 (3H, m), 3.25-2.76 (6H, m), 2.64-2.54 (1H, m), 2.02 (3H, s), 1.98-1.80 (1H, m.)

Example 102

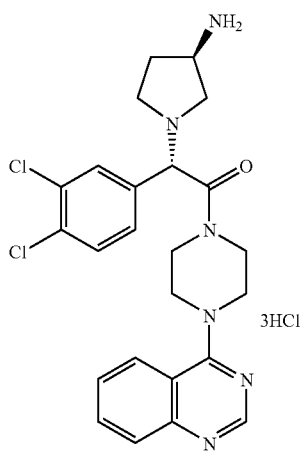

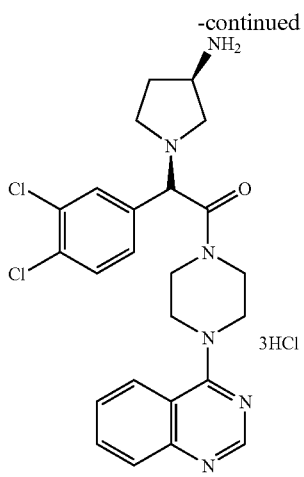

Preparation of (2R,3'R)-2-(3'-Amino-pyrrolidin-1-yl)-2-(3,4-dichlorophenyl)-1-(4-quinazolin-4-yl-piperazin-1-yl)-ethanone trihydrochloride and (2S,3R)-2-(3'-Amino-pyrrolidin-1-yl)-2-(3,4-dichlorophenyl)-1-(4-quinazolin-4-yl-piperazin-1-yl)-ethanone trihydrochloride Step 1: To a solution of glyoxylic acid monohydrate (1.0 g, 10.9 mmol) and (3R)-3-Boc-amino-pyrrolidine (2.06 g, 11.1 mmol) in 65 mL DCE was added 3,4-dichlorophenyl boronic acid (2.11 g, 11.1 mmol). The reaction mixture was heated to reflux and stirred 16 hours, after which it was cooled to room temperature, diluted with DCM, and extracted with 1M Na₂CO₃. The basic aqueous layer was extracted with EtOAc, and the combined extracts were washed with 1N NaOH, dried (Na₂SO₄), filtered, and concentrated. The resulting residue was dissolved in minimal DCM, and the product was triturated by the addition of ether. The resulting solids were isolated by vacuum filtration, washed with ether, and dried in vacuo to give one diastereomer of (3'R)-(3'-Boc-amino-pyrrolidin-1-yl)-(3,4-difluorophenyl)-acetic acid (1.53 g, 36%) as a tan powder, which will be referred to as Diastereomer 1.
$^1$H NMR (DMSO-d6, 400 MHz) δ 7.63 (s, 1H), 7.45 (d, J=8.2 Hz, 1H), 7.33 (d, J=8.0 Hz, 1H), 7.09 (d, J=6.4 Hz, 0.2H), 6.95 (d, J=6.4 Hz, 0.8H), 3.92-3.78 (m, 1H), 3.51 (s, 0.25H), 3.49 (s, 0.75H), 3.40-3.30 (m, 1H), 2.77-2.69 (m, 0.2H), 2.64-2.53 (m, 1.8H), 2.42-2.33 (m, 1H), 2.31-2.17 (m, 1H), 2.01-1.88 (m, 1H), 1.58-1.46 (m, 1), 1.36 (s, 9H). LCMS (APCI)+ m/z 389 [M+H]$_+$; HPLC Rt 2.17 min.

The basic aqueous layer from above was carefully acidified to about pH 6.5 with solid KHSO₄ until CO₂ evolution ceased. The oily mixture was then extracted with EtOAc, and the combined extracts were dried (Na₂SO₄), filtered, and concentrated. The resulting residue was dissolved in minimal DCM, and the product was triturated by the addition of ether. The resulting solids were isolated by vacuum filtration, washed with ether, and dried in vacuo to give the other diastereomer of (3'R)-(3'-Boc-amino-pyrrolidin-1-yl)-(3,4-difluorophenyl)-acetic acid (0.67 g, 16%) as a tan powder, which will be referred to as Diastereomer 2. $^1$H NMR (DMSO-d6, 400 MHz) δ 7.68 (s, 1H), 7.67-7.58 (m, 1.25H), 7.46-7.37 (m, 1H), 7.13-7.03 (m, 0.75H), 4.20 (d, J=6.6 Hz, 1H), 3.97 (br s, 1H), 3.11-3.00 (m, 0.5H), 2.90-2.76 (m, 1.5H), 2.74-2.63 (m, 0.5H), 2.63-2.52 (m, 1H), 2.47-2.37 (m, 0.5H), 2.13-1.97 (m, 1H), 1.74-1.60 (m, 1H), 1.36 (s, 9H). LCMS (APCI)+ m/z 389 [M+H]$_+$; HPLC Rt 2.17 min.

Step 2, (Diastereomer 1): To a solution of 4-Piperazin-1-ylquinazoline (30 mg, 0.14 mmol) and Diastereomer 1 (65 mg, 0.17 mmol) in 1.2 mL 3:1 DCM:THF were added successively HOBt.H2O (21 mg, 0.14 mmol) and DCC (34 mg, 0.17 mmol). The reaction mixture was stirred at room temperature 3.5 hours, after which it was diluted with DCM, vacuum filtered through compressed celite, and rinsed with DCM. The filtrate was then stirred with 2N NaOH and extracted with DCM. The combined extracts were dried (Na₂SO₄), filtered and concentrated. The crude was purified on silica (1:4 DCM:ethyl acetate to 30:1 DCM:MeOH gradient) to give (3'R)-2-(3'-Boc-amino-pyrrolidin-1-yl)-2-(3,4-dichlorophenyl)-1-(4-quinazolin-4-yl-piperazin-1-yl)-ethanone. This was then dissolved in 1.2 mL dioxane, and 1.5 mL 4M HCl/dioxane was added. The resulting suspension was stirred at room temperature 16 hours, after which it was concentrated to dryness. The solids were dissolved in minimal MeOH, and the product was triturated with ether. The resulting solids were isolated by filtration through a fritted funnel with nitrogen pressure, rinsed with ether, and dried in vacuo to give one diasteomer of (3'R)-2-(3'-amino-pyrrolidin-1-yl)-2-(3,4-dichlorophenyl)-1-(4-quinazolin-4-yl-piperazin-1-yl)-ethanone trihydrochloride (67 mg, 81%) as a pale yellow powder. $^1$H NMR (D₂O, 400 MHz) δ 8.45 (s, 1H), 7.91 (d, J=8.0 Hz, 1H), 7.89 (d, J=7.8 Hz, 1H), 7.67 (d, J=8.4 Hz, 1H), 7.59 (d, J=7.8 Hz, 1H), 7.56 (s, 1H), 7.51 (d, J=8.4 Hz, 1H), 7.33 (d, J=8.4 Hz, 1H), 5.54 (s, 0.75H), 5.52 (s, 0.25H), 4.25-3.95 (m, 5H), 3.77-3.35 (m, 7H), 3.26-3.06 (m, 1H), 2.60-2.40 (m, 1H), 2.19-1.94 (m, 1H). LCMS (APCI)+ m/z 485 [M+H]$^+$; HPLC Rt 1.71 min.

Step 2, Diastereomer 2: 4-Piperazin-1-ylquinazoline was acylated with Diastereomer 2 following Step 2 for Diastereomer 1 above, to furnish the other diastereomer of (3'R)-2-(3-amino-pyrrolidin-1-yl)-2-(3,4-dichlorophenyl)-1-(4-quinazolin-4-yl-piperazin-1-yl)-ethanone trihydrochloride (60 mg, 72%) as a pale yellow powder. $^1$H NMR (D₂O, 400 MHz) δ 8.45 (s, 1H), 7.91 (d, J=7.8 Hz, 1H), 7.89 (d, J=7.8 Hz, 1H), 7.67 (d, J=8.4 Hz, 1H), 7.59 (d, J=8.0 Hz, 1H), 7.55 (s, 1H), 7.49 (d, J=8.2 Hz, 1H), 7.32 (d, J=7.6 Hz, 1H), 5.46 (d, J=12.7 Hz, 1H), 4.24-3.95 (m, 5H), 3.82-3.44 (m, 6H), 3.40-3.28 (m, 0.5H), 3.20-3.10 (m, 1H), 3.10-2.98 (m, 0.5H), 2.56-2.36 (m, 1H), 2.15-1.92 (m, 1H). LCMS (APCI)+m/z 485 [M+H]$_+$; HPLC Rt 1.69 min.

Example 103

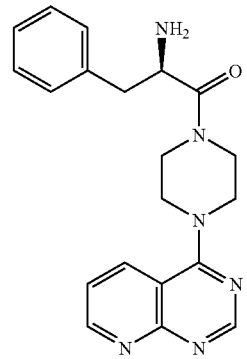 [SMILES: N[C@H](Cc1ccccc1)C(=O)N1CCN(c2ncnc3ncccc23)CC1]

The preparation of (2R)-2-amino-3-phenyl-1-(4-pyrido[2,3-d]pyrimidin-4-yl-piperazin-1-yl)-propan-1-one trihydochloride Step 1: 2-aminonicotinic acid (7 g) and formamide (22.8 g) were heated at 167 C (internal temperature) for 2.5 hours.

After cooling, the solid was recrystallized from 100 mL of hot water to give Pyrido[2,3-d]pyrimidin-4-ol as pale yellow powder (5.2 g, 69.7%). ¹H NMR (DMSO, 400 MHz) δ 12.60 (br, 1H), 8.90 (br, 1H), 8.50 (m, 1H), 8.37 (s, 1H), 7.50 (m, 1H). R$_t$ 0.87 min. MS (ESI+) [M+H]$^+$148.

Step 2: The Pyrido[2,3-d]pyrimidin-4-ol (3 g) in POCl$_3$ (45 mL) was stirred at reflux for 3 hours. The excess POCl$_3$ was removed. The residue was added 10 mL of cold water and extracted with EtOAc (2×30 mL). The combined organic layer was washed with brine and dried over sodium sulfate. After removal of solvent, it gave 4-chloropyrido[2,3-d]pyrimidine as yellow solid (0.3 g, 7.6%). ¹H NMR (CDCl$_3$, 400 MHz) δ 9.38 (br, 1H), 9.31 (s, 1H), 8.62 (d, 1H), 7.75 (m, 1H).

Step 3: The 4-chloro-pyrido[2,3-d]pyrimidine (0.3 g) and piperazine (1.6 g) in Ethanol (10 mL) was refluxed for 1 hour. The solvent was removed and 50 mL of toluene was added. The toluene was removed in vacuo. The resulting solid was used directly for the next step without purification. R$_t$ 1.93 min. MS (ESI+) [M+H]$^+$216.

Step 4: DIEA (0.74 mL) and HBTU (1.3 g) was added to the solution of (2R)-2-tert-butoxycarbonylamino-3-phenyl-propionic acid (0.092 g) in THF (5 mL) at 0° C. The mixture was stirred at room temperature for 20 minutes, and then 4-piperazin-1-yl-pyrido[2,3-d]pyrimidine (0.31 g) was added. The reaction was stirred at room temperature for 1 hour. 20 mL of EtOAc was added and the organic layer was separated. The aqueous layer extracted with EtOAc (20 mL). The combined organic layer was washed with saturated sodium bicarbonate (20 mL) and dried over sodium sulfate. After removal of solvent, the residue was purified by flash chromatography (10:1=DCM:MeOH) to give [1-benzyl-2-oxo-2-(4-pyrido[2,3-d]pyrimidin-4-yl-piperazin-yl)-ethyl-carbamic acid tert-butyl ester as white foam solid (0.392 g, 58.9%). ¹H NMR (CDCl$_3$, 400 MHz) δ 9.11 (br, 1H), 8.92 (s, 1H), 8.15 (d, 1H), 7.40 (m, 1H), 7.20-7.33 (m, 5H), 5.42 (m, 1H), 4.85 (m, 1H), 3.78-3.82 (m, 2H), 3.61-3.70 (m, 2H), 3.50-3.58 (m, 2H), 3.15-3.20 (m, 1H), 3.08-3.12 (m, 2H), 1.42 (s, 9H). R$_t$ 2.23 min. MS (ESI+) [M+H]$^+$463.

Step 5: [1-benzyl-2-oxo-2-(4-pyrido[2,3-d]pyrimidin-4-yl-piperazin-yl)-ethyl-carbamic acid tert-butyl ester (0.046 mg) was dissolved in DCM (5 mL) and HCl/dioxane (0.5 mL) was added. The suspension was stirred at room temperature for 3 hours, after which it was concentrated to give (2R)-2-amino-3-phenyl-1-(4-pyrido[2,3-d]pyrimidin-4-yl-piperazin-1-yl)-propan-1-one trihydrochloride (0.031 g, 86%). R$_t$ 1.55 min. MS (ESI+) [M+H]$^+$363.

Example 104

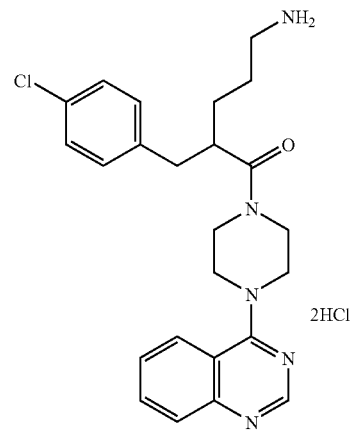 [SMILES: NCCCC(Cc1ccc(Cl)cc1)C(=O)N1CCN(c2ncnc3ccccc23)CC1 ; "2HCl"]

Preparation of 5-amino-2-(4-chlorobenzyl)-1-(4-quinazolin-4-yl-piperazin-1-yl)-pentan-1-one dihydrochloride Step 1: To a −78° C. solution of LHMDS (1.0M, 5.3 mL, 5.3 mmol) in 10 mL THF was added by syringe a solution of Boc-2-piperidone (1.0 g, 5.0 mmol) in 8 mL THF. The reaction mixture was stirred at −78° C. for 1 hour, after which a 0° C. solution of 4-chlorobenzyl bromide (1.1 g, 5.3 mmol) in 5 mL THF was added quickly by syringe. The reaction mixture was stirred 1 hour at −78° C., warmed to 0° C., stirred another 1 hour, then quenched with 17 mL 3M LiOH solution. The reaction mixture was then stirred 15 hours at room temperature, after which it was diluted with H$_2$O and washed with ether. The aqueous layer was acidified with solid KHSO$_4$, extracted with DCM, and the extracts were dried (Na$_2$SO$_4$), filtered, and concentrated to give 5-Boc-amino-2-(4-chlorobenzyl)-pentanoic acid (1.0 g, 60%) as a clear, colorless syrup. LCMS (APCI−) m/z 340 [M−H]$^−$; Rt: 2.37 min.

Step 2: A solution of EDCI (100 mg, 0.54 mmol), HOBt.H20 (82 mg, 0.54 mmol), 5-Boc-amino-2-(4-chlorobenzyl)-pentanoic acid (170 mg, 0.50 mmol), and TEA (190 μL, 1.4 mmol) in 3 mL DMF was stirred 10 minutes, and solid 4-piperazin-1-yl-quinazoline dihydrochloride (130 mg, 0.45 mmol) was added. The reaction mixture was stirred at room temperature 15 hours, after which water was added. The reaction mixture was extracted with DCM, and combined extracts washed with sat NaHCO$_3$, dried (Na$_2$SO$_4$), filtered, and concentrated. The crude was purified on silica gel (1:1 to 1:9 DCM:EtOAc) to give 5-Boc-amino-2-(4-chlorobenzyl)-1-(4-quinazolin-4-yl-piperazin-1-yl)-pentan-1-one. LCMS (APCI+) m/z 538 [M+H]$^+$; Rt: 3.12 min.

Step 3: To a solution of 5-Boc-amino-2-(4-chlorobenzyl)-1-(4-quinazolin-4-yl-piperazin-1-yl)-pentan-1-one in 1.5 mL dioxane was added 2.5 mL 4M HCl/dioxane. The resulting suspension was stirred at room temperature 17 hours, after which it was concentrated to dryness. The solids were dissolved in minimal MeOH, and the product was triturated by the addition of ether. The solids were isolated by filtration through a fritted funnel with nitrogen pressure, rinsed with ether, and dried in vacuo to give 5-amino-2-(4-chlorobenzyl)-

1-(4-quinazolin-4-yl-piperazin-1-yl)-pentan-1-one dihydrochloride (110 mg, 46%) as a white powder. $^1$H NMR (CD$_3$OD, 400 MHz) δ 8.71 (1H, d, J 2.0 Hz), 8.20 (1H, d, J 8.7 Hz), 8.05 (1H, t, J 7.8 Hz), 7.84-7.75 (2H, m), 7.31-7.22 (4H, m), 4.40-4.30 (1H, m), 4.29-4.20 (1H, m), 4.12-4.02 (1H, m), 3.92-3.66 (4H, m), 3.53-3.42 (1H, m), 3.29-3.21 (1H, m), 2.97-2.81 (4H, m), 1.87-1.62 (4H, m). LCMS (APCI+) m/z 438 [M+H]$^+$; Rt: 1.98 min.

Example 105

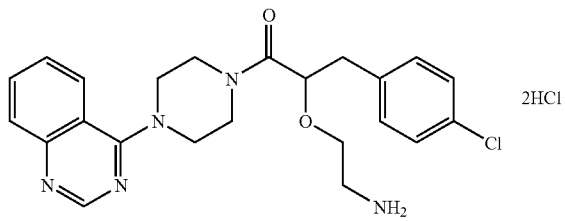 [SMILES: NCCOC(Cc1ccc(Cl)cc1)C(=O)N1CCN(c2ncnc3ccccc23)CC1 ; "2HCl"]

Preparation of 2-(2-Amino-ethoxy)-3-(4-chlorophenyl)-1-(4-quinazolin-4-yl-piperazin-1-yl)-propan-1-one dihydrochloride The PS-CDI (175 mg, 0.181 mmol), HOBt monohydrate (214 mg, 0.140 mmol), 4-piperazin-1-yl-quinazoline dihydrochloride (52 mg, 0.181 mmol), and 2-(2-tert-butoxycarbonylamino-ethoxy)-3-(4-chlorophenyl)-propionic acid (48 mg, 0.140 mmol; prepared by alkylation of (2-Boc-amino-ethoxy)-acetic acid ethyl ester with 4-chlorobenzylbromide according to procedures described in the literature: Nizal S. Chandrakumar et al. *J. Med. Chem.* 1992, 35, 2928-2938) were suspended/dissolved in 2.5 mL of chloroform (plus 3-5 drops THF). The mixture was shaken at room temperature overnight, then treated with MP-CO$_3$ (330 mg, 0.838 mmol) for two hours. The mixture was vacuum filtered, rinsed with chloroform, and concentrated in vacuo. The residue was purified on silica gel (1:19 DCM:EtOAc) to afford 2-(2-Boc-amino-ethoxy)-3-(4-chlorophenyl)-1-(4-quinazolin-4-yl-piperazin-1-yl)-propan-1-one. This material was dissolved in 1.0 mL of 1,4-dioxane and treated with 1.5 mL of 4M HCl in 1,4-dioxane affording slow precipitation. The mixture was sonicated briefly and stirred at room temperature overnight to completion. The resulting suspension was concentrated in vacuo, and the solids were suspended in diethyl ether, filtered under nitrogen pressure, and dried in vacuo to afford 2-(2-amino-ethoxy)-3-(4-chlorophenyl)-1-(4-quinazolin-4-yl-piperazin-1-yl)-propan-1-one dihydrochloride as a yellow powder (13 mg, 18%). LCMS (APCI+) m/z 440 [M+H]$^+$. HPLC R$_2$=1.75 min.

Example 106

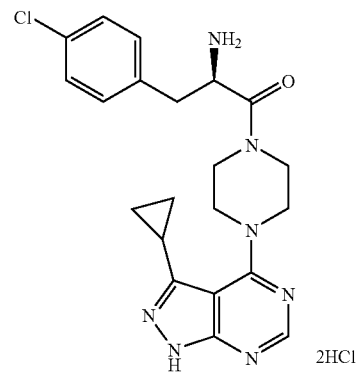 [SMILES: N[C@H](Cc1ccc(Cl)cc1)C(=O)N1CCN(c2ncnc3[nH]nc(C4CC4)c23)CC1 ; "2HCl"]

Preparation of (2R)-2-Amino-3-(4-chlorophenyl[4-(3-cyclopropyl-1H-pyrazolo[3,4-d]pyrimidin-4-yl)-piperazin-1-yl]-propan-1-one dihydrochloride Step 1: To a stirred solution of LDA (9.85 mL, 1.5 M, 15.8 mmol) in THF (20 mL) was added dropwise a solution of 4,6-dichloropyrimidine (2.00 g, 13.4 mmol) in THF (12 mL) at −78° C. After stirring for 1.5 hours, a solution of cyclopropanecarbaldehyde (1.05 g, 15.0 mmol) in THF (10 mL) was added dropwise. The solution was stirred at −78° C. for 1 hour and then quenched by addition of water (10 mL). The reaction mixture was allowed to warm to room temperature and partitioned between EtOAc and water. The organic layer was washed with brine, dried and concentrated. The residue was purified by column chromatography (hexanes/EtOAc, 3:1) to give Cyclopropyl-(4,6-dichloro-pyrimidin-5-yl)-methanol (2.36 g, 80%) as a yellow oil. $^1$H NMR (CDCl$_3$, 400 MHz) δ 8.70 (s, 1H), 4.56 (m, 1H), 2.63 (d, J=8.0 Hz, 1H), 1.70 (m, 1H), 0.76 (m, 1H), 0.55 (m, 2H).

Step 2: To a vigorously stirred solution of Cyclopropyl-(4,6-dichloro-pyrimidin-5-yl)-methanol (0.84 g, 3.8 mmol) in anhydrous acetone (12 mL) was added portionwise chromium (VI) oxide (1.2 g, 12 mmol) at 0° C. The mixture was stirred at 0° C. for 30 minutes. The excess of the oxidizing agent was destroyed by the addition of isopropanol (2 mL). After stirring for 15 minutes, the reaction mixture was poured into saturated NaHCO$_3$ solution and filtered through Celite. The filtrate was extracted with EtOAc. The combined organic layers were washed with brine, dried and concentrated. The residue was purified by column chromatography (hexanes:EtOAc, 6:1) to give Cyclopropyl-(4,6-dichloro-pyrimidin-5-yl)-methanone (0.80 g, 96%) as a colorless oil. $^1$H NMR (CDCl$_3$, 400 MHz) δ 8.83 (s, 1H), 2.26 (m, 1H), 1.46 (m, 2H), 1.26 (m, 2H).

Step 3: A mixture of Cyclopropyl-(4,6-dichloro-pyrimidin-5-yl)-methanone (0.75 g, 3.5 mmol), anhydrous hydrazine (0.13 mL, 4.1 mmol) and THF (35 mL) was stirred at room temperature for 4 hours. The reaction was partitioned between water and EtOAc. The organic layer was washed with brine, dried and passed through a short silica gel pad to give 4-Chloro-3-cyclopropyl-1H-pyrazolo[3,4-d]pyrimidine (0.50 g, 74%) as a white solid. ¹H NMR (CDCl₃, 400 MHz) δ 11.87 (s, 1H), 8.80 (s, 1H), 2.55 (m, 1H), 1.15 (m, 2H), 1.14 (m, 2H).

Step 4: 4-(3-Cyclopropyl-1H-pyrazolo[3,4-d]pyrimidin-4-yl)-piperazine-1-carboxylic acid tert-butyl ester was prepared by the procedures described in Example 40, Step 1, substituting 4-chloro-5-iodopyrimidine with 4-Chloro-3-cyclopropyl-1H-pyrazolo[3,4-d]pyrimidine. LCMS (APCI+) m/z 345 [M+H]⁺; Rt=2.52 min.

Step 5: 3-Cyclopropyl-4-piperazin-1-yl-1H-pyrazolo[3,4-d]pyrimidine dihydrochloride was prepared by the procedures described in Example 34, Step 3, substituting (2R)-{1-(4-Chlorobenzyl)-2-[4-(1H-indazol-5-yl)-piperazin-1-yl]-2-oxo-ethyl}-carbamic acid tert-butyl ester with 4-(3-cyclopropyl-1H-pyrazolo[3,4-d]pyrimidin-4-yl)-piperazine-1-carboxylic acid tert-butyl ester. ¹H NMR (DMSO-d₆, 400 MHz) δ 8.58 (s, 1H), 4.60 (m, 4H), 3.53 (m, 4H), 2.36 (m, 1H), 1.31 (m, 2H), 1.14 (m, 2H). LCMS (APCI+) m/z 245 [M+H]⁺; Rt=1.02 min.

Step 6: (2R)-2-Amino-3-(4-chlorophenyl)-1-[4-(3-cyclopropyl-1H-pyrazolo[3,4-d]pyrimidin-4-yl)-piperazin-1-yl]-propan-1-one dihydrochloride was prepared by substituting 4-Piperazin-1-yl-6,7,8,9-tetrahydro-5H-1,3,9-triaza-fluorene dihydrochloride with 3-cyclopropyl-4-piperazin-1-yl-1H-pyrazolo[3,4-d]pyrimidine dihydrochloride in Example 81, Step 3. ¹H NMR (CD₃OD, 400 MHz) δ 8.48 (s, 1H), 7.40 (d, J=8.4 Hz, 2H), 7.34 (d, J=8.4 Hz, 2H), 4.77 (m, 1H), 4.24 (m, 3H), 3.87 (m, 2H), 3.74 (m, 2H), 3.25 (m, 1H), 3.16 (m, 2H), 2.27 (m, 1H), 1.28 (m, 2H), 1.10 (m, 2H). LCMS (APCI+) m/z 426, 428 [M+H]⁺; Rt=1.88 min.

Example 107

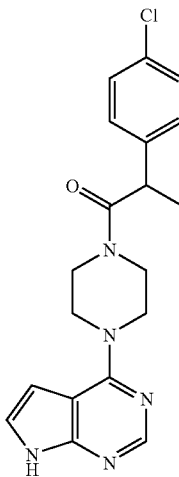

Preparation of 2-(3,4-Dichlorophenyl)-3-(1H-imidazol-4-yl)-1-[4-(7H-pyrrolo[2,3-d]pyrimidin-4-yl)-piperazin-1-yl]-propan-1-one dihydrochloride Step 1: 4-[2-(3,4-Dichlorophenyl)-2-methoxycarbonylethyl]-imidazole-1-carboxylic acid tert-butyl ester was prepared by the procedures described in Example 78, Step 1, substituting 3-tert-butoxycarbonylamino-propionic acid tert-butyl ester with (3,4-Dichlorophenyl)-acetic acid methyl ester and substituting 4-Bromo-1-bromomethyl-2-fluorobenzene with 4-Bromomethyl-imidazole-1-carboxylic acid tert-butyl ester (prepared from 4(5)-hydroxymethylimidazole hydrochloride according to the literature: *J. Med. Chem.* 1997, 40, 2208). ¹H NMR (CDCl₃, 400 MHz) δ 7.96 (s, 1H), 7.42 (s, 1H), 7.38 (d, J=8.0 Hz, 1H), 7.16 (d, J=8.0 Hz, 1H), 7.02 (s, 1H), 4.08 (t, J=7.6 Hz, 1H), 3.66 (s, 3H), 3.32 (dd, J=14.4 Hz, J=8.4 Hz, 1H), 2.92 (dd, J=14.4 Hz, J=6.8 Hz, 1H). LCMS (APCI+) m/z 299, 301, 303 [M-Boc+H]⁺; Rt=3.72 min.

Step 2: 2-(3,4-Dichlorophenyl)-3-(1H-imidazol-4-yl)-propionic acid was prepared by the procedures described in Example 78, Step 2, substituting 3-tert-Butoxycarbonylamino-2-(4-trifluoromethylbenzyl)-propionic acid ethyl ester with 4-[2-(3,4-Dichlorophenyl)-2-methoxycarbonylethyl]imidazole-1-carboxylic acid tert-butyl ester. ¹H NMR (CD₃OD, 400 MHz) δ 8.25 (s, 1H), 7.51 (s, 1H), 7.42 (d, J=8.0 Hz, 1H), 7.26 (d, J=8.0 Hz, 1H), 7.00 (s, 1H), 3.84 (m, 1H), 3.38 (m, 1H), 3.00 (dd, J=14.4 Hz, J=6.8 Hz, 1H). LCMS (APCI+) m/z 285, 287, 289 [M+H]⁺; Rt=1.54 min.

Step 3: 2-(3,4-Dichlorophenyl)-3-(1H-imidazol-4-yl)-1-[4-(7H-pyrrolo[2,3-d]pyrimidin-4-yl)-piperazin-1-yl]-propan-1-one was prepared by substituting 5-piperazin-1-yl-1H-indazole with 4-Piperazin-1-yl-7H-pyrrolo[2,3-d]pyrimidine dihydrochloride and substituting (D)-Boc-4-chlorophenylalanine with 2-(3,4-Dichlorophenyl)-3-(1H-imidazol-4-yl)-propionic acid in Example B-1, Step 2. The free amine was converted to HCl salt by treatment with HCl in Ether. ¹H NMR (CD₃OD, 400 MHz) δ 8.76 (s, 1H), 8.32 (s, 1H), 7.52 (m, 2H), 7.38 (s, 1H), 7.29 (m, 2H), 6.92 (s, 1H), 4.58 (m, 1H), 3.70-4.20 (m, 7H), 3.63 (m, 1H), 3.43 (m, 1H), 3.16 (m, 1H). LCMS (APCI+) m/z 470, 472, 474 [M+H]⁺; Rt=2.15 min.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups.

What is claimed is:

1. A compound including resolved enantiomers, diastereomers, solvates and pharmaceutically acceptable salts thereof, said compound comprising Formula I:

A-L-CR    I where:
CR is quinoline, wherein said quinoline is optionally substituted with one or more groups selected from halogen, hydroxyl, cyano, nitro, azido, —NR²¹SO₂R²⁴, —SO₂NR²¹R²², —NR²¹S(O)R⁴, —S(O)NR²¹R²², —C(O)R²¹, —C(O)OR²¹, —OC(O)R²¹, —OC(O)OR²¹, —NR²¹C(O)OR²⁴, —NR²¹C(=NR²¹)NR²²R²³, —NR²¹C(O)R²², —C(O)NR²¹R²², —SR²¹, —S(O)R²⁴, —SO₂R²⁴, —NR²¹R²², —NR²¹C(O)NR²²R²³, —NR²¹C(NCN)NR²²R²³, —OR²¹, C₁-C₄ alkyl, C₁-C₆ heteroalkyl, C₂-C₆ alkenyl, C₂-C₆ heteroalkenyl, C₂-C₆ alkynyl, C₂-C₆ heteroalkynyl, C₃-C₆ cycloalkyl, C₃-C₆ heterocycloalkyl, aryl, heteroaryl, arylalkyl and heteroarylalkyl, wherein any of said alkyl, heteroalkyl, alkenyl, heteroalkenyl, alkynyl, heteroalkynyl, cycloalkyl, heterocycloalkyl, aryl, heteroaryl, arylalkyl and heteroarylalkyl are further optionally substituted with one or more groups selected from halogen, hydroxyl, cyano, nitro, azido, fluoromethyl, difluoromethyl, trifluoromethyl, C₁-C₆ alkyl, C₂-C₆ alkenyl, C₂-C₆ alkynyl, C₁-C₆ heteroalkyl, C₂-C₆ heteroalkenyl, C₂-C₆ heteroalkynyl, C₃-C₆ cycloalkyl, C₃-C₆ heterocycloalkyl, —SR²¹, —S(O)R²⁴, —SO₂R²⁴, —C(O)R²¹, C(O)OR²¹, —C(O)NR²¹R²², —NR²¹R²² and —OR²¹, and wherein each heteroaryl of CR is selected from pyridinyl, imidazolyl, pyrimidinyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl;

L is selected from:

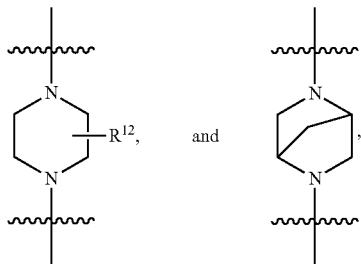

where $R^{12}$ is hydrogen, halogen, hydroxy, cyano, nitro, amino, azido, $C_1$-$C_5$ alkyl, $C_2$-$C_5$ alkenyl, $C_2$-$C_5$ alkynyl, $C_1$-$C_5$ heteroalkyl, $C_2$-$C_5$ heteroalkenyl or $C_2$-$C_5$ heteroalkynyl, wherein any of said alkyl, alkenyl, alkynyl, heteroalkyl, heteroalkenyl, and heteroalkynyl are optionally substituted with one or more groups independently selected from halogen, cyano, nitro, amino, azido, $C_1$-$C_4$ alkyl, fluoromethyl, difluoromethyl, trifluoromethyl, methoxy, fluoromethoxy, difluoromethoxy and trifluoromethoxy;

A is

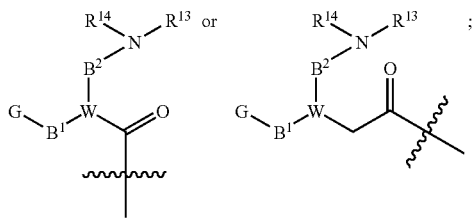

W is N or $CR^{15}$, provided that when L is a substituted or unsubstituted piperazinylene, W must be $CR^{15}$;

G is hydrogen, alkyl, heteroalkyl, alkenyl, heteroalkenyl, alkynyl, heteroalkynyl, cycloalkyl, heterocycloalkyl, aryl or heteroaryl, wherein any of said alkyl, heteroalkyl, alkenyl, heteroalkenyl, alkynyl, heteroalkynyl, cycloalkyl, heterocycloalkyl, aryl or heteroaryl is optionally substituted with one or more groups selected from halogen, hydroxyl, cyano, amino, nitro, azido, —$NR^{21}SO_2R^{24}$, $SO_2NR^{21}R^{22}$, —$NR^{21}S(O)R^4$, —$S(O)NR^{21}R^{22}$, —$C(O)R^{21}$, —$C(O)OR^{21}$, —$OC(O)R^{21}$, —$OC(O)OR^{21}$, —$NR^{21}C(O)OR^{24}$, —$NR^{21}C(=NR^{21})NR^{22}R^{23}$, —$NR^{21}C(O)R^{22}$, —$C(O)NR^{21}R^{22}$, —$SR^{21}$, —$S(O)R^{24}$, —$SO_2R^{24}$, —$NR^{21}R^{22}$, $NR^{21}C(O)NR^{22}R^{23}$, —$NR^{21}C(NCN)NR^{22}R^{23}$, —$OR^{21}$, $C_1$-$C_4$ alkyl, $C_1$-$C_4$ heteroalkyl, $C_2$-$C_4$ alkenyl, $C_2$-$C_4$ heteroalkenyl, $C_2$-$C_4$ alkynyl, $C_2$-$C_4$ heteroalkynyl, cycloalkyl, heterocycloalkyl aryl and heteroaryl;

$B^1$ and $B^2$ are independently absent or $C_1$-$C_4$ alkylene, $C_1$-$C_4$ heteroalkylene, $C_2$-$C_4$ alkenylene, $C_2$-$C_4$ heteroalkenylene, $C_2$-$C_4$ alkynylene, $C_2$-$C_4$ heteroalkynylene, $C_3$-$C_6$ cycloalkylene, and $C_3$-$C_6$ heterocycloalkylene, wherein any of said alkylene, heteroalkylene, alkenylene, heteroalkenylene, alkynylene, heteroalkynylene, cycloalkylene or heterocycloalkylene is optionally substituted with one or more groups independently selected from halogen, hydroxyl, cyano, nitro, azido, $C_1$-$C_4$ alkyl, $C_1$-$C_4$ heteroalkyl, $C_2$-$C_4$ alkenyl, $C_2$-$C_4$ heteroalkenyl, $C_2$-$C_4$ alkynyl, $C_2$-$C_4$ heteroalkynyl, $NR^{21}R^{22}$ and $OR^{21}$;

$R^{21}$, $R^{22}$ and $R^{23}$ independently are hydrogen, $C_1$-$C_6$ alkyl, $C_2$-$C_6$ alkenyl, $C_2$-$C_6$ alkynyl, $C_1$-$C_6$ heteroalkyl, $C_2$-$C_6$ heteroalkenyl, $C_2$-$C_6$ heteroalkynyl, $C_3$-$C_6$ cycloalkyl, $C_3$-$C_6$ heterocycloalkyl, aryl, arylalkyl, heteroaryl or heteroarylalkyl;

$R^{24}$ is $C_1$-$C_6$ alkyl, $C_2$-$C_6$ alkenyl, $C_2$-$C_6$ alkynyl, $C_1$-$C_6$ heteroalkyl, $C_2$-$C_6$ heteroalkenyl, $C_2$-$C_6$ heteroalkynyl, $C_3$-$C_6$ cycloalkyl, $C_3$-$C_6$ heterocycloalkyl, aryl, arylalkyl, heteroaryl or heteroarylalkyl;

or any two of $R^{21}$, $R^{22}$, $R^{23}$ or $R^{24}$ together with the atom(s) to which they are attached form a 4 to 10 membered carbocyclic, aryl, heteroaryl or heterocyclic ring, wherein any of said carbocyclic, aryl, heteroaryl or heterocyclic rings are optionally substituted with one or more groups independently selected from halogen, cyano, nitro, trifluoromethyl, difluoromethoxy, trifluoromethoxy, azido, aryl, heteroaryl, arylalkyl, heteroarylalkyl, heterocyclyl, and heterocyclylalkyl;

$R^{13}$ and $R^{14}$ are independently hydrogen, hydroxyl, cyano, $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, $C_1$-$C_6$ cycloalkyl, $C_1$-$C_6$ heterocycloalkyl, aryl, heteroaryl, arylalkyl, heteroarylalkyl, —$C(O)R^{21}$, $C(O)OR^{21}$, $C(=NR^{21})NR^{22}R^{23}$ or —$SO_2R^{24}$, wherein any of said alkyl, alkenyl, alkynyl, cycloalkyl, heterocycloalkyl, aryl, heteroaryl, heteroalkyl, heteroalkenyl, heteroalkynyl, arylalkyl or heteroarylalkyl is optionally substituted with one or more groups independently selected from halogen, hydroxyl, cyano, amino, nitro, azido, —$NR^{21}SO_2R^{24}$, —$SO_2NR^{21}R^{22}$, —$NR^{21}S(O)R^4$, —$S(O)NR^{21}R^{22}$, —$C(O)R^{21}$, —$C(O)OR^{21}$, —$OC(O)R^{21}$, —$OC(O)OR^{21}$, —$NR^{21}C(O)OR^{24}$, —$NR^{21}C(=NR^{21})NR^{22}R^{23}$, —$NR^{21}C(O)R^{22}$, —$C(O)NR^{21}R^{22}$, —$SR^{21}$, —$S(O)R^{24}$, —$SO_2R^{24}$, —$NR^{21}R^{22}$, —$NR^{21}C(O)NR^{22}R^{23}$, —$NR^{21}C(NCN)NR^{22}R^{23}$, —$OR^{21}$, $C_1$-$C_4$ alkyl, $C_1$-$C_4$ heteroalkyl, $C_2$-$C_4$ alkenyl, $C_2$-$C_4$ heteroalkenyl, $C_2$-$C_4$ alkynyl, $C_2$-$C_4$ heteroalkynyl, cycloalkyl, heterocycloalkyl aryl and heteroaryl, and wherein any $R^{21}$ of the group —$C(O)R^{21}$ of $R^{13}$ and $R^{14}$ is hydrogen, $C_1$-$C_6$ alkyl, $C_1$-$C_6$ alkenyl, $C_1$-$C_6$ alkynyl, $C_1$-$C_6$ heteroalkenyl, $C_1$-$C_6$ heteroalkynyl, $C_3$-$C_6$ cycloalkyl, $C_3$-$C_6$ heterocycloalkyl, aryl, arylalkyl, heteroaryl or heteroarylalkyl;

or $R^{13}$ and $R^{14}$ together with the atoms to which they are attached form a 4 to 10 membered carbocyclic, aryl, heteroaryl or heterocyclic ring, wherein any of said carbocyclic, aryl, heteroaryl and heterocyclic rings are optionally substituted with one or more groups independently selected from halogen, cyano, nitro, azido, $C_1$-$C_4$ alkyl, $C_1$-$C_4$ heteroalkyl, $C_2$-$C_4$ alkenyl, $C_2$-$C_4$ heteroalkenyl, $C_2$-$C_4$ alkynyl, $C_2$-$C_4$ heteroalkynyl, $NR^{21}R^{22}$ and $OR^{21}$;

or $R^{13}$ and an atom of $B^2$ together with N form a 4 to 10 membered carbocyclic, aryl, heteroaryl or heterocyclic ring, wherein any of said carbocyclic, aryl, heteroaryl and heterocyclic rings are optionally substituted with one or more groups independently selected from halogen, cyano, nitro, azido, $C_1$-$C_4$ alkyl, $C_1$-$C_4$ heteroalkyl, C₂-C₄ alkenyl, C₂-C₄ heteroalkenyl, C₂-C₄ alkynyl, C₂-C₄ heteroalkynyl, NR²¹R²² and OR²¹;

R¹⁵ is hydrogen, C₁-C₄ alkyl, C₁-C₄ heteroalkyl, C₂-C₄ alkenyl, C₂-C₄ heteroalkenyl, C₂-C₄ alkynyl or C₂-C₄ heteroalkynyl, wherein any of said alkyl, heteroalkyl, alkenyl, heteroalkenyl, alkynyl or heteroalkynyl is optionally substituted with one or more groups independently selected from halogen, hydroxyl, cyano, nitro, azido, NR²¹R²² and OR²¹;

or R¹³ and R¹⁵ together with atoms to which they are attached form a 3 to 10 membered carbocyclic, aryl, heteroaryl or heterocyclic ring, wherein any of said carbocyclic, aryl, heteroaryl and heterocyclic rings are optionally substituted with one or more groups independently selected from halogen, cyano, nitro, azido, C₁-C₄ alkyl, C₁-C₄ heteroalkyl, C₂-C₄ alkenyl, C₂-C₄ heteroalkenyl, C₂-C₄ alkynyl, C₂-C₄ heteroalkynyl, NR²¹R²² and OR²¹;

or, when W is CR¹⁵, R¹⁵ and an atom of B¹ or B² together with C, form a 3 to 10 membered carbocyclic, aryl, heteroaryl or heterocyclic ring, wherein any of said carbocyclic, aryl, heteroaryl and heterocyclic rings are optionally substituted with one or more groups independently selected from halogen, cyano, nitro, azido, C₁-C₄ alkyl, C₁-C₄ heteroalkyl, C₂-C₄ alkenyl, C₂-C₄ heteroalkenyl, C₂-C₄ alkynyl, C₂-C₄ heteroalkynyl, NR²¹R²² and OR²¹.

2. The compound of claim 1, where CR is:

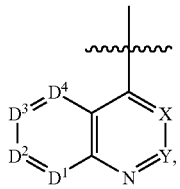

where X is CR¹;
Y is CR²;
D¹, D², D³ and D⁴ are independently CR⁴;
R¹ is hydrogen, halogen, hydroxyl, cyano, nitro, azido, fluoromethyl, difluoromethyl, trifluoromethyl, methoxy, fluoromethoxy, difluoromethoxy, trifluoromethoxy, amino, aminomethyl, dimethylamino, aminoethyl, diethylamino or ethoxy;
R² is hydrogen, halogen, hydroxyl, cyano, nitro, amino, azido, C₁-C₄ alkyl, C₁-C₄ heteroalkyl, C₂-C₄ alkenyl, C₂-C₄ heteroalkenyl, C₂-C₄ alkynyl, C₂-C₄ heteroalkynyl, C₁-C₆ cycloalkyl, C₁-C₆ heterocycloalkyl, C₁-C₆ aryl, or C₁-C₆ heteroaryl, wherein any of said alkyl, heteroalkyl, alkenyl, heteroalkenyl, alkynyl, heteroalkynyl, cycloalkyl, heterocycloalkyl, aryl or heteroaryl are further optionally substituted with one or more groups independently selected from halogen, hydroxyl, cyano, nitro, azido, fluoromethyl, difluoromethyl, trifluoromethyl, methoxy, fluoromethoxy, difluoromethoxy, trifluoromethoxy, amino, aminomethyl, dimethylamino, aminoethyl, diethylamino and ethoxy; and
R⁴ is hydrogen, hydroxyl, cyano, amino, nitro, azido, alkyl, heteroalkyl, alkenyl, heteroalkenyl, alkynyl, heteroalkynyl, cycloalkyl, heterocycloalkyl, aryl, arylalkyl, heteroaryl, heteroarylalkyl, —NR²¹SO₂R²⁴, —SO₂NR²¹R²², —NR²¹S(O)R⁴, —S(O)NR²¹, —C(O)R²¹, —C(O)OR²¹, —OC(O)R²¹, —OC(O)OR²¹, —NR²¹C(O)OR²⁴, —NR²¹C(=NR²¹)NR²²R²³, —NR²¹C(O)R²², —C(O)NR²¹R²², —SR²¹, —S(O)R²⁴, —SO₂R²⁴, —NR²¹R²², —NR²¹C(O)NR²²R²³, —NR²¹C(NCN)NR²²R²³ or —OR²¹, wherein any of said alkyl, heteroalkyl, alkenyl, heteroalkenyl, alkynyl, heteroalkynyl, cycloalkyl, heterocycloalkyl, aryl, arylalkyl, heteroaryl or heteroarylalkyl, is optionally substituted with one or more groups independently selected from halogen, hydroxyl, cyano, amino, nitro, azido, —NR²¹SO₂R²⁴, —SO₂NR²¹R²², —NR²¹S(O)R⁴, —S(O)NR²¹R²², —C(O)R²¹, —C(O)OR²¹, —OC(O)R²¹, —OC(O)OR²¹, —NR²¹C(O)OR²⁴, —NR²¹C(=NR²¹)NR²²R²³, —NR²¹C(O)R²², —C(O)NR²¹R²², —SR²¹, —S(O)R²⁴, —SO₂R²⁴, —NR²¹R²², —NR²¹C(O)NR²²R²³, —NR²¹C(NCN)NR²²R²³, —OR²¹, C₁-C₄ alkyl, C₁-C₄ heteroalkyl, C₂-C₄ alkenyl, C₂-C₄ heteroalkenyl, C₂-C₄ alkynyl, C₂-C₄ heteroalkynyl, cycloalkyl, heterocycloalkyl, aryl and heteroaryl, and wherein said alkyl, heteroalkyl, alkenyl, heteroalkenyl, alkynyl, heteroalkynyl, cycloalkyl, heterocycloalkyl, aryl and heteroaryl may optionally be further optionally substituted with one or more groups independently selected from halogen, hydroxyl, cyano, amino, nitro, azido, C₁-C₄ alkyl, C₁-C₄ heteroalkyl, C₂-C₄ alkenyl, C₂-C₄ heteroalkenyl, C₂-C₄ alkynyl, C₂-C₄ heteroalkynyl, cycloalkyl, heterocycloalkyl, aryl and heteroaryl, —NR²¹R²², and —OR²¹.

3. The compound of claim 1, where L is:

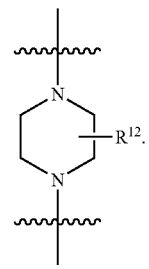

4. The compound of claim 2, where A is:

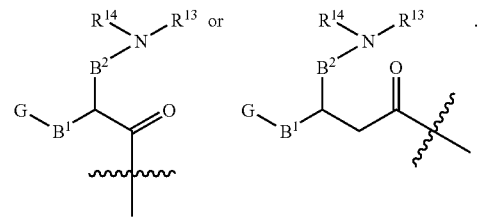

5. The compound of claim 2, where A is:

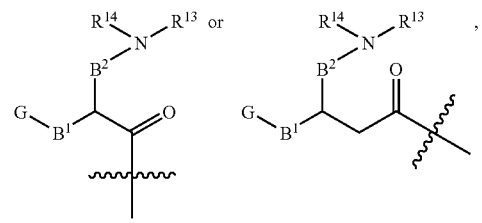

where G is hydrogen, alkyl, cycloalkyl, heterocycloaryl, aryl or heteroaryl, wherein any of said alkyl, cycloalkyl, heterocycloalkyl, aryl or heteroaryl is optionally substituted with one or more groups selected from halogen, hydroxyl, cyano, amino, nitro, azido, —NR$^{21}$SO$_2$R$^{24}$, —SO$_2$NR$^{21}$R$^{22}$, —NR$^{21}$S(O)R$^{4}$, —S(O)NR$^{21}$R$^{22}$, —C(O)R$^{21}$, —C(O)OR$^{21}$, —OC(O)R$^{21}$, —OC(O)OR$^{21}$, —NR$^{21}$C(O)OR$^{24}$, —NR$^{21}$C(=NR$^{21}$)NR$^{22}$R$^{23}$, —NR$^{21}$C(O)R$^{22}$, —C(O)NR$^{21}$R$^{22}$, —SR$^{21}$, —S(O)R$^{24}$, —SO$_2$R$^{24}$, —NR$^{21}$R$^{22}$, —NR$^{21}$C(O)NR$^{22}$R$^{23}$, —NR$^{21}$C(NCN)NR$^{22}$R$^{23}$, —βOR$^{21}$, C$_1$-C$_4$ alkyl, C$_2$-C$_4$ alkenyl, C$_2$-C$_4$ alkynyl, cycloalkyl, heterocycloalkyl aryl and heteroaryl.

6. The compound of claim 1, where A is:

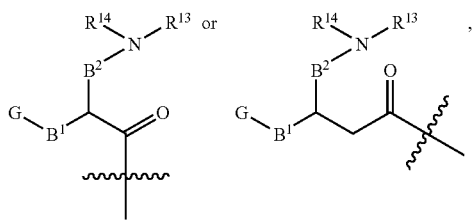

where G is hydrogen, alkyl, cycloalkyl, heterocycloaryl, aryl or heteroaryl, wherein any of said alkyl, cycloalkyl, heterocycloalkyl, aryl or heteroaryl is optionally substituted with one or more groups selected from halogen, hydroxyl, cyano, amino, nitro, azido, —NR$^{21}$SO$_2$R$^{24}$, —SO$_2$NR$^{21}$R$^{22}$, —NR$^{21}$S(O)R$^{4}$, —S(O)NR$^{21}$R$^{22}$, —C(O)R$^{21}$, —C(O)OR$^{21}$, —OC(O)R$^{21}$, —OC(O)OR$^{21}$, —NR$^{21}$C(O)OR$^{24}$, —NR$^{21}$C(=NR$^{21}$)NR$^{22}$R$^{23}$, —NR$^{21}$C(O)R$^{22}$, —C(O)NR$^{21}$R$^{22}$, —SR$^{21}$, —S(O)R$^{24}$, —SO$_2$R$^{24}$, —NR$^{21}$R$^{22}$, —NR$^{21}$C(O)NR$^{22}$R$^{23}$, —NR$^{21}$C(NCN)NR$^{22}$R$^{23}$, —OR$^{21}$, C$_1$-C$_4$ alkyl, C$_2$-C$_4$ alkenyl, C$_2$-C$_4$ alkynyl, cycloalkyl, heterocycloalkyl aryl and heteroaryl.

7. The compound of claim 1, wherein A comprises:

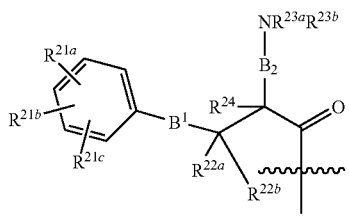

where B$^1$ and B$^2$ are, independently, absent or C$_1$-C$_4$ alkylene;

R$^{21a}$-R$^{21c}$ are independently H, halogen, CH$_3$, CF$_3$, CH$_3$O, CN, NO$_2$, NH$_2$, Ph, OH, or OCH$_2$Ph;

R$^{22a}$, R$^{22b}$, and R$^{22c}$ are independently H, CH$_3$, or halogen;

R$^{23a}$ is H; and

R$^{23b}$ is H, CH$_3$, CH$_2$NH$_2$, CH$_2$NHCH$_2$, CH$_2$CH$_2$NH$_2$, CH$_2$CH$_2$NHCH$_2$, CH$_2$CH$_2$N(CH$_2$)$_2$, —(C=O)CH$_2$NH$_2$ or —(C=O)CH$_2$CH$_2$NH$_2$;

or R$^{23a}$ and R$^{23b}$ are joined to complete a 5 or 6 membered heterocyclic ring.

8. The compound of claim 3, wherein A comprises:

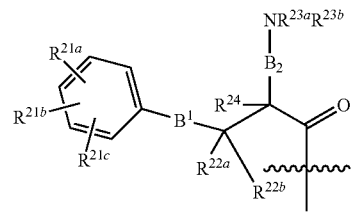

where B$^1$ and B$^2$ are, independently, absent or C$_1$-C$_4$ alkylene;

R$^{21a}$-R$^{21c}$ are independently H, halogen, CH$_3$, CF$_3$, CH$_3$O, CN, NO$_2$, NH$_2$, Ph, OH, or OCH$_2$Ph;

R$^{22a}$, R$^{22b}$, and R$^{24}$ are independently H, CH$_3$, or halogen;

R$^{23a}$ is H; and

R$^{23b}$ is H, CH$_3$, CH$_2$NH$_2$, CH$_2$NHCH$_2$, CH$_2$CH$_2$NH$_2$, CH$_2$CH$_2$NHCH$_2$, CH$_2$CH$_2$N(CH$_2$)$_2$, —(C=O)CH$_2$NH$_2$ or —(C=O)CH$_2$CH$_2$NH$_2$;

or R$^{23a}$ and R$^{23b}$ are joined to complete a 5 or 6 membered heterocyclic ring.

9. The compound of claim 1, wherein A comprises:

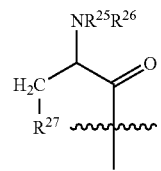

wherein R$^{25}$ and R$^{26}$ are independently H or CH$_3$; and

R$^{27}$ is 1-naphthyl, 2-naphthyl, 3'-benzylthienyl, 2'-thienyl, 2'-pyridyl, 3'-pyridyl, 4'-pyridyl, 4'-thiazolyl, or 3,3-diphenyl.

10. The compound of claim 3, wherein A comprises:

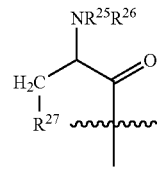

wherein R$^{25}$ and R$^{26}$ are independently H or CH$_3$, and

R$^{27}$ is 1-naphthyl, 2-naphthyl, 3'-benzylthienyl, 2'-thienyl, 2'-pyridyl, 3'-pyridyl, 4'-pyridyl, 4'-thiazolyl, or 3,3-diphenyl.

11. The compound of claim 1, where A is:

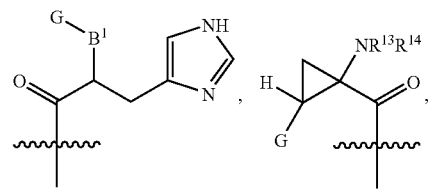

-continued

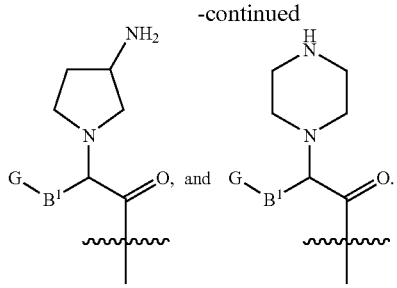

12. The compound of claim 3, where A is:

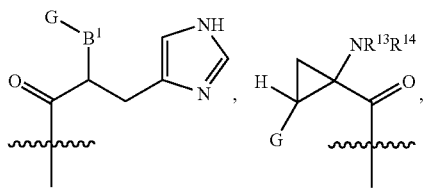

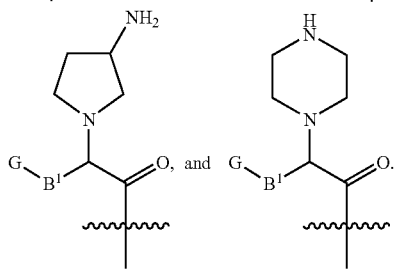

13. The compound of claim 3, where A is a D- or L-amino acid selected from the naturally occurring amino acids, 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone.

14. The compound of claim 13, wherein the amino acid is alanine, phenylalanine, histidine, or tryptophan.

15. The compound of claim 1, wherein the compound is:

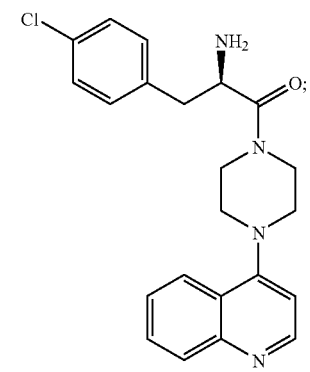 [SMILES: N[C@H](Cc1ccc(Cl)cc1)C(=O)N1CCN(c2ccnc3ccccc23)CC1]

including resolved enantiomers, diastereomers, solvates and pharmaceutically acceptable salts thereof.

16. A composition comprising a compound of claim 1 and a pharmaceutically acceptable carrier.

17. A composition comprising a compound of claim 2 and a pharmaceutically acceptable carrier.

18. A composition comprising a compound of claim 3 and a pharmaceutically acceptable carrier.

19. A composition comprising a compound of claim 5 and a pharmaceutically acceptable carrier.

20. A composition comprising a compound of claim 15 and a pharmaceutically acceptable carrier.

\* \* \* \* \*

UNITED STATES PATENT AND TRADEMARK OFFICE
CERTIFICATE OF CORRECTION

Page 1 of 2

PATENT NO. : 8,680,114 B2
APPLICATION NO. : 12/567258
DATED : March 25, 2014
INVENTOR(S) : Mitchell et al.

It is certified that error appears in the above-identified patent and that said Letters Patent is hereby corrected as shown below:

In the Claims
In Claim 1, Column 153, Line 5:
Replace:
thiadiazolyl, thiadiazolyl
With:
thiadiazolyl In Claim 1, Column 153, Line 63:
Replace:
heterocycloalkyl aryl
With:
heterocycloalkyl, aryl In Claim 1, Column 154, Line 47:
Replace:
heterocycloalkyl aryl
With:
heterocycloalkyl, aryl In Claim 1, Column 154, Lines 49-50:
Replace:
$C_1$-$C_6$ alkyl, $C_1$-$C_6$ alkenyl, $C_1$-$C_6$ alkynyl, $C_1$-$C_6$ heteroalkenyl, $C_1$-$C_6$ heteroalkynyl,
With:
$C_1$-$C_6$ alkyl, $C_2$-$C_6$ alkenyl, $C_2$-$C_6$ alkynyl, $C_2$-$C_6$ heteroalkenyl, $C_2$-$C_6$ heteroalkynyl, Signed and Sealed this
Ninth Day of August, 2016

Michelle K. Lee
*Director of the United States Patent and Trademark Office*

CERTIFICATE OF CORRECTION (continued)
U.S. Pat. No. 8,680,114 B2

In the Claims
In Claim 2, Column 155, Line 66:
Replace:
-S(O)NR$^{21}$,
With:
-S(O)NR$^{21}$R$^{22}$ In Claim 2, Column 156, Line 21-22:
Replace:
may optionally be further optionally substituted
With:
may optionally be further substituted In Claim 5, Column 157, Line 11:
Replace:
-βOR$^{21}$,
With:
-OR$^{21}$ In Claim 5, Column 157, Lines 11-12:
Replace:
heterocycloalkyl aryl
With:
heterocycloalkyl, aryl In Claim 5, Column 157, Lines 40-41:
Replace:
heterocycloalkyl aryl
With:
heterocycloalkyl, aryl In Claim 13, Column 160, Line 2:
Replace:
cirtulline,
With:
citrulline,